(12) United States Patent
Anderson et al.

(10) Patent No.: US 11,613,533 B2
(45) Date of Patent: Mar. 28, 2023

(54) COMPOUNDS USEFUL FOR INHIBITING RET KINASE

(71) Applicant: Eli Lilly and Company, Indianapolis, IN (US)

(72) Inventors: Erin D. Anderson, Boulder, CO (US); Steven W. Andrews, Longmont, CO (US); Kevin R. Condroski, Lafayette, CO (US); Thomas C. Irvin, Erie, CO (US); Gabrielle R. Kolakowski, Longmont, CO (US); Manoj Kumar, Longmont, CO (US); Elizabeth A. McFaddin, Nederland, CO (US); Megan McKenney, Boulder, CO (US); Michael J. Munchhof, Corvallis, MT (US); Michael B. Welch, Westminster, CO (US)

(73) Assignee: Eli Lilly and Company, Indianapolis, IN (US)

( * ) Notice: Subject to any disclaimer, the term of this patent is extended or adjusted under 35 U.S.C. 154(b) by 99 days.

(21) Appl. No.: 17/238,370

(22) Filed: Apr. 23, 2021

(65) Prior Publication Data
US 2021/0363140 A1 Nov. 25, 2021

Related U.S. Application Data

(60) Provisional application No. 63/015,933, filed on Apr. 27, 2020.

(51) Int. Cl.
| C07D 413/14 | (2006.01) |
|---|---|
| C07D 231/38 | (2006.01) |
| C07D 413/12 | (2006.01) |
| C07D 417/12 | (2006.01) |

(52) U.S. Cl.
CPC ......... *C07D 413/14* (2013.01); *C07D 231/38* (2013.01); *C07D 413/12* (2013.01); *C07D 417/12* (2013.01); *C07B 2200/05* (2013.01)

(58) Field of Classification Search
CPC ............... C07D 413/14; C07D 231/38; C07D 413/12
See application file for complete search history.

(56) References Cited

U.S. PATENT DOCUMENTS 10,183,928 B2 * 1/2019 Kim .................. A61P 35/00
2017/0267661 A1 9/2017 Kim et al.

FOREIGN PATENT DOCUMENTS

| WO | 2014/141187 A1 | 9/2014 |
|---|---|---|
| WO | 2017/145050 A1 | 8/2017 |
| WO | 2020/035065 A1 | 2/2020 |

OTHER PUBLICATIONS

International Search Report and Written Opinion in International Application No. PCT/US2021/028836, dated Jul. 2, 2021, 6 pages.

* cited by examiner

*Primary Examiner* — Kamal A Saeed
(74) *Attorney, Agent, or Firm* — Bradley W Crawford

(57) ABSTRACT

Provided herein are RET kinase inhibitors according to the formula:

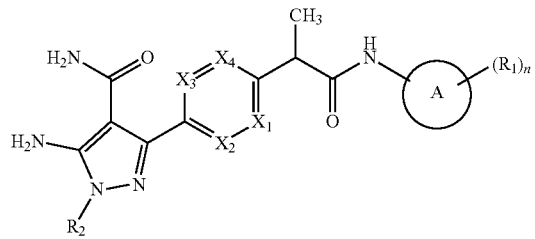

pharmaceutically acceptable salts thereof, pharmaceutical compositions thereof, and methods for their use in the treatment of diseases that can be treated with a RET kinase inhibitor, including RET-associated diseases and disorders. A, $R_1$, n, $X_1$, $X_2$, $X_3$, $X_4$, and $R_2$ have the meanings given in the specification.

25 Claims, No Drawings
Specification includes a Sequence Listing.

COMPOUNDS USEFUL FOR INHIBITING RET KINASE

BACKGROUND

The Rearranged during transfection (RET) kinase is a single-pass transmembrane receptor belonging to the tyrosine kinase superfamily that is required for normal development, maturation, and maintenance of several tissues and cell types. The extracellular portion of the RET kinase contains four calcium-dependent cadherin-like repeats involved in ligand binding and a juxtamembrane cysteine-rich region necessary for the correct folding of the RET extracellular domain, while the cytoplasmic portion of the receptor includes two tyrosine kinase subdomains.

RET signaling is mediated by the binding of a group of 35 soluble proteins of the glial cell line-derived neurotrophic factor (GDNF) family ligands (GFLs), which also includes neurturin (NTRN), artemin (ARTN), and persephin (PSPN). Unlike other receptor tyrosine kinases, RET does not directly bind to GFLs and requires an additional co-receptor, which can be one of four GDNF family receptor-α(GFRα) family members that are tethered to the cell surface by a glycosylphosphatidylinositol linkage. GFLs and GFRα family members form binary complexes that in turn bind to RET and recruit it into cholesterol-rich membrane subdomains where RET signaling occurs.

Upon binding of the ligand-co-receptor complex, RET dimerization and autophosphorylation on intracellular tyrosine residues recruits adaptor and signaling proteins to stimulate multiple downstream pathways. Adaptor protein binding to these docking sites leads to activation of Ras-MAPK and PI3K-Akt/mTOR signaling pathways or to recruitment of the CBL family of ubiquitin ligases that functions in RET downregulation of the RET-mediated functions.

Disruptions in normal RET activity due to abnormal RET expression stemming from genetic alterations in the RET kinase, including protein-gene fusions and activating point mutations, lead to overactive RET signaling and uncontrolled cell growth, e.g., various cancer types and certain gastrointestinal disorders such as irritable bowel syndrome (IBS). The ability to inhibit abnormal RET activity in patients with cancer or other disorders related to overactive RET signaling would be of great benefit to those patients. Additionally, some RET kinase genetic alterations are altering the conformational structure of a RET kinase to such an extent that a given RET kinase inhibitor may be less effective (or ineffective). In such cases, new RET kinase inhibitors that are effective to the modified RET kinase would greatly benefit patients.

SUMMARY

Compounds of the formula:

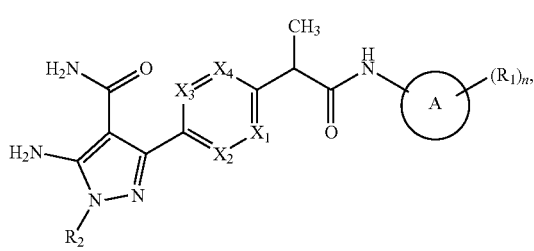

(I)

pharmaceutically acceptable salts thereof, and pharmaceutical compositions thereof, are provided herein. In formula (I), A can be a five- or six-member aryl or heteroaryl; $R_1$ can be hydrogen, halogen, $C_1$-$C_6$ alkyl, $C_1$-$C_6$ heteroalkyl, —($C_0$-$C_4$ alkyl)($C_5$-$C_6$ heteroalkyl), —($C_0$-$C_4$ alkyl)($C_3$-$C_7$ cycloalkyl), —($C_0$-$C_4$ heteroalkyl)(C3-$C_7$ cycloalkyl), —($C_0$-$C_4$ alkyl)($C_4$-$C_7$ cycloheteroalkyl), —($C_0$-$C_4$ heteroalkyl)(C3-$C_7$ cycloheteroalkyl), —($C_0$-$C_4$ alkyl)($C_4$-$C_{10}$ bicyclic), —($C_0$-$C_4$ alkyl)(C5-$C_6$ aryl), —($C_0$-$C_4$ alkyl)($C_5$-$C_6$ heteroaryl), —($C_0$-$C_4$ alkyl)($C_4$-$C_{10}$ heterobicyclic), $C_5$-$C_{12}$ spirane, $C_5$-$C_{12}$ heterospirane, adamantane, difluoromethylsulfane, or pentafluorosulfane, wherein each $R_1$ is optionally substituted with one or more groups that are independently halogen, cyano, hydroxyl, oxo, methyl, methoxy, hydroxymethyl, ethyl, ethoxy, hydroxyethyl, methylamine, N,N-diethylmethylamine, or mono-, di-, or tri-halomethyl, and wherein two $R_1$ groups can fuse to form a ring structure that includes a portion of A and is optionally aromatic, and n is 1, 2, 3, 4 or 5; $X_1$, $X_2$, $X_3$, and $X_4$ each can be independently N, CH, C—$CH_3$, C—$CH_2$—OH, C—$OCH_3$, C—$CH_2$—$OCH_3$ or C-halogen; and $R_2$ can be $C_1$-$C_4$ alkyl, —($C_0$-$C_4$ alkyl)($C_3$-$C_7$ cycloalkyl), —($C_0$-$C_4$ alkyl)($C_4$-$C_7$ heterocycloalkyl), —($C_0$-$C_4$ alkyl)($C_4$-$C_{10}$ bicyclic), with each being optionally substituted with one or more groups that are independently deuterium, halogen, cyano, hydroxyl, oxo, methyl, methoxy, hydroxymethyl, ethyl, ethoxy, hydroxyethyl, cyclopropyl, or mono-, di-, or tri-halomethyl. The compounds of formula (I) contain a chiral center providing an R-enantiomeric form and an S-enantiomeric form as shown here:

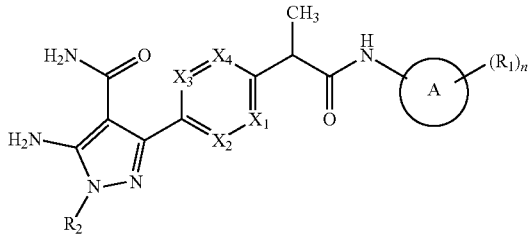

(R-enantiomer)

(II)

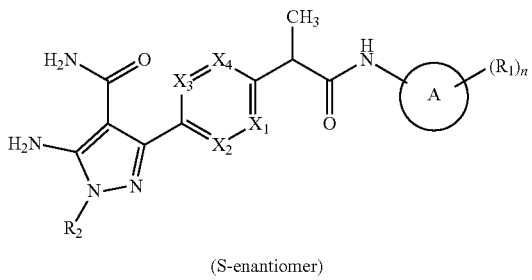

(S-enantiomer)

(III)

The R-enantiomer and S-enantiomer, pharmaceutically acceptable salts thereof, and pharmaceutical compositions thereof, in which A, $R_1$, n, $X_1$, $X_2$, $X_3$, $X_4$, and $R_2$ are defined herein are also provided. It is understood that formulas II and III are subspecies of formula I, and thus, references to formula I throughout this application also apply to formulas II and III.

Methods of using the compounds of formulas I, II, or III, pharmaceutically acceptable salts thereof, and pharmaceutical compositions thereof, to treat cancer, in particular for the treatment of cancer with abnormal RET expression (e.g., a RET-associated cancer like medullary thyroid cancer or RET fusion lung cancer) are also provided. The methods include administering a therapeutically effective amount of a compound of formulas I, II, or III, or a pharmaceutically acceptable salt thereof, to a patient in need.

Also provided herein, are compounds of formulas I, II, and III, and pharmaceutically acceptable salts thereof, for use in therapy. Further provided herein, are the compounds of formulas I, II, and III, and pharmaceutically acceptable salts thereof, for use in the treatment of cancer, in particular for use in the treatment of cancer with abnormal RET expression (e.g., a RET-associated cancer like medullary thyroid cancer or RET fusion lung cancer). The use of compounds of formulas I, II, and III, or pharmaceutically acceptable salts thereof, in the manufacture of a medicament for treating cancer, in particular for use in the treatment of cancer with abnormal RET expression (e.g., a RET-associated cancer like medullary thyroid cancer or RET fusion lung cancer), is also provided.

DESCRIPTION

Novel RET kinase inhibitor compounds are described herein. These new compounds could address the need for potent, effective treatment of disorders associated with abnormal RET activity, e.g., IBS or cancer, especially cancer stemming from overactive RET signaling (i.e., RET-associated cancers). More specifically, these new compounds could address the need for potent, effective treatment of RET-associated cancers such as lung cancer (e.g., small cell lung carcinoma or non-small cell lung carcinoma), thyroid cancer (e.g., papillary thyroid cancer, medullary thyroid cancer, differentiated thyroid cancer, recurrent thyroid cancer, or refractory differentiated thyroid cancer), thyroid adenoma, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, or cervical cancer.

The compounds described herein are compounds of formula (I):

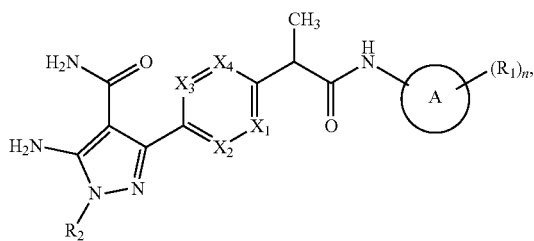

or pharmaceutically acceptable salts thereof. In formula (I),
A is a five- or six-member aryl or heteroaryl;
Each $R_1$ can be attached to A at various chemically appropriate positions and is independently hydrogen, halogen, $C_1$-$C_6$ alkyl, $C_1$-$C_6$ heteroalkyl, —($C_0$-$C_4$ alkyl)($C_5$-$C_6$ heteroalkyl), —($C_0$-$C_4$ alkyl)($C_3$-$C_7$ cycloalkyl), —($C_0$-$C_4$ heteroalkyl)($C_3$-$C_7$ cycloalkyl), —($C_0$-$C_4$ alkyl)($C_4$-$C_7$ cycloheteroalkyl), —($C_0$-$C_4$ heteroalkyl)($C_3$-$C_7$ cycloheteroalkyl), —($C_0$-$C_4$ alkyl)($C_4$-$C_{10}$ bicyclic), —($C_0$-$C_4$ alkyl) ($C_5$-$C_6$ aryl), —($C_0$-$C_4$ alkyl)($C_5$-$C_6$ heteroaryl), —($C_0$-$C_4$ alkyl)($C_4$-$C_{10}$ heterobicyclic), $C_5$-$C_{12}$ spirane, $C_5$-$C_{12}$ heterospirane, adamantane, difluoromethylsulfane, or pentafluorosulfane, wherein each $R_1$ is optionally substituted with one or more groups that are independently halogen, cyano, hydroxyl, oxo, methyl, methoxy, hydroxymethyl, ethyl, ethoxy, hydroxy ethyl, methylamine, N,N-diethylmethylamine, or mono-, di-, or tri-halomethyl, and wherein two $R_1$ groups can fuse to form a ring structure that includes a portion of A and is optionally aromatic, and n is 1, 2, 3, 4, or 5;

$X_1$, $X_2$, $X_3$, and $X_4$ are each independently N, CH, C—CH$_3$, C—CH$_2$—OH, C—OCH$_3$, C—CH$_2$—OCH$_3$ or C-halogen; and $R_2$ is $C_1$-$C_4$ alkyl, —($C_0$-$C_4$ alkyl)($C_3$-$C_7$ cycloalkyl), —($C_0$-$C_4$ alkyl)($C_4$-$C_7$ heterocycloalkyl), —($C_0$-$C_4$ alkyl) ($C_4$-$C_{10}$ bicyclic) each optionally substituted with one or more groups that are independently deuterium, halogen, cyano, hydroxyl, oxo, methyl, methoxy, hydroxymethyl, ethyl, ethoxy, hydroxyethyl, cyclopropyl, or mono-, di-, or tri-halomethyl.

While n is defined as 1, 2, 3, 4, or 5, some A-rings have 5 positions that may accommodate an $R_1$ group, while others do not. For example, phenyl has 5 substitutable positions, pyrazoles have three substitutable positions, while an isoxazole has only two. Thus, the maximum value of the variable n can depend on the identity of the A-ring.

The specific chemical naming conventions used herein are intended to be familiar to one of skill in the chemical arts. Some terms are defined specifically for additional clarity.

As used herein, the term alkyl means saturated linear or branched-chain monovalent hydrocarbon radicals of one to four atoms, e.g., "$C_1$-$C_4$ alkyl." In cases where a zero is indicated, e.g., $C_0$-$C_4$ alkyl, this component of the substituent group can be absent, thus, if a $C_5$ heterocycloalkyl substituent is at the $R_2$ position in formula (I), the $C_5$ heterocycloalkyl substituent would be described by the —($C_0$-$C_4$ alkyl)($C_4$-$C_7$ heterocycloalkyl) substituent as described for $R_2$ (i.e., the substituent group would be —($C_0$) ($C_5$ heterocycloalkyl). Examples include, but are not limited to, methyl, ethyl, propyl, 1-propyl, isopropyl, and butyl. Similarly, as used herein, the term heteroalkyl means saturated linear or branched-chain monovalent alkyl molecules as defined herein containing one or more heteroatoms that have replaced carbon(s) in the alkyl chain.

As used herein, the term $C_5$-$C_6$ aryl refers to a functional group or substituent derived from an aromatic ring containing five to seven carbon atoms and no heteroatoms. As used herein, the term $C_5$-$C_6$ heteroaryl refers to a functional group or substituent derived from an aromatic ring containing carbon atoms and one or more heteroatoms (e.g., nitrogen, oxygen, or sulphur) as part of the aromatic ring such that that ring contains from five to seven atoms. Examples of aryl and heteroaryl groups include, but are not limited to, benzene, pyridine, pyrazine, pyrimidine, pyridazine, furan, pyrrole, thiophene, imidazole, pyrazole, oxazole, isoxazole, and thiazole.

As used herein, the term $C_3$-$C_7$ cycloalkyl means a cyclic alkyl molecule containing three to seven carbon atoms. Examples of $C_3$-$C_7$ cycloalkyls include, but are not limited to, cyclopropyl, cyclobutyl, and cyclopentyl. Similarly, as used herein, the term $C_4$-$C_7$ cycloheteroalkyl means a cycloalkyl molecule as defined herein, containing four to seven total atoms and including one or more hetero atoms that have replaced carbon(s) in the cycloalkyl chain.

As used herein, the term $C_4$-$C_{10}$ bicyclic refers to a group having two or more fused or bridged rings made from four to ten carbon atoms. When the $C_4$-$C_{10}$ bicyclic group is fused, the two rings share two adjacent atoms. When the $C_4$-$C_{10}$ bicyclic group is bridged, the two rings share three or more atoms. Bicyclic molecules can be all aliphatic, all aromatic, or mixed aromatic and aliphatic. The term $C_4$-$C_{10}$ heterobicyclic refers to $C_4$-$C_{10}$ bicyclic groups as defined that also include one or more hetero atoms. Examples of bridged $C_4$-$C_8$ bicycloalkyl molecules useful with the compounds of formula (I) include, but are not limited to:

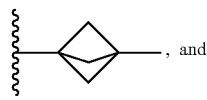

3-methyl-bicyclo[1.1.1]pentyl

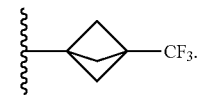

3-(trifluoromethyl)-bicyclo[1.1.1]pentyl

As used herein, the term $C_5$-$C_{12}$ spirane refers to a group having two or more rings made from seven to twelve carbon atoms connected through a single common carbon atom. Similarly, the term $C_5$-$C_{12}$ heterospirane refers to a group having two or more rings made from seven to twelve atoms including carbon and at least one hetero atom joined by a spirocyclic linkage through a carbon atom, wherein each ring has three to six ring atoms (with one carbon atom being common to both rings), and wherein two of the ring atoms are nitrogen atoms. Examples of $C_5$-$C_{12}$ spiranes and heterospiranes useful with the compounds of formula (I) include, but are not limited to:

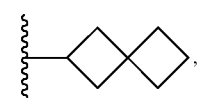

spiro[3.3]heptanyl

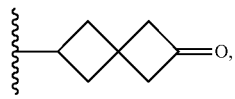

spiro[3.3]heptan-2-onyl

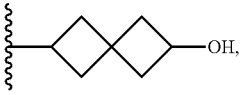

spiro[3.3]heptan-2-olyl

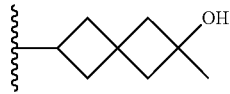

2-methylspiro[3.3]heptan-2-olyl

7-methyl-7-azaspiro[3.5]nonanyl

8-methyl-8-azaspiro[4.5]decanyl

As used herein, the term halogen means fluoro (F), chloro (Cl), bromo (Br), or iodo (I).

As used herein, the term oxo means an oxygen that is double-bonded to a carbon atom.

In the compounds of formula (I), A-$(R_1)_n$ can be

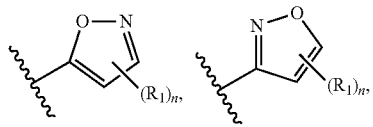

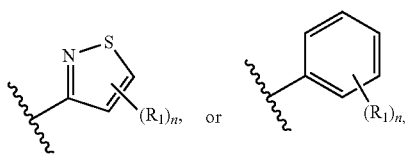

wherein a wavy line indicates the connection point of A to the backbone as shown in formula (I).

In one embodiment, in the compounds of formula (I), A-$(R_1)_n$ is

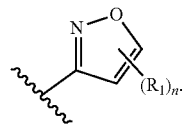

In an embodiment, in the compounds of formula (I), A-$(R_1)_n$ is

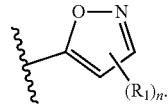

In another embodiment, in the compounds of formula (I), A-$(R_1)_n$ is

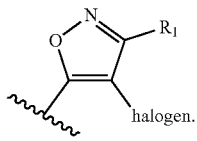

In a preferred embodiment, the halogen is F or Cl.

In yet another embodiment, in the compounds of formula (I), A-(R₁)ₙ is

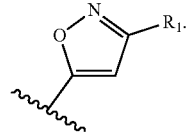

In another embodiment, in the compounds of formula (I), A-(R₁)ₙ can be

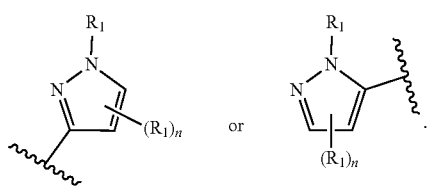

In an embodiment, in the compounds of formula (I), A-(R₁)ₙ is

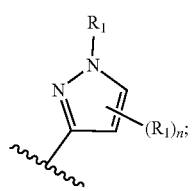

and n is 1.

In a further embodiment, in the compounds of formula (I), A-(R₁)ₙ is

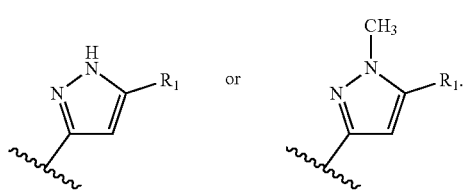

In an embodiment, A-(R₁)ₙ is a phenyl substituted with (R₁)ₙ. In a further embodiment, n is 1-4, or 1-3, or 1-2, or 1, or 2, or 2-4, or 2-5. In some embodiments when A-(R₁)ₙ is a phenyl substituted with (R₁)ₙ, two R₁ groups fuse to form a ring structure that includes a portion of A and is optionally aromatic, the resulting A-ring is optionally substituted, as described herein.

In some embodiments, in the compounds of formula (I), each R₁ is independently selected from the group consisting of H, —CH₃, —CH₂C(CH₃)₃, —C(CH₃)₂CF₃,

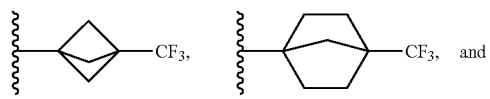

-continued

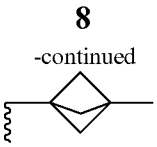

In further embodiments, in the compounds of formula (I), at least one R₁ group is H or CH₃.

In another embodiment, in the compounds of formula (I), at least one R₁ is halogen,

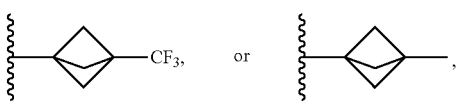

—CH₂C(CH₃)₃, 2-chloro-4-fluorophenyl, 2,4-dichlorophenyl, —CH₂C(CH₃)₃, —C(CH₃)₂CF₃,

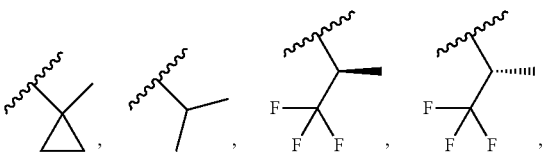

—C(CH₃)₂CH₂CH₃, —C(CH₃)₂CF₂CH₃, —C(CH₃)₂CH₂CF₃, —C(CH₃)₃, or CF₃.

In yet another embodiment, at least one R₁ is halogen, —CH₂C(CH₃)₃,

In still yet another embodiment, at least one R₁ is CH₃, —CH₂C(CH₃)₃, —C(CH₃)₂CF₃, C(CH₃)₂CH₂CH₃, —C(CH₃)₂CF₂CH₃, —C(CH₃)₂CH₂CF₃, —C(CH₃)₃, or CF₃.

In another embodiment, at least one R₁ is an optionally substituted C₅-C₁₂ spirane.

In still another embodiment, at least one R₁ is difluoromethylsulfane, or pentafluorosulfane.

In yet still another embodiment, at least one R₁ is 2-fluoro-4-chlorophenyl; 2-chloro-4-fluorophenyl; 2,4-dichlorophenyl; or 2,4-difluorophenyl.

In the compounds of formula (I), R₂ can be

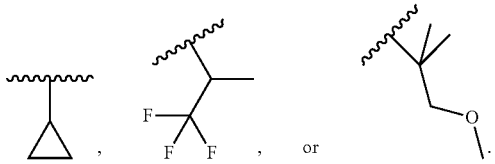

where the wavy line indicates connection the backbone.

In some embodiments, in the compounds of formula (I), $R_2$ is —$CH(CH_3)_2$, —$CH(CF_3)CH_3$, —$CH(CH_3)CHF_2$, or

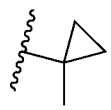

In other embodiments, in the compounds of formula (I), $R_2$ is

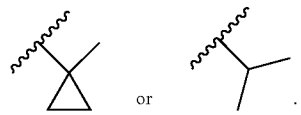

In another embodiment, in the compounds of formula (I), $R_2$ is

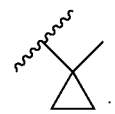

In still another embodiment, in the compounds of formula (I), $R_2$ is

In some embodiments, in the compounds of formula (I), $R_2$ is deuterated, i.e., it contains at least one deuterium. In some further embodiments, deuterated $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$.

In some embodiments, $R_2$ is —$CH(CD_3)_2$.

In various embodiments, $X_1$, $X_2$, $X_3$, and $X_4$ are CH.

In other embodiments, $X_1$, $X_2$, $X_3$, and $X_4$ are each independently CH, C—$CH_3$, C—$CH_2$—OH, C—$OCH_3$, C—$CH_2$—$OCH_3$ or C-halogen, wherein at least one of $X_1$, $X_2$, $X_3$, and $X_4$ is not CH.

In some embodiments, two of $X_1$, $X_2$, $X_3$, and $X_4$ are CH, while the other two are C-halogen. In a further embodiment, $X_1$ and $X_2$ are CF, and $X_3$ and $X_4$ are CH.

In various embodiments, three of $X_1$, $X_2$, $X_3$, and $X_4$ are CH, while one is C-halogen. In a further embodiment, $X_2$ is CF, while $X_1$, $X_3$ and $X_4$ are CH.

In still other embodiments, one of $X_1$, $X_2$, $X_3$, and $X_4$ is N.

In a further embodiment, $X_2$ is N and at least two of $X_1$, $X_3$, and $X_4$ is CH.

In a still further embodiment, $X_1$ is N and at least two of $X_2$, $X_3$, and $X_4$ is CH.

In all of the above embodiments, it is understood that the definitions of variables apply to the non-salt forms "or a pharmaceutically acceptable salt thereof."

One of skill in the art will appreciate that compounds as described by formula (I), or pharmaceutically acceptable salts thereof, contain at least one chiral center, the position of which is indicated by an φ in formula (I)$^φ$:

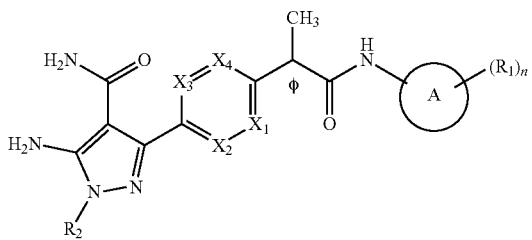

(other chiral centers may also be created by various optional substitution patterns of Ru and $R_2$ and can create further diastereomer sets). One of skill in the art will also appreciate that the Cahn-Ingold-Prelog (R) or (S) designations for chiral centers will vary depending upon the substitution patterns around a chiral center. The chiral center noted in the compound of formula (I) provides an R-enantiomeric form shown by formula (II) and an S-enantiomeric from shown by formula (III):

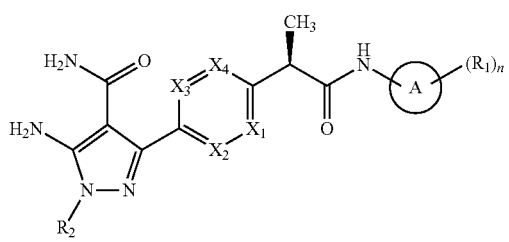

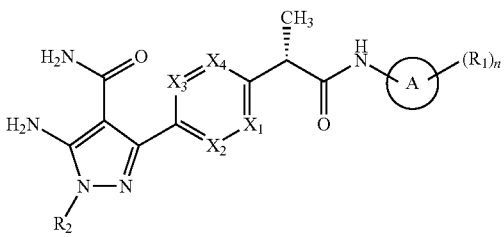

Compounds of formula (II) and formula (III) or pharmaceutically acceptable salts thereof, in which A, $R_1$, n, $X_1$, $X_2$, $X_3$, $X_4$, and $R_2$ are defined as for formula (I), are also provided herein. If multiple chiral centers are present, then diastereomers may also be present.

In one aspect, in the compounds of formulas (I), (II) and/or (III), $R_2$ is isopropyl; $X_1$, $X_2$, $X_3$, and $X_4$ are CH; A-$(R_1)_n$ is (III)

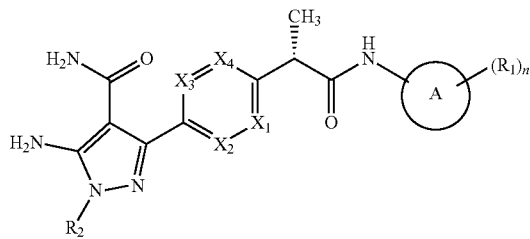

where R$_1$ is selected from the group consisting of H, —CH$_3$, —CH$_2$C(CH$_3$)$_3$, —C(CH$_3$)$_2$CF$_3$,

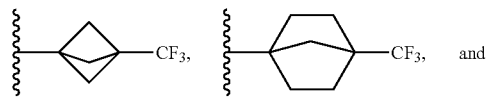 and

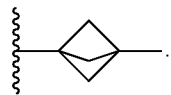.

In another aspect, in the compounds of formulas (I), (II) and/or (III), R$_2$ is isopropyl; three of X$_1$, X$_2$, X$_3$, and X$_4$ are CH, while one of X$_1$, X$_2$, X$_3$, and X$_4$ is N; A-(R$_1$)$_n$ is

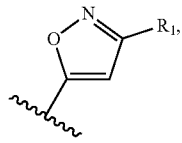

where R$_1$ is selected from the group consisting of H, —CH$_3$, —CH$_2$C(CH$_3$)$_3$, —C(CH$_3$)$_2$CF$_3$,

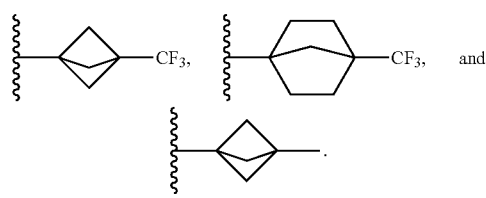

In an aspect, in the compounds of formulas (I), (II) and/or (III), R$_2$ is

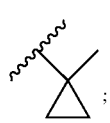;

X$_1$, X$_2$, X$_3$, and X$_4$ are CH; A-(R$_1$)$_n$ is

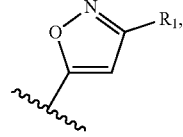

where R$_1$ is selected from the group consisting of H, —CH$_3$, —CH$_2$C(CH$_3$)$_3$, —C(CH$_3$)$_2$CF$_3$,

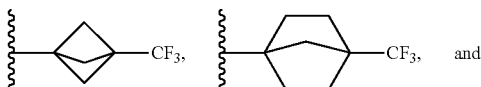 and

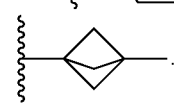.

In a further aspect, in the compounds of formulas (I), (II) and/or (III), R$_2$ is

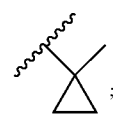;

three of X$_1$, X$_2$, X$_3$, and X$_4$ are CH, while one of X$_1$, X$_2$, X$_3$, and X$_4$ is N; A-(R$_1$)$_n$ is

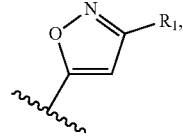

where R$_1$ is selected from the group consisting of H, —CH$_3$, —CH$_2$C(CH$_3$)$_3$, —C(CH$_3$)$_2$CF$_3$,

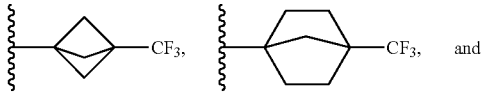 and

In a further aspect, in the compounds of formulas (I), (II) and/or (III), R$_2$ is —CH(CH$_3$)CF$_2$D, —CH(CD$_3$)$_2$, —CH(CF$_3$)CD$_3$, —CH(CH$_3$)CDF$_2$, —CD(CD$_3$)$_2$, or —CD(CH$_3$)CD$_3$; X$_1$, X$_2$, X$_3$, and X$_4$ are CH; A-(R$_1$)$_n$ is

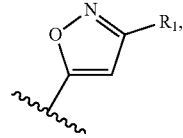

where $R_1$ is selected from the group consisting of H, —$CH_3$, —$CH_2C(CH_3)_3$, —$C(CH_3)_2CF_3$,

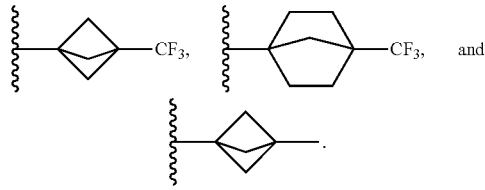

In a yet still further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; three of $X_1$, $X_2$, $X_3$, and $X_4$ are CH, while one of $X_1$, $X_2$, $X_3$, and $X_4$ is N; A-$(R_1)_n$ is

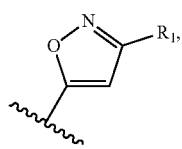

where $R_1$ is selected from the group consisting of H, —$CH_3$, —$CH_2C(CH_3)_3$, —$C(CH_3)_2CF_3$,

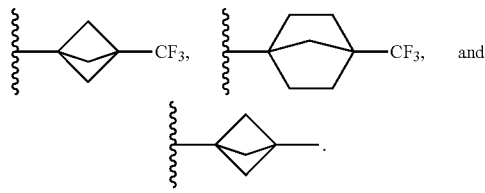

In one aspect, in the compounds of formulas (I), (II) and/or (III), $R_2$ is isopropyl; $X_1$, $X_2$, $X_3$, and $X_4$ are CH; A-$(R_1)_n$ is

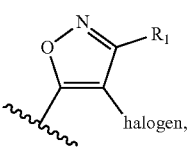

where $R_1$ is selected from the group consisting of H, —$CH_3$, —$CH_2C(CH_3)_3$, —$C(CH_3)_2CF_3$,

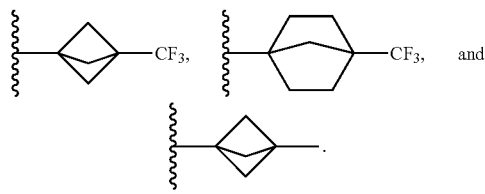

In another aspect, in the compounds of formulas (I), (II) and/or (III), $R_2$ is isopropyl; three of $X_1$, $X_2$, $X_3$, and $X_4$ are CH, while one of $X_1$, $X_2$, $X_3$, and $X_4$ is N; A-$(R_1)_n$ is

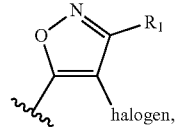

where $R_1$ is selected from the group consisting of H, —$CH_3$, —$CH_2C(CH_3)_3$, —$C(CH_3)_2CF_3$,

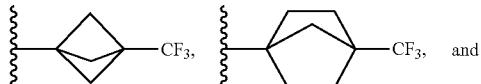

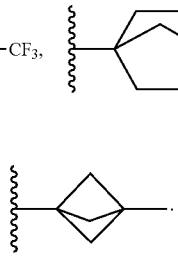

In an aspect, in the compounds of formulas (I), (II) and/or (III), $R_2$ is

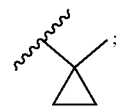

$X_1$, $X_2$, $X_3$, and $X_4$ are CH; A-$(R_1)_n$ is

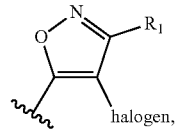

where $R_1$ is selected from the group consisting of H, —$CH_3$, —$CH_2C(CH_3)_3$, —$C(CH_3)_2CF_3$,

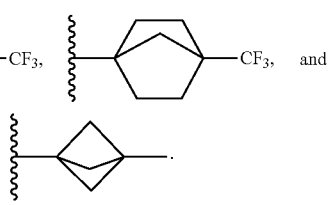

In a further aspect, in the compounds of formulas (I), (II) and/or (III), $R_2$ is

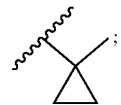 [SMILES: *C1(C)CC1]

three of $X_1$, $X_2$, $X_3$, and $X_4$ are CH, while one of $X_1$, $X_2$, $X_3$, and $X_4$ is N; $A\text{-}(R_1)_n$ is

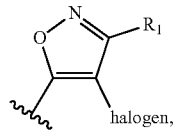

where $R_1$ is selected from the group consisting of H, —$CH_3$, —$CH_2C(CH_3)_3$, —$C(CH_3)_2CF_3$,

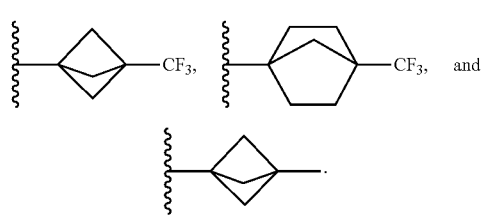

In a further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; $X_1$, $X_2$, $X_3$, and $X_4$ are CH; $A\text{-}(R_1)_n$ is

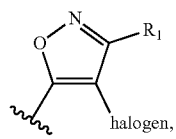

where $R_1$ is selected from the group consisting of H, —$CH_3$, —$CH_2C(CH_3)_3$, —$C(CH_3)_2CF_3$,

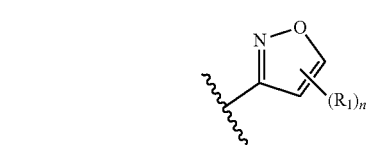

In a yet still further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; three of $X_1$, $X_2$, $X_3$, and $X_4$ are CH, while one of $X_1$, $X_2$, $X_3$, and $X_4$ is N; $A\text{-}(R_1)_n$ is

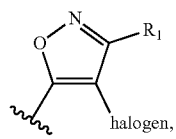

where $R_1$ is selected from the group consisting of H, —$CH_3$, —$CH_2C(CH_3)_3$, —$C(CH_3)_2CF_3$,

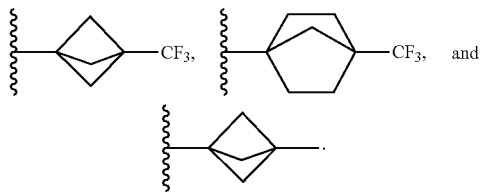

In another aspect, in the compounds of formulas (I), (II) and/or (III), $R_2$ is isopropyl; $X_1$, $X_2$, $X_3$, and $X_4$ are CH; $A\text{-}(R_1)_n$ is

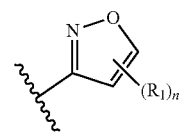

where each $R_1$ is selected from the group consisting of H, —$CH_3$, —$CH_2C(CH_3)_3$, —$C(CH_3)_2CF_3$,

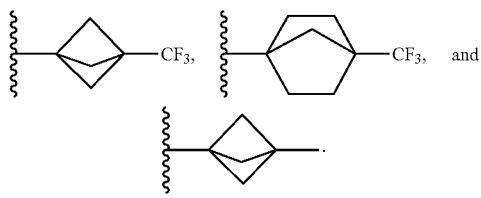

In an aspect, in the compounds of formulas (I), (II) and/or (III), $R_2$ is isopropyl; three of $X_1$, $X_2$, $X_3$, and $X_4$ are CH, while one of $X_1$, $X_2$, $X_3$, and $X_4$ is N; $A\text{-}(R_1)_n$ is

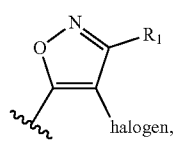

where each $R_1$ is selected from the group consisting of H, —$CH_3$, —$CH_2C(CH_3)_3$, —$C(CH_3)_2CF_3$,

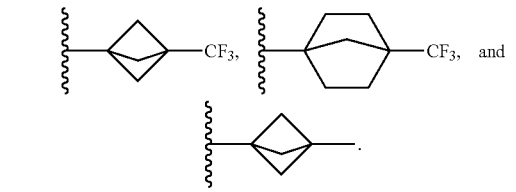

In an aspect, in the compounds of formulas (I), (II) and/or (III), $R_2$ is

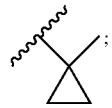

$X_1$, $X_2$, $X_3$, and $X_4$ are CH; A-$(R_1)_n$ is

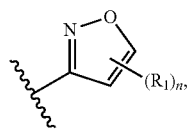

where each $R_1$ is selected from the group consisting of H, —$CH_3$, —$CH_2C(CH_3)_3$, —$C(CH_3)_2CF_3$,

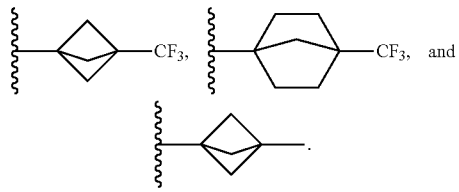

In a further aspect, in the compounds of formulas (I), (II) and/or (III), $R_2$ is

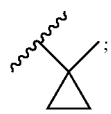

three of $X_1$, $X_2$, $X_3$, and $X_4$ are CH, while one of $X_1$, $X_2$, $X_3$, and $X_4$ is N; A-$(R_1)_n$ is

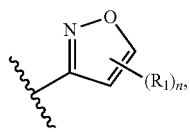

where each $R_1$ is selected from the group consisting of H, —$CH_3$, —$CH_2C(CH_3)_3$, —$C(CH_3)_2CF_3$,

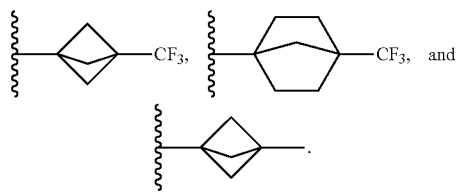

In a further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; $X_1$, $X_2$, $X_3$, and $X_4$ are CH; A-$(R_1)_n$ is

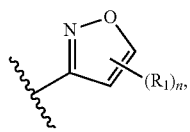

where each $R_1$ is selected from the group consisting of H, —$CH_3$, —$CH_2C(CH_3)_3$, —$C(CH_3)_2CF_3$,

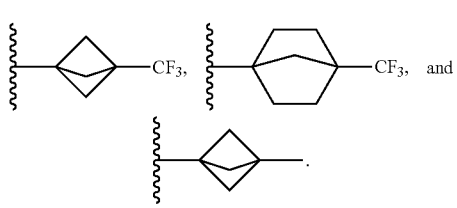

In a yet still further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; three of $X_1$, $X_2$, $X_3$, and $X_4$ are CH, while one of $X_1$, $X_2$, $X_3$, and $X_4$ is N; A-$(R_1)_n$ is

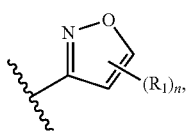

where each $R_1$ is selected from the group consisting of H, —$CH_3$, —$CH_2C(CH_3)_3$, —$C(CH_3)_2CF_3$

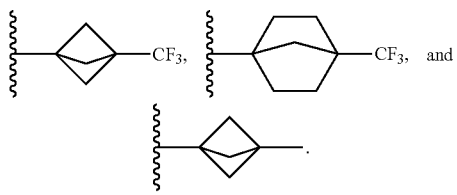

In one aspect, in the compounds of formulas (I), (II) and/or (III), $R_2$ is isopropyl; $X_1$, $X_2$, $X_3$, and $X_4$ are CH; A-$(R_1)_n$ is

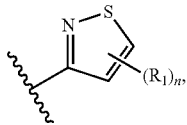

where each $R_1$ is selected from the group consisting of H, —$CH_3$, —$CH_2C(CH_3)_3$, —$C(CH_3)_2CF_3$,

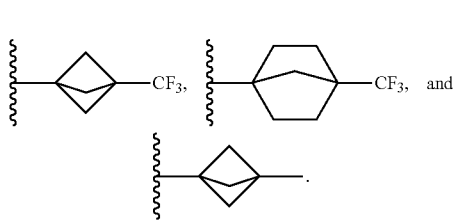

In another aspect, in the compounds of formulas (I), (II) and/or (III), $R_2$ is isopropyl; three of $X_1$, $X_2$, $X_3$, and $X_4$ are CH, while one of $X_1$, $X_2$, $X_3$, and $X_4$ is N; A-$(R_1)_n$ is

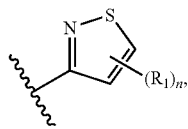

where each $R_1$ is selected from the group consisting of H, —CH$_3$, —CH$_2$C(CH$_3$)$_3$, —C(CH$_3$)$_2$CF$_3$,

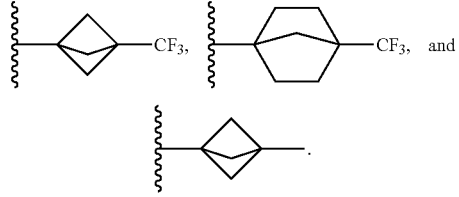

In an aspect, in the compounds of formulas (I), (II) and/or (III), $R_2$ is

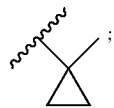 [SMILES: *C1(C)CC1]

$X_1$, $X_2$, $X_3$, and $X_4$ are CH; A-(R$_1$)$_n$ is

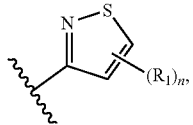

where each $R_1$ is selected from the group consisting of H, —CH$_3$, —CH$_2$C(CH$_3$)$_3$, —C(CH$_3$)$_2$CF$_3$,

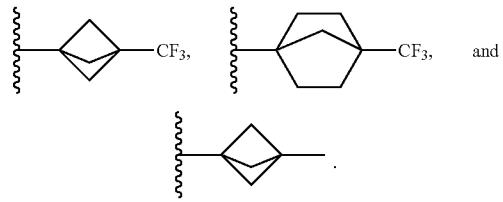

In a further aspect, in the compounds of formulas (I), (II) and/or (III), $R_2$ is

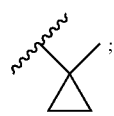

three of $X_1$, $X_2$, $X_3$, and $X_4$ are CH, while one of $X_1$, $X_2$, $X_3$, and $X_4$ is N; A-(R$_1$)$_n$ is

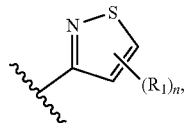

where each $R_1$ is selected from the group consisting of H, —CH$_3$, —CH$_2$C(CH$_3$)$_3$, —C(CH$_3$)$_2$CF$_3$,

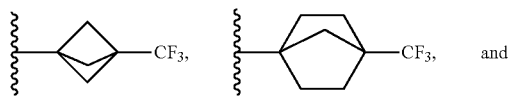

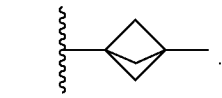

In a further aspect, in the compounds of formulas (I), (II) and/or (III), $R_2$ is —CH(CH$_3$)CF$_2$D, —CH(CD$_3$)$_2$, —CH(CF$_3$)CD$_3$, —CH(CH$_3$)CDF$_2$, —CD(CD$_3$)$_2$, or —CD(CH$_3$)CD$_3$; $X_1$, $X_2$, $X_3$, and $X_4$ are CH; A-(R$_1$)$_n$ is

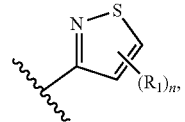

where each $R_1$ is selected from the group consisting of H, —CH$_3$, —CH$_2$C(CH$_3$)$_3$, —C(CH$_3$)$_2$CF$_3$,

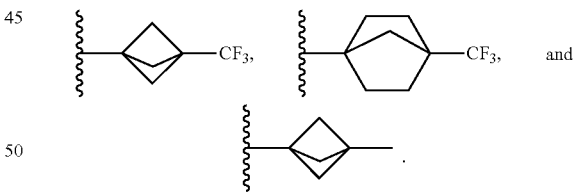

In a yet still further aspect, in the compounds of formulas (I), (II) and/or (III), $R_2$ is —CH(CH$_3$)CF$_2$D, —CH(CD$_3$)$_2$, —CH(CF$_3$)CD$_3$, —CH(CH$_3$)CDF$_2$, —CD(CD$_3$)$_2$, or —CD(CH$_3$)CD$_3$; three of $X_1$, $X_2$, $X_3$, and $X_4$ are CH, while one of $X_1$, $X_2$, $X_3$, and $X_4$ is N; A-(R$_1$)$_n$ is

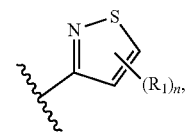

where each $R_1$ is selected from the group consisting of H, —$CH_3$, —$CH_2C(CH_3)_3$, —$C(CH_3)_2CF_3$,

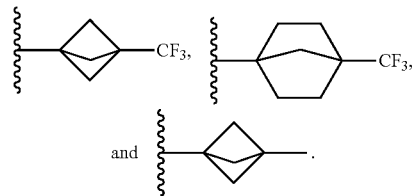

and

In one aspect, in the compounds of formulas (I), (II) and/or (III), $R_2$ is isopropyl; $X_1$, $X_2$, $X_3$, and $X_4$ are CH; A-$(R_1)_n$ is

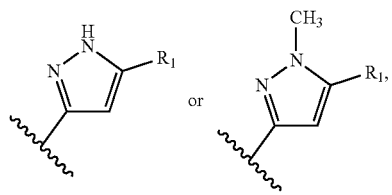

where $R_1$ is selected from the group consisting of H, —$CH_3$, —$CH_2C(CH_3)_3$, —$C(CH_3)_2CF_3$,

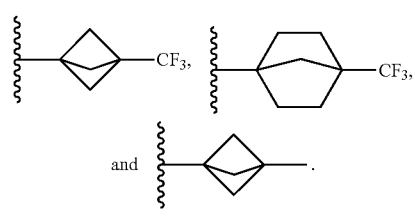

In another aspect, in the compounds of formulas (I), (II) and/or (III), $R_2$ is isopropyl; three of $X_1$, $X_2$, $X_3$, and $X_4$ are CH, while one of $X_1$, $X_2$, $X_3$, and $X_4$ is N; A-$(R_1)_n$

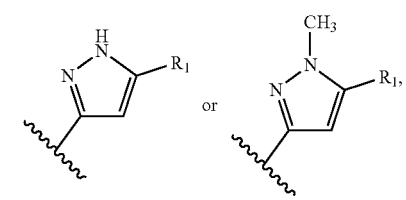

where $R_1$ is selected from the group consisting of H, —$CH_3$, —$CH_2C(CH_3)_3$, —$C(CH_3)_2CF_3$,

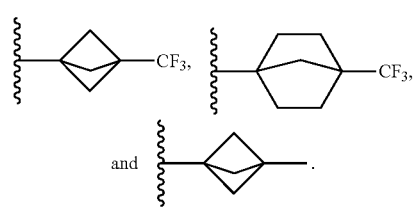

In an aspect, in the compounds of formulas (I), (II) and/or (III), $R_2$ is

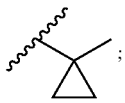 [SMILES: *C1(C)CC1]

$X_1$, $X_2$, $X_3$, and $X_4$ are CH; A-$(R_1)_n$ is

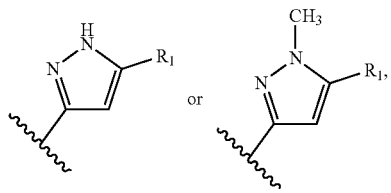

where $R_1$ is selected from the group consisting of H, —$CH_3$, —$CH_2C(CH_3)_3$, —$C(CH_3)_2CF_3$,

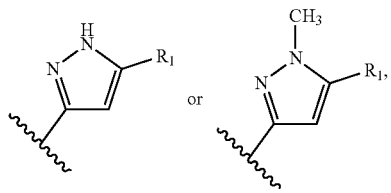

In a further aspect, in the compounds of formulas (I), (II) and/or (III), $R_2$ is

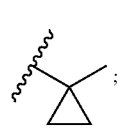 [SMILES: *C1(C)CC1]

three of $X_1$, $X_2$, $X_3$, and $X_4$ are CH, while one of $X_1$, $X_2$, $X_3$, and $X_4$ is N; A-$(R_1)_n$ is

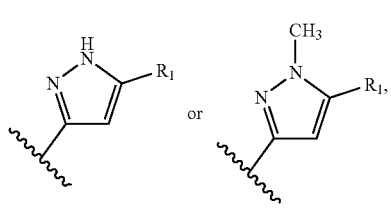

where $R_1$ is selected from the group consisting of H, —$CH_3$, —$CH_2C(CH_3)_3$, —$C(CH_3)_2CF_3$,

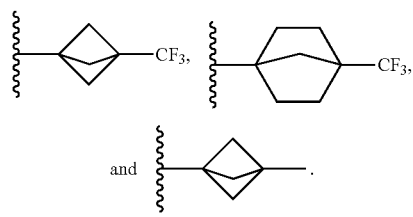

and

In a further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; $X_1$, $X_2$, $X_3$, and $X_4$ are CH; A-$(R_1)_n$ is

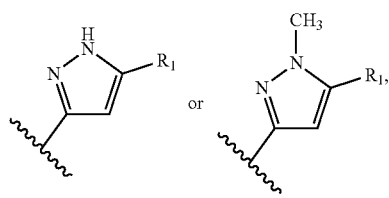

or where $R_1$ is selected from the group consisting of H, —$CH_3$, —$CH_2C(CH_3)_3$, —$C(CH_3)_2CF_3$,

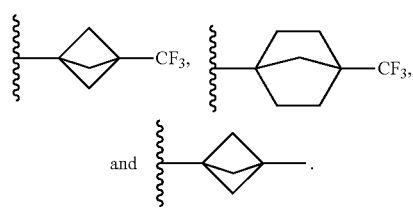

and

In a yet still further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; three of $X_1$, $X_2$, $X_3$, and $X_4$ are CH, while one of $X_1$, $X_2$, $X_3$, and $X_4$ is N; A-$(R_1)_n$ is

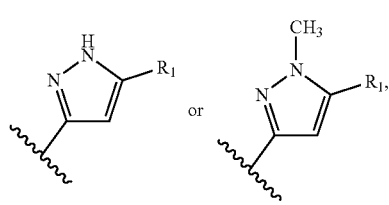

or where $R_1$ is selected from the group consisting of H, —$CH_3$, —$CH_2C(CH_3)_3$, —$C(CH_3)_2CF_3$,

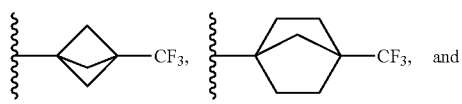

and

-continued

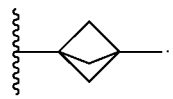

In one aspect, in the compounds of formulas (I), (II) and/or (III), $R_2$ is isopropyl; $X_1$, $X_2$, $X_3$, and $X_4$ are CH; A-$(R_1)_n$ is

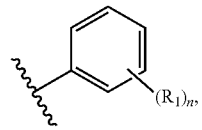

where each $R_1$ is selected from the group consisting of H, —$CH_3$, —$CH_2C(CH_3)_3$, —$C(CH_3)_2CF_3$,

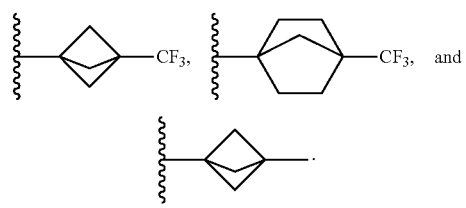

and

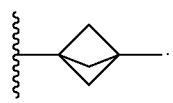

In another aspect, in the compounds of formulas (I), (II) and/or (III), $R_2$ is isopropyl; three of $X_1$, $X_2$, $X_3$, and $X_4$ are CH, while one of $X_1$, $X_2$, $X_3$, and $X_4$ is N; A-$(R_1)_n$ is

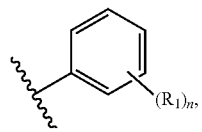

where each $R_1$ is selected from the group consisting of H, —$CH_3$, —$CH_2C(CH_3)_3$, —$C(CH_3)_2CF_3$,

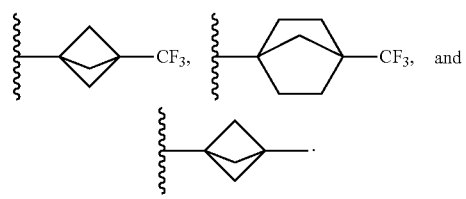

and

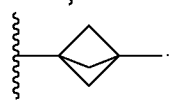

In an aspect, in the compounds of formulas (I), (II) and/or (III), $R_2$ is

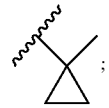

$X_1$, $X_2$, $X_3$, and $X_4$ are CH; A-$(R_1)_n$ is

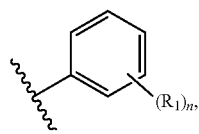

where each $R_1$ is selected from the group consisting of H, —$CH_3$, —$CH_2C(CH_3)_3$, —$C(CH_3)_2CF_3$,

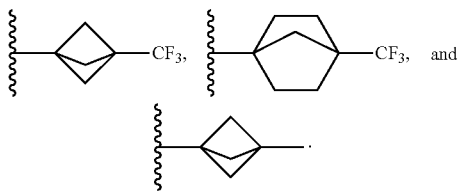

In a further aspect, in the compounds of formulas (I), (II) and/or (III), $R_2$ is

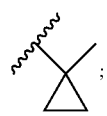

three of $X_1$, $X_2$, $X_3$, and $X_4$ are CH, while one of $X_1$, $X_2$, $X_3$, and $X_4$ is N; A-$(R_1)_n$ is

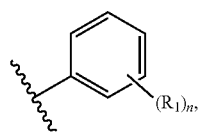

where each $R_1$ is selected from the group consisting of H, —$CH_3$, —$CH_2C(CH_3)_3$, —$C(CH_3)_2CF_3$,

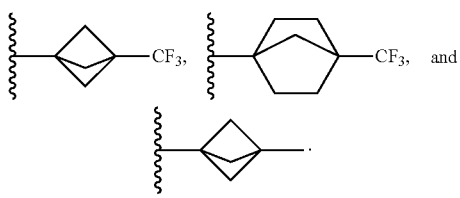

In a further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; $X_1$, $X_2$, $X_3$, and $X_4$ are CH; A-$(R_1)_n$ is

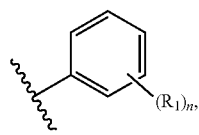

where each $R_1$ is selected from the group consisting of H, —$CH_3$, —$CH_2C(CH_3)_3$, —$C(CH_3)_2CF_3$,

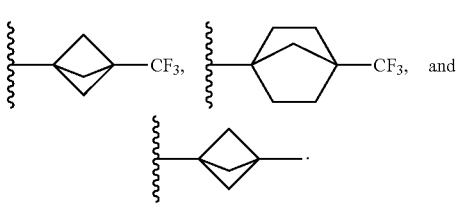

In a yet still further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; three of $X_1$, $X_2$, $X_3$, and $X_4$ are CH, while one of $X_1$, $X_2$, $X_3$, and $X_4$ is N; A-$(R_1)_n$ is

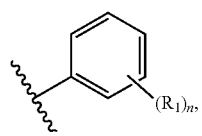

where each $R_1$ is selected from the group consisting of H, —$CH_3$, —$CH_2C(CH_3)_3$, —$C(CH_3)_2CF_3$,

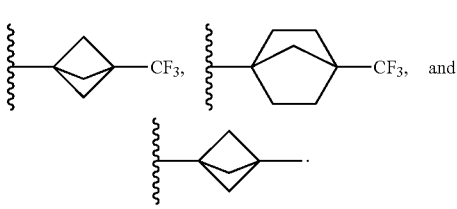

In another aspect, in the compounds of formulas (I), (II) and/or (III), $R_2$ is isopropyl; $X_1$, $X_2$, $X_3$, and $X_4$ are CH; A-$(R_1)_n$ is

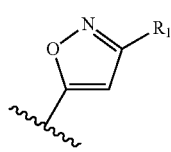

where $R_1$ is halogen,

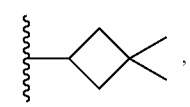 [SMILES: *C1CC(C)(C)C1]

—$CH_2C(CH_3)_3$, 2-chloro-4-fluorophenyl, 2,4-dichlorophenyl, —$CH_2C(CH_3)_3$, —$C(CH_3)_2CF_3$,

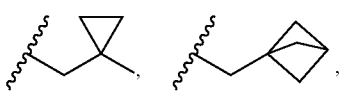

-continued

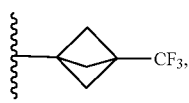

—C(CH₃)₂CH₂CH₃, —C(CH₃)₂CF₂CH₃, —C(CH₃)₂CH₂CF₃, —C(CH₃)₃,

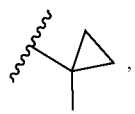

or CF₃.

In an aspect, in the compounds of formulas (I), (II) and/or (III), $R_2$ is isopropyl; three of $X_1$, $X_2$, $X_3$, and $X_4$ are CH, while one of $X_1$, $X_2$, $X_3$, and $X_4$ is N; $A-(R_1)_n$ is

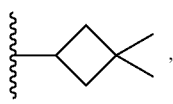

where $R_1$ is halogen,

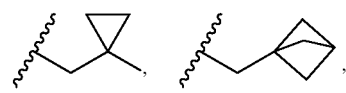

—CH₂C(CH₃)₃, 2-chloro-4-fluorophenyl, 2,4-dichlorophenyl, —CH₂C(CH₃)₃, —C(CH₃)₂CF₃

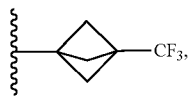

—C(CH₃)₂CH₂CH₃, —C(CH₃)₂CF₂CH₃, —C(CH₃)₂CH₂CF₃, —C(CH₃)₃,

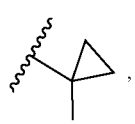

or CF₃.

In an aspect, in the compounds of formulas (I), (II) and/or (III), $R_2$ is

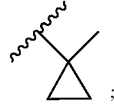

$X_1$, $X_2$, $X_3$, and $X_4$ are CH; $A-(R_1)_n$ is

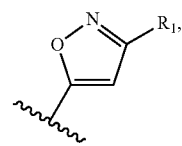

where $R_1$ is halogen,

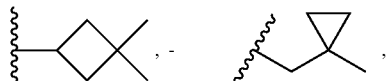
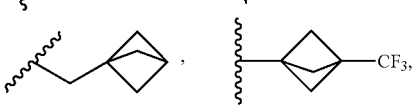

CH₂C(CH₃)₃, 2-chloro-4-fluorophenyl, 2,4-dichlorophenyl, —CH₂C(CH₃)₃, —C(CH₃)₂CF₃, C(CH₃)₂CH₂CH₃, —C(CH₃)₂CF₂CH₃, C(CH₃)₂CH₂CF₃, —C(CH₃)₃,

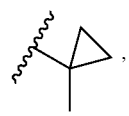

or CF₃.

In a further aspect, in the compounds of formulas (I), (II) and/or (III), $R_2$ is

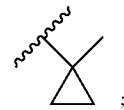

three of $X_1$, $X_2$, $X_3$, and $X_4$ are CH, while one of $X_1$, $X_2$, $X_3$, and $X_4$ is N; $A-(R_1)_n$ is

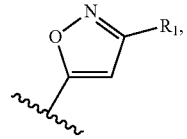

where $R_1$ is halogen,

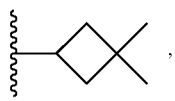 [SMILES: *C1CC(C)(C)C1]

—$CH_2C(CH_3)_3$, 2-chloro-4-fluorophenyl, 2,4-dichlorophenyl, —$CH_2C(CH_3)_3$, —$C(CH_3)_2CF_3$,

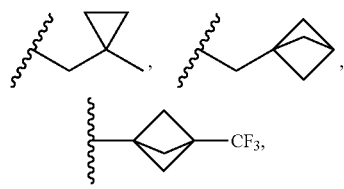

—$C(CH_3)_2CH_2CH_3$, —$C(CH_3)_2CF_2CH_3$, —$C(CH_3)_2CH_2CF_3$, —$C(CH_3)_3$,

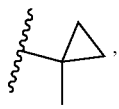

or $CF_3$.

In a further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; $X_1$, $X_2$, $X_3$, and $X_4$ are CH; A-$(R_1)_n$ is

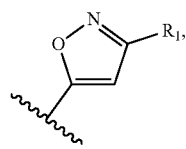

where $R_1$ is halogen,

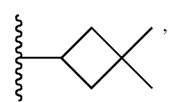 [SMILES: *C1CC(C)(C)C1]

—$CH_2C(CH_3)_3$, 2-chloro-4-fluorophenyl, 2,4-dichlorophenyl, —$CH_2C(CH_3)_3$, —$C(CH_3)_2CF_3$,

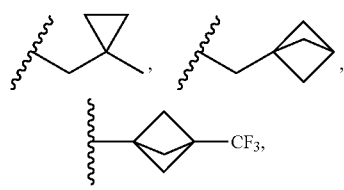

—$C(CH_3)_2CH_2CH_3$, —$C(CH_3)_2CF_2CH_3$, —$C(CH_3)_2CH_2CF_3$, —$C(CH_3)_3$,

or $CF_3$.

In a yet still further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; three of $X_1$, $X_2$, $X_3$, and $X_4$ are CH, while one of $X_1$, $X_2$, $X_3$, and $X_4$ is N; A-$(R_1)_n$ is

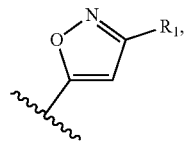

where $R_1$ is halogen,

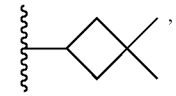 [SMILES: *C1CC(C)(C)C1]

—$CH_2C(CH_3)_3$, 2-chloro-4-fluorophenyl, 2,4-dichlorophenyl, —$CH_2C(CH_3)_3$, —$C(CH_3)_2CF_3$,

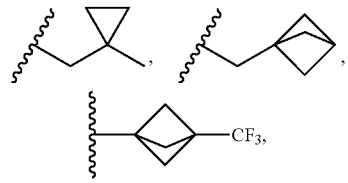

—$C(CH_3)_2CH_2CH_3$, —$C(CH_3)_2CF_2CH_3$, —$C(CH_3)_2CH_2CF_3$, —$C(CH_3)_3$,

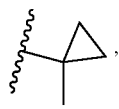 [SMILES: *C1(C)CC1]

or $CF_3$.

In another aspect, in the compounds of formulas (I), (II) and/or (III), $R_2$ is isopropyl; $X_1$, $X_2$, $X_3$, and $X_4$ are CH; A-$(R_1)_n$ is

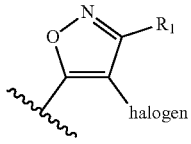

where R₁ is halogen,

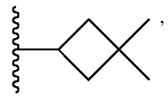

—CH₂C(CH₃)₃, 2-chloro-4-fluorophenyl, 2,4-dichlorophenyl, —CH₂C(CH₃)₃, —C(CH₃)₂CF₃,

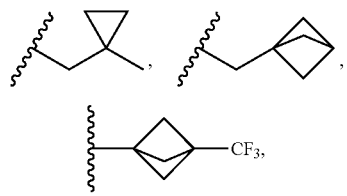

—C(CH₃)₂CH₂CH₃, —C(CH₃)₂CF₂CH₃, —C(CH₃)₂CH₂CF₃, —C(CH₃)₃,

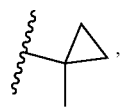

or CF₃.

In an aspect, in the compounds of formulas (I), (II) and/or (III), R₂ is isopropyl; three of X₁, X₂, X₃, and X₄ are CH, while one of X₁, X₂, X₃, and X₄ is N; A-(R₁)ₙ is

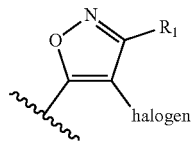

where R₁ is halogen is halogen,

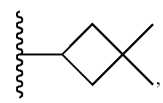

—CH₂C(CH₃)₃, 2-chloro-4-fluorophenyl, 2,4-dichlorophenyl, —CH₂C(CH₃)₃, —C(CH₃)₂CF₃,

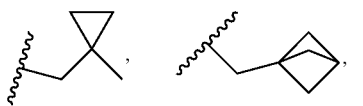

—C(CH₃)₂CH₂CH₃, —C(CH₃)₂CF₂CH₃, —C(CH₃)₂CH₂CF₃, —C(CH₃)₃,

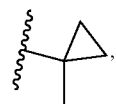

or CF₃.

In an aspect, in the compounds of formulas (I), (II) and/or (III), R₂ is

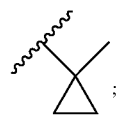 [SMILES: *C1(C)CC1]

X₁, X₂, X₃, and X₄ are CH; A-(R₁)ₙ is

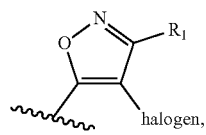

where R₁ is halogen,

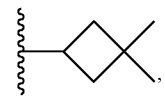 [SMILES: *C1CC(C)(C)C1]

CH₂C(CH₃)₃, 2-chloro-4-fluorophenyl, 2,4-dichlorophenyl, —CH₂C(CH₃)₃, —C(CH₃)₂CF₃,

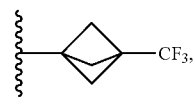

—C(CH₃)₂CH₂CH₃, —C(CH₃)₂CF₂CH₃, —C(CH₃)₂CH₂CF₃, —C(CH₃)₃,

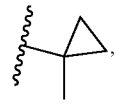

or CF₃.

In a further aspect, in the compounds of formulas (I), (II) and/or (III), R₂ is

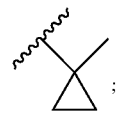 [SMILES: *C1(C)CC1]

three of $X_1$, $X_2$, $X_3$, and $X_4$ are CH, while one of $X_1$, $X_2$, $X_3$, and $X_4$ is N; $A\text{-}(R_1)_n$ is

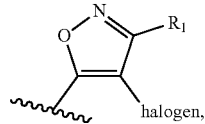

where $R_1$ is halogen,

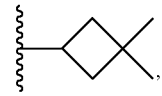

—$CH_2C(CH_3)_3$, 2-chloro-4-fluorophenyl, 2,4-dichlorophenyl, —$CH_2C(CH_3)_3$, —$C(CH_3)_2CF_3$,

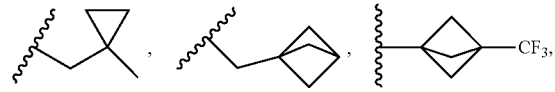

—$C(CH_3)_2CH_2CH_3$, —$C(CH_3)_2CF_2CH_3$, —$C(CH_3)_2CH_2CF_3$, —$C(CH_3)_3$,

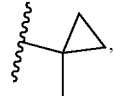

or $CF_3$.

In a further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; $X_1$, $X_2$, $X_3$, and $X_4$ are CH; $A\text{-}(R_1)_n$ is

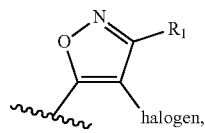

where $R_1$ is halogen,

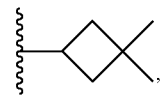 [SMILES: *C1CC(C)(C)C1]

—$CH_2C(CH_3)_3$, 2-chloro-4-fluorophenyl, 2,4-dichlorophenyl, —$CH_2C(CH_3)_3$, —$C(CH_3)_2CF_3$,

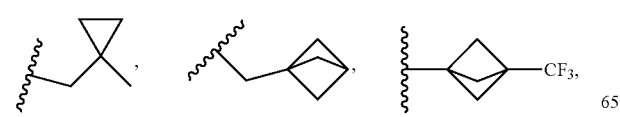

—$C(CH_3)_2CH_2CH_3$, —$C(CH_3)_2CF_2CH_3$, —$C(CH_3)_2CH_2CF_3$, —$C(CH_3)_3$,

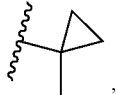 [SMILES: *C1(C)CC1]

or $CF_3$.

In a yet still further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; three of $X_1$, $X_2$, $X_3$, and $X_4$ are CH, while one of $X_1$, $X_2$, $X_3$, and $X_4$ is N; $A\text{-}(R_1)_n$ is

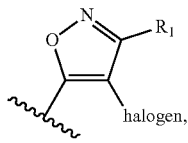

where $R_1$ is halogen,

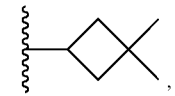 [SMILES: *C1CC(C)(C)C1]

—$CH_2C(CH_3)_3$, 2-chloro-4-fluorophenyl, 2,4-dichlorophenyl, —$CH_2C(CH_3)_3$, —$C(CH_3)_2CF_3$,

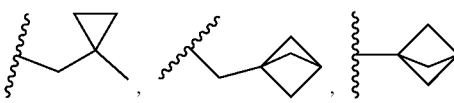

—$C(CH_3)_2CH_2CH_3$, —$C(CH_3)_2CF_2CH_3$, —$C(CH_3)_2CH_2CF_3$, —$C(CH_3)_3$,

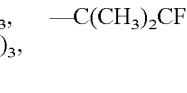

or $CF_3$.

In another aspect, in the compounds of formulas (I), (II) and/or (III), $R_2$ is isopropyl; $X_1$, $X_2$, $X_3$, and $X_4$ are CH; $A\text{-}(R_1)_n$ is

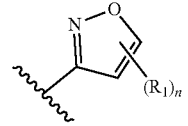

where at least one $R_1$ is halogen

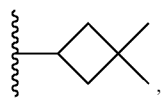,

—$CH_2C(CH_3)_3$, 2-chloro-4-fluorophenyl, 2,4-dichlorophenyl, —$CH_2C(CH_3)_3$, —$C(CH_3)_2CF_3$,

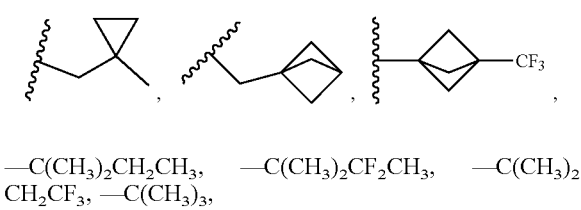

—$C(CH_3)_2CH_2CH_3$, —$C(CH_3)_2CF_2CH_3$, —$C(CH_3)_2CH_2CF_3$, —$C(CH_3)_3$,

, or $CF_3$.

In an aspect, in the compounds of formulas (I), (II) and/or (III), $R_2$ is isopropyl; three of $X_1$, $X_2$, $X_3$, and $X_4$ are CH, while one of $X_1$, $X_2$, $X_3$, and $X_4$ is N; A-$(R_1)_n$ is

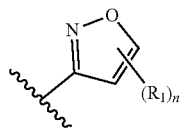

where at least one $R_1$ is halogen,

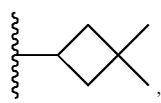 [SMILES: *C1CC(C)(C)C1]

—$CH_2C(CH_3)_3$, 2-chloro-4-fluorophenyl, 2,4-dichlorophenyl, —$CH_2C(CH_3)_3$, —$C(CH_3)_2CF_3$,

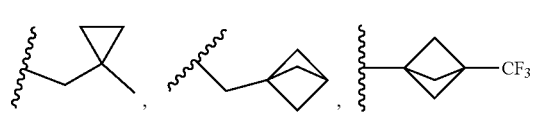

—$C(CH_3)_2CH_2CH_3$, —$C(CH_3)_2CF_2CH_3$, —$C(CH_3)_2CH_2CF_3$, —$C(CH_3)_3$,

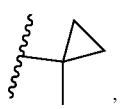 [SMILES: *C1(C)CC1], or $CF_3$.

In an aspect, in the compounds of formulas (I), (II) and/or (III), $R_2$ is

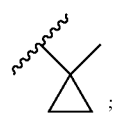;

$X_1$, $X_2$, $X_3$, and $X_4$ are CH; A-$(R_1)_n$ is

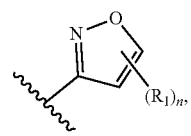, where at least one $R_1$ is halogen,

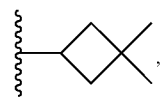,

—$CH_2C(CH_3)_3$, 2-chloro-4-fluorophenyl, 2,4-dichlorophenyl, —$CH_2C(CH_3)_3$, —$C(CH_3)_2CF_3$,

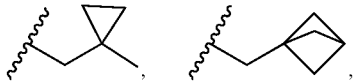

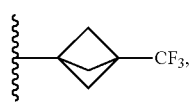

—$C(CH_3)_2CH_2CH_3$, —$C(CH_3)_2CF_2CH_3$, —$C(CH_3)_2CH_2CF_3$, —$C(CH_3)_3$,

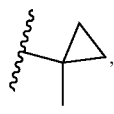, or $CF_3$.

In a further aspect, in the compounds of formulas (I), (II) and/or (III), $R_2$ is

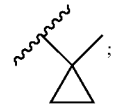;

three of $X_1$, $X_2$, $X_3$, and $X_4$ are CH, while one of $X_1$, $X_2$, $X_3$, and $X_4$ is N; $A-(R_1)_n$ is

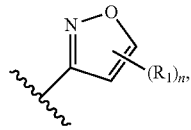

where at least one $R_1$ is halogen,

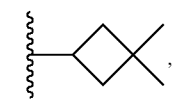

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

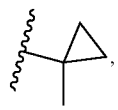

or CF$_3$.

In a further aspect, in the compounds of formulas (I), (II) and/or (III), $R_2$ is —CH(CH$_3$)CF$_2$D, —CH(CD$_3$)$_2$, —CH(CF$_3$)CD$_3$, —CH(CH$_3$)CDF$_2$, —CD(CD$_3$)$_2$, or —CD(CH$_3$)CD$_3$; $X_1$, $X_2$, $X_3$, and $X_4$ are CH; $A-(R_1)_n$ is

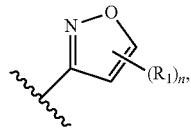

where at least one $R_1$ is halogen,

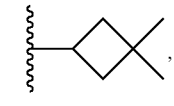

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

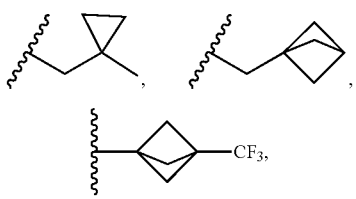

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

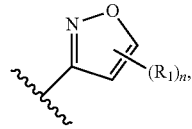

or CF$_3$.

In a yet still further aspect, in the compounds of formulas (I), (II) and/or (III), $R_2$ is —CH(CH$_3$)CF$_2$D, —CH(CD$_3$)$_2$, —CH(CF$_3$)CD$_3$, —CH(CH$_3$)CDF$_2$, —CD(CD$_3$)$_2$, or —CD(CH$_3$)CD$_3$; three of $X_1$, $X_2$, $X_3$, and $X_4$ are CH, while one of $X_1$, $X_2$, $X_3$, and $X_4$ is N; $A-(R_1)_n$ is

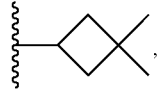

where at least one $R_1$ is halogen,

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

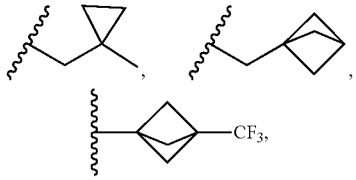

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

or CF$_3$.

In one aspect, in the compounds of formulas (I), (II) and/or (III), R$_2$ is isopropyl; X$_1$, X$_2$, X$_3$, and X$_4$ are CH; A-(R$_1$)$_n$ is

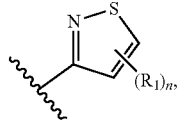

where at least one R$_1$ is halogen,

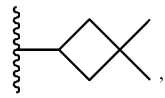

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

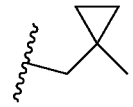 , 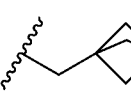 , 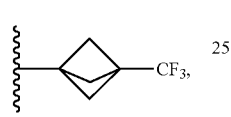

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

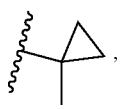

or CF$_3$.

In another aspect, in the compounds of formulas (I), (II) and/or (III), R$_2$ is isopropyl; three of X$_1$, X$_2$, X$_3$, and X$_4$ are CH, while one of X$_1$, X$_2$, X$_3$, and X$_4$ is N; A-(R$_1$)$_n$ is

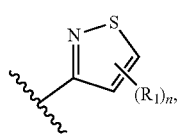

where at least one R$_1$ is halogen,

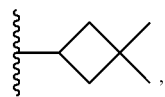

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$ —C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

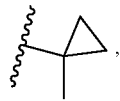

or CF$_3$.

In an aspect, in the compounds of formulas (I), (II) and/or (III), R$_2$ is

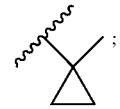 ;

X$_1$, X$_2$, X$_3$, and X$_4$ are CH; A-(R$_1$)$_n$ is

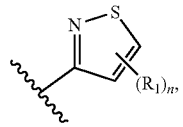

where at least one R$_1$ is halogen,

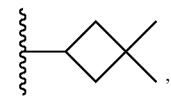

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$, —C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

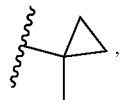 [SMILES: *C1(C)CC1]

or CF$_3$.

In a further aspect, in the compounds of formulas (I), (II) and/or (III), R$_2$ is

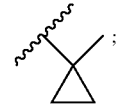 ;

three of $X_1$, $X_2$, $X_3$, and $X_4$ are CH, while one of $X_1$, $X_2$, $X_3$, and $X_4$ is N; $A-(R_1)_n$ is

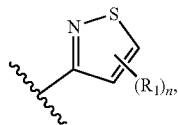

where at least one $R_1$ is halogen,

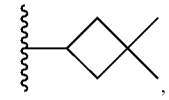

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

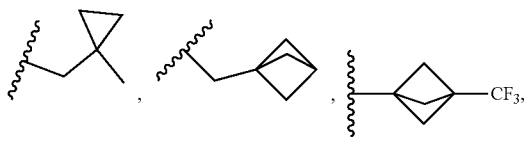

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

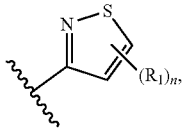

or CF$_3$.

In a further aspect, in the compounds of formulas (I), (II) and/or (III), $R_2$ is —CH(CH$_3$)CF$_2$D, —CH(CD$_3$)$_2$, —CH(CF$_3$)CD$_3$, —CH(CH$_3$)CDF$_2$, —CD(CD$_3$)$_2$, or —CD(CH$_3$)CD$_3$; $X_1$, $X_2$, $X_3$, and $X_4$ are CH; $A-(R_1)_n$ is

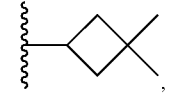

where at least one $R_1$ is halogen,

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

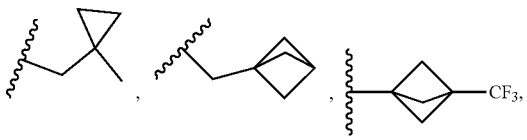

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

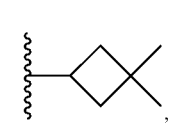 [SMILES: *C1CC(C)(C)C1]

or CF$_3$.

In a yet still further aspect, in the compounds of formulas (I), (II) and/or (III), $R_2$ is —CH(CH$_3$)CF$_2$D, —CH(CD$_3$)$_2$, —CH(CF$_3$)CD$_3$, —CH(CH$_3$)CDF$_2$, —CD(CD$_3$)$_2$, or —CD(CH$_3$)CD$_3$; three of $X_1$, $X_2$, $X_3$, and $X_4$ are CH, while one of $X_1$, $X_2$, $X_3$, and $X_4$ is N; $A-(R_1)_n$ is

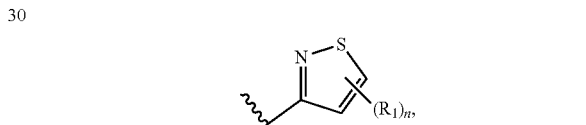

where at least one $R_1$ is halogen,

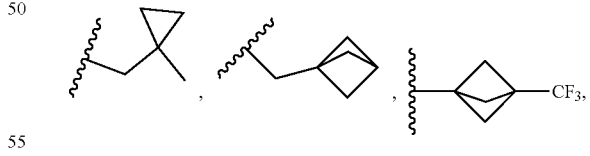

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$, —C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

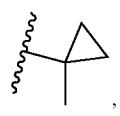

or CF$_3$.

In another aspect, in the compounds of formulas (I), (II) and/or (III), R$_2$ is isopropyl; X$_1$, X$_2$, X$_3$, and X$_4$ are CH; A-(R$_1$)$_n$ is

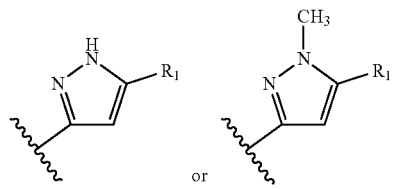

or where R$_1$ is halogen,

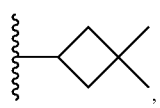

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

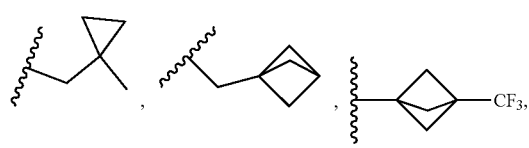

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

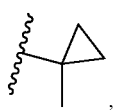

or CF$_3$.

In an aspect, in the compounds of formulas (I), (II) and/or (III), R$_2$ is isopropyl; three of X$_1$, X$_2$, X$_3$, and X$_4$ are CH, while one of X$_1$, X$_2$, X$_3$, and X$_4$ is N; A-(R$_1$)$_n$ is

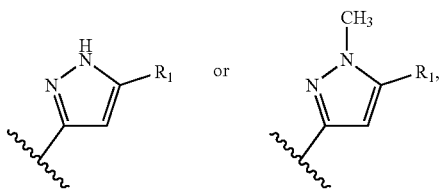

where R$_1$ is halogen,

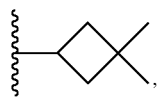 [SMILES: *C1CC(C)(C)C1]

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

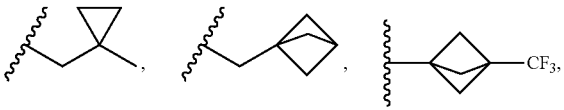

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

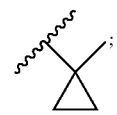 [SMILES: *C1(C)CC1]

or CF$_3$.

In an aspect, in the compounds of formulas (I), (II) and/or (III), R$_2$ is

X$_1$, X$_2$, X$_3$, and X$_4$ are CH; A-(R$_1$)$_n$ is

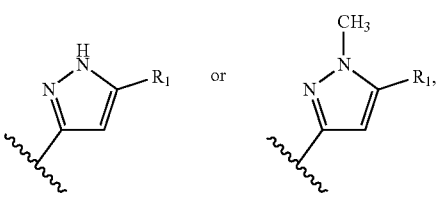

where R$_1$ is halogen,

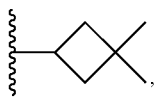

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

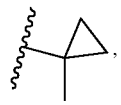 [SMILES: *C1(C)CC1]

or CF$_3$.

In a further aspect, in the compounds of formulas (I), (II) and/or (III), $R_2$ is

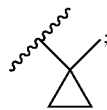 [SMILES: *C1(C)CC1]

three of $X_1$, $X_2$, $X_3$, and $X_4$ are CH, while one of $X_1$, $X_2$, $X_3$, and $X_4$ is N; A-$(R_1)_n$ is

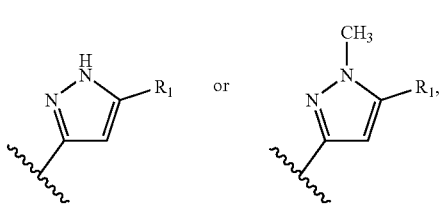

where $R_1$ is halogen,

—$CH_2C(CH_3)_3$, 2-chloro-4-fluorophenyl, 2,4-dichlorophenyl, —$CH_2C(CH_3)_3$, —$C(CH_3)_2CF_3$,

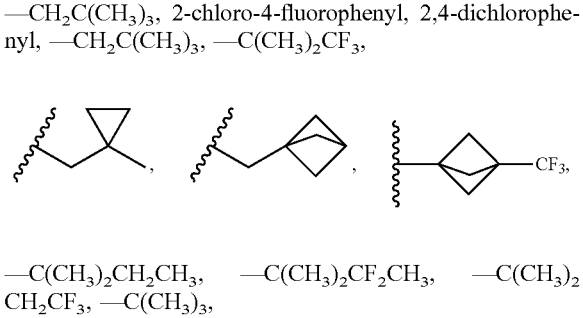

—$C(CH_3)_2CH_2CH_3$, —$C(CH_3)_2CF_2CH_3$, —$C(CH_3)_2CH_2CF_3$, —$C(CH_3)_3$,

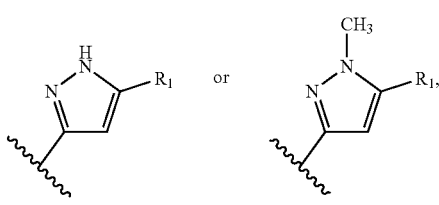

or $CF_3$.

In a further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; $X_1$, $X_2$, $X_3$, and $X_4$ are CH; A-$(R_1)_n$ is

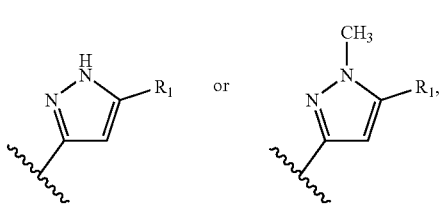

where $R_1$ is halogen,

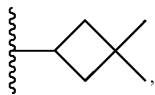

—$CH_2C(CH_3)_3$, 2-chloro-4-fluorophenyl, 2,4-dichlorophenyl, —$CH_2C(CH_3)_3$, —$C(CH_3)_2CF_3$,

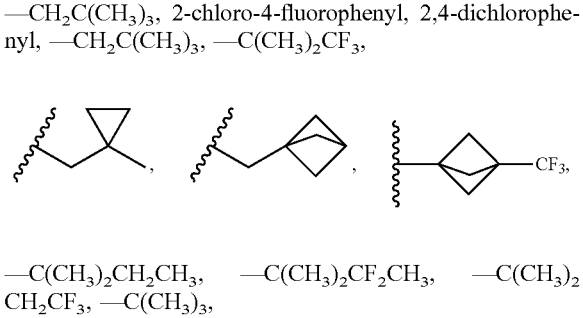

—$C(CH_3)_2CH_2CH_3$, —$C(CH_3)_2CF_2CH_3$, —$C(CH_3)_2CH_2CF_3$, —$C(CH_3)_3$,

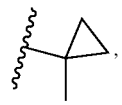 [SMILES: *C1(C)CC1]

or $CF_3$.

In a yet still further aspect, in the compounds of formulas (I), (II) and/or (III), $R_2$ is —$CH(CH_3)CF_2D$, —$CH(CD_3)_2$, —$CH(CF_3)CD_3$, —$CH(CH_3)CDF_2$, —$CD(CD_3)_2$, or —$CD(CH_3)CD_3$; three of $X_1$, $X_2$, $X_3$, and $X_4$ are CH, while one of $X_1$, $X_2$, $X_3$, and $X_4$ is N; A-$(R_1)_n$ is

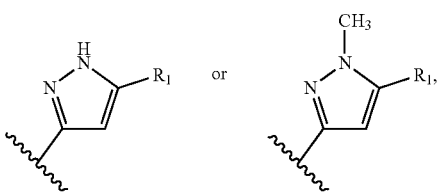

where $R_1$ is halogen,

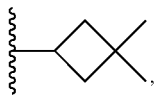

—$CH_2C(CH_3)_3$, 2-chloro-4-fluorophenyl, 2,4-dichlorophenyl, —$CH_2C(CH_3)_3$, —$C(CH_3)_2CF_3$,

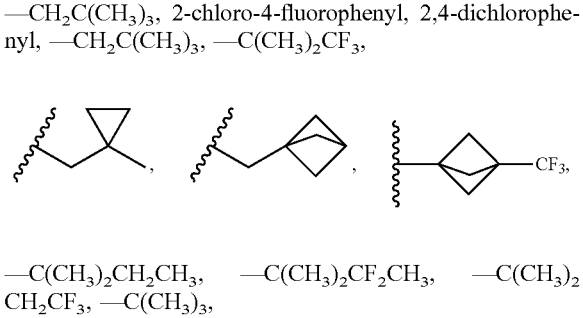

—$C(CH_3)_2CH_2CH_3$, —$C(CH_3)_2CF_2CH_3$, —$C(CH_3)_2CH_2CF_3$, —$C(CH_3)_3$,

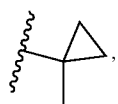

or CF$_3$.

In one aspect, in the compounds of formulas (I), (II) and/or (III), R$_2$ is isopropyl; X$_1$, X$_2$, X$_3$, and X$_4$ are CH; A-(R$_1$)$_n$ is

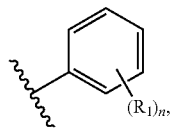

where each R$_1$ is halogen,

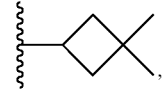 [SMILES: *C1CC(C)(C)C1]

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

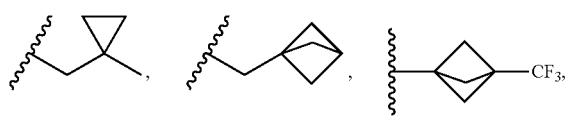

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

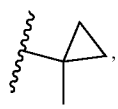

or CF$_3$.

In another aspect, in the compounds of formulas (I), (II) and/or (III), R$_2$ is isopropyl; three of X$_1$, X$_2$, X$_3$, and X$_4$ are CH, while one of X$_1$, X$_2$, X$_3$, and X$_4$ is N; A-(R$_1$)$_n$ is

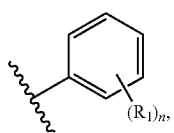

where each R$_1$ is halogen,

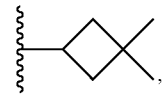 [SMILES: *C1CC(C)(C)C1]

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

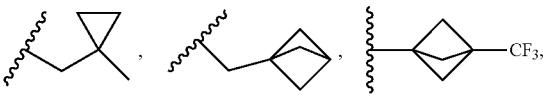

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

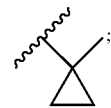 [SMILES: *C1(C)CC1]

or CF$_3$.

In an aspect, in the compounds of formulas (I), (II) and/or (III), R$_2$ is

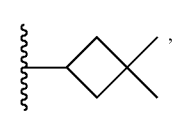

X$_1$, X$_2$, X$_3$, and X$_4$ are CH; A-(R$_1$)$_n$ is

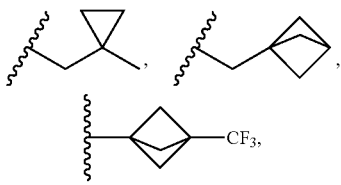

where each R$_1$ is halogen,

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$, —C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

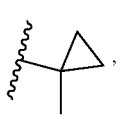

or CF$_3$.

In a further aspect, in the compounds of formulas (I), (II) and/or (III), R$_2$ is

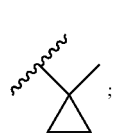

three of X$_1$, X$_2$, X$_3$, and X$_4$ are CH, while one of X$_1$, X$_2$, X$_3$, and X$_4$ is N; A-(R$_1$)$_n$ is

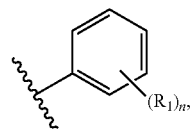

where each R$_1$ is halogen,

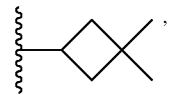 [SMILES: *C1CC(C)(C)C1]

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

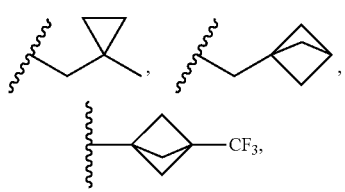

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

or CF$_3$.

In a further aspect, in the compounds of formulas (I), (II) and/or (III), R$_2$ is —CH(CH$_3$)CF$_2$D, —CH(CD$_3$)$_2$, —CH(CF$_3$)CD$_3$, —CH(CH$_3$)CDF$_2$, —CD(CD$_3$)$_2$, or —CD(CH$_3$)CD$_3$; X$_1$, X$_2$, X$_3$, and X$_4$ are CH; A-(R$_1$)$_n$ is

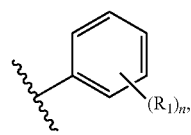

where each R$_1$ is halogen

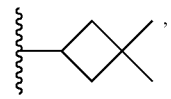 [SMILES: *C1CC(C)(C)C1]

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

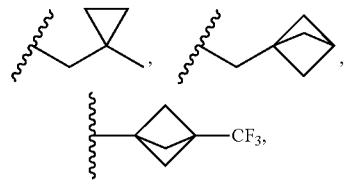

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

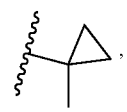

or CF$_3$.

In a yet still further aspect, in the compounds of formulas (I), (II) and/or (III), R$_2$ is —CH(CH$_3$)CF$_2$D, —CH(CD$_3$)$_2$, —CH(CF$_3$)CD$_3$, —CH(CH$_3$)CDF$_2$, —CD(CD$_3$)$_2$, or —CD(CH$_3$)CD$_3$; three of X$_1$, X$_2$, X$_3$, and X$_4$ are CH, while one of X$_1$, X$_2$, X$_3$, and X$_4$ is N; A-(R$_1$)$_n$ is

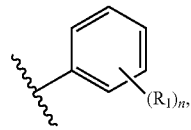

where each R$_1$ is halogen,

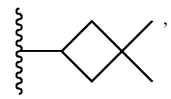

—CH$_2$C(CH$_3$)$_3$, 2-chloro-4-fluorophenyl, 2,4-dichlorophenyl, —CH$_2$C(CH$_3$)$_3$, —C(CH$_3$)$_2$CF$_3$,

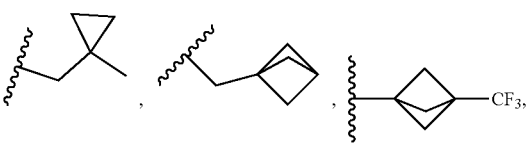

—C(CH$_3$)$_2$CH$_2$CH$_3$, —C(CH$_3$)$_2$CF$_2$CH$_3$, —C(CH$_3$)$_2$CH$_2$CF$_3$, —C(CH$_3$)$_3$,

, or CF₃.

Whenever a variable is defined as "each," for example, "each R₁ is . . ." it is understood that the definition of the variable at each occurrence is independently selected from the groups contained in the definition. Thus, for example, if a phenyl is substituted with four R₁ groups, the identity of each R₁ group is independently selected from the groups listed in the definition of R₁. Accordingly, all four R1 groups may be the same or they may all be different or some of the groups may be the same, while others are different.

Specific enantiomers may be prepared beginning with chiral reagents or by stereo-selective or stereo-specific synthetic techniques. Alternatively, single enantiomers may be isolated from mixtures of different chiral forms by standard chiral chromatographic or crystallization techniques at any convenient point in the synthesis of compounds of formula (I), formula (II), and formula (III). All individual enantiomers, as well as mixtures of the enantiomers of the compounds of formula (II) and formula (III) including racemates are intended to be included herein.

Specific examples of the compounds of formula (I) including the forms of formula (II) and formula (III) are shown in the Examples below. A subset of useful molecules from the Examples is shown in Table A.

TABLE A

| Example # | Structure |
|---|---|
| 1 (Isomer 1) | 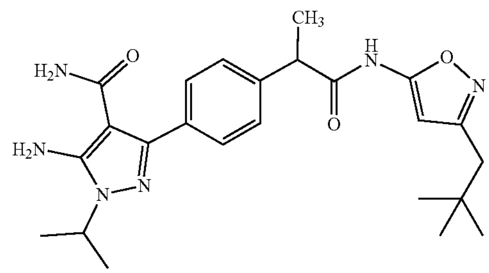 [SMILES: CC(C(=O)Nc1cc(CC(C)(C)C)no1)c1ccc(-c2nn(C(C)C)c(N)c2C(N)=O)cc1] |
| 15 (Isomer 1) | 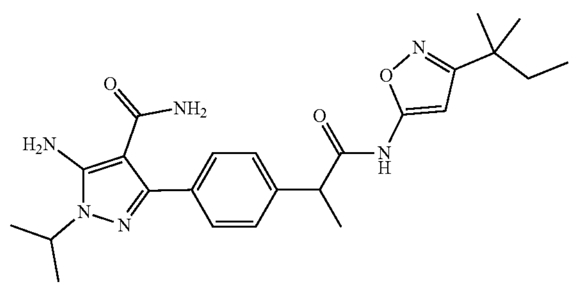 [SMILES: CCC(C)(C)c1cc(NC(=O)C(C)c2ccc(-c3nn(C(C)C)c(N)c3C(N)=O)cc2)on1] |
| 17 (Isomer 1) | 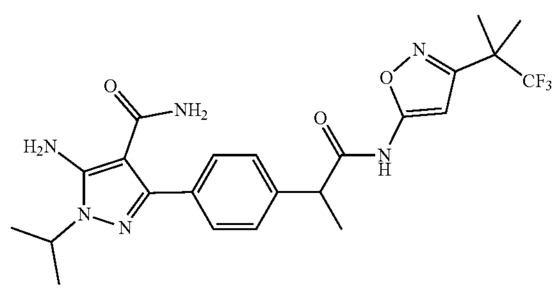 [SMILES: CC(C(=O)Nc1cc(C(C)(C)C(F)(F)F)no1)c1ccc(-c2nn(C(C)C)c(N)c2C(N)=O)cc1] |
| 31 (Isomer 1) | 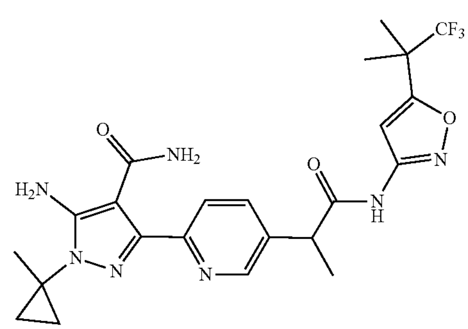 [SMILES: CC(C(=O)Nc1cc(C(C)(C)C(F)(F)F)on1)c1ccc(-c2nn(C3(C)CC3)c(N)c2C(N)=O)nc1] |

TABLE A-continued

| Example # | Structure |
|---|---|
| 33 (Isomer 1) | 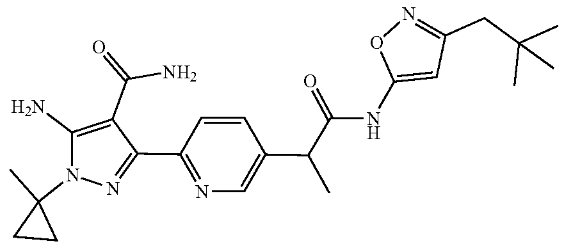 [SMILES: CC(C(=O)Nc1cc(CC(C)(C)C)no1)c1ccc(-c2nn(C3(C)CC3)c(N)c2C(N)=O)nc1] |
| 35 (Isomer 1) | 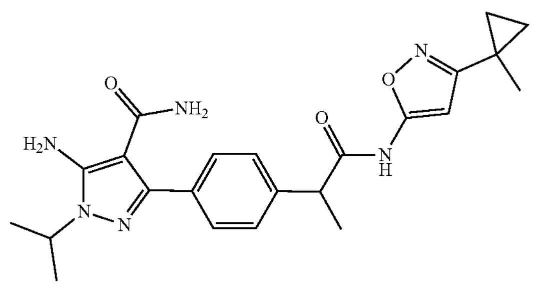 [SMILES: CC(C(=O)Nc1cc(C2(C)CC2)no1)c1ccc(-c2nn(C(C)C)c(N)c2C(N)=O)cc1] |
| 45 (Isomer 1) | 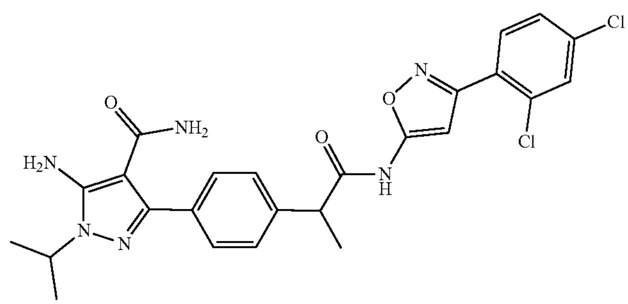 [SMILES: CC(C(=O)Nc1cc(-c2ccc(Cl)cc2Cl)no1)c1ccc(-c2nn(C(C)C)c(N)c2C(N)=O)cc1] |
| 52 (Isomer 2) | 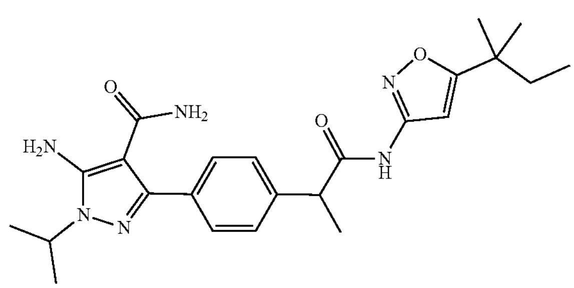 [SMILES: CCC(C)(C)c1cc(NC(=O)C(C)c2ccc(-c3nn(C(C)C)c(N)c3C(N)=O)cc2)no1] |
| 64 (Isomer 2) | 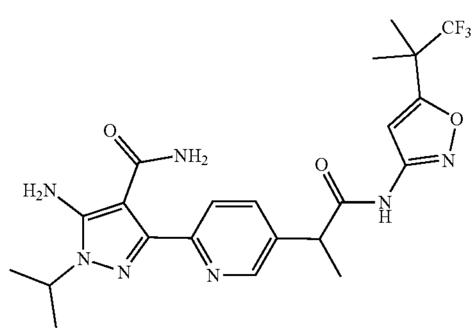 [SMILES: CC(C(=O)Nc1cc(C(C)(C)C(F)(F)F)on1)c1ccc(-c2nn(C(C)C)c(N)c2C(N)=O)nc1] |

TABLE A-continued
| Example # | Structure |
|---|---|
| 66 (Isomer 2) | 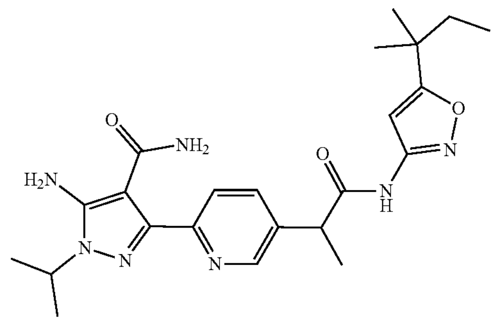 [SMILES: CCC(C)(C)c1cc(NC(=O)C(C)c2ccc(-c3nn(C(C)C)c(N)c3C(N)=O)nc2)no1] |
| 68 (Isomer 2) | 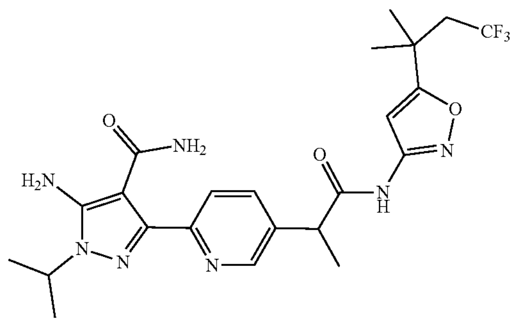 [SMILES: CC(C(=O)Nc1cc(C(C)(C)CC(F)(F)F)on1)c1ccc(-c2nn(C(C)C)c(N)c2C(N)=O)nc1] |
| 70 (Isomer 2) | 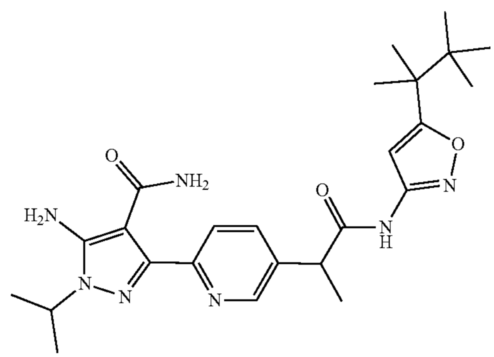 [SMILES: CC(C(=O)Nc1cc(C(C)(C)C(C)(C)C)on1)c1ccc(-c2nn(C(C)C)c(N)c2C(N)=O)nc1] |
| 76 (Isomer 2) | 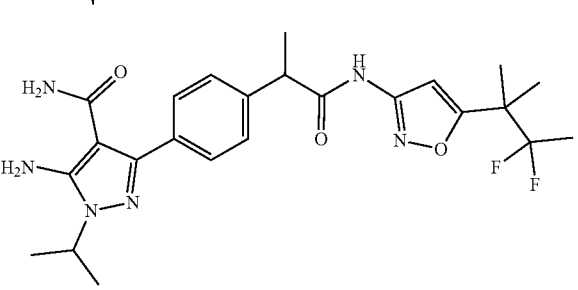 |
| 80 (Isomer 2) | 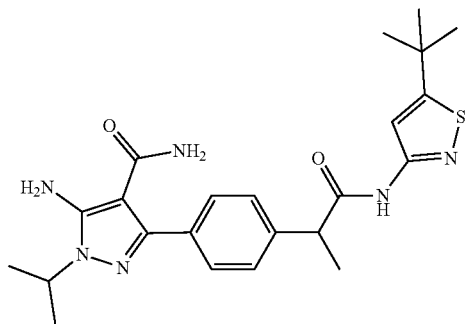 [SMILES: CC(C(=O)Nc1cc(C(C)(C)C)sn1)c1ccc(-c2nn(C(C)C)c(N)c2C(N)=O)cc1] |

TABLE A-continued
| Example # | Structure |
|---|---|
| 81 (Isomer 1) | 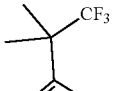 |
| 84 (Isomer 2) | 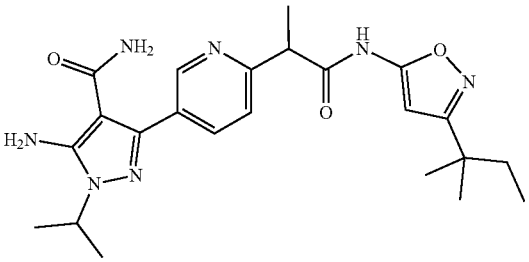 [SMILES: CCC(C)(C)c1cc(NC(=O)C(C)c2ccc(-c3nn(C(C)C)c(N)c3C(N)=O)cn2)on1] |
| 90 (Isomer 2) | 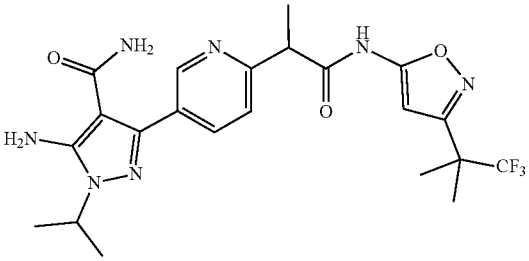 [SMILES: CC(C(=O)Nc1cc(C(C)(C)C(F)(F)F)no1)c1ccc(-c2nn(C(C)C)c(N)c2C(N)=O)cn1] |
| 94 (Isomer 2) | 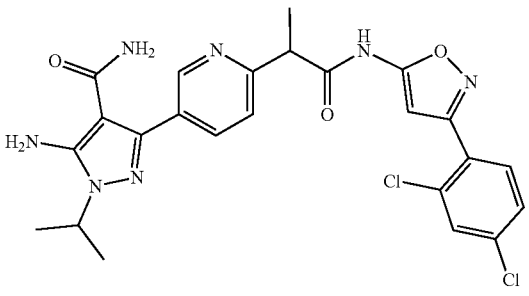 [SMILES: CC(C(=O)Nc1cc(-c2ccc(Cl)cc2Cl)no1)c1ccc(-c2nn(C(C)C)c(N)c2C(N)=O)cn1] |
| 98 (Isomer 1) | 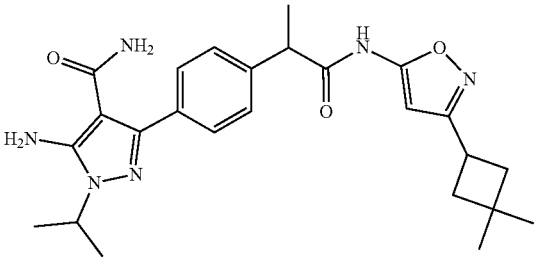 [SMILES: CC(C(=O)Nc1cc(C2CC(C)(C)C2)no1)c1ccc(-c2nn(C(C)C)c(N)c2C(N)=O)cc1] |

TABLE A-continued

| Example # | Structure |
|---|---|
| 36c (Isomer 1) | 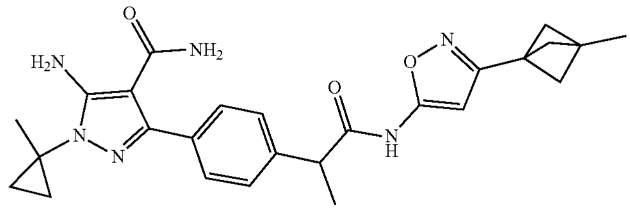 [SMILES: CC(C(=O)Nc1cc(C23CC(C)(C2)C3)no1)c1ccc(-c2nn(C3(C)CC3)c(N)c2C(N)=O)cc1] |
| 36g (Isomer 1) | 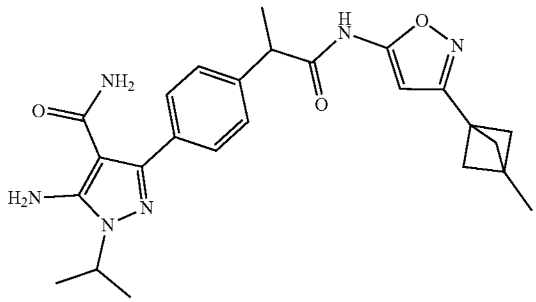 [SMILES: CC(C(=O)Nc1cc(C23CC(C)(C2)C3)no1)c1ccc(-c2nn(C(C)C)c(N)c2C(N)=O)cc1] |
| 36h (Isomer 1) | 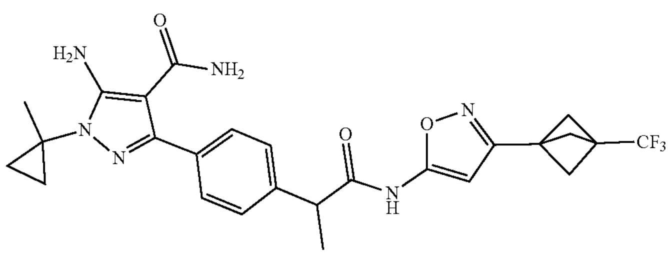 [SMILES: CC(C(=O)Nc1cc(C23CC(C(F)(F)F)(C2)C3)no1)c1ccc(-c2nn(C3(C)CC3)c(N)c2C(N)=O)cc1] |
| 36t (Isomer 1) | 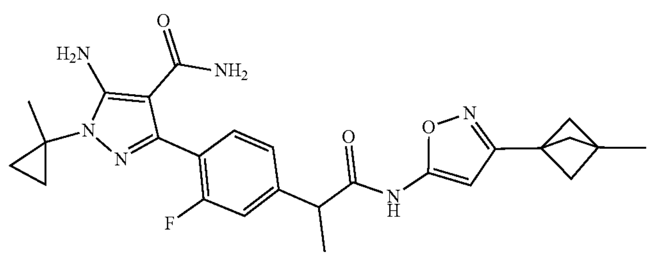 [SMILES: CC(C(=O)Nc1cc(C23CC(C)(C2)C3)no1)c1ccc(-c2nn(C3(C)CC3)c(N)c2C(N)=O)c(F)c1] |
| 36v (Isomer 1) | 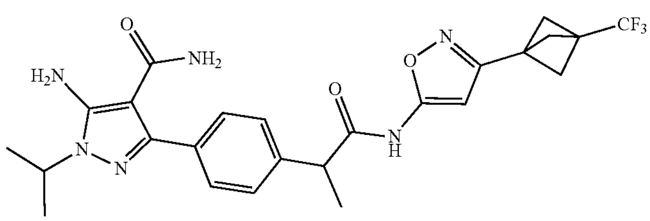 [SMILES: CC(C(=O)Nc1cc(C23CC(C(F)(F)F)(C2)C3)no1)c1ccc(-c2nn(C(C)C)c(N)c2C(N)=O)cc1] |
| 36zf (Isomer 1) | 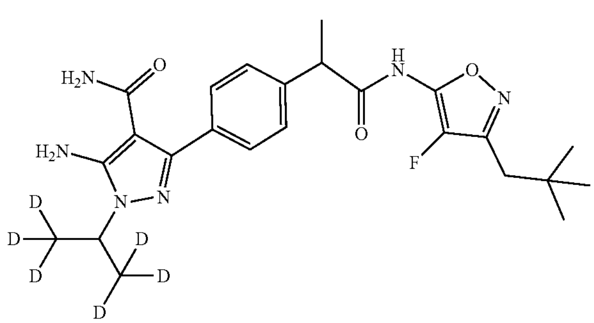 [SMILES: [2H]C([2H])([2H])C(n1nc(-c2ccc(C(C)C(=O)Nc3onc(CC(C)(C)C)c3F)cc2)c(C(N)=O)c1N)C([2H])([2H])[2H]] |

The structures drawn in Table A do not indicate absolute stereochemistry at the backbone chiral position (shown by φ in formula (I)$^φ$). However, the isomers can be separated by chiral chromatography as described in the Examples below and differing activity is often noted between the isomers. Thus, in each of the Examples in Table A, the noted isomer (i.e., Isomer 1 or Isomer 2) could be the R-enantiomeric form as differentiated over the S-enantiomeric form (or vice versa) of the molecule. Both the R-enantiomeric form and the S-enantiomeric form are indicated below in the examples and both forms are intended to be included in the disclosure herein.

Compounds of formula (I) including the forms of formula (II) and formula (III) also can be deuterated at specific positions and such deuterated forms are understood to be disclosed herein where a hydrogen can be replaced by a deuterium in a disclosed molecule.

The compounds of formulas (I), (II), and (III) described herein may form pharmaceutically acceptable salts. Such pharmaceutically acceptable salts of the compounds of formulas (I), (II), and (III) are intended to be included. Pharmaceutically acceptable salts and common methodology for preparing them are well known in the art (see, e.g., P. Stahl, et al. *Handbook of Pharmaceutical Salts; Properties, Selection and Use*, 2$^{nd}$ Revised Edition (Wiley-VCH, 2011); S. M. Berge, et al., "Pharmaceutical Salts," *Journal of Pharmaceutical Sciences*, Vol. 66, No. 1, January 1977).

The compounds of formulas (I), (II), and (III) as described herein are generally effective over a wide dosage range. For example, dosages per day fall within the range of about 1 mg/kg to about 200 mg/kg. Further, the compounds of formulas (I), (II), and (III) as described herein can be administered, for example, in an amount of about 1 mg/kg to about 150 mg/kg, about 1 mg/kg to about 100 mg/kg, about 5 mg/kg to about 150 mg/kg, about 5 mg/kg to about 100 mg/kg, about 20 mg/kg to about 40 mg/kg, about 25 mg/kg to about 35 mg/kg, about 50 mg/kg to about 70 mg/kg, about 55 mg/kg to about 65 mg/kg, about 90 mg/kg to about 110 mg/kg, about 95 mg/kg to about 105 mg/kg, or about 50 mg/kg to about 150 mg/kg. Additionally, the compounds of formulas (I), (II), and (III) as described herein can be administered, for example, in an amount of about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 105 mg/kg, about 110 mg/kg, about 115 mg/kg, about 120 mg/kg, about 125 mg/kg, about 130 mg/kg, about 135 mg/kg, about 140 mg/kg, about 145 mg/kg, about 150 mg/kg, about 155 mg/kg, about 160 mg/kg, about 165 mg/kg, about 170 mg/kg, about 175 mg/kg, about 180 mg/kg, about 185 mg/kg, about 190 mg/kg, about 195 mg/kg, or about 200 mg/kg. Daily administration can be once-daily or in multiple doses, e.g., twice-daily (BID) administration. It will be understood that the amount of a compound actually administered will be determined by a physician, in light of the relevant circumstances, including the condition to be treated, the chosen route of administration, the actual compound or compounds administered, the age, weight, and response of the individual patient, and the severity of the patient's symptoms.

The compounds of formulas (I), (II), and (III) as described herein can be formulated as pharmaceutical compositions that can be administered by a variety of routes. Such pharmaceutical compositions and processes for preparing the same are well known in the art (see, e.g., *Remington; The Science and Practice of Pharmacy* (A. Gennaro, et al., eds., 21st ed., Mack Publishing Co., 2005)). Specifically, the compounds of formulas (I), (II), and (III), as described herein, or pharmaceutically acceptable salts thereof, can be combined with one or more pharmaceutically acceptable carriers, diluents, or excipients. More particularly, the compounds described herein by formulas (I), (II), and (III) can be formulated as pharmaceutical compositions. Further, the compounds of formulas (I), (II), and (III) as described herein, or pharmaceutically acceptable salts thereof, can be combined with one or more other therapeutic agents. For example, the compounds of formulas (I), (II), and (III) as described herein, or pharmaceutically acceptable salts thereof, can be a component in a pharmaceutical composition for the treatment of cancer in combination with one or more pharmaceutically acceptable carriers, diluents, or excipients, and optionally with one or more additional therapeutic agents. Pharmaceutical compositions containing the compounds of formulas (I), (II), and (III) as described herein, or pharmaceutically acceptable salts thereof, can be used in the methods described herein.

The term "treating" (or "treat" or "treatment") as used herein refers to restraining, slowing, stopping, or reversing the progression or severity of an existing symptom, condition or disorder.

As used herein, the term "irritable bowel syndrome" or "IBS" means gastrointestinal disorders including, but not limited to, diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, and inflammatory bowel disease.

As used herein, the terms "cancer" and "cancerous" refer to or describe the physiological condition in patients that is typically characterized by unregulated cell proliferation. Included in this definition are benign and malignant cancers. By "early stage cancer" or "early stage tumor" is meant a cancer that is not advanced or metastatic or is classified as a Stage 0, I, or II cancer. Examples of cancer include, but are not limited to, lung cancer (e.g., small cell lung carcinoma or non-small cell lung carcinoma), thyroid cancer (e.g., papillary thyroid cancer, medullary thyroid cancer, differentiated thyroid cancer, recurrent thyroid cancer, or refractory differentiated thyroid cancer), thyroid adenoma, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, and cervical cancer.

The term "RET-associated disease or disorder" as used herein refers to diseases or disorders associated with or having a dysregulation of a RET gene, a RET kinase (also called herein RET kinase protein), or the expression or activity or level of any (e.g., one or more) of the same (e.g., any of the types of dysregulation of a RET gene, a RET kinase, a RET kinase domain, or the expression or activity or level of any of the same described herein).

The term "RET-associated cancer" as used herein refers to cancers associated with or having a dysregulation of a RET gene, a RET kinase (also called herein RET kinase protein), or expression or activity, or level of any of the same. Non-limiting examples of a RET-associated cancer are described herein.

The phrase "dysregulation of a RET gene, a RET kinase, or the expression or activity or level of any of the same" refers to a genetic mutation. Examples of such genetic mutations causing dysregulation of a RET gene, a RET kinase, or the expression or activity or level of any of the same include, but are not limited to, a RET gene translocation that results in the expression of a fusion protein, a deletion in a RET gene that results in the expression of a RET protein that includes a deletion of at least one amino acid as compared to the wild-type RET protein, a mutation in a RET gene that results in the expression of a RET protein with one or more point mutations, or an alternative spliced version of a RET mRNA that results in a RET protein having a deletion of at least one amino acid in the RET protein as compared to the wild-type RET protein or a RET gene amplification that results in overexpression of a RET protein or an autocrine activity resulting from the overexpression of a RET gene in a cell that results in a pathogenic increase in the activity of a kinase domain of a RET protein (e.g., a constitutively active kinase domain of a RET protein) in a cell. A dysregulation of a RET gene, a RET protein, or expression or activity, or level of any of the same, can be a mutation in a RET gene that encodes a RET protein that is constitutively active or has increased activity as compared to a protein encoded by a RET gene that does not include the mutation. For example, a dysregulation of a RET gene, a RET protein, or expression or activity, or level of any of the same, can be the result of a gene or chromosome translocation which results in the expression of a fusion protein that contains a first portion of RET that includes a functional kinase domain, and a second portion of a partner protein (i.e., that is not RET). In some examples, dysregulation of a RET gene, a RET protein, or expression or activity or level of any of the same can be a result of a gene translocation of one RET gene with another non-RET gene.

Methods for the treatment of RET-associated diseases or disorders, in particular for the treatment of IBS or cancer with abnormal RET expression, using the compounds of formulas (I), (II), and (III) as described herein are provided. Examples of cancers with abnormal RET expression include cancers caused by dysregulation of a RET gene, a RET kinase, or the expression or activity or level of any of the same. One such method of treating RET-associated diseases or disorders such as IBS or cancer includes administering a therapeutically effective amount of to a patient in need thereof. Another method of treating RET-associated diseases or disorders such as IBS or cancer includes a) detecting a dysregulation of a RET gene, a RET kinase, or the expression or activity or level of any of the same in a sample from the patient; and b) administering a therapeutically effective amount of a compound of formula I or a pharmaceutically acceptable salt.

The dysregulation of a RET gene, a RET kinase, or the expression or activity or level of any of the same can be the result of one or more chromosome translocations or inversions resulting in a RET gene fusion (i.e., the genetic translocations result in an expressed protein that is a fusion protein containing residues from a non-RET partner protein and including a minimum of a functional RET kinase domain). Non-limiting examples of RET fusion partners and their associated cancers include ACBD5 (papillary thyroid cancer); AFAP1 (NSCLC); AFAP1L2 (papillary thyroid cancer); AKAP13 (papillary thyroid cancer); BCR (chronic myelomonocytic leukemia); C10orf118 (papillary thyroid cancer); CCDC6 (also called PTC1, D10S170, or H4) (NSCLC, colon cancer, papillary thyroid cancer, adenocarcinomas, lung adenocarcinoma, metastatic colorectal cancer, adenosquamous carcinomas, breast cancer); CCDC188C (NSCLC); CEP55 (diffuse gastric cancer); CGNL1 (pancreatic cancer); CLIP1 (adenocarcinoma); CUX1 (lung adenocarcinoma); DLG5 (non-anaplastic thyroid cancer); DOCK1 (NSCLC); EML4 (papillary thyroid cancer); ERC1 (also called ELKS) (papillary thyroid cancer, breast cancer); ETV6 (salivary cancer); FGFR1OP (CMML, primary myelofibrosis with secondary acute myeloid leukemia); FKBP15 (papillary thyroid cancer); FOXP4 (lung adenocarcinoma); FRMD4A (NSCLC); GOLGA5 (also called PTC5) (papillary thyroid cancer, spitzoid neoplasms); H4L (various); HOOK3 (papillary thyroid cancer); HRH4-RET (thyroid cancer and/or papillary thyroid cancer); HTIF1 (various); KIAA1217 (also called SKT) (papillary thyroid cancer, lung adenocarcinoma, NSCLC); KIAA1468 (also called PTC9 and RFG9) (papillary thyroid cancer, lung adenocarcinoma); KIF13A (NSCLC); KIF5B (NSCLC, ovarian cancer, spitzoid neoplasms, lung adenocarcinoma, adenosquamous carcinomas); KTN1 (also called PTC8) (papillary thyroid cancer); MBD1 (also known as PCM1) (papillary thyroid cancer); MPRIP (NSCLC); MYH10 (infantile myofibromatosis); MYH13 (medullary thyroid cancer); NCOA4 (also called PTC3, ELE1, and RFG) (papillary thyroid cancer, NSCLC, colon cancer, salivary gland cancer, metastatic colorectal cancer, lung adenocarcinoma, adenosquamous carcinomas diffuse sclerosing variant of papillary thyroid cancer, breast cancer, acinic cell cancer, mammary analog secretory cancer); OLFM4 (Small-bowel cancer); PARD3 (NSCLC); PCM1 (papillary thyroid cancer); PIBF1 (bronchiolus lung cell cancer); PICALM (NSCLC); PPFIBP2 (papillary thyroid cancer); PRKAR1A (also called PTC2) (papillary thyroid cancer); PTClex9 (a novel CCDC6 rearrangement) (metastatic papillary thyroid cancer); PTC4 (a novel NCO4/ELE1 rearrangement) (papillary thyroid cancer); RAB61P2 (papillary thyroid cancer); RASAL2 (Sarcoma); RASGEF1A (breast cancer); RBPMS (NSCLC); RFG8 (papillary thyroid cancer); RRBP1 (colon cancer); RUFY1 (colorectal cancer); RUFY2 (NSCLC; papillary thyroid cancer); RUFY3 (papillary thyroid cancer); SLC12A2 (NSCLC); SORBS2 (papillary thyroid cancer); SPECC1L (papillary thyroid cancer; thyroid gland cancer); SQSTM1 (papillary thyroid cancer); TAF3 (pancreatic cancer); TBL1XR1 (papillary thyroid cancer, thyroid gland cancer); TFG (pancreatic cancer); TIF1G (various); TRIM24 (also called PTC6) (papillary thyroid cancer); TRIM27 (also called RFP) (papillary thyroid cancer); AKAP13 (papillary thyroid cancer); TRIM33 (also called PTC7 and RFG7) (NSCLC, papillary thyroid cancer); and UEVLD (papillary thyroid cancer). The fusion protein can be, for example, KIF5B-RET. Other RET fusion proteins may not be included in the listing herein or are not yet known; however, the compounds of formulas (I), (II), and (III) and methods for their use as described herein are expected to be effective inhibitors.

The dysregulation of a RET gene, a RET kinase, or expression or activity or level of any of the same, can be caused by one or more point mutations, insertions, or deletions in a RET gene (compared to wildtype RET). For reference, the sequence of mature human RET protein (SEQ ID NO: 1) is provided here:

```
MAKATSGAAG LRLLLLLLLP LLGKVALGLY FSRDAYWEKL

YVDQAAGTPL LYVHALRDAP EEVPSFRLGQ HLYGTYRTRL

HENNWICIQE DTGLLYLNRS LDHSSWEKLS VRNRGFPLLT

VYLKVFLSPT SLREGECQWP GCARVYFSFF NTSFPACSSL

KPRELCFPET RPSFRIRENR PPGTFHQFRL LPVQFLCPNI

SVAYRLLEGE GLPFRCAPDS LEVSTRWALD REQREKYELV

AVCTVHAGAR EEVVMVPFPV TVYDEDDSAP TFPAGVDTAS

AVVEFKRKED TVVATLRVFD ADVVPASGEL VRRYTSTLLP

GDTWAQQTFR VEHWPNETSV QANGSFVRAT VHDYRLVLNR

NLSISENRTM QLAVLVNDSD FQGPGAGVLL LHFNVSVLPV

SLHLPSTYSL SVSRRARRFA QIGKVCVENC QAFSGINVQY

KLHSSGANCS TLGVVTSAED TSGILFVNDT KALRRPKCAE

LHYMVVATDQ QTSRQAQAQL LVTVEGSYVA EEAGCPLSCA

VSKRRLECEE CGGLGSPTGR CEWRQGDGKG ITRNFSTCSP

STKTCPDGHC DVVETQDINI CPQDCLRGSI VGGHEPGEPR

GIKAGYGTCN CFPEEEKCFC EPEDIQDPLC DELCRTVIAA

AVLFSFIVSV LLSAFCIHCY HKFAHKPPIS SAEMTFRRPA

QAFPVSYSSS GARRPSLDSM ENQVSVDAFK ILEDPKWEFP

RKNLVLGKTL GEGEFGKVVK ATAFHLKGRA GYTTVAVKML

KENASPSELR DLLSEFNVLK QVNHPHVIKL YGACSQDGPL

LLIVEYAKYG SLRGFLRESR KVGPGYLGSG GSRNSSSLDH

PDERALTMGD LISFAWQISQ GMQYLAEMKL VHRDLAARNI

LVAEGRKMKI SDFGLSRDVY EEDSYVKRSQ GRIPVKWMAI

ESLFDHIYTT QSDVWSFGVL LWEIVTLGGN PYPGIPPERL

FNLLKTGHRM ERPDNCSEEM YRLMLQCWKQ EPDKRPVFAD

ISKDLEKMMV KRRDYLDLAA STPSDSLIYD DGLSEEETPL

VDCNNAPLPR ALPSTWIENK LYGMSDPNWP GESPVPLTRA

DGTNTGFPRY PNDSVYANWM LSPSAAKLMD TFDS
```

Non-limiting examples of activating RET kinase protein point mutations, insertions, or deletions as compared to wild-type RET kinase can occur at the following amino acid positions: 2, 3, 4, 5, 6, 7, 8, 11, 12, 13, 20, 32 (e.g., S32L), 34 (e.g., D34S), 40 (e.g., L40P), 56 (e.g., L56M), 64 (e.g., P64L), 67 (e.g., R67H), 114 (e.g., R114H), 136 (e.g., glutamic acid to stop codon), 145 (e.g., V145G), Amino acid position 180 (e.g., arginine to stop codon), 200, 292 (e.g., V292M), 294, 321 (e.g., G321R), 330 (e.g., R330Q), 338 (e.g., T338I), 360 (e.g., R360W), 373 (e.g., alanine to frameshift), 393 (e.g., F393L), 423 (e.g., G423R), 432, 446 (e.g., G446R), 505-506 (6-Base Pair In-Frame Germline Deletion in Exon 7), 510 (e.g., A510V), 511 (e.g., E511K), 513 (e.g., G513D), (e.g., C515R, C515S, C515W), 525 (e.g., R525W), 531 (e.g., C531R, or 9 base pair duplication), 532 (e.g., duplication), 533 (e.g., G533C, G533S), 550 (e.g., G550E), 591 (e.g., V591I), 593 (e.g., G593E), 595 (e.g., E595D and E595A), 600 (e.g., R600Q), 602 (e.g., I602V), 603 (e.g., K603Q, K603E), 606 (e.g., Y606C), 609 (e.g., C609Y, C609S, C609G, C609R, C609F, C609W, C609C), 611 (e.g., C611R, C611S, C611G, C611Y, C611F, C611W), 616 (e.g., E616Q), 618 (e.g., C618S, C618Y, C618R, C618T, C618G, C618F, C618W), 620 (e.g., C620S, C620W, C620R, C620G, C620L, C620Y, C620F), (e.g., E623K), 624 (e.g., D624N), 630 (e.g., C630A, C630R, C630S, C630Y, C630F, C630W, C630G), 631 (e.g., D631N, D631Y, D631A, D631G, D631V, D631E), 632 (e.g., E632K, E632G), 632-633 (6-Base Pair In-Frame Germline Deletion in Exon 11), 633 (e.g., 9 base pair duplication), 634 (e.g., C634W, C634Y, C634S, C634R, C634F, C634G, C634L, C634A, or C634T, or an insertion ELCR, or a 12 base pair duplication, or in combination with A640G, A641A, or A641T) (e.g., causing MTC), 634/852 (e.g., C634R/I852M), 635 (e.g., R635G), 636 (e.g., T636P, T636M), 648 (e.g., V648I), 649 (e.g., S649L), 664 (e.g., A664D), 665 (e.g., H665Q), 666 (e.g., K666E, K666M, K666N, K666R), 675 (T675T, silent nucleotide change), 686 (e.g., S686N), 689 (e.g., S689T), (e.g., G691S), 694 (e.g., R694Q), 700 (e.g., M700L), 706 (e.g., V706M, V706A), splice variant (e.g., E713K), 732 (e.g., E732K), 736 (e.g., G736R), 748 (e.g., G748C), 765 (e.g., S765P), 766 (e.g., P766S, P766M6), 768 (e.g., E768Q, E768D), 769 (e.g., L769L), 770 (e.g., R770Q), 771 (e.g., D771N), 777 (e.g., N777S), 778 (e.g., V778I), 781 (e.g., Q781R), 788 (e.g., I788I), 790 (e.g., L790F, L790T), 791 (e.g., Y791F, Y791N), 791/852 (e.g., Y791F/I852M), 802, 804 (e.g., V804L, V804M, V804E, V804G, V804S) (e.g., causing MTC), 804/918 (e.g., V804M/M918T, V804L/M918T), 805 (e.g., E805K), 804/805 (e.g., V804M/E805K), 806 (e.g., Y806F, Y806C, Y806H, Y806Y), 810 (e.g., G810R, G810S, G810A, G810C, G810V), 818 (e.g., E818K), 819 (e.g., S819I), 823 (e.g., G823E), 826 (e.g., Y826M, Y826S), 833 (e.g., R833C), 841 (e.g., P841L, P841P), (e.g., E843D), 844 (e.g., R844W, R844Q, R844L), 848 (e.g., M848T), 852 (e.g., I852M), 865 (e.g., L865V), 870 (e.g., L870F), 873 (e.g., R873W), 876 (e.g., A876V), 881 (e.g., L881V), 882, 883 (e.g., A883F, A883P, A883S, A883T, A883Y), 884 (e.g., E884K), 886 (e.g., R886W), 891 (e.g., S891A), 897 (e.g., R897Q), 898 (e.g., D898V), (e.g., Y900F), 901 (e.g., E901K), 904 (e.g., S904F, S904C), 905 (e.g., Y905F), 907 (e.g., K907E, K907M), 908 (e.g., R908K), 911 (e.g., G911D), 912 (e.g., R912P, R912Q), (e.g., M918T, M918V, M918L, M918R) (e.g., causing MTC), 919 (e.g., A919V), (e.g., E921K), 922 (e.g., S922P, S922Y), 930 (e.g., T930M), 961 (e.g., F961L), 972 (e.g., R972G), 981 (e.g., Y981F), 982 (e.g., R982C), 1009 (e.g., M1009V), 1015 (e.g., Y1015F), 1017 (e.g., D1017N), 1041 (e.g., V1041G), 1064 (e.g., M1064T), 1096 (e.g., Y1096F), RET+3, In-Frame Deletion in Exons 6 and 11, 3 bp In-Frame Deletion in Exon 15, Nucleotide position 2136+2 (e.g., 2136+2T>G), del632-636 ins6. The RET kinase protein point mutations/insertions/deletions can be, for example, M918T, M918V, C634W, V804L, or V804M. Other RET kinase protein point mutations/insertions/deletions may not be included in the listing herein or are not yet known; however, the compounds of formulas (I), (II), and (III) and methods for their use as described herein are expected to be effective inhibitors.

A dysregulation of a RET gene, a RET kinase, or expression or activity or level of any of the same, can also include a splice variation in a RET mRNA which results in an expressed protein that is an alternatively spliced variant of RET having at least one residue deleted (as compared to the wild-type RET kinase) resulting in a constitutive activity of a RET kinase domain.

A "RET kinase inhibitor" as defined herein refers to compounds that inhibit RET activity using a measurement such as the Biological Assays described below in the examples.

In some cases, a RET kinase containing a mutation, insertion, or deletion is more resistant to inhibition of its phosphotransferase activity by one or more first RET kinase inhibitor(s), as compared to a wildtype RET kinase or a RET kinase not including the same mutation. Such mutations may not decrease the sensitivity of the cancer cell or tumor having the RET kinase to treatment a compound of formulas (I), (II), and (III) as described herein (e.g., as compared to a cancer cell or a tumor that does not include the particular RET inhibitor resistance mutation). In these cases, a RET inhibitor resistance mutation can result in a RET kinase that has one or more of an increased $V_{max}$, a decreased $K_m$ for ATP, and an increased $K_D$ for a first RET kinase inhibitor, when in the presence of a first RET kinase inhibitor, as compared to a wildtype RET kinase or a RET kinase not having the same mutation in the presence of the same first RET kinase inhibitor.

In other cases, a RET kinase containing a mutation, insertion, or deletion, has increased resistance to a compound of formulas (I), (II), and (III) as described herein, as compared to a wildtype RET kinase or a RET kinase not including the same mutation. In such cases, a RET inhibitor resistance mutation can result in a RET kinase that has one or more of an increased $V_{max}$, a decreased $K_m$, and a decreased $K_D$ in the presence of a compound of formulas (I), (II), and (III) as described herein, as compared to a wildtype RET kinase or a RET kinase not having the same mutation in the presence of the same compound of formulas (I), (II), and (III) as described herein.

Examples of RET inhibitor resistance mutations can include point mutations, insertions, or deletions in and near the ATP binding site in the tertiary structure of RET kinase, including, but not limited to, the gatekeeper residue, P-loop residues, residues in or near the DFG motif, and ATP cleft solvent front amino acid residues. Additional examples of these types of mutations include changes in residues that may affect enzyme activity and/or drug binding including but are not limited to residues in the activation loop, residues near or interacting with the activation loop, residues contributing to active or inactive enzyme conformations, changes including mutations, deletions, and insertions in the loop proceeding the C-helix and in the C-helix. Specific residues or residue regions that at which mutations are known to create RET inhibitor resistance include but are not limited to the following amino acids (based on the human wildtype RET protein sequence (SEQ ID NO: 1)): 732 (e.g., E732K); 788 (e.g., I788N); 804 (e.g., V804M, V804L, V804E); 804/805 (e.g., V804M/E805K); 806 (e.g., Y806C, Y806E, Y806S, Y806H, Y806N); 810 (e.g., G810A, G810C, G810R, G810S, G810V); and 865 (e.g., L865V). Further examples of RET inhibitor resistance mutation positions include, but are not limited to, the following amino acids (based on the human wildtype RET protein sequence (SEQ ID NO: 1)): L730P, G731V, E732K, G733V, E734K, L760M, K761E, E762K, N763D, A764V, S765N, P766A, S767C, E768K, L779M, I788M, M868R, K869E, L870Q, V871M, H872R, R873P, D874Y, L881R, L895M, S896N, R897C, D898Y, V899G, Y900D, E901K, E902K, D903Y, S904C, Y905D, V906M, K907E, R908P, S909C, Q910R, G911C, and R912P. These mutations (which may also include single or multiple amino acid changes, insertions within or flanking the sequences, and deletions within or flanking the sequences) are thought to induce a steric hindrance and/or an active conformational effect that changes inhibitor binding characteristics.

Compounds of formulas (I), (II), and (III) as described herein may be useful in treating patients that develop cancers with certain RET inhibitor resistance mutations. For example, resistance mutations that result in an increased resistance to a RET inhibitor like a substitution at amino acid position 804 (e.g., V804M, V804L, or V804E), and/or one or more other RET inhibitor resistance mutations like those discussed above may be treated by either dosing in combination or as a follow-up therapy to existing drug treatments. For example, if a patient is treated with a first RET kinase inhibitor and the patient develops a RET inhibitor resistance mutation, the patient could then be subsequently treated with a compound of formulas (I), (II), and (III) as described herein, or pharmaceutically acceptable salts thereof (assuming that the compound of formulas (I), (II), and (III) as described herein is a suitable inhibitor of the particular RET kinase inhibitor mutation present). As another example, if a patient is known to have a particular RET kinase inhibitor mutation (or multiple mutations), the patient could simultaneously be treated with multiple RET kinase inhibitors including a compound (or compounds) of formulas (I), (II), and (III) as described herein, or pharmaceutically acceptable salts thereof that are effective against the RET kinase inhibitor mutation(s) present). Examples of currently known RET kinase inhibitors include alectinib, BLU6864, cabozantinib, dovitinib, foretinib, lenvatinib, ponatinib, pralsetinib, selpercatinib, sorafenib, sunitinib, and vandetanib.

The types of cancers that can be treated using the methods described herein include hematological cancer or solid tumor cancer. Examples of the types of cancer that can be treated using a compound of formulas (I), (II), and (III) as described herein include lung cancer (e.g., small cell lung carcinoma or non-small cell lung carcinoma), thyroid cancer (e.g., papillary thyroid cancer, medullary thyroid cancer, differentiated thyroid cancer, recurrent thyroid cancer, or refractory differentiated thyroid cancer), thyroid adenoma, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, and cervical cancer. Specifically, the types of cancer can be lung cancer or thyroid cancer. More specifically, the cancer can be non-small cell lung carcinoma or medullary thyroid cancer. Further examples of the types of cancers that can be treated using the compounds of formulas (I), (II), and (III) and the methods as described herein include acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromocytoma, pituitary cancer, plasma cell neoplasm, pleuropulmonary blastoma, pregnancy and breast cancer, primary central nervous system lymphoma, primary peritoneal cancer, prostate cancer, rectal cancer, colon cancer, colonic neoplasms, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

Examples of the types of hematological cancers that can be treated using the compounds of formulas (I), (II), and (III) and the methods as described herein include leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In one embodiment, the hematological cancer (e.g., the hematological cancer that is a RET-associated cancer) is AML or CMML.

Examples of the types of solid tumor cancers that can be treated using the compounds of formulas (I), (II), and (III) and the methods as described herein include thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma.

A compound of formulas (I), (II), and (III) as described herein, or pharmaceutically acceptable salts thereof, can be used in the manufacture of a medicament for the treatment of RET-associated diseases or disorders such as IBS or cancer. Cancers that can be treated using such a medicament are described herein above. Use of a compound of formulas (I), (II), or (III) as described herein, or pharmaceutically acceptable salts thereof, in the manufacture of a medicament can also include a step of performing an in vitro assay using a biological sample from a patient, determining the presence of a dysregulation of a RET gene, a RET kinase, or expression or activity or level of any of the same, and administering a therapeutically effective amount of the compound of formulas (I), (II), and (III) as described herein, to the patient if a dysregulation of a RET gene, a RET kinase, or expression or activity or level of any of the same is present. In these uses, the biological sample can be a tumor sample and the tumor sample can be analyzed using methods known to those of skill in the art such as genomic/DNA sequencing. Additionally, in these uses the sample can be obtained from the patient prior to the first administration of the compound of formulas (I), (II), and (III) as described herein. In these uses of the compound of formulas (I), (II), and (III) as described herein in a therapy can be based upon a patient being selected for treatment by having at least one dysregulation of a RET gene, a RET kinase, or expression or activity or level of any of the same. Also, in these uses a compound of formulas (I), (II), and (III), as described herein, or pharmaceutically acceptable salts thereof, may be administered to the patient at a dose of about 1 mg/kg to 200 mg/kg (effective dosage sub-ranges are noted herein above).

The compounds of formulas (I), (II), and (III) as described herein or pharmaceutically acceptable salts thereof, may be prepared by a variety of procedures known in the art, as well as the Preparations and Examples below. The specific synthetic steps for each of the routes described may be combined in different ways, or in conjunction with steps from different schemes, to prepare compounds of formulas (I), (II), and (III) or pharmaceutically acceptable salts thereof. The products of each step in the schemes below can be recovered by conventional methods well known in the art, including extraction, evaporation, precipitation, chromatography, filtration, trituration, and crystallization. The reagents and starting materials are readily available to one of ordinary skill in the art.

Certain stereochemical centers have been left unspecified and certain substituents have been eliminated in the following schemes for the sake of clarity and are not intended to limit the teaching of the schemes in any way. Furthermore, individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). For example, the following molecule has two chiral centers designated by a φ(as above in formula (I)φ) and an asterisk (*) to show a second chiral center. There are four possible isomers of this molecule that can be isolated without the absolute stereochemistry being determined, i.e., these diastereomer pairs can be RR, RS, SR, and SS. In cases where stereochemistry is not determined, the molecules may be differentiated by their retention time on a chiral column.

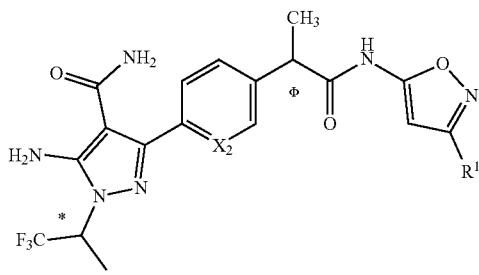

For example, the designations "isomer 1" and "isomer 2" refer to the compounds that elute from chiral chromatography first and second, respectively, under the conditions described herein and if chiral chromatography is initiated early in the synthesis, the same designation is applied to subsequent intermediates and examples. Similarly, when diastereomers are also present, the designations "diastereomer A" and "diastereomer B" in addition to the isomer 1 and isomer 2 designations are used. Additionally, the intermediates described in the following schemes may contain a number of nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Certain abbreviations are defined as follows: "ACN" refers to acetonitrile; "ATP" refers to adenosine triphosphate; "BSA" refers to Bovine Serum Albumin; "n-BuLi" refers to n-butyl lithium; "DCM" refers to dichloromethane or methylene chloride; "DEA" refers to diethylamine; "DIPEA" refers to N,N-diisopropylethylamine or N-ethyl-N-isopropyl-propan-2-amine; "DMA" refers to dimethylamine; "DMF" refers to N,N-dimethylformamide; "DMSO" refers to dimethyl sulfoxide; "DTT" refers to dithiothreitol; "Et$_3$N" refers to triethylamine; "EtOAc" refers to ethyl acetate; "ee" refers to enantiomeric excess; "Et$_2$O" refers to diethyl ether; "EtOH" refers to ethanol or ethyl alcohol; "FA" refers to formic acid; "GST" refers to glutathione S-transferase; "HEK" refers to human embryonic kidney; "hr" or "hrs" refers to hour or hours; "HTRF" refers to homogeneous time resolved fluorescence; "IgG" refers to immunoglobulin G; "IPA" refers to isopropyl alcohol or isopropanol; "KOAc" refers to potassium acetate; "LDA" refers to lithium diisopropylamide; "MeOH" refers to methanol or methyl alcohol; "MeTHF" refers to 2-methyltetrahydrofuran; "min" refers to minute or minutes; "Mn (dpm)3" refers to manganese(3+) tris[(3Z)-2,2,6,6-tetramethyl-5-oxo-3-hepten-3-olate]; "MtBE" refers to methyl tert-butyl ether; "NaOAc" refers to sodium acetate; "NBS" refers to N-bromosuccinimide; "NMI" refers to 1-methylimidazole or N-methylimidazole; "PBS-T" refers to Phosphate Buffered Saline+Tween®20; "Pd(dppf)Cl$_2$)" refers to [1,1' bis(diphenylphosphino)ferrocene]dichloropalladium (II); "PE" refers to petroleum ether; "PhSiH$_3$" refers to phenylsilane; "RT" refers to room temperature; "TCHF" refers to tetramethylchloroformamidinium hexafluorophosphate; "tert-BuOH" refers to tert butyl alcohol; "TCFH" refers to N,N,N',N'-tetramethylchloroformamidinium hexafluorophosphate; "TFA" refers to trifluoroacetic acid; "THF" refers to tetrahydrofuran; and "T3P®" refers to propanephosphonic acid anhydride, 2,4,6-tripropyl-1,3,5,2,4,6-trioxatriphosphorinane-2,4,6-trioxide, or PPACA; "t$_{(R)}$" refers to retention time and "WT" refers to wild-type.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally similar compounds and the procedures described in the Preparations and Examples which follow including any novel procedures. Intermediates and processes useful for the synthesis of the compounds described by formula (I) are intended to be included in this description.

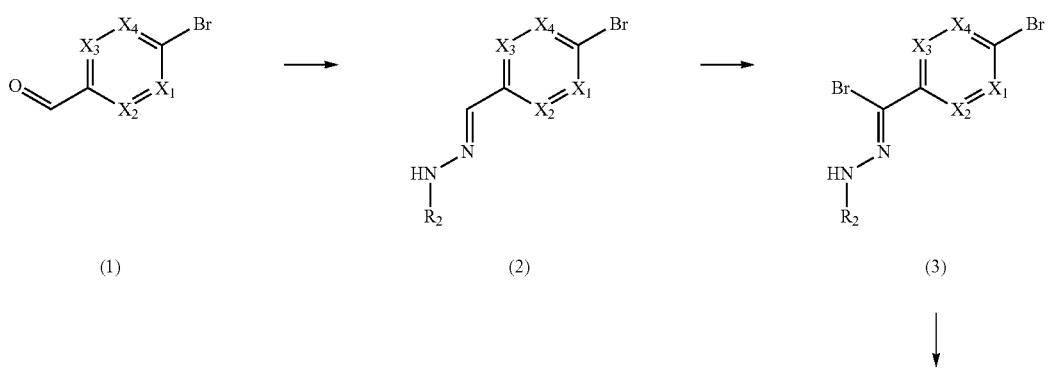

Scheme 1

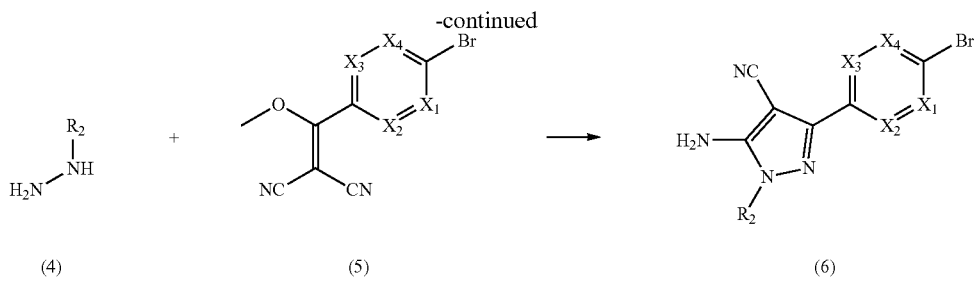

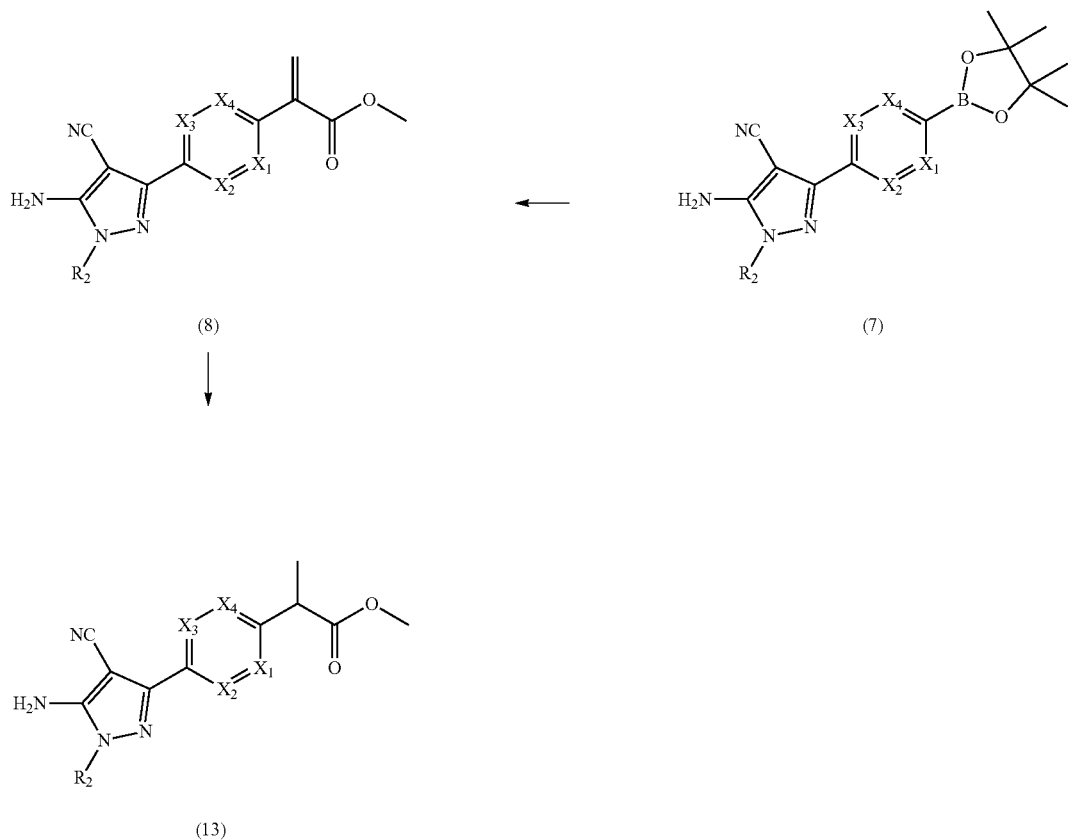

Scheme 1 depicts the preparation of the compounds of (13), which can be used to prepare the compounds of formulas (I), (II), and (III). A person of ordinary skill in the art will recognize that aryl aldehyde (1) may undergo condensation with alkyl hydrazine (4) to furnish hydrazone (2). Hydrazone (2) may be halogenated by employing reagents well known in the art to provide hydrazonoyl bromide (3). Amino pyrazole (6) may be formed via condensation of hydrazonoyl bromide (3) with malononitrile and an ensuing annulation. Amino pyrazole (6) may also be synthesized by reacting the appropriately substituted hydrazine (4) with the appropriate dinitrile Michael acceptor (5). Borylation of aryl bromide (6) under typical Miyaura reaction conditions may provide boronic ester (7). Treatment of boronic ester (7) with the appropriate metal catalyst and halide may afford α,β unsaturated ester (8). Reduction of olefin (8) may be achieved under reductive conditions such as a hydrogen atmosphere and suitable metal catalyst, preferably Pd/C, to furnish the α-methyl ester (13).

Scheme 2

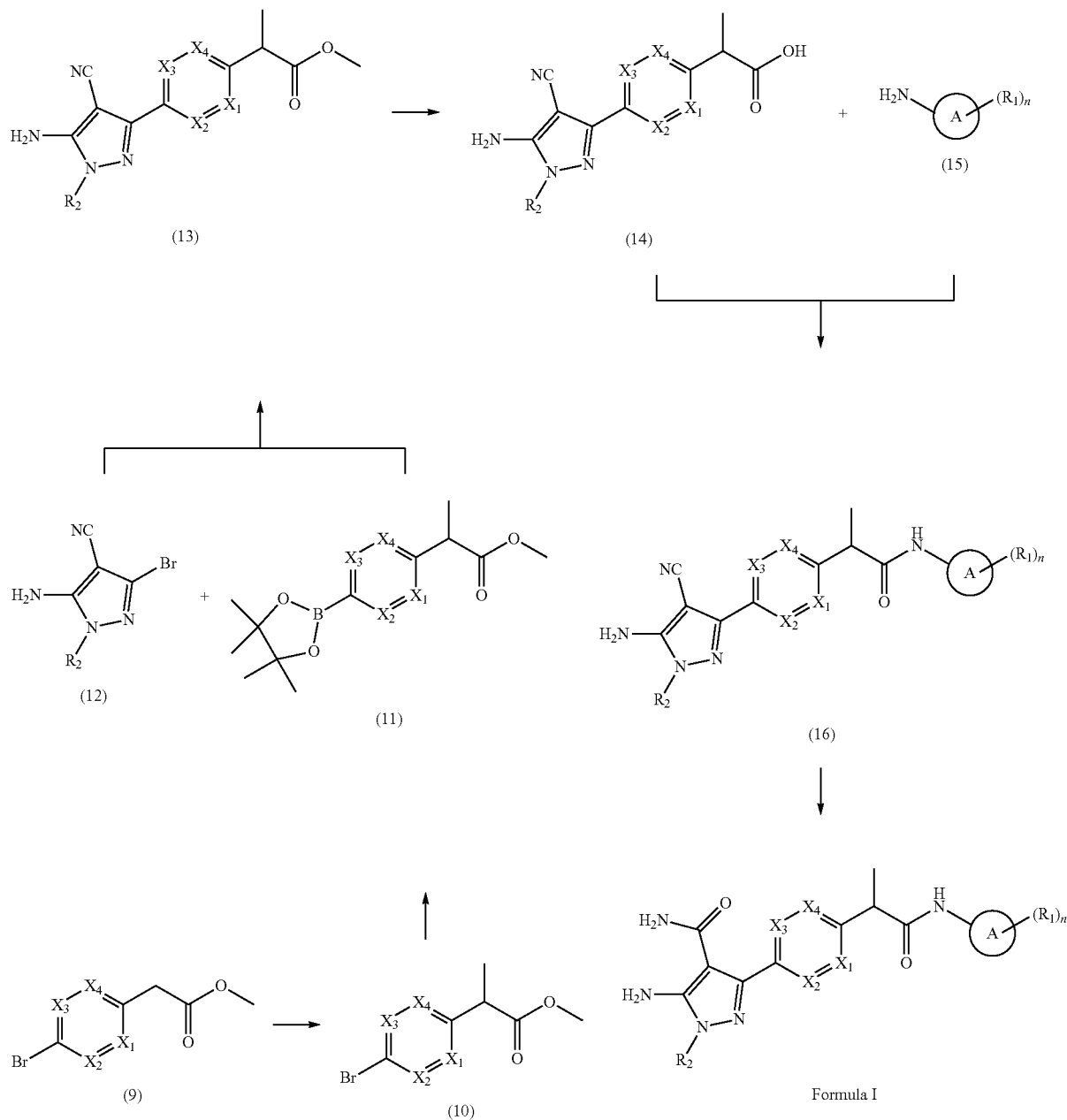

Scheme 2 depicts the preparation of the compounds of formulas (I), (II), and (III), as described herein. The skilled artisan will recognize that an alternative synthesis of α-methyl ester (13) may be achieved by α-methylation of methyl acetate (9) under archetypal enolate alkylation conditions to provide a methyl ester (10). Borylation via Miyaura conditions of the aryl bromide (10) may furnish boronate (11) in essentially the same manner as described for the boranate (7) in Scheme 1. Treatment of boronate ester (11) with the appropriate bromopyrazole (12) and metal catalyst, under Suzuki coupling conditions may afford α-methyl ester (13). Carboxylic acid (14) may be obtained by saponification of ester (13) with the proper nucleophilic base. The enantiomers of the carboxylic acid (14) may be separated using chiral separation techniques well known in the art or separated at a later step in the synthesis. Carboxylic acid (14) and primary amine (15) may be joined by utilizing the appropriate amide coupling reagent under conditions suitable for amide bond formation to provide (16). The nitrile moiety of amino pyrazole (16) may be converted to compounds of formulas (I), (II), and (III), as described herein, under a variety of conditions such as metal catalyzed hydration, acidic hydrolysis, and oxidation. The enantiomers may be separated using chiral separation techniques well known in the art to give the compounds of formulas (I), (II), and (III), as described herein.

PREPARATIONS AND EXAMPLES

Preparation 1

Methyl 2-(5-bromo-2-pyridyl)propanoate

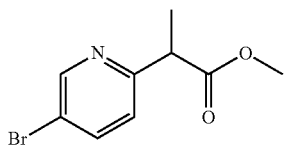

To methyl 2-(5-bromopyridin-2-yl)acetate (4.20 g, 17.5 mmol) in THF (84 mL) under N2 and at −20° C. is added 60% NaH (w/w) in mineral oil (771 mg, 19.3 mmol). The mixture is stirred at −20° C. until gas evolution has subsided. To the reaction mixture is then added iodomethane (4.4 mL, 70.1 mmol). The mixture is stirred for 5 min at −20° C. after which time it is allowed to warm to RT. After 1 hr the reaction mixture is concentrated under reduced pressure and dried under vacuum. To the residue is added DCM (15 mL), $H_2O$ (10 mL) and saturated aqueous $NaHCO_3$ solution (10 mL). The organic layer is separated, dried over $Na_2SO_4$, filtered, and concentrated under reduced pressure. The crude material is purified by silica gel flash chromatography eluting with a gradient of EtOAc in DCM from 0% to 20% to give the title compound as a colorless oil (3.16 g, 68.59%).

Preparation 2

Methyl 2-[4-(2,2-dicyano-1-hydroxy-vinyl)phenyl]propanoate

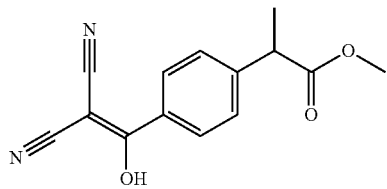 [SMILES: COC(=O)C(C)c1ccc(C(O)=C(C#N)C#N)cc1]

60% NaH (w/w) in mineral oil (3.85 g, 96.091 mmol) is added to THF (180 mL) in portions at RT under $N_2$. To this mixture is added malononitrile (3.17 g, 48.046 mmol) in THF (20 mL) dropwise at 0-10° C. and the mixture is stirred for 30 min at RT. To this mixture is added methyl 2-(4-chlorocarbonylphenyl)propanoate (13 g, crude) in THF (30 mL) dropwise at 0° C. and the mixture is stirred for 2 hrs at RT. The resulting mixture is used directly without further purification.

Preparation 2a

2-[(4-Bromo-2,3-difluoro-phenyl)-hydroxy-methylene]propanedinitrile

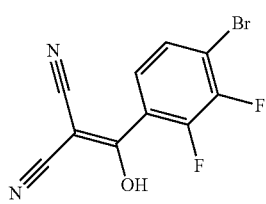 [SMILES: N#CC(C#N)=C(O)c1ccc(Br)c(F)c1F]

To a stirred mixture of NaH (1.68 g, 42.13 mmol, 60%) in THF (100 mL) is added malononitrile (1.53 g, 23.160 mmol) in THF (100 mL) dropwise at 0° C. under $N_2$. The mixture is stirred for 30 min at RT under $N_2$. To the above mixture is added 4-bromo-2,3-difluorobenzoyl chloride in THF (10 mL) dropwise at 0° C. The mixture is stirred for additional 2 hr at RT. The mixture is used without further purification.

Preparation 3

Methyl 2-[4-(2,2-dicyano-1-methoxyeth-1-en-1-yl)phenyl]propanoate

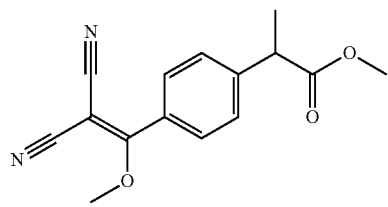 [SMILES: COC(=O)C(C)c1ccc(C(OC)=C(C#N)C#N)cc1]

To crude methyl 2-[4-(2,2-dicyano-1-hydroxy-vinyl)phenyl]propanoate in THF solution is added dimethyl sulfate (7.67 g, 60.810 mmol) dropwise at RT under $N_2$ and the mixture is stirred overnight at 80° C. under $N_2$. The mixture is allowed to cool to RT and quenched with $H_2O$ (300 mL). The mixture is extracted with EtOAc (3×300 mL) and the combined organic extracts are washed with saturated aqueous NaCl solution (3×500 mL), dried over anhydrous $Na_2SO_4$, filtered, and concentrated under reduced pressure. The residue is purified by silica gel column chromatography, eluting with hexanes/EtOAc (6:1-1:1) to give the title compound (5 g, 36.49% over 3 steps) as a yellow oil. $^1$H NMR ($d_6$-DMSO) δ 7.71-7.62 (m, 2H), 7.59-7.50 (m, 2H), 4.00-3.93 (m, 1H), 3.90 (s, 3H), 3.63 (s, 3H), 1.44 (d, 3H).

Preparation 3a

2-[(4-Bromo-2,3-difluoro-phenyl)-methoxy-methylene]propanedinitrile

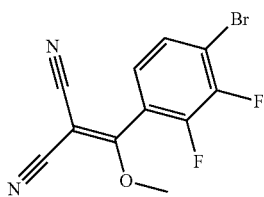 [SMILES: COC(=C(C#N)C#N)c1ccc(Br)c(F)c1F]

To crude 2-[(4-bromo-2,3-difluoro-phenyl)-hydroxymethylene]propanedinitrile is added dimethyl sulfate (3.35 g, 26.56 mmol) dropwise at RT. The mixture is stirred overnight at 80° C. under $N_2$. The mixture is cooled to RT. The reaction is quenched with $H_2O$ at RT. The mixture is extracted with EtOAc (3×100 mL). The combined organic extracts are washed with brine (3×100 mL), dried over anhydrous $Na_2SO_4$, filtered and the filtrate is concentrated under reduced pressure. The residue is purified by silica gel column chromatography, eluting with PE/EtOAc (3:1-2:1) to give the title compound (5.0 g, 75.5% over 3 steps) as a light grey solid. $^1$H NMR (300 MHz, $CDCl_3$) δ7.64-7.54 (m, 1H), 7.18-7.11 (m, 1H), 3.99 (d, 3H).

Preparation 3b

2-[(4-Bromo-2-fluorophenyl)(methoxy)methylidene]propanedinitrile

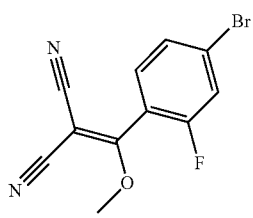 [SMILES: COC(=C(C#N)C#N)c1ccc(Br)cc1F]

Into a solution of 2-(4-bromo-2-fluorobenzoyl)propanedinitrile (23.40 g, 87.62 mmol) in THF (300 mL), is added dimethyl sulfate (13.26 g, 105.13 mmol) and the mixture is stirred overnight at 80° C. under $N_2$. The solution is cooled to RT and concentrated under reduced pressure. The crude product is dissolved in EtOAc (200 mL) and diluted with $H_2O$ (200 mL). The mixture is extracted with EtOAc (3×200 mL) and the organic extract is washed with brine (2×100 mL), dried over anhydrous $Na_2SO_4$, and concentrated under reduced pressure. The crude product is purified by silica gel chromatography eluting with a gradient of 5:1 to 3:1 PE to EtOAc to give the title product (23.5 g, 95.4%) as brown semi-solid. ES/MS m/z ($^{79}$Br/$^{81}$Br) 265.0/267.0 [M+H]$^+$.

Preparation 4

5,5-Difluoro-4,4-dimethyl-3-oxohexanenitrile

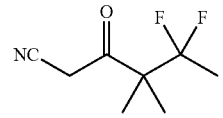

To a stirred mixture of LDA (20.81 mL, 41.62 mmol) in THF (100 mL) is added ACN (1.82 g, 44.33 mmol) in THF dropwise at −70° C. The mixture is stirred for 30 min at −70° C. To the above mixture is added ethyl 3,3-difluoro-2,2-dimethylbutanoate (5 g, 27.75 mmol) in THF dropwise at −70° C. and the mixture is slowly warmed to RT. The reaction is quenched by the addition of sat. $NH_4Cl$ (aq.) (30 mL) at 0° C. and extracted with PE (200 mL). The aqueous phase is acidified to pH=3 with HCl (aq.) (1 N) and extracted with EtOAc (3×100 mL). The EtOAc extracts are washed with saturated aqueous NaCl solution (3×50 mL), dried over anhydrous $Na_2SO_4$, filtered, and the filtrate is concentrated under reduced pressure to give the title compound (1.9 g, 39.09%) as a brown oil which is used without further purification. $^1$H NMR ($CDCl_3$) δ3.79 (s, 2H), 1.63 (t, 3H), 1.34 (s, 6H).

Preparation 5

4-(3-Bicyclo[1.1.1]pentanyl)-3-oxo-butanenitrile

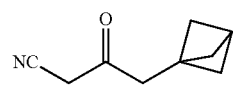 [SMILES: N#CCC(=O)CC12CC(C1)C2]

60% NaH (w/w) in mineral oil (140 mg, 3.5 mmol) in THF (1 mL) is added dropwise to a stirring solution of benzyl 2-(3-bicyclo[1.1.1]pentanyl)acetate (504 mg, 2.33 mmol) and ACN (134 μL, 2.56 mmol) in THF (8 mL, 0.3 M) at RT. The reaction mixture is heated and stirred at 60° C. for 25 min. The reaction mixture is quenched with ice $H_2O$ (10 mL), acidified to pH 5 with HCl (c) and extracted with EtOAc (3×10 mL). The combined organic extracts are washed with saturated aqueous NaCl solution (10 mL), dried over anhydrous $Na_2SO_4$, and concentrated under reduced pressure to give the title compound (350 mg).

Preparation 5a

3-[3-Methylbicyclo[1.1.1]pentan-1-yl]-3-oxopropanenitrile

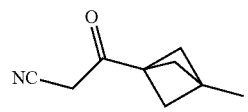

To THF (5.00 mL) is added n-BuLi (1.71 mL, 4.28 mmol, 2.5 M in THF) at 0° C. under $N_2$. To the mixture is added ACN (187.42 mg, 4.56 mmol) in THF (5 mL) dropwise over 5 min at −78° C. under N₂. The mixture is stirred for 1 hr at −78° C. To the mixture is added methyl 3-methylbicyclo[1.1.1]pentane-1-carboxylate (400.00 mg, 2.85 mmol) in THF (5 mL) dropwise at −78° C. under N₂. The mixture is stirred for 1 hr at RT. The reaction is quenched by the addition of saturated NH₄Cl aq. (20 mL) at 0° C. The mixture is acidified to pH 4 with HCl (1 N) aq. and extracted with DCM (3×50 mL). The combined organic extracts are washed with brine (2×100 mL), dried over anhydrous Na₂SO₄, filtered and concentrated under reduced pressure, to give the title compound (360 mg, 84.5%) as a brown liquid.

Preparation 5b

3-Oxo-3-[3-(trifluoromethyl)bicyclo[1.1.1]pentan-1-yl]propanenitrile

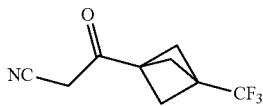 [SMILES: N#CCC(=O)C12CC(C(F)(F)F)(C1)C2]

n-BuLi (0.83 mL, 2.087 mmol, 2.5 M in hexanes) is added to THF (10 mL) at 0° C. under N₂. ACN (91.34 mg, 2.23 mmol) in THF (2 mL) is added dropwise over 2 min at −78° C. under N₂ and the reaction is stirred for 1 hr at −78° C. Methyl 3-(trifluoromethyl)bicyclo[1.1.1]pentane-1-carboxylate (270.00 mg, 1.39 mmol) in THF (2 mL) is added dropwise to the reaction mixture at −78° C. and the reaction is stirred at RT for 12 hr. The reaction is quenched by the addition of sat. NH₄Cl (aq., 20 mL), acidified to pH=4 with concentrated HCl, and extracted with DCM (3×50 mL). The combined organic extracts are washed with brine, dried over anhydrous Na₂SO₄, filtered and concentrated under reduced pressure. The crude product (290 mg) is used without further purification. ¹H NMR (300 MHz, CDCl₃) δ3.54 (s, 2H), 2.39 (s, 6H).

The following compound in Table 1 is prepared essentially as described for 3-oxo-3-[3-(trifluoromethyl)bicyclo[1.1.1]pentan-1-yl]propanenitrile, adjusting reaction time to determine completion of the reaction, and purification conditions as appropriate. The reaction can be allowed to warm to RT after the carboxylate is added. n-BuLi can be added in hexanes or THF.

Preparation 6 tert-Butyl N-(tert-butoxycarbonylamino)-N-(2-methoxy-1,1-dimethyl-ethyl)carbamate

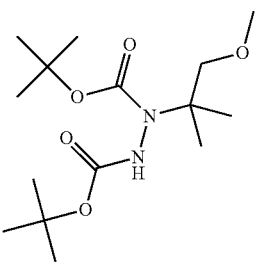 [SMILES: COCC(C)(C)N(NC(=O)OC(C)(C)C)C(=O)OC(C)(C)C]

To a stirred solution of Mn(dpm)³ (60.31 mg, 0.100 mmol) in IPA (20.00 mL) is added 3-methoxy-2-methyl-prop-1-ene (860.00 mg, 9.984 mmol), PhSiH₃ (1.08 g, 9.984 mmol), and (E)-N-[(tert-butoxycarbonyl)imino](tert-butoxy)formamide (3.45 g, 14.98 mmol) in portions at 0° C. under N₂. The resulting mixture is stirred for 2 hrs at RT under N₂ and concentrated under vacuum. H₂O (15 mL) is added, and the resulting mixture is extracted with EtOAc (3×30 mL). The combined organic extracts are washed with saturated aqueous NaCl solution (2×20 mL), dried over anhydrous Na₂SO₄, filtered, and concentrated under reduced pressure. The residue is purified by silica gel column chromatography, eluting with a gradient of PE/EtOAc (10:1 to 7:3) to give the title compound (1.8 g, 56.62%) as a colorless oil. ¹H NMR (CDCl₃) δ3.38-3.32 (m, 5H), 1.49-1.46 (m, 24H).

Preparation 7 tert-Butyl N-(1-methylcyclopropyl)-N-nitroso-carbamate

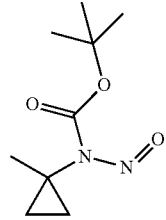

To a stirred solution of tert-butyl N-(1-methylcyclopropyl)carbamate (2.00 g, 11.68 mmol) in DCM (20.00 mL) is

TABLE 1

| Prep. No. | Chemical name | Structure |
|---|---|---|
| 5c | 3-Oxo-3-[4-(trifluoromethyl)bicyclo[2.2.1]heptan-1-yl]propanenitrile | | added tert-butyl nitrite (2.40 g, 23.36 mmol) in portions at RT under $N_2$ and the mixture is stirred for 2 hrs at RT under $N_2$. The mixture is concentrated under reduced pressure and the residue is purified by silica gel column chromatography, eluting with PE/EtOAc (25/1 to 20/1) to give the title compound (1.3 g, 55.59%) as a brown liquid. $^1$H NMR ($d_6$-DMSO) δ1.59 (s, 9H), 1.10 (s, 3H), 0.86-0.84 (m, 2H), 0.70-0.65 (m, 2H).

Preparation 8

(1-Methylcyclopropyl)hydrazine hydrochloride

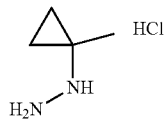

To a stirred solution of tert-butyl N-(1-methylcyclopropyl)-N-nitroso-carbamate (1.20 g, 5.99 mmol) in 4 N HCl (8.00 mL) is added Zn (783.98 mg, 11.99 mmol) in portions at 0° C. under $N_2$ and the mixture is stirred for 12 hrs at RT under $N_2$. The mixture is filtered, the filter cake is washed with $H_2O$ (3×10 mL), and the filtrate is concentrated under reduced pressure to give the title compound (2 g, crude) as an off-white solid which is used directly without further purification. $^1$H NMR ($d_6$-DMSO) δ1.30 (s, 3H), 0.77-0.73 (m, 2H), 0.54-0.50 (m, 2H).

Preparation 9

(1-Methoxy-2-methylpropan-2-yl)hydrazine hydrochloride

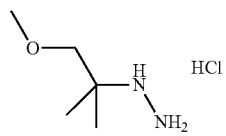

A solution of tert-butyl N-(tert-butoxycarbonylamino)-N-(2-methoxy-1,1-dimethyl-ethyl)carbamate (1.6 g, 5.00 mmol) in HCl (gas) in 1,4-dioxane (15.00 mL) is stirred for 6 hrs at RT under $N_2$. The mixture is concentrated under vacuum and triturated with $Et_2O$ (3×10 mL) to give the title compound (400 mg, 52%) as a semi-solid. $^1$H NMR ($d_6$-DMSO) δ3.36 (s, 2H), 3.32 (s, 3H), 1.17 (s, 6H).

Preparation 10

(1,1,1-Trifluoro-2-methylpropan-2-yl)hydrazine dihydrochloride

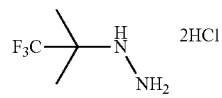

To a stirred mixture of N'-(1,1,1-trifluoro-2-methylpropan-2-yl)benzohydrazide (7.50 g) in $H_2O$ (40.00 mL) is added HCl (c) (40.00 mL) in portions at RT under $N_2$. The resulting mixture is stirred for 12 hrs at 80° C. under $N_2$. The mixture is allowed to cool to RT and concentrated under reduced pressure. The resulting solid is triturated with $Et_2O$ (30 mL) and the precipitated solids are collected by filtration and washed with $Et_2O$ (3×30 mL) to give the title compound (4.0 g, 61%) as an off-white solid. $^1$H NMR ($d^6$-DMSO) δ9.55 (br, s, 2H), 5.60 (br, s, 3H), 1.34 (s, 6H).

Preparation 11

N-[(E)-(4-Bromophenyl)methyleneamino]propan-2-amine

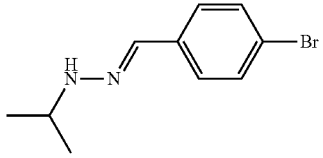

A solution of 4-bromo-benzaldehyde (100.00 g, 540.48 mmol), isopropylhydrazine hydrochloride (65.75 g, 594.53 mmol), and DIPEA (76.84 g, 594.53 mmol) in DMF (500 mL) is stirred for 3 hrs at 80° C. under $N_2$. The reaction is cooled to RT. The resulting mixture is used directly without workup or further purification. ES/MS m/z ($^{79}$Br/$^{81}$Br) 241.1/243.1 [M+H]$^+$.

The following compounds in Table 1a are prepared essentially as described for N-[(E)-(4-bromophenyl)methyleneamino]propan-2-amine using the appropriate reagents and adjusting reaction times to determine completion of the reactions.

TABLE 1a

| Prep. No. | Chemical name | Structure | ES/MS (m/z) (M + H) |
|---|---|---|---|
| 12 | 5-Bromo-2-[(1E)-[2-(1-methylcyclopropyl)hydrazin-1-ylidene]methyl]pyridine | 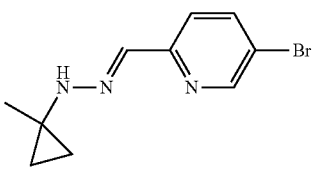 | 254.0, 256.0 |

TABLE 1a-continued

| Prep. No. | Chemical name | Structure | ES/MS (m/z) (M + H) |
|---|---|---|---|
| 13 | 5-Bromo-2-[(1E)-[2-(1,1,1-trifluoropropan-2-yl)hydrazin-1-ylidene]methyl]pyridine | 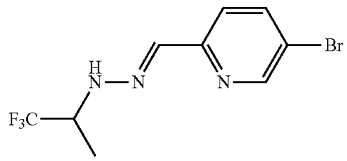 [SMILES: CC(N/N=C/c1ccc(Br)cn1)C(F)(F)F] | 295.9, 297.9 |

Preparation 13a

N'-[(2Z/E)-1-bromo-1,1-difluoropropan-2-ylidene]benzohydrazide

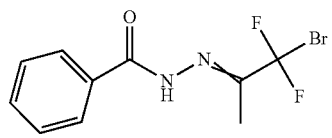 [SMILES: CC(=NNC(=O)c1ccccc1)C(F)(F)Br]

To a crude solution of 1-bromo-1,1-difluoro-propan-2-one (200 mL of 3/1 Et$_2$O/toluene) is added benzohydrazide (23.62 g) in sealed tube at RT under N$_2$. The mixture is stirred 2 hrs at 50° C. under N$_2$. The mixture is allowed to cool to RT. The precipitated solids are collected by filtration and washed with toluene (3×100 mL) to give the title compound (28 g, 34%, over 2 steps, purity 62% on $^1$H-NMR) as a white solid.

Preparation 13b (Z/E)-N-[(2,2,2-Trideuterio-1-methyl-ethylidene)amino]benzamide

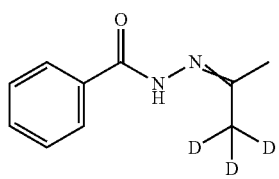 [SMILES: [2H]C([2H])([2H])C(C)=NNC(=O)c1ccccc1]

To a stirred mixture of 1,1,1-trideuteriopropan-2-one (0.24 g, 3.93 mmol) in THF (50 mL) is added benzohydrazide (2.14 g, 15.71 mmol, dissolved in THF (10 mL)) dropwise at −78° C. under N$_2$. The mixture is stirred for 2 hrs at −78° C. The mixture is diluted with EtOAc (200 mL). The organic phase is washed with H$_2$O (2×50 mL) and brine (50 mL), dried over anhydrous Na$_2$SO$_4$, filtered, and the filtrate is concentrated under reduced pressure to give the title compound which is used directly without further purification. ES/MS (m/z) 180.1 (M+H).

Preparation 13c

N-[[2,2,2-Trideuterio-1-(trideuteriomethyl)ethylidene]amino]benzamide

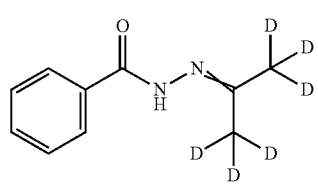 [SMILES: [2H]C([2H])([2H])C(=NNC(=O)c1ccccc1)C([2H])([2H])[2H]]

To a stirred solution of benzohydrazide (5.00 g, 36.723 mmol) in MeOH (100.00 mL) is added 1,1,1,3,3,3-hexadeuteriopropan-2-one (2.35 g, 36.723 mmol) dropwise at RT. The mixture is stirred overnight at RT and then concentrated under reduced pressure to give the title compound (5 g, 74.70%) as a white solid. ES/MS (m/z) 183.3 (M+H).

Preparation 13d

N'-(2,2,2-Trideuterio-1-methyl-ethyl)benzohydrazide

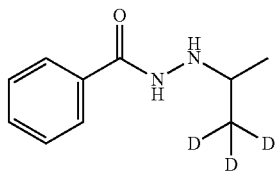 [SMILES: [2H]C([2H])([2H])C(C)NNC(=O)c1ccccc1]

To a stirred mixture of (Z/E)-N-[(2,2,2-trideuterio-1-methyl-ethylidene)amino]benzamide (695 mg, 3.88 mmol) in MeOH (5 mL) is added NaBH$_4$ (293.40 mg, 7.76 mmol) in portions at 0° C. The mixture is stirred at rt for 1 hr. The mixture is diluted with EtOAc (100 mL), washed with H$_2$O (30 mL), brine (30 mL), dried over anhydrous Na$_2$SO$_4$, filtered, and concentrated under reduced pressure. The residue is purified by silica gel column chromatography, eluting with PE:EtOAc (3:1~1:3) to give the title compound (280 mg, 39.8%) as a white solid. ES/MS (m/z) 182.2 (M+H).

Preparation 13e

N'-[2,2,2-Trideuterio-1-(trideuteriomethyl)ethyl]benzohydrazide

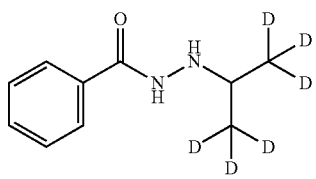 [SMILES: [2H]C([2H])([2H])C(NNC(=O)c1ccccc1)C([2H])([2H])[2H]]

To a stirred solution of N-[[2,2,2-Trideuterio-1-(trideuteriomethyl)ethylidene]amino]benzamide (2.00 g, 10.97 mmol) in MeOH (30.00 mL) is added NaBH$_4$ (0.81 g, 21.95 mmol) in portions at RT. The mixture is stirred for 2 hrs. The reaction is quenched with H$_2$O (50 mL) and extracted with DCM (3×50 mL). The combined organic extracts are washed with H$_2$O (3×50 mL), dried over anhydrous Na$_2$SO$_4$, and concentrated under reduced pressure to give the title compound (1.9 g, 93.96%) as a white solid. ES/MS (m/z) 185.3 (M+H).

Preparation 13f

N'-(1,2,2,2-Tetradeuterio-1-methyl-ethyl)benzohydrazide

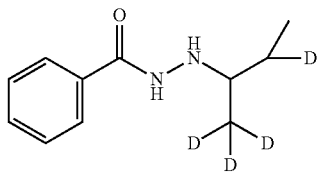 [SMILES: [2H]C(C)C(NNC(=O)c1ccccc1)C([2H])([2H])[2H]]

To a stirred mixture of (Z/E)-N-[(2,2,2-trideuterio-1-methyl-ethylidene)amino]benzamide (695.00 mg, 3.88 mmol) in CD$_3$OD (5 mL) is added NaBD$_4$ (326.15 mg, 7.77 mmol) in portions at 0° C. The mixture is stirred at RT for 1 hr. The mixture is diluted with EtOAc (100 mL) and washed with H$_2$O (30 mL) brine (30 mL), dried over anhydrous Na$_2$SO$_4$, filtered, and the filtrate is concentrated under reduced pressure. The residue is purified by silica gel chromatography eluting with PE:EtOAc (3:1~1:3) to give the title compound (260 mg, 36.6%) as a white solid. ES/MS (m/z) 183.2 (M+H).

The following compound in Table 1b is prepared essentially as described for N'-(1,2,2,2-tetradeuterio-1-methyl-ethyl)benzohydrazide using the appropriate reagents and adjusting reaction times to determine completion of the reactions. NaBD$_4$ can be added at RT and can be used without further purification.

TABLE 1b

| Prep. No. | Chemical name | Structure | ES/MS (m/z) (M + H) |
|---|---|---|---|
| 13g | N'-[1,2,2,2-Tetradeuterio-1-(trideuteriomethyl)ethyl]benzohydrazide | 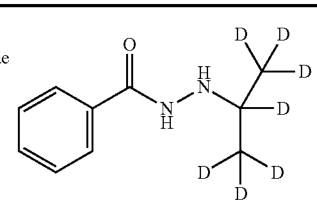 | 186.3 |

Preparation 13h

N'-(2-bromo-2,2-difluoro-1-methyl-ethyl)benzohydrazide

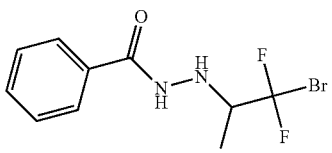 [SMILES: CC(NNC(=O)c1ccccc1)C(F)(F)Br]

To a stirred solution of N'-[(2E)-1-bromo-1,1-difluoropropan-2-ylidene]benzohydrazide (12 g, 41.22 mmol) in THF (100 mL) is added BH$_3$-THF (82.45 mL, 82.45 mmol, 1 M in THF) dropwise at 0° C. under N$_2$. The mixture is stirred for 12 hrs at RT under N$_2$. The reaction is quenched by the addition of MeOH (5 mL) at 0° C. The mixture is diluted with H$_2$O (50 mL) and extracted with DCM (3×50 mL). The combined organic extracts are washed with brine (2×100 mL), dried over anhydrous Na$_2$SO$_4$, filtered, and concentrated under reduced pressure. The residue is purified by silica gel column chromatography, eluting with PE/EtOAc (8/1 to 6/1) to give the title compound (7 g, 57%) as a white solid. $^1$H NMR (400 MHz, CDCl$_3$) δ 7.78-7.73 (m, 2H), 7.60-7.53 (m, 1H), 7.52-7.45 (m, 2H), 3.57-3.49 (m, 1H), 1.45 (d, 3H).

Preparation 13i

[2,2,2-Trideuterio-1-(trideuteriomethyl)ethyl]hydrazine.HCl

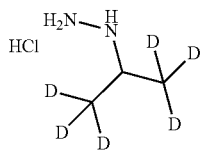

A mixture of N'-[2,2,2-trideuterio-1-(trideuteriomethyl)ethyl]benzohydrazide (500 mg, 2.71 mmol) in HCl (5.00 mL, conc) is stirred overnight at 80° C. The mixture is allowed to cool to RT and concentrated under reduced pressure. The crude product is triturated with Et$_2$O (3 mL). The resulting precipitate is filtered, and the filter cake is washed with Et$_2$O (3×2 mL) to give the title compound (180 mg, 56.88%) as a white solid.

The following compounds in Table 1c are prepared essentially as described for [2,2,2-trideuterio-1-(trideuteriomethyl)ethyl]hydrazine.HCl using the appropriate reagents and adjusting reaction times to determine completion of the reactions.

TABLE 1c

| Prep. No. | Chemical name | Structure |
|---|---|---|
| 13j | (2,2,2-Trideuterio-1-methyl-ethyl)hydrazine•HCl | 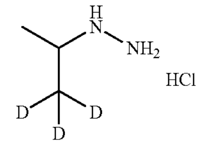 |
| 13k | (1,2,2,2-Tetradeuterio-1-methyl-ethyl)hydrazine•HCl | 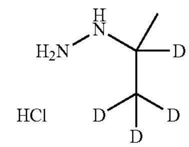 |
| 13l | [1,2,2,2-Tetradeuterio-1-(trideuteriomethyl)ethyl]hydrazine•HCl | 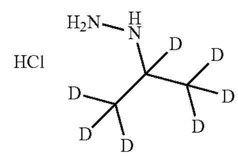 [SMILES: Cl ; [2H]C([2H])([2H])C([2H])(NN)C([2H])([2H])[2H]] |
| 13m | (1-Bromo-1,1-difluoropropan-2-yl)hydrazine•HCl | 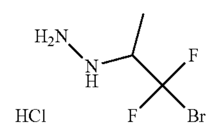 |

Preparation 14

(1Z)-4-Bromo-N-isopropyl-benzohydrazonoyl bromide

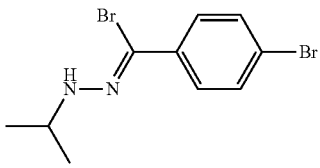

To N-[(E)-(4-bromophenyl)methyleneamino]propan-2-amine is added NBS (106.04 g, 595.77 mmol) in DMF dropwise and the mixture is stirred for 3 hrs at 0° C. under N$_2$. The resulting mixture is used directly without workup or further purification.

The following compounds in Table 2 are prepared essentially as described for (1Z)-4-bromo-N-isopropyl-benzohydrazonoyl bromide using the appropriate reagents and adjusting reaction times to determine completion of the reactions.

TABLE 2

| Prep. No. | Chemical name | Structure | ES/MS (m/z) (M + H) |
|---|---|---|---|
| 15 | (Z)-5 Bromo-N-(1-methylcyclopropyl)pyridine-2-carbohydrazonoyl bromide | 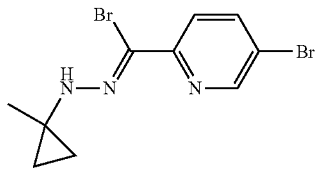 | 333.9 |
| 16 | (Z)-5-Bromo-N-(1,1,1-trifluoropropan-2-yl)pyridine-2-carbohydrazonoyl bromide | 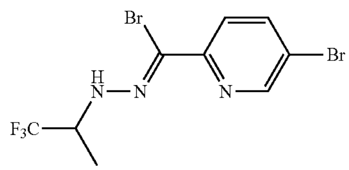 [SMILES: CC(N/N=C(\Br)c1ccc(Br)cn1)C(F)(F)F] | 373.9, 377.9 |

Preparation 17

5-Amino-3-(4-bromophenyl)-1-isopropylpyrazole-4-carbonitrile

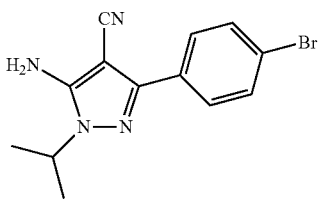 [SMILES: CC(C)n1nc(-c2ccc(Br)cc2)c(C#N)c1N]

A solution of sodium ethoxide (91.88 g, 1.351 mol) and propanedinitrile (39.24 g, 594.53 mmol) in EtOH (400 mL) is stirred for 1 hr at 0° C. under $N_2$. The crude solution of (1Z)-4-bromo-N-isopropyl-benzohydrazonoyl bromide is added to the mixture. The mixture is stirred for 2 hrs at RT. The mixture is concentrated under reduced pressure, diluted with $H_2O$ (3 L), and the resulting precipitated solids are collected by filtration, washed with $H_2O$ (3×200 mL), and the solid is dried in an oven at 50° C. to give the title compound (127 g, 73.7% over 3 steps). ES/MS (m/z) ($^{79}Br/^{81}Br$ 305/307 (M+H).

The following compounds in Table 3 are prepared essentially as described for 5-amino-3-(4-bromophenyl)-1-isopropylpyrazole-4-carbonitrile using the appropriate reagents, adjusting reaction times to determine completion of the reactions and purification conditions if appropriate. The crude reaction can be diluted with $H_2O$, extracted with EtOAc, and purified with chromatography using appropriate conditions.

TABLE 3

| Prep. No. | Chemical name | Structure | ES/MS (m/z) (M + H) |
|---|---|---|---|
| 18 | 5-Amino-3-(5-bromopyridin-2-yl)-1-(1-methylcyclopropyl)pyrazole-4-carbonitrile | 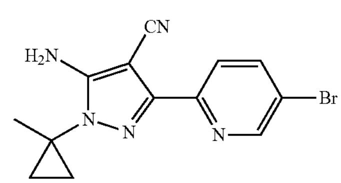 [SMILES: CC1(n2nc(-c3ccc(Br)cn3)c(C#N)c2N)CC1] | 318.0, 320.0 |
| 19 | 5-Amino-3-(5-bromopyridin-2-yl)-1-(1,1,1-trifluoropropan-2-yl)pyrazole-4-carbonitrile | 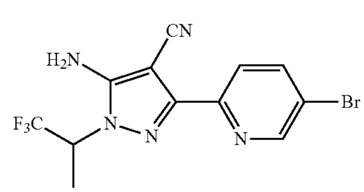 [SMILES: CC(n1nc(-c2ccc(Br)cn2)c(C#N)c1N)C(F)(F)F] | 360.0, 362.0 |

Preparation 20

5-Amino-3-(4-bromophenyl)-1-(1-methylcyclopropyl)pyrazole-4-carbonitrile

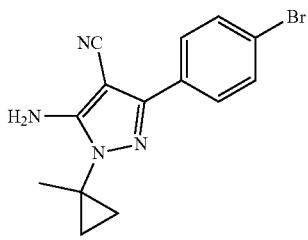 [SMILES: CC1(n2nc(-c3ccc(Br)cc3)c(C#N)c2N)CC1]

(1-Methylcyclopropyl)hydrazine hydrochloride (1.63 g, 13.30 mmol), THF (20 mL), Et$_3$N (3.08 g, 30.41 mmol), and 2-[(4-bromophenyl)(methoxy)methylidene]propanedinitrile (1.00 g, 3.80 mmol) are added together and stirred for 6 hrs at 50° C. The resulting mixture is diluted with EtOAc (100 mL), washed with H$_2$O (2×30 mL), and saturated aqueous NaCl solution (20 mL). The organic phase is concentrated under reduced pressure. The residue is purified by reverse Combi-flash chromatography with the following conditions: C18; ACN in H$_2$O (0.1% NH$_4$HCO$_3$), UV 254 nm eluting with a gradient of 70% to 100% in 15 mins to give the title compound (375 mg, 31%) as an off-white solid. ES/MS m/z ($^{79}$Br/$^{81}$Br) 317.0/319.0 [M+H]$^+$.

The following compounds in Table 3a are prepared essentially as described for 5-amino-3-(4-bromophenyl)-1-(1-methylcyclopropyl)pyrazole-4-carbonitrile using the appropriate reagents, adjusting reaction times to determine completion of the reactions. The Et$_3$N can be added dropwise. The crude reaction can be concentrated to dryness and purified as appropriate.

Preparation 20c

5-Amino-3-(4-bromo-2-fluorophenyl)-1-(1-methylcyclopropyl)pyrazole-4-carbonitrile

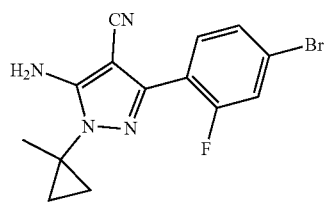

A solution of 2-[(4-bromo-2-fluorophenyl)(methoxy)methylidene]propanedinitrile (1.50 g, 5.34 mmol), (1-methylcyclopropyl)hydrazine HCl (1.96 g, 15.99 mmol) and Et$_3$N (2.70 g, 26.682 mmol) in EtOH (20.00 mL) is stirred for 1 hr at RT under N$_2$. The mixture is concentrated under reduced pressure and the residue is purified by silica gel chromatography, eluting with a gradient of 3:1 to 2:1 PE:EtOAc to give the title compound (1.2 g, 67.09%) as a light yellow solid. ES/MS m/z ($^{79}$Br/$^{81}$Br) 335.1/337.1 [M+H]$^+$.

The following compounds in Table 3b are prepared essentially as described for 5-amino-3-(4-bromo-2-fluorophenyl)-1-(1-methylcyclopropyl)pyrazole-4-carbonitrile using the appropriate reagents, adjusting reaction times to determine completion of the reactions and purification conditions if appropriate. The reaction can be stirred at 50° C. and the hydrazine can be the free amine if available.

TABLE 3a

| Prep. No. | Chemical name | Structure | ES/MS (m/z) (M + H) |
|---|---|---|---|
| 20a | 5-Amino-3-(4-bromo-2,3-difluorophenyl)-1-isopropylpyrazole-4-carbonitrile | 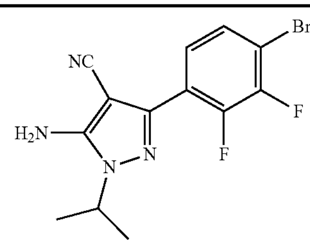 | 528.0/526.0 |
| 20b | 5-Amino-1-(1-bromo-1,1-difluoropropan-2-yl)-3-(4-bromophenyl)pyrazole-4-carbonitrile | 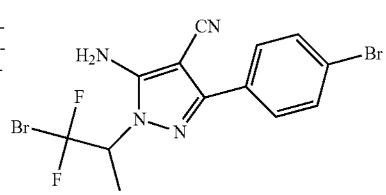 | 418.9/420.9/422.9 |

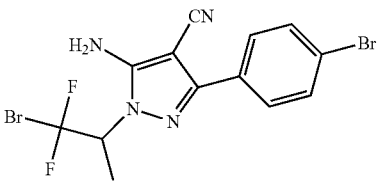 [SMILES: CC(n1nc(-c2ccc(Br)cc2)c(C#N)c1N)C(F)(F)Br]

TABLE 3b

| Prep. No. | Chemical name | Structure | ES/MS (m/z) (M + H) |
|---|---|---|---|
| 20d | Methyl 2-[4-[5-amino-4-cyano-1-(2,2,2-trideuterio-1-methyl-ethyl)pyrazol-3-yl]phenyl]propanoate | 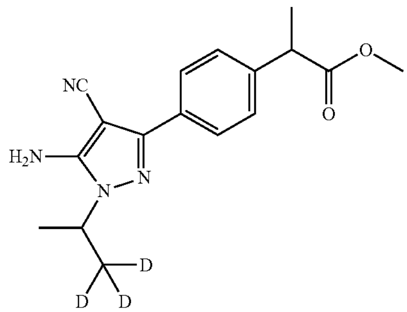 [SMILES: [2H]C([2H])([2H])C(C)n1nc(-c2ccc(C(C)C(=O)OC)cc2)c(C#N)c1N] | 316.3 |
| 20e | Methyl 2-[4-[5-amino-4-cyano-1-(1,2,2,2-tetradeuterio-1-methyl-ethyl)pyrazol-3-yl]phenyl]propanoate | 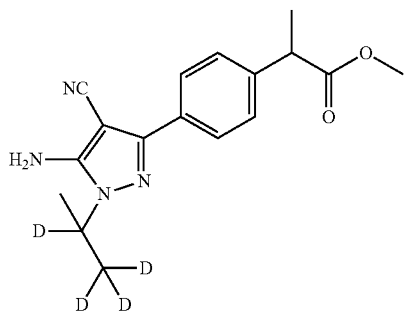 [SMILES: [2H]C([2H])([2H])C([2H])(C)n1nc(-c2ccc(C(C)C(=O)OC)cc2)c(C#N)c1N] | 317.3 |
| 20f | 5-Amino-3-(4-bromophenyl)-1-(1,1-difluoropropan-2-yl)pyrazole-4-carbonitrile | 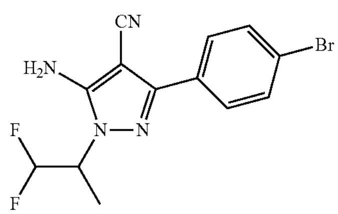 [SMILES: CC(C(F)F)n1nc(-c2ccc(Br)cc2)c(C#N)c1N] | 340.9/342.9 |
| 20g | 5-Amino-3-(4-bromophenyl)-1-[2,2,2-trifluoro-1-(trideuteriomethyl)ethyl]pyrazole-4-carbonitrile | 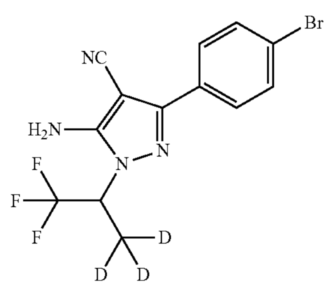 [SMILES: [2H]C([2H])([2H])C(n1nc(-c2ccc(Br)cc2)c(C#N)c1N)C(F)(F)F] | 360.1/362.1 |

Preparation 20h

5-Amino-3-(4-bromophenyl)-1-(2-deuterio-2,2-difluoro-1-methyl-ethyl)pyrazole-4-carbonitrile

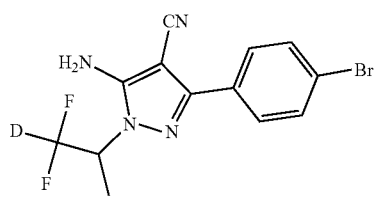 [SMILES: [2H]C(F)(F)C(C)n1nc(-c2ccc(Br)cc2)c(C#N)c1N]

To a stirred solution of 5-amino-1-(1-bromo-1,1-difluoropropan-2-yl)-3-(4-bromophenyl)pyrazole-4-carbonitrile (300.00 mg, 0.71 mmol, co-evaporated with 2×CD$_3$OD) in CD$_3$COOD (3.00 mL) is added Zn (467.14 mg, 7.14 mmol, co-evaporated with 2×CD$_3$OD) in portions at RT under N$_2$. The mixture is stirred for 1 hr at 80° C. under N$_2$. The mixture is allowed to cool to RT and quenched with EtOAc. The mixture is filtered, the filter cake is washed with EtOAc (3×10 mL) and concentrated under reduced pressure. The residue is purified by silica gel column chromatography, eluting with PE/EtOAc (2:1-1:1) to give the title compound (100 mg, 40.92%) as a yellow solid. $^1$H NMR (300 MHz, d$_6$-DMSO) δ7.79-7.65 (m, 4H), 7.00 (s, 2H), 4.93-4.68 (m, 1H), 1.48 (d, 3H).

Preparation 20i

Methyl 2-[4-[5-amino-4-cyano-1-[2,2,2-trideuterio-1-(trideuteriomethyl)ethyl]pyrazol-3-yl]phenyl]propanoate

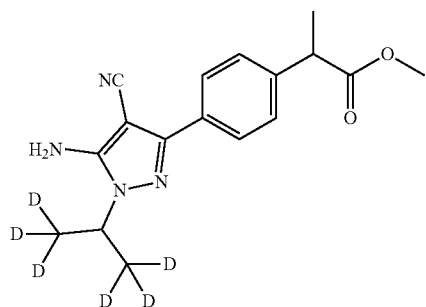 [SMILES: [2H]C([2H])([2H])C(n1nc(-c2ccc(C(C)C(=O)OC)cc2)c(C#N)c1N)C([2H])([2H])[2H]]

A solution of methyl 2-[4-(2,2-dicyano-1-methoxyeth-1-en-1-yl)phenyl]propanoate (500 mg, 1.85 mmol), [2,2,2-trideuterio-1-(trideuteriomethyl)ethyl]hydrazine.HCl (648 mg, 5.56 mmol) and Et$_3$N (936 mg, 9.25 mmol) in EtOH (20 mL) is stirred for 1 hr at RT. The solution is diluted with H$_2$O (30 mL) and extracted with EtOAc (3×50 mL). The organic layer is dried over anhydrous Na$_2$SO$_4$ and concentrated under reduced pressure to give the title compound (650 mg, crude) as a light yellow solid. The crude product is used without further purification. ES/MS (m/z) 319.40 (M+H).

Preparation 21 tert-Butyl N-tert-butoxycarbonyl-N-(4-cyano-2-isopropyl-pyrazol-3-yl)carbamate

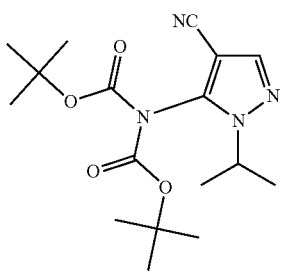 [SMILES: CC(C)n1ncc(C#N)c1N(C(=O)OC(C)(C)C)C(=O)OC(C)(C)C]

To a stirred solution of 5-amino-1-isopropyl-pyrazole-4-carbonitrile (13.58 g, 85.0 mmol) in THF (170 mL) are added successively N,N-dimethylpyridin-4-amine (1.05 g, 8.50 mmol), Et$_3$N (36 mL, 0.255 mol), and tert-butoxycarbonyl tert-butyl carbonate (40.81 g, 0.187 mol). The reaction mixture is stirred at RT overnight. The reaction mixture is quenched with a saturated aqueous solution of NH$_4$Cl (15 mL). The aqueous layer is extracted with EtOAc (3×20 mL) and the combined organic extracts are washed with saturated aqueous NaCl solution, dried over Na$_2$SO$_4$, filtered, and concentrated under reduced pressure. The crude is purified by silica gel flash chromatography eluting with a gradient of EtOAc in cyclohexane from 2% to 30% to give the title compound as a pale yellow solid (9.29 g, 31%) and a second batch as a pale yellow solid (4.86 g, 16%) which combined gives 14.15 g, 47% yield.

Preparation 22

Methyl 2-[5-[5-(tert-butoxycarbonylamino)-4-cyano-1-isopropyl-pyrazol-3-yl]-2-pyridyl]propanoate

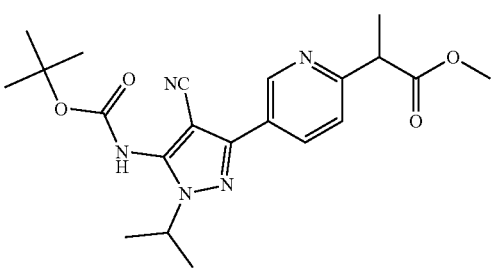 [SMILES: COC(=O)C(C)c1ccc(-c2nn(C(C)C)c(NC(=O)OC(C)(C)C)c2C#N)cn1]

and

Preparation 23

Methyl 2-[5-[5-[bis(tert-butoxycarbonyl)amino]-4-cyano-1-isopropyl-pyrazol-3-yl]-2-pyridyl]propanoate

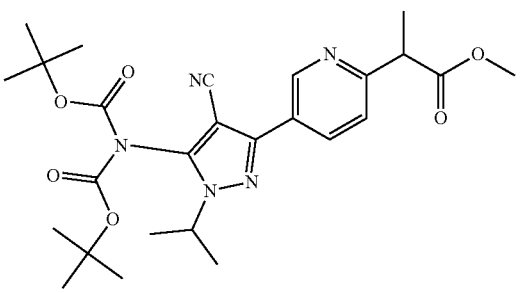 [SMILES: COC(=O)C(C)c1ccc(-c2nn(C(C)C)c(N(C(=O)OC(C)(C)C)C(=O)OC(C)(C)C)c2C#N)cn1]

tert-Butyl N-tert-butoxycarbonyl-N-(4-cyano-2-isopropyl-pyrazol-3-yl)carbamate (4.02 g, 11.5 mmol), 4,4,5,5-tetramethyl-2-(4,4,5,5-tetramethyl-1,3,2-dioxaborolan-2-yl)-1,3,2-dioxaborolane (2.39 g, 9.42 mmol), di-μ- methoxybis(1,5-cyclooctadiene)diiridium (CAS #12148-71-9) (1:2) (136 mg, 0.21 mmol) and 4-tert-butyl-2-(4-tert-butyl-2-pyridyl)pyridine (112 mg, 0.41 mmol) are added together under vacuum, THF (11.60 mL) is added, and the reaction is kept under $N_2$. The mixture is stirred and heated at 80° C. for 6 hrs. The reaction mixture is cooled to RT and stirred overnight. The reaction mixture is concentrated under reduced pressure and the residue is dissolved in a mixture of DCM/EtOAc 3:1 (10 mL) and this solution is passed through a pad of silica gel and washed with DCM/EtOAc 3:1 (2×10 mL). The filtrates are combined, concentrated under reduced pressure, and dried under vacuum to give a crude residue. To the crude material is added $Cs_2CO_3$ (8049 mg, 24.6 mmol), methyl 2-(5-bromo-2-pyridyl)propanoate (2.00 g, 8.19 mmol), Pd(dppf)Cl$_2$ DCM (342 mg, 0.410 mmol) and 4 Å molecular sieves (5 g). The reaction mixture is then degassed by vacuum/$N_2$ (3×) and heated to 100° C. for 2 hrs. The reaction is cooled to RT, filtered through a bed of Perlite and the bed of Perlite being washed with THF (3×60 mL). The organic solutions are combined, concentrated under reduced pressure, and dried under vacuum. To the residue is added DCM (60 mL), $H_2O$ (80 mL) and saturated aqueous NaHCO$_3$ solution (60 mL). The organic layer is separated, dried over anhydrous $Na_2SO_4$, concentrated under reduced pressure, and dried under vacuum. The crude material is purified by silica gel flash chromatography eluting with a gradient of EtOAc in DCM from 0% to 20% to give the Preparation 22 title compound (2.47 g, 68.53%) and Preparation 23 title compound. The material of Preparation 23 is further purified with silica gel chromatography eluting with a gradient of 10% to 80% EtOAc in cyclohexane to give the title compound of Preparation 23.

Preparation 24

5-Amino-1-isopropyl-3-[4-(4,4,5,5-tetramethyl-1,3,2-dioxaborolan-2-yl)phenyl]pyrazole-4-carbonitrile

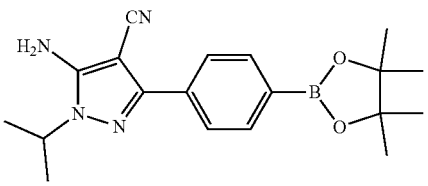 [SMILES: CC(C)n1nc(-c2ccc(B3OC(C)(C)C(C)(C)O3)cc2)c(C#N)c1N]

A mixture of 5-amino-3-(4-bromophenyl)-1-isopropylpyrazole-4-carbonitrile (100 g, 327.68 mmol), bis(pinacolato)diboron (91.53 g, 360.444 mmol), KOAc (48.24 g, 491.52 mmol), and Pd(dppf)Cl$_2$ (11.99 g, 16.38 mmol) in 1,4-dioxane (1 L) is stirred for 6 hrs at 80° C. under $N_2$. The mixture is allowed to cool to RT. The resulting mixture is filtered, washed with EtOAc (3×100 mL), and concentrated under reduced pressure. The residue is purified by silica gel column chromatography, eluting with PE/EtOAc (10:1-5:1) to give the title compound (100 g, 86.6%) as a brown solid. ES/MS (m/z) 353.2 (M+H).

The following compounds in Table 4 are prepared essentially as described for 5-amino-1-isopropyl-3-[4-(4,4,5,5-tetramethyl-1,3,2-dioxaborolan-2-yl)phenyl]pyrazole-4-carbonitrile using the appropriate reagents, adjusting reaction times to determine completion of the reactions, and adjusting purification conditions if appropriate. The material can also be filtered without work-up and used without further purification.

TABLE 4

| Prep. No. | Chemical name | Structure | ES/MS (m/z) (M + H) |
|---|---|---|---|
| 25 | 5-Amino-1-isopropyl-3-[5-(4,4,5,5-tetramethyl-1,3,2-dioxaborolan-2-yl)pyridin-2-yl]pyrazole-4-carbonitrile | 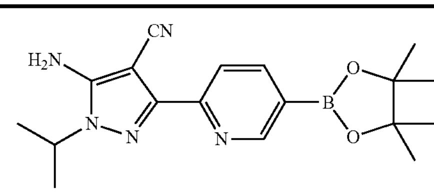 | 354.20 |
| 26 | 5-Amino-1-(1-methylcyclopropyl)-3-[4-(4,4,5,5-tetramethyl-1,3,2-dioxaborolan-2-yl)phenyl]pyrazole-4-carbonitrile | 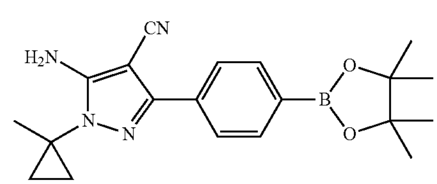 | 365.2 |
| 27c | 5-Amino-3-[4-(4,4,5,5-tetramethyl-1,3,2-dioxaborolan-2-yl)phenyl]-1-(1,1,1-trifluoropropan-2-yl)pyrazole-4-carbonitrile | 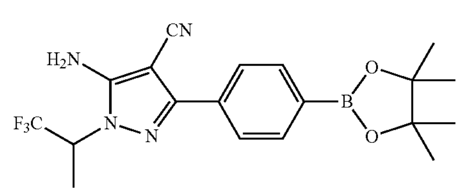 [SMILES: CC(n1nc(-c2ccc(B3OC(C)(C)C(C)(C)O3)cc2)c(C#N)c1N)C(F)(F)F] | 407.2 |

TABLE 4-continued

| Prep. No. | Chemical name | Structure | ES/MS (m/z) (M + H) |
|---|---|---|---|
| 28 | 5-Amino-1-(1-methylcyclopropyl)-3-[5-(4,4,5,5-tetramethyl-1,3,2-dioxaborolan-2-yl)pyridin-2-yl]pyrazole-4-carbonitrile | 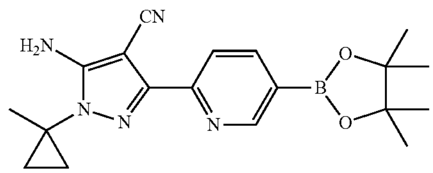 | 284.2 |
| 29 | 5-Amino-3-[5-(4,4,5,5-tetramethyl-1,3,2-dioxaborolan-2-yl)pyridin-2-yl]-1-(1,1,1-trifluoropropan-2-yl)pyrazole-4-carbonitrile | 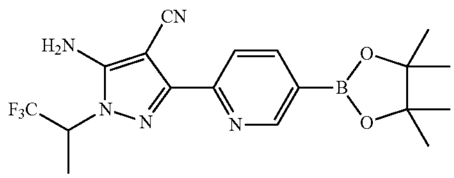 [SMILES: CC(n1nc(-c2ccc(B3OC(C)(C)C(C)(C)O3)cn2)c(C#N)c1N)C(F)(F)F] | 326.2 |
| 29a | 5-Amino-1-(1,1-difluoropropan-2-yl)-3-[4-(4,4,5,5-tetramethyl-1,3,2-dioxaborolan-2-yl)phenyl]pyrazole-4-carbonitrile | 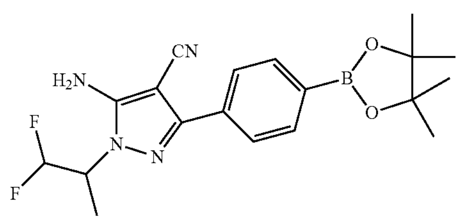 [SMILES: CC(C(F)F)n1nc(-c2ccc(B3OC(C)(C)C(C)(C)O3)cc2)c(C#N)c1N] | 389.1 |
| 29b | 5-Amino-3-[2,3-difluoro-4-(4,4,5,5-tetramethyl-1,3,2-dioxaborolan-2-yl)phenyl]-1-isopropyl-pyrazole-4-carbonitrile | 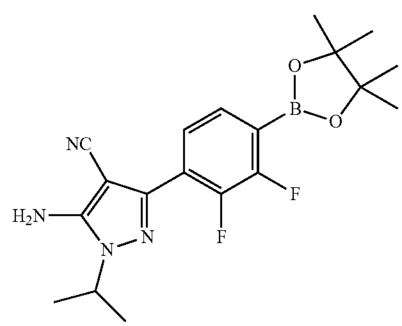 [SMILES: CC(C)n1nc(-c2ccc(B3OC(C)(C)C(C)(C)O3)c(F)c2F)c(C#N)c1N] | |
| 29c | 5-Amino-3-[4-(4,4,5,5-tetramethyl-1,3,2-dioxaborolan-2-yl)phenyl]-1-[2,2,2-trifluoro-1-(trideuteriomethyl)ethyl]pyrazole-4-carbonitrile | 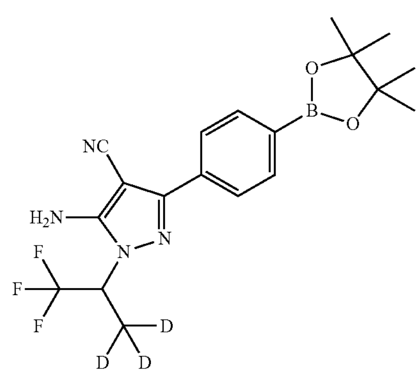 [SMILES: [2H]C([2H])([2H])C(n1nc(-c2ccc(B3OC(C)(C)C(C)(C)O3)cc2)c(C#N)c1N)C(F)(F)F] | 410.3 |
| 29e | 5-Amino-1-(2-deuterio-2,2-difluoro-1-methyl-ethyl)-3-[4-(4,4,5,5-tetramethyl-1,3,2-dioxaborolan-2-yl)phenyl]pyrazole-4-carbonitrile | 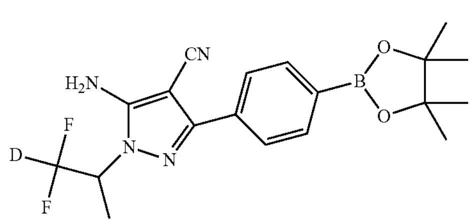 [SMILES: [2H]C(F)(F)C(C)n1nc(-c2ccc(B3OC(C)(C)C(C)(C)O3)cc2)c(C#N)c1N] | 390.1 |

Alternate Preparation 26

5-Amino-1-(1-methylcyclopropyl)-3-[4-(4,4,5,5-tetramethyl-1,3,2-dioxaborolan-2-yl)phenyl]pyrazole-4-carbonitrile

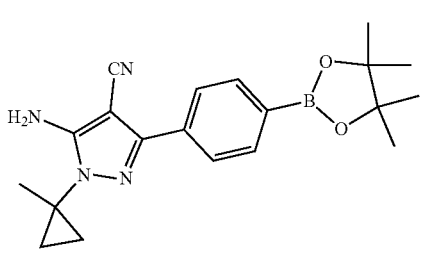

5-Amino-3-(4-bromophenyl)-1-(1-methylcyclopropyl) pyrazole-4-carbonitrile (350 mg, 1.10 mmol), bis(pinacolato)diboron (560.41 mg, 2.21 mmol), KOAc (325 mg, 3.31 mmol), and Pd(dppf)Cl$_2$ (121 mg, 0.17 mmol) are added together in dioxane (5.00 mL). The solution is stirred for 2 hrs at 80° C. under N$_2$. The mixture is filtered and used directly without purification. ES/MS (m/z) 365.2 (M+H).

Preparation 29f

5-Amino-3-[2-fluoro-4-(4,4,5,5-tetramethyl-1,3,2-dioxaborolan-2-yl)phenyl]-1-(1-methylcyclopropyl) pyrazole-4-carbonitrile

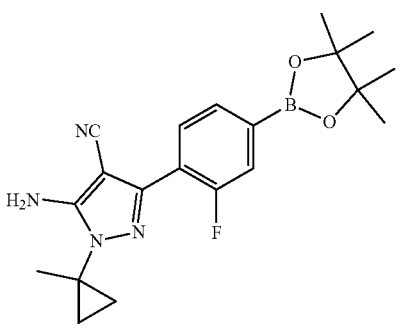 [SMILES: CC1(n2nc(-c3ccc(B4OC(C)(C)C(C)(C)O4)cc3F)c(C#N)c2N)CC1]

A solution of 5-amino-3-(4-bromo-2-fluorophenyl)-1-(1-methylcyclopropyl)pyrazole-4-carbonitrile (700 mg, 2.09 mmol), 4,4,5,5-tetramethyl-2-(tetramethyl-1,3,2-dioxaborolan-2-yl)-1,3,2-dioxaborolane (636.40 mg, 2.51 mmol), Pd(dppf)Cl$_2$·CH$_2$Cl$_2$ (341.10 mg, 0.42 mmol) and KOAc (614.89 mg, 6.26 mmol) in dioxane (10.00 mL) is stirred for 1 hr at 80° C. under N$_2$. The solution is cooled to RT, filtered, and the filter cake is washed with 1,4-dioxane (2×3 mL). The mixture is used directly without further purification. ES/MS (m/z) 383.3 (M+H).

Preparation 29 g

Methyl 2-[4-[5-amino-4-cyano-1-(1-methylcyclopropyl)pyrazol-3-yl]-3-fluorophenyl]prop-2-enoate

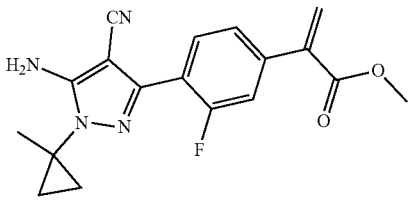

A solution of 5-amino-3-[2-fluoro-4-(4,4,5,5-tetramethyl-1,3,2-dioxaborolan-2-yl)phenyl]-1-(1-methylcyclopropyl) pyrazole-4-carbonitrile (980 mg, 2.56 mmol), methyl 2-(trifluoromethanesulfonyloxy)prop-2-enoate (1200.61 mg, 5.13 mmol), Pd(dppf)Cl$_2$·CH$_2$Cl$_2$ (418.73 mg, 0.51 mmol) and K$_2$CO$_3$ (708.65 mg, 5.128 mmol) in dioxane/H$_2$O (4:1, 10 mL) is stirred for 1 hr at 80° C. under N$_2$. The solution is cooled to RT and concentrated to dryness under reduced pressure. The residue is purified by silica gel chromatography, eluting with a gradient of 3:1 to 2:1 PE:EtOAc to give the title compound (430 mg, 49.28%) as a yellow solid. ES/MS (m/z) 341.2 (M+H).

Preparation 30

Methyl 2-[4-(5-amino-4-cyano-1-isopropyl-pyrazol-3-yl)phenyl]prop-2-enoate

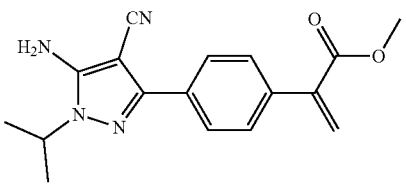 [SMILES: C=C(C(=O)OC)c1ccc(-c2nn(C(C)C)c(N)c2C#N)cc1]

A mixture of 5-amino-1-isopropyl-3-[4-(4,4,5,5-tetramethyl-1,3,2-dioxaborolan-2-yl)phenyl]pyrazole-4-carbonitrile (100.00 g, 283.89 mmol), methyl 2-(trifluoromethanesulfonyloxy)prop-2-enoate (99.71 g, 425.83 mmol), K$_2$CO$_3$ (117.71 g, 851.67 mmol) and Pd(dppf)Cl$_2$ (10.39 g, 14.19 mmol) in 1,4-dioxane (1 L) and H$_2$O (250 mL) is stirred overnight at 90° C. under N$_2$. The mixture is allowed to cool to RT. The resulting mixture is filtered, and the filter cake is washed with EtOAc (3×100 mL). The filtrate is concentrated under reduced pressure, diluted with H$_2$O (500 mL), and extracted with EtOAc (3×500 mL). The combined organic extracts are washed with saturated aqueous NaCl solution (3×200 mL), dried over anhydrous Na$_2$SO$_4$, filtered, and concentrated under reduced pressure. The residue is purified by silica gel column chromatography, eluting with PE/EtOAc (10:1-3:1) to give the title compound (43 g, 48.8%) as a yellow solid. ES/MS (m/z): 311.2 (M+H).

The following compounds in Table 5 are prepared essentially as described for methyl 2-[4-(5-amino-4-cyano-1-isopropyl-pyrazol-3-yl)phenyl]prop-2-enoate using the appropriate reagents and adjusting reaction times to determine completion of the reactions. Temperature is varied from 80-90° C. and dioxane and H$_2$O can be used as solvents.

TABLE 5

| Prep. No. | Chemical name | Structure | ES/MS (m/z) (M + H) |
|---|---|---|---|
| 31 | Methyl 2-[6-(5-amino-4-cyano-1-isopropylpyrazol-3-yl)pyridin-3-yl]prop-2-enoate | 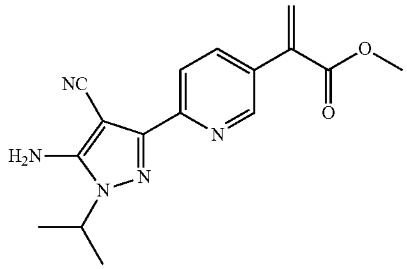 [SMILES: C=C(C(=O)OC)c1ccc(-c2nn(C(C)C)c(N)c2C#N)nc1] | 312.10 |
| 32* | Methyl 2-[4-[5-amino-4-cyano-1-(1-methylcyclopropyl)pyrazol-3-yl]phenyl]prop-2-enoate | 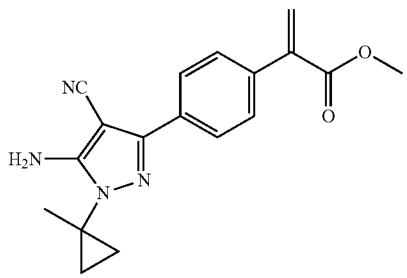 [SMILES: C=C(C(=O)OC)c1ccc(-c2nn(C3(C)CC3)c(N)c2C#N)cc1] | 323.1 |
| 33 | Methyl 2-[4-[5-amino-4-cyano-1-(1,1,1-trifluoropropan-2-yl)pyrazol-3-yl]phenyl]prop-2-enoate | 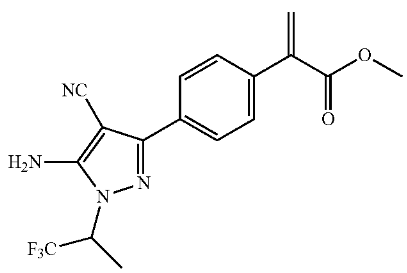 [SMILES: C=C(C(=O)OC)c1ccc(-c2nn(C(C)C(F)(F)F)c(N)c2C#N)cc1] | 365.1 |
| 34 | Methyl 2-[6-[5-amino-4-cyano-1-(1-methylcyclopropyl)pyrazol-3-yl]pyridin-3-yl]prop-2-enoate | 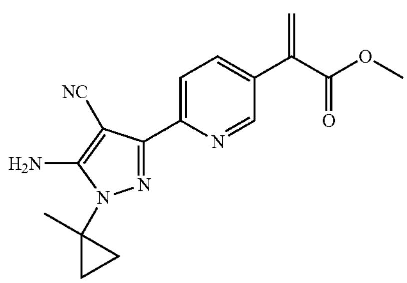 [SMILES: C=C(C(=O)OC)c1ccc(-c2nn(C3(C)CC3)c(N)c2C#N)nc1] | 324.1 |
| 35 | Methyl 2-[6-[5-amino-4-cyano-1-(1,1,1-trifluoropropan-2-yl)pyrazol-3-yl]pyridin-3-yl]prop-2-enoate | 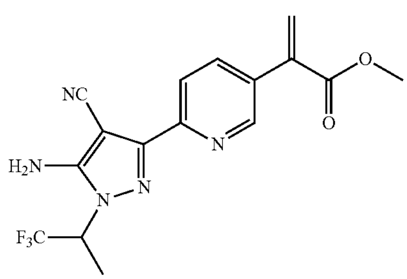 [SMILES: C=C(C(=O)OC)c1ccc(-c2nn(C(C)C(F)(F)F)c(N)c2C#N)nc1] | 366.1 |

TABLE 5-continued

| Prep. No. | Chemical name | Structure | ES/MS (m/z) (M + H) |
|---|---|---|---|
| 35a | Methyl-2-[4-[5-amino-4-cyano-1-(1,1-difluoropropan-2-yl)pyrazol-3-yl]phenyl]prop-2-enoate | 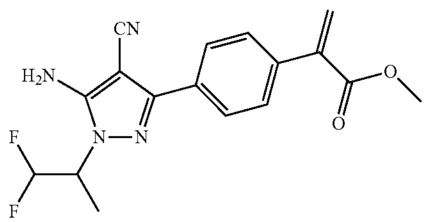 [SMILES: C=C(C(=O)OC)c1ccc(-c2nn(C(C)C(F)F)c(N)c2C#N)cc1] | 347.0 |
| 35b | Methyl 2-[4-(5-amino-4-cyano-1-isopropylpyrazol-3-yl)-2,3-difluorophenyl]prop-2-enoate | 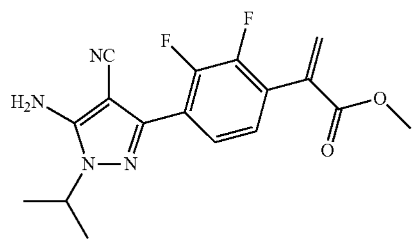 [SMILES: C=C(C(=O)OC)c1ccc(-c2nn(C(C)C)c(N)c2C#N)c(F)c1F] | 347.2 |
| 35c | Methyl 2-[4-[5-amino-4-cyano-1-[2,2,2-trifluoro-1-(trideuteriomethyl)ethyl]pyrazol-3-yl]phenyl]prop-2-enoate | 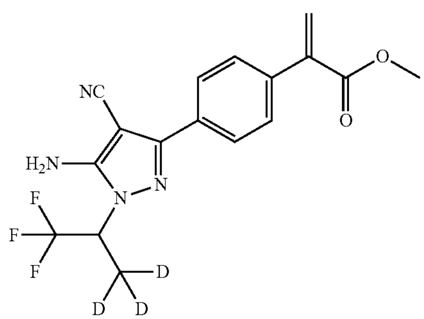 [SMILES: [2H]C([2H])([2H])C(n1nc(-c2ccc(C(=C)C(=O)OC)cc2)c(C#N)c1N)C(F)(F)F] | 368.2 |
| 35d | Methyl 2-[4-[5-amino-4-cyano-1-(2-deuterio-2,2-difluoro-1-methyl-ethyl)pyrazol-3-yl]phenyl]prop-2-enoate | 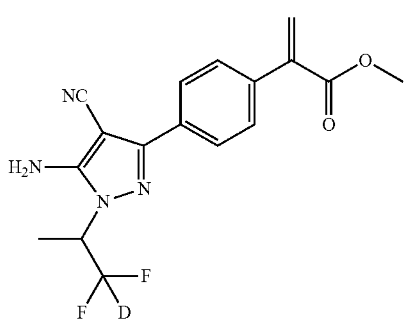 [SMILES: [2H]C(F)(F)C(C)n1nc(-c2ccc(C(=C)C(=O)OC)cc2)c(C#N)c1N] | 348.0 |

*The title compound is purified by reverse combi-chromatography with the following conditions: C18; ACN in H$_2$O (0.1% NH$_4$HCO$_3$) eluting with a gradient of 70% to 100% in 15 mins; UV 254 nm.

Alternate Preparation 32

Methyl 2-[4-[5-amino-4-cyano-1-(1-methylcyclopropyl)pyrazol-3-yl]phenyl]prop-2-enoate

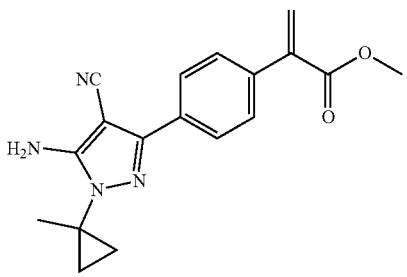 [SMILES: C=C(C(=O)OC)c1ccc(-c2nn(C3(C)CC3)c(N)c2C#N)cc1]

5-Amino-1-(1-methylcyclopropyl)-3-[4-(4,4,5,5-tetramethyl-1,3,2-dioxaborolan-2-yl)phenyl]pyrazole-4-carbonitrile (400 mg, 1.10 mmol), methyl 2-(trifluoromethanesulfonyloxy)prop-2-enoate (642.95 mg, 2.7 5 mmol), K₂CO₃ (455 mg, 3.30 mmol), and Pd(dppf)Cl₂ (85 mg, 0.09 mmol) are added together in dioxane (6.00 mL) and H₂O (1.50 mL). The solution is stirred for 2 hrs at 80° C. The mixture is diluted with EtOAc (100 mL), washed with H₂O (2×30 mL), and brine (20 mL). The organic phase is separation and concentrated under reduced pressure. The residue is purified by reversed combi-chromatography with following conditions: C18; eluting with a gradient of ACN in H₂O (0.1% NH₄HCO₃) to give the title compound (280 mg, 78.5) as a brown solid. ES/MS (m/z) 323.1 (M+H).

Preparation 36

Methyl 2-[4-[5-amino-4-cyano-1-[1,1,1-trifluoropropan-2-yl]pyrazol-3-yl]phenyl]prop-2-enoate, Isomer 1 and

Preparation 37

Methyl 2-[4-[5-amino-4-cyano-1-[1,1,1-trifluoropropan-2-yl]pyrazol-3-yl]phenyl]prop-2-enoate, Isomer 2

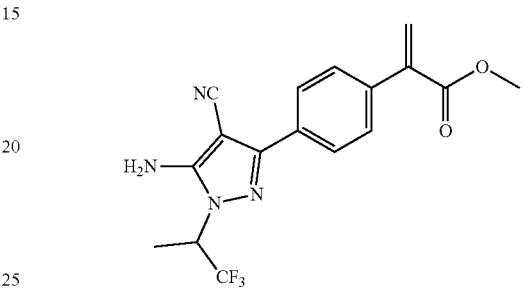

Methyl 2-[4-[5-amino-4-cyano-1-(1,1,1-trifluoropropan-2-yl)pyrazol-3-yl]phenyl]prop-2-enoate (2.00 g) is purified by Prep-HPLC with the following conditions: Column: N—(R,R)-Whelk-O1 4.6*50 mm, 3.5 μm; mobile phase A: mobile phase B: MeOH (0.1% DEA), with flow rate of 2 mL/min; eluting with 10% B, UV 254 nm; $t_{(R)}$ Isomer 1 is 6.7 min; $t_{(R)}$ Isomer 2 is 7.2; (700 mg, 35.0%, 100% ee) as a yellow solid and (700 mg, 35.0%, 100% ee) as a yellow solid.

The following compounds in Table 6 are prepared essentially as described for methyl 2-[4-[5-amino-4-cyano-1-[1,1,1-trifluoropropan-2-yl]pyrazol-3-yl]phenyl]prop-2-enoate, Isomer 1 and methyl 2-[4-[5-amino-4-cyano-1-[1,1,1-trifluoropropan-2-yl]pyrazol-3-yl]phenyl]prop-2-enoate, Isomer 2 using the appropriate purification conditions.

TABLE 6

| Prep. No. | Chemical name | Structure | $t_{(R)}$, min |
|---|---|---|---|
| 38 | Methyl 2-(6-[5-amino-4-cyano-1-[1,1,1-trifluoropropan-2-yl]pyrazol-3-yl]pyridin-3-yl)prop-2-enoate, Isomer 1 | 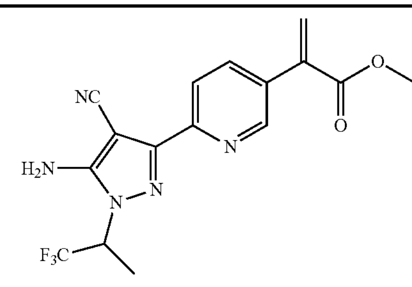 | 6.7 |
| 39 | Methyl 2-(6-[5-amino-4-cyano-1-[1,1,1-trifluoropropan-2-yl]pyrazol-3-yl]pyridin-3-yl)prop-2-enoate, Isomer 2 | 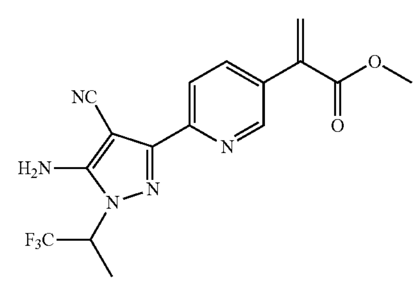 [SMILES: C=C(C(=O)OC)c1ccc(-c2nn(C(C)C(F)(F)F)c(N)c2C#N)nc1] | 7.2 |

TABLE 6-continued

| Prep. No. | Chemical name | Structure | $t_{(R)}$, min |
|---|---|---|---|
| 39a[1] | Methyl-2-[4-[5-amino-4-cyano-1-(1,1-difluoropropan-2-yl)pyrazol-3-yl]phenyl]prop-2-enoate, Isomer 1 | 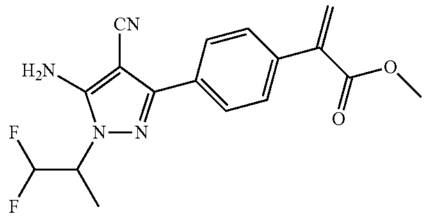 [SMILES: C=C(C(=O)OC)c1ccc(-c2nn(C(C)C(F)F)c(N)c2C#N)cc1] | 5 |
| 39b[1] | Methyl-2-[4-[5-amino-4-cyano-1-(1,1-difluoropropan-2-yl)pyrazol-3-yl]phenyl]prop-2-enoate, Isomer 2 | 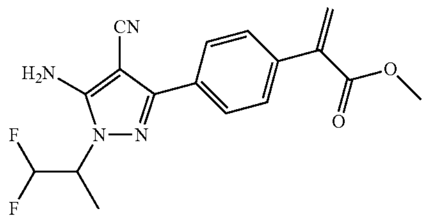 [SMILES: C=C(C(=O)OC)c1ccc(-c2nn(C(C)C(F)F)c(N)c2C#N)cc1] | 7.4 |
| 39c[3] | Methyl 2-[4-[5-amino-4-cyano-1-[2,2,2-trifluoro-1-(trideuteriomethyl)ethyl]pyrazol-3-yl]phenyl]prop-2-enoate, Isomer 1 | 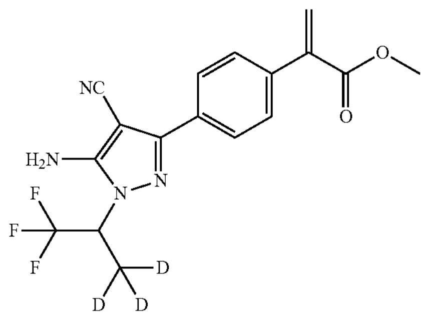 [SMILES: [2H]C([2H])([2H])C(n1nc(-c2ccc(C(=C)C(=O)OC)cc2)c(C#N)c1N)C(F)(F)F] | 5.16 |
| 39d[3] | Methyl 2-[4-[5-amino-4-cyano-1-[2,2,2-trifluoro-1-(trideuteriomethyl)ethyl]pyrazol-3-yl]phenyl]prop-2-enoate, Isomer 2 | 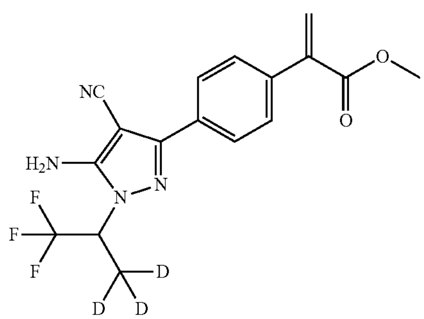 [SMILES: [2H]C([2H])([2H])C(n1nc(-c2ccc(C(=C)C(=O)OC)cc2)c(C#N)c1N)C(F)(F)F] | 7.65 |
| 39e[2] | Methyl 2-[4-[5-amino-4-cyano-1-(2-deuterio-2,2-difluoro-1-methyl-ethyl)pyrazol-3-yl]phenyl]prop-2-enoate, Isomer 1 | 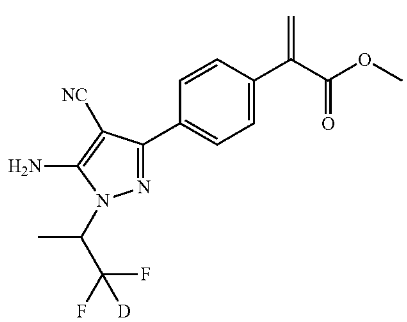 [SMILES: [2H]C(F)(F)C(C)n1nc(-c2ccc(C(=C)C(=O)OC)cc2)c(C#N)c1N] | 10.8 |

TABLE 6-continued

| Prep. No. | Chemical name | Structure | t(R), min |
|---|---|---|---|
| 39f[2] | Methyl 2-[4-[5-amino-4-cyano-1-(2-deuterio-2,2-difluoro-1-methyl-ethyl)pyrazol-3-yl]phenyl]prop-2-enoate, Isomer 2 | 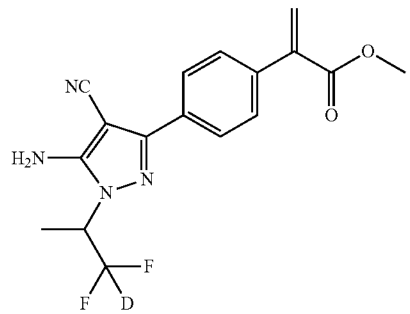 [SMILES: [2H]C(F)(F)C(C)n1nc(-c2ccc(C(=C)C(=O)OC)cc2)c(C#N)c1N] | 13.6 |

[1]CHIRALPAK IG, 2*25 cm, 5 μm; eluting with 30% EtOH in hexanes (10 mM NH$_3$—MeOH), flow rate: 20 mL/min, UV 234/274 nm
[2]CHIRALART Amylose-SA, 2*25 cm, 5 μm; eluting with 10% EtOH in hexanes (0.5% 2 M NH$_3$—MeOH) flow rate 20 mL/min, 210/220 nm.
[3]CHIRALPAK IH, 2.0*2.5 cm, 5 μm eluting with 40% EtOH in hexanes (10 mM NH$_3$—MeOH), flow rate 20 mL/min, UV 235.275.

Preparation 40

Methyl 2-[4-(5-amino-4-cyano-1-isopropylpyrazol-3-yl)phenyl]propanoate

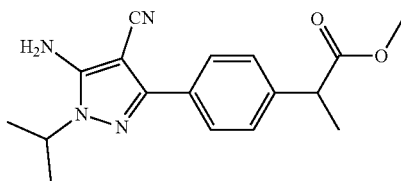

A mixture of methyl 2-[4-(5-amino-4-cyano-1-isopropyl-pyrazol-3-yl)phenyl]prop-2-enoate (43.00 g, 138.55 mmol) and 50% Pd/C (43.00 g) in MeOH (1 L) is stirred for 4 hrs at RT under N$_2$. The resulting mixture is filtered (through diatomaceous earth if needed) and the filter cake is washed with MeOH (300 ml). The filtrate is concentrated under reduced pressure to give the title compound (40 g, 92.4%) as a yellow solid. ES/MS (m/z) 313.2 (M+H).

The following compounds in Table 7 are prepared essentially as described for methyl 2-[4-(5-amino-4-cyano-1-isopropylpyrazol-3-yl)phenyl]propanoate using the appropriate reagents, using a balloon of hydrogen if appropriate, using 10-50% Pd/C, and adjusting reaction times to determine completion of the reactions. The products can also be purified by silica gel chromatography eluting with a solvent system such as PE:EtOAc of 2:1 to 1:1.

TABLE 7

| Prep. No. | Chemical name | Structure | ES/MS (m/z) (M + H) |
|---|---|---|---|
| 41 | Methyl 2-[6-(5-amino-4-cyano-1-isopropylpyrazol-3-yl)pyridin-3-yl]propanoate | 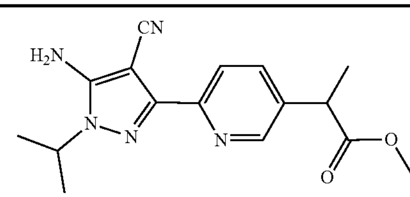 | 314.20 |
| 42 | Methyl 2-[4-[5-amino-4-cyano-1-(1-methylcyclopropyl)pyrazol-3-yl]phenyl]propanoate | 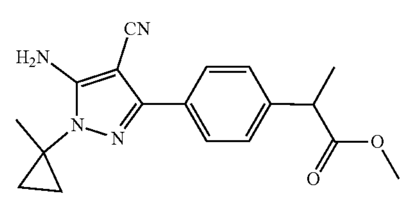 | 325.1 |
| 43 | Methyl 2-(4-[5-amino-4-cyano-1-[1,1,1-trifluoropropan-2-yl]pyrazol-3-yl]phenyl)propanoate, Isomer 1 | 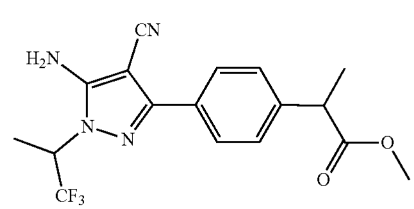 [SMILES: COC(=O)C(C)c1ccc(-c2nn(C(C)C(F)(F)F)c(N)c2C#N)cc1] | 367.2 |

TABLE 7-continued

| Prep. No. | Chemical name | Structure | ES/MS (m/z) (M + H) |
|---|---|---|---|
| 44 | Methyl 2-(4-[5-amino-4-cyano-1-[1,1,1-trifluoropropan-2-yl]pyrazol-3-yl]phenyl)propanoate, Isomer 2 | 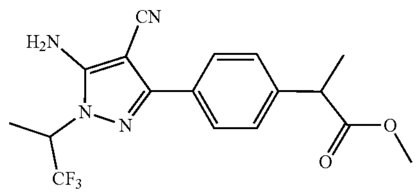 [SMILES: COC(=O)C(C)c1ccc(-c2nn(C(C)C(F)(F)F)c(N)c2C#N)cc1] | 367.3 |
| 45 | Methyl 2-[6-[5-amino-4-cyano-1-(1-methylcyclopropyl)pyrazol-3-yl]pyridin-3-yl]propanoate | 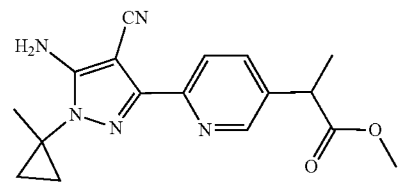 | 326.1 |
| 46 | Methyl 2-(6-[5-amino-4-cyano-1-[1,1,1-trifluoropropan-2-yl]pyrazol-3-yl]pyridin-3-yl)propanoate, Isomer 1e | 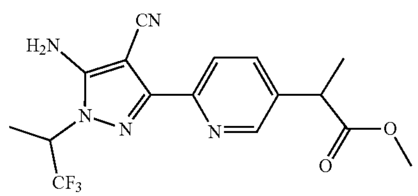 [SMILES: COC(=O)C(C)c1ccc(-c2nn(C(C)C(F)(F)F)c(N)c2C#N)nc1] | 368.2 |
| 47 | Methyl 2-(6-[5-amino-4-cyano-1-[1,1,1-trifluoropropan-2-yl]pyrazol-3-yl]pyridin-3-yl)propanoate, Isomer 2 | 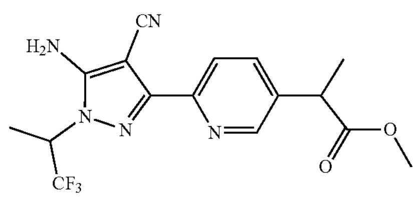 [SMILES: COC(=O)C(C)c1ccc(-c2nn(C(C)C(F)(F)F)c(N)c2C#N)nc1] | 368.1 |
| 47a[1] | Methyl 2-(4-[5-amino-4-cyano-1-[1,1-difluoropropan-2-yl]pyrazol-3-yl]phenyl)propanoate, Isomer 1 | 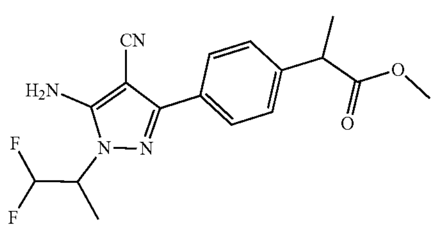 [SMILES: COC(=O)C(C)c1ccc(-c2nn(C(C)C(F)F)c(N)c2C#N)cc1] | 349.1 |
| 47b[1] | Methyl 2-(4-[5-amino-4-cyano-1-[1,1-difluoropropan-2-yl]pyrazol-3-yl]phenyl)propanoate, Isomer 2 | 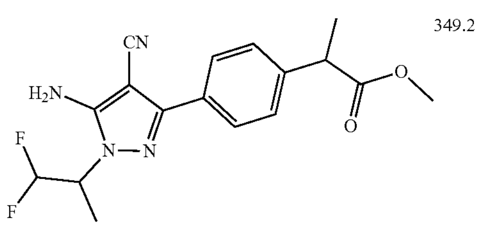 | 349.2 |
| 47c | Methyl 2-[4-(5-amino-4-cyano-1-isopropylpyrazol-3-yl)-2,3-difluorophenyl]propanoate | 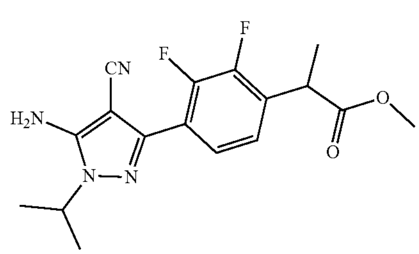 [SMILES: COC(=O)C(C)c1ccc(-c2nn(C(C)C)c(N)c2C#N)c(F)c1F] | 349.2 |

TABLE 7-continued

| Prep. No. | Chemical name | Structure | ES/MS (m/z) (M + H) |
|---|---|---|---|
| 47d[1] | Methyl 2-[4-[5-amino-4-cyano-1-[2,2,2-trifluoro-1-(trideuteriomethyl)ethyl]pyrazol-3-yl]phenyl]propanoate, Isomer 1 | 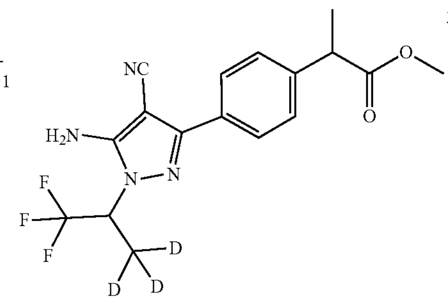 | 370.2 |
| 47e[1] | Methyl 2-[4-[5-amino-4-cyano-1-[2,2,2-trifluoro-1-(trideuteriomethyl)ethyl]pyrazol-3-yl]phenyl]propanoate, Isomer 2 | 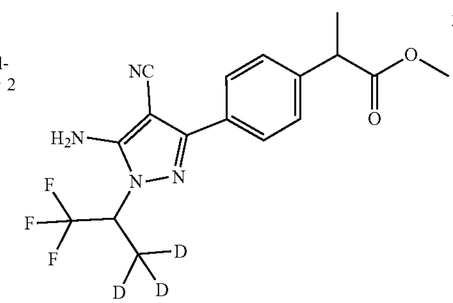 | 370.2 |
| 47f[1] | Methyl 2-[4-[5-amino-4-cyano-1-(2-deuterio-2,2-difluoro-1-methyl-ethyl)pyrazol-3-yl]phenyl]propanoate, Isomer 1 | 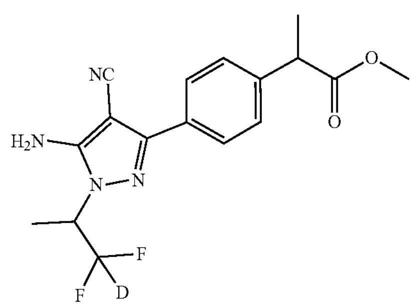 [SMILES: [2H]C(F)(F)C(C)n1nc(-c2ccc(C(C)C(=O)OC)cc2)c(C#N)c1N] | 350.1 |
| 47g | Methyl 2-[4-[5-amino-4-cyano-1-(2-deuterio-2,2-difluoro-1-methyl-ethyl)pyrazol-3-yl]phenyl]propanoate, Isomer 2 | 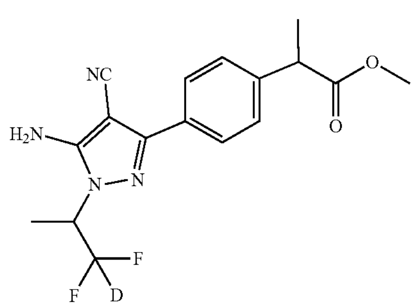 [SMILES: [2H]C(F)(F)C(C)n1nc(-c2ccc(C(C)C(=O)OC)cc2)c(C#N)c1N] | 350.15 |

[1]PD(OH)$_2$/C is catalyst and DCM is solvent used

Alternate Preparation 42

Methyl 2-[4-[5-amino-4-cyano-1-(1-methylcyclopropyl)pyrazol-3-yl]phenyl]propanoate

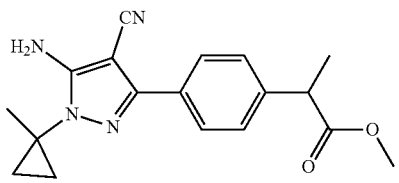

Methyl 2-[4-[5-amino-4-cyano-1-(1-methylcyclopropyl)pyrazol-3-yl]phenyl]prop-2-enoate (260 mg, 0.81 mmol), MeOH (15.00 mL) and 50% Pd/C (275 mg) are added together. The solution is stirred for 2 hrs at RT under H₂. The mixture is filtered, and the solution is concentrated under vacuum to give the title compound (240 mg, 91%) as a light yellow solid. The crude product is used directly without further purification. ES/MS (m/z) 325.1 (M+H).

Alternate Preparation 42

Methyl 2-[4-[5-amino-4-cyano-1-(1-methylcyclopropyl)pyrazol-3-yl]phenyl]propanoate To a stirred solution of methyl 2-[4-(2,2-dicyano-1-methoxyeth-1-en-1-yl)phenyl]propanoate (4.00 g, 14.80 mmol) and (1-methylcyclopropyl)hydrazine hydrochloride (1.81 g, 14.80 mmol) in THF (50.00 mL) is added Et₃N (7.49 g, 73.99 mmol) dropwise at RT under N₂. The mixture is stirred for 1 hr at 50° C. under N₂. The mixture is diluted with H₂O (50 mL) and extracted with EtOAc (3×100 mL). The combined organic extracts are washed with brine (3×200 mL), dried over anhydrous Na₂SO₄, filtered, and the filtrate is concentrated under reduced pressure. The residue is purified by silica gel column chromatography, eluting with hexanes/EtOAc (5:1-1:1) to give the title compound (3.8 g, 79.16%) as an off-white solid. ES/MS (m/z) 325.2 (M+H).

Preparation 47h

Methyl 2-[4-[5-amino-4-cyano-1-(1-methylcyclopropyl)pyrazol-3-yl]-3-fluorophenyl]propanoate

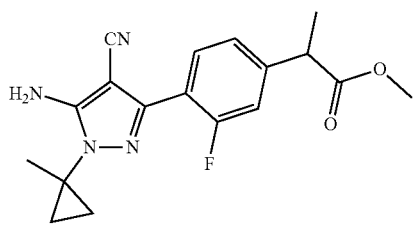

To a solution of methyl 2-[4-[5-amino-4-cyano-1-(1-methylcyclopropyl)pyrazol-3-yl]-3-fluorophenyl]prop-2-enoate (410 mg, 1.21 mmol) in MeOH (10 mL) is added Pd/C (10%, 0.64 g). The mixture is hydrogenated at RT for 1 hr using a H₂ balloon. The mixture is filtered, the filter cake is washed with MeOH (3×50 mL) and the filtrate is concentrated under reduced pressure to give the title compound (340 mg, 82.44%) as a dark yellow solid. ES/MS (m/z) 343.2 (M+H).

Preparation 48

Methyl 2-[4-[5-amino-4-cyano-1-(1,1,1-trifluoro-2-methylpropan-2-yl)pyrazol-3-yl]phenyl]propanoate

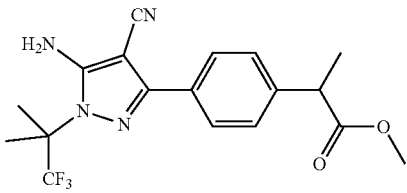 [SMILES: COC(=O)C(C)c1ccc(-c2nn(C(C)(C)C(F)(F)F)c(N)c2C#N)cc1]

To a stirred mixture of methyl 2-[4-(2,2-dicyano-1-methoxyeth-1-en-1-yl)phenyl]propanoate (400.00 mg, 1.48 mmol) and (1,1,1-trifluoro-2-methylpropan-2-yl)hydrazine dihydrochloride (210.33 mg, 1.48 mmol) in EtOH (5.00 mL) is added Et₃N (449.25 mg, 4.44 mmol) in portions at RT under N₂. The resulting mixture is stirred for 2 hrs at 50° C. under N₂. The mixture is allowed to cool to RT and concentrated under reduced pressure. The residue is purified by silica gel column chromatography, eluting with a gradient of PE/EtOAc (2/1 to 1/1) to give the title compound (270 mg, 47%) as an off-white solid. ES/MS (m/z) 381.2 (M+H).

The following compound in Table 8 is prepared essentially as described for methyl 2-[4-[5-amino-4-cyano-1-(1,1,1-trifluoro-2-methylpropan-2-yl)pyrazol-3-yl]phenyl]propanoate using the appropriate reagents, adjusting reaction times to determine completion of the reactions, and adjusting purification conditions if needed. The reaction can be stirred from RT-50° C. and used without purification.

TABLE 8

| Prep. No. | Chemical name | Structure | ES/MS (m/z) (M + H) |
|---|---|---|---|
| 49 | Methyl 2-[4-[5-amino-4-cyano-1-(1-methoxy-2-methylpropan-2-yl)pyrazol-3-yl]phenyl]propanoate | 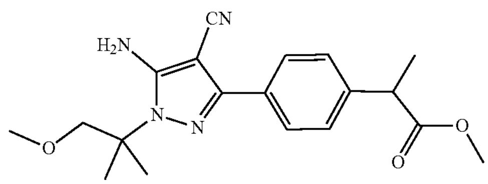 | 357.1 |
| 49a | Methyl 2-[4-[5-amino-4-cyano-1-(2,2,2-trideuterio-1-methyl-ethyl)pyrazol-3-yl]phenyl]propanoate | 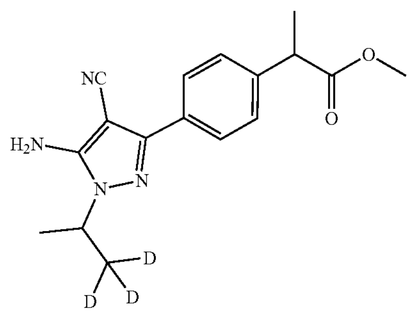 [SMILES: [2H]C([2H])([2H])C(C)n1nc(-c2ccc(C(C)C(=O)OC)cc2)c(C#N)c1N] | 316.3 |
| 49b | Methyl 2-[4-[5-amino-4-cyano-1-(1,2,2,2-tetradeuterio-1-methyl-ethyl)pyrazol-3-yl]phenyl]propanoate | 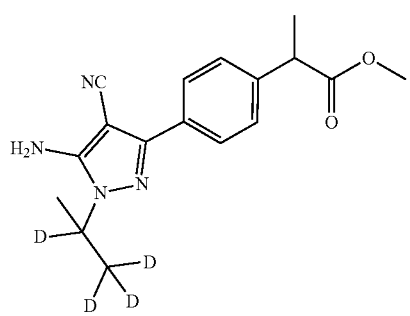 [SMILES: [2H]C([2H])([2H])C([2H])(C)n1nc(-c2ccc(C(C)C(=O)OC)cc2)c(C#N)c1N] | 317.3 |
| 49c | Methyl 2-[4-[5-amino-4-cyano-1-[1,2,2,2-tetradeuterio-1-(trideuteriomethyl)ethyl]pyrazol-3-yl]phenyl]propanoate | 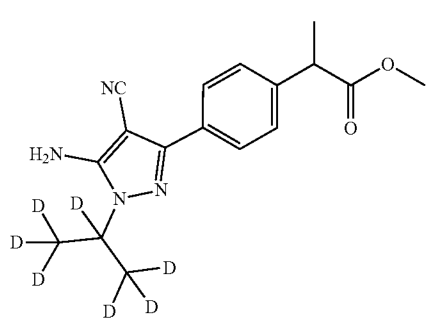 [SMILES: [2H]C([2H])([2H])C([2H])(n1nc(-c2ccc(C(C)C(=O)OC)cc2)c(C#N)c1N)C([2H])([2H])[2H]] | 320.1 |

Preparation 50

Lithium; 2-[5-[5-(tert-butoxycarbonylamino)-4-cyano-1-isopropyl-pyrazol-3-yl]-2-pyridyl]propanoate

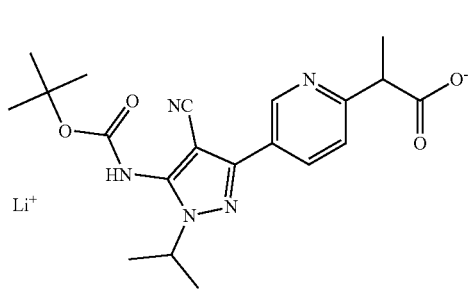 [SMILES: CC(C(=O)[O-])c1ccc(-c2nn(C(C)C)c(NC(=O)OC(C)(C)C)c2C#N)cn1 ; [Li+]]

Methyl 2-[5-[5-(tert-butoxycarbonylamino)-4-cyano-1-isopropyl-pyrazol-3-yl]-2-pyridyl]propanoate (100 mg, 0.227 mmol), methyl 2-[5-[5-[bis(tert-butoxycarbonyl)amino]-4-cyano-1-isopropyl-pyrazol-3-yl]-2-pyridyl]propanoate (958 mg, 1.87 mmol) are added together in MeOH (8.20 mL). LiOH (142 mg, 5.69 mmol) is solubilized in $H_2O$ (2.46 mL) and is added to the mixture. The reaction mixture is stirred at RT for 18 hrs and concentrated under reduced pressure to give the title compound (926 mg, 111.39%).

Preparation 51

2-[4-(5-Amino-4-cyano-1-isopropylpyrazol-3-yl)phenyl]propanoic acid

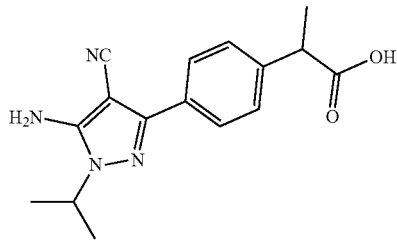 [SMILES: CC(C(=O)O)c1ccc(-c2nn(C(C)C)c(N)c2C#N)cc1]

A mixture of methyl 2-[4-(5-amino-4-cyano-1-isopropylpyrazol-3-yl)phenyl]propanoate (40.00 g, 128.05 mmol) and NaOH (25.61 g, 640.26 mmol) in MeOH (500 mL) and $H_2O$ (500 mL) is stirred for 5 hrs at 50° C. The mixture is allowed to cool to RT. The resulting mixture is concentrated under reduced pressure, diluted with $H_2O$ (500 mL), and the aqueous layer is extracted with EtOAc (2×300 mL). The aqueous layer is acidified to pH 3-4 with 6 N HCl and the resulting precipitated solids are collected by filtration, washed with $H_2O$ (3×50 mL), and dried under vacuum to give the title compound (34 g, 89.0%) as a light yellow solid. ES/MS (m/z) 299.2 (M+H).

The following compounds in Table 9 are prepared essentially as described for 2-[4-(5-amino-4-cyano-1-isopropylpyrazol-3-yl)phenyl]propanoic acid and stirring at RT until completion.

TABLE 9

| Prep. No. | Chemical name | Structure | ES/MS (m/z) (M + H) |
|---|---|---|---|
| 52 | 2-[6-(5-Amino-4-cyano-1-isopropylpyrazol-3-yl)pyridin-3-yl]propanoic acid | 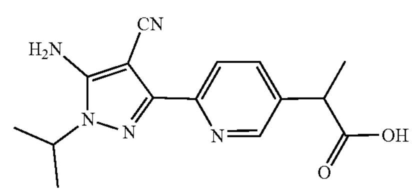 [SMILES: CC(C(=O)O)c1ccc(-c2nn(C(C)C)c(N)c2C#N)nc1] | 300.10 |
| 53[1] | 2-[5-[5-(tert-Butoxycarbonylamino)-4-cyano-1-isopropyl-pyrazol-3-yl]-2-pyridyl]propanoic acid | 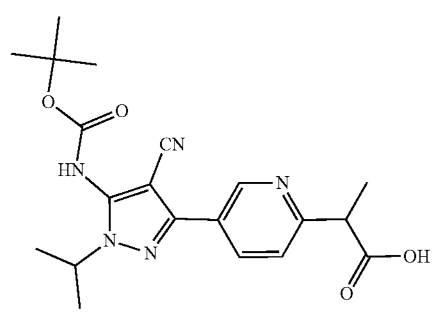 [SMILES: CC(C(=O)O)c1ccc(-c2nn(C(C)C)c(NC(=O)OC(C)(C)C)c2C#N)cn1] | |

[1] 2 M NaOH used with no extra $H_2O$, after acidification with potassium bisulfate, the mixture and is cooled at 0 °C. for 1 hr and the title compound is filtered, collected, dried, used directly without further purification.

Preparation 54

2-(6-[5-Amino-4-cyano-1-[1,1,1-trifluoropropan-2-yl]pyrazol-3-yl]pyridin-3-yl)propanoic acid, Isomer 1

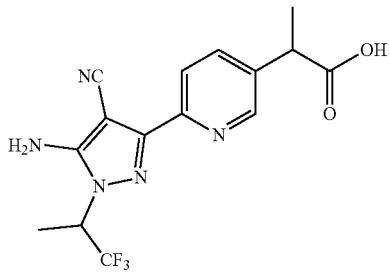 [SMILES: CC(C(=O)O)c1ccc(-c2nn(C(C)C(F)(F)F)c(N)c2C#N)nc1]

To a stirred solution of methyl 2-(6-[5-amino-4-cyano-1-[1,1,1-trifluoropropan-2-yl]pyrazol-3-yl]pyridin-3-yl)propanoate, Isomer 2 (1.30 g, 3.53 mmol) in THF (16.00 mL) and H$_2$O (4.00 mL) is added LiOH (253.56 mg, 10.59 mmol) in portions at RT under N$_2$. The resulting mixture is stirred for 2 hrs at RT under N$_2$. The mixture is concentrated under reduced pressure, diluted with H$_2$O (20 mL), and acidified to pH 3 with HCl (c). The resulting mixture is extracted with EtOAc (3×50 mL). The combined organic extracts are washed with saturated aqueous NaCl solution (2×100 mL), dried over anhydrous Na$_2$SO$_4$, filtered, and concentrated under reduced pressure to give the title compound (1.2 g, 96%) as a light yellow solid. ES/MS (m/z) 353.9 (M+H).

The following compounds in Table 10 are prepared essentially as described for 2-(6-[5-amino-4-cyano-1-[-1,1,1-trifluoropropan-2-yl]pyrazol-3-yl]pyridin-3-yl)propanoic acid, Isomer 1 using the appropriate reagents at RT to 50° C. and adjusting reaction times to determine completion of the reactions. LiOH can be added portionwise or in a single amount depending on the scale of the reaction.

TABLE 10

| Prep. No. | Chemical name | Structure | ES/MS (m/z) (M + H) |
|---|---|---|---|
| 55 | 2-(4-[5-Amino-4-cyano-1-[1,1,1-trifluoropropan-2-yl]pyrazol-3-yl]phenyl)propanoic acid, Isomer 1 | 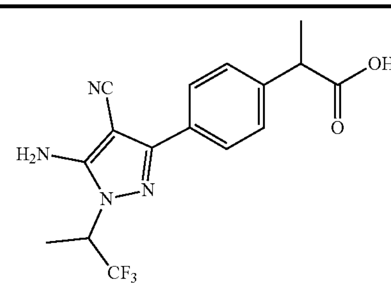 | 353.1 |
| 56 | 2-(4-[5-Amino-4-cyano-1-[1,1,1-trifluoropropan-2-yl]pyrazol-3-yl]phenyl)propanoic acid, Isomer 2 | 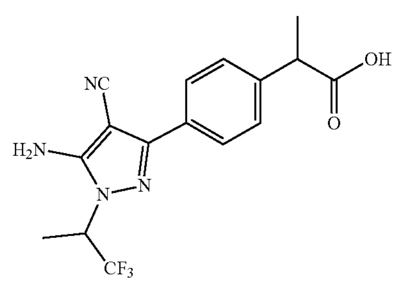 [SMILES: CC(C(=O)O)c1ccc(-c2nn(C(C)C(F)(F)F)c(N)c2C#N)cc1] | 353.3 |
| 57 | 2-[4-[5-Amino-4-cyano-1-(1,1,1-trifluoro-2-methylpropan-2-yl)pyrazol-3-yl]phenyl]propanoic acid | 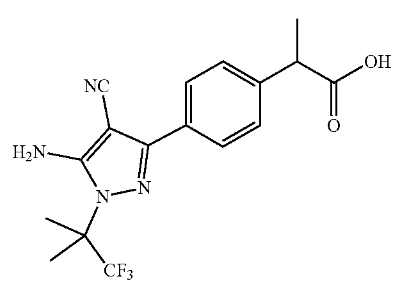 [SMILES: CC(C(=O)O)c1ccc(-c2nn(C(C)(C)C(F)(F)F)c(N)c2C#N)cc1] | 367.0 |

TABLE 10-continued

| Prep. No. | Chemical name | Structure | ES/MS (m/z) (M + H) |
|---|---|---|---|
| 58 | 2-[4-[5-Amino-4-cyano-1-(1-methoxy-2-methylpropan-2-yl)pyrazol-3-yl]phenyl]propanoic acid | 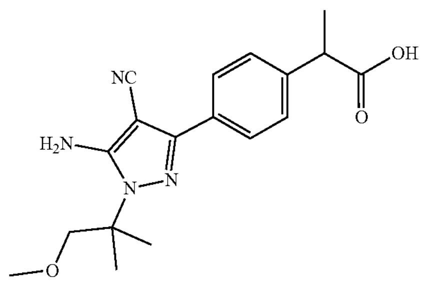 [SMILES: COCC(C)(C)n1nc(-c2ccc(C(C)C(=O)O)cc2)c(C#N)c1N] | 343.1 |
| 59 | 2-[6-[5-Amino-4-cyano-1-(1-methylcyclopropyl)pyrazol-3-yl]pyridin-3-yl]propanoic acid | 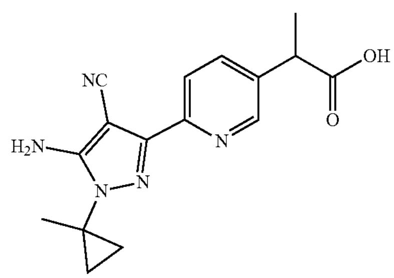 [SMILES: CC(C(=O)O)c1ccc(-c2nn(C3(C)CC3)c(N)c2C#N)nc1] | 312.1 |
| 60 | 2-(6-[5-Amino-4-cyano-1-[1,1,1-trifluoropropan-2-yl]pyrazol-3-yl]pyridin-3-yl)propanoic acid, Isomer 2 | 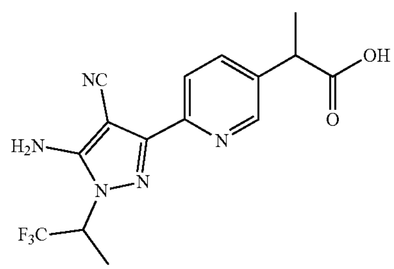 [SMILES: CC(C(=O)O)c1ccc(-c2nn(C(C)C(F)(F)F)c(N)c2C#N)nc1] | 354.0 |
| 60a | 2-[4-[5-Amino-4-cyano-1-(2,2,2-trideuterio-1-methyl-ethyl)pyrazol-3-yl]phenyl]propanoic acid | 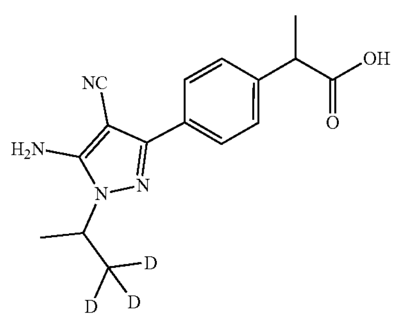 [SMILES: [2H]C([2H])([2H])C(C)n1nc(-c2ccc(C(C)C(=O)O)cc2)c(C#N)c1N] | 302.2 |
| 60b | 2-[4-[5-Amino-4-cyano-1-(1,2,2,2-tetradeuterio-1-methyl-ethyl)pyrazol-3-yl]phenyl]propanoic acid | 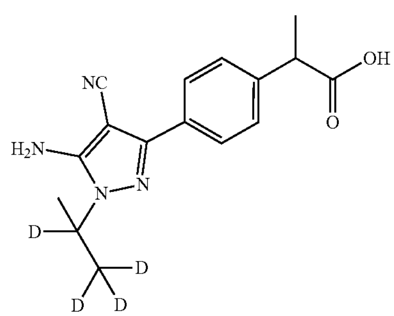 [SMILES: [2H]C([2H])([2H])C([2H])(C)n1nc(-c2ccc(C(C)C(=O)O)cc2)c(C#N)c1N] | 303.3 |

TABLE 10-continued

| Prep. No. | Chemical name | Structure | ES/MS (m/z) (M + H) |
|---|---|---|---|
| 60c | 2-[4-[5-Amino-4-cyano-1-[1,2,2,2-tetradeuterio-1-(trideuteriomethyl)ethyl]pyrazol-3-yl]phenyl]propanoic acid | 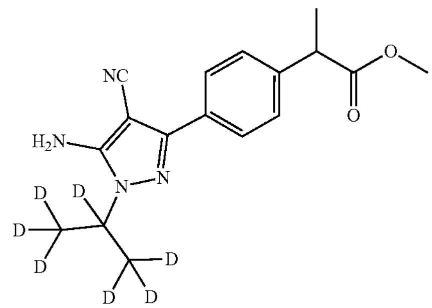 [SMILES: [2H]C([2H])([2H])C([2H])(n1nc(-c2ccc(C(C)C(=O)OC)cc2)c(C#N)c1N)C([2H])([2H])[2H]] | 306.2 |
| 60d | 2-(4-[5-Amino-4-cyano-1-[1,1-difluoropropan-2-yl]pyrazol-3-yl]phenyl)propanic acid, Isomer 1 | 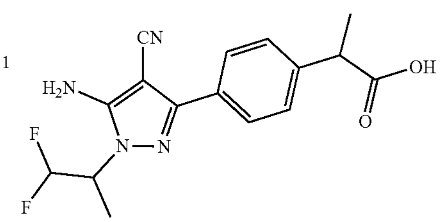 | |
| 60e | 2-(4-[5-Amino-4-cyano-1-[1,1-difluoropropan-2-yl]pyrazol-3-yl]phenyl)propanic acid, Isomer 2 | 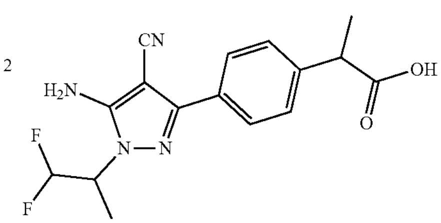 | 335.1 |
| 60f | 2-[4-(5-Amino-4-cyano-1-isopropylpyrazol-3-yl)-2,3-difluorophenyl]propanoic acid | 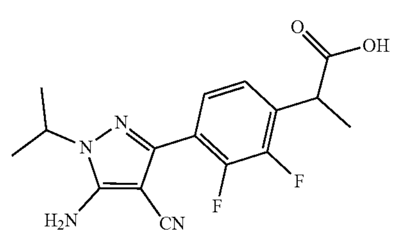 [SMILES: CC(C(=O)O)c1ccc(-c2nn(C(C)C)c(N)c2C#N)c(F)c1F] | 335.1 |
| 60g | 2-[4-[5-Amino-4-cyano-1-[2,2,2-trifluoro-1-(trideuteriomethyl)ethyl]pyrazol-3-yl]phenyl]propanoic acid, Isomer 1 | 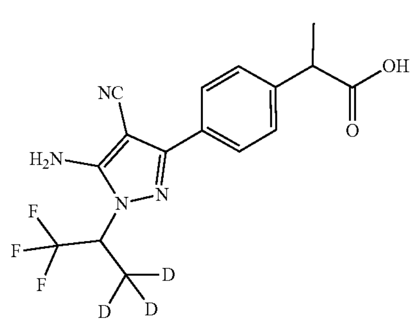 [SMILES: [2H]C([2H])([2H])C(n1nc(-c2ccc(C(C)C(=O)O)cc2)c(C#N)c1N)C(F)(F)F] | 356.2 |

TABLE 10-continued

| Prep. No. | Chemical name | Structure | ES/MS (m/z) (M + H) |
|---|---|---|---|
| 60h | 2-[4-[5-Amino-4-cyano-1-[2,2,2-trifluoro-1-(trideuteriomethyl)ethyl]pyrazol-3-yl]phenyl]propanoic acid, Isomer 2 | 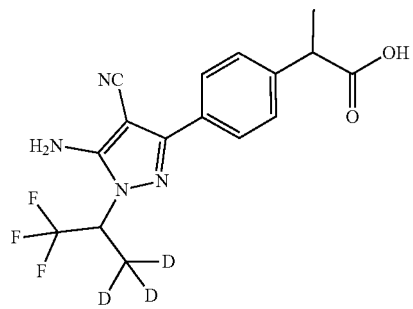 [SMILES: [2H]C([2H])([2H])C(n1nc(-c2ccc(C(C)C(=O)O)cc2)c(C#N)c1N)C(F)(F)F] | 356.2 |
| 60i | 2-[4-[5-Amino-4-cyano-1-(2-deuterio-2,2-difluoro-1-methyl-ethyl)pyrazol-3-yl]phenyl]propanoic acid, Isomer 1 | 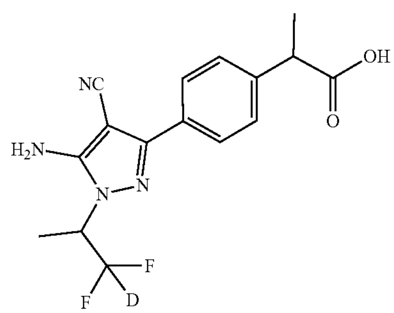 [SMILES: [2H]C(F)(F)C(C)n1nc(-c2ccc(C(C)C(=O)O)cc2)c(C#N)c1N] | 336.2 |
| 60j | 2-[4-[5-Amino-4-cyano-1-(2-deuterio-2,2-difluoro-1-methyl-ethyl)pyrazol-3-yl]phenyl]propanoic acid, Isomer 2 | 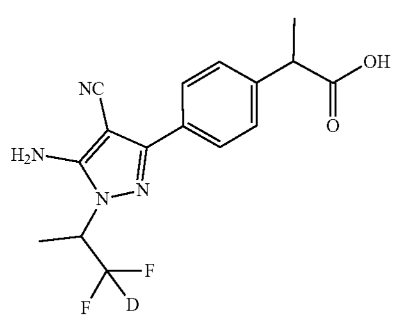 [SMILES: [2H]C(F)(F)C(C)n1nc(-c2ccc(C(C)C(=O)O)cc2)c(C#N)c1N] | 335.9 |

Preparation 60k

2-[4-[5-Amino-4-cyano-1-[2,2,2-trideuterio-1-(trideuteriomethyl)ethyl]pyrazol-3-yl]phenyl]propanoic acid

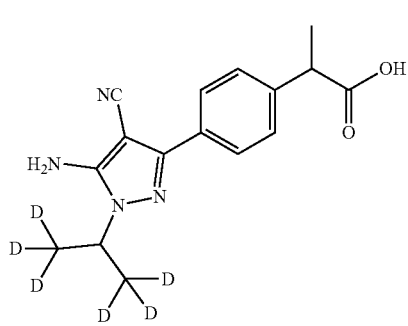 [SMILES: [2H]C([2H])([2H])C(n1nc(-c2ccc(C(C)C(=O)O)cc2)c(C#N)c1N)C([2H])([2H])[2H]]

A solution of methyl 2-[4-[5-amino-4-cyano-1-[2,2,2-trideuterio-1-(trideuteriomethyl)ethyl]pyrazol-3-yl]phenyl]propanoate (630 mg, 1.98 mmol) and LiOH (143 mg, 5.94 mmol) in MeOH/H$_2$O (25 mL, 4:1) is stirred for 1 hr at RT. The solution is extracted with EtOAc (2×5 mL). The aqueous layer is acidified with HCl (2 M) and extracted with EtOAc (3×50 mL). The organic extract is dried over anhydrous Na$_2$SO$_4$ and concentrated under reduced pressure to give the title compound (460 mg, crude) as a light yellow solid. The product is washed with Et$_2$O (10 mL) used directly without further purification. ES/MS (m/z) 305.20 (M+H).

Preparation 60l

2-[4-[5-Amino-4-cyano-1-(1-methylcyclopropyl)pyrazol-3-yl]phenyl]propanoic acid

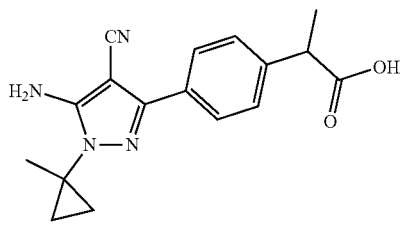 [SMILES: CC(C(=O)O)c1ccc(-c2nn(C3(C)CC3)c(N)c2C#N)cc1]

Methyl 2-[4-[5-amino-4-cyano-1-(1-methylcyclopropyl)pyrazol-3-yl]phenyl]propanoate (220.00 mg, 0.68 mmol), MeOH (2.00 mL), H$_2$O (2.00 mL), and NaOH (109 mg, 2.71 mmol) are added together. The solution is stirred for 2 hrs at 50° C. and then MeOH is removed under reduced pressure. The pH of the mixture is adjusted to with 4 N HCl and the mixture is extracted with EtOAc (2×50 mL). The combined organic extracts are washed with H$_2$O (2×15 mL), washed with brine (10 mL) and concentrated to give the title compound (240 mg, 100% crude) as an off-white solid. The crude product is used directly without further purification. ES/MS (m/z) 311.2 (M+H).

Preparation 60m

2-[4-[5-Amino-4-cyano-1-(1-methylcyclopropyl)pyrazol-3-yl]-3-fluorophenyl]propanoic acid

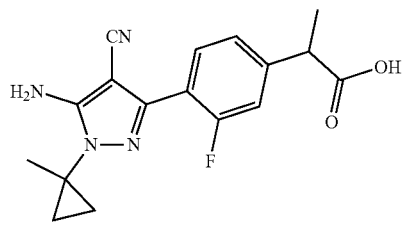 [SMILES: CC(C(=O)O)c1ccc(-c2nn(C3(C)CC3)c(N)c2C#N)c(F)c1]

A solution of methyl 2-[4-[5-amino-4-cyano-1-(1-methylcyclopropyl)pyrazol-3-yl]-3-fluorophenyl]propanoate (340 mg, 0.99 mmol) and LiOH (118.91 mg, 4.96 mmol) in THF/H$_2$O (4:1, 5.00 mL) is stirred for 1 hr at 50° C. under N$_2$. The solution is cooled to RT and the mixture is acidified to pH=3 with HCl (aq. 1 N). The mixture is extracted with EtOAc (3×100 mL). The combined organic extracts are washed with brine (2×20 mL), dried over anhydrous Na$_2$SO$_4$, filtered, and the filtrate is concentrated under reduced pressure to give the title compound (280 mg, 85.87%) as a light yellow solid. ES/MS (m/z) 329.2 (M+H).

Preparation 61

2-[4-(5-Amino-4-cyano-1-isopropylpyrazol-3-yl)phenyl]propanoic acid, Isomer 1 and

Preparation 62

2-[4-(5-Amino-4-cyano-1-isopropylpyrazol-3-yl)phenyl]propanoic acid, Isomer 2

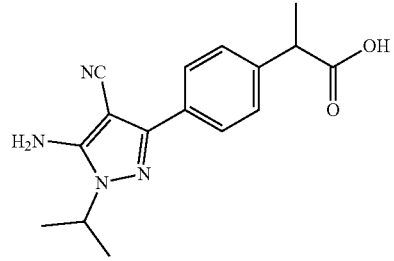 [SMILES: CC(C(=O)O)c1ccc(-c2nn(C(C)C)c(N)c2C#N)cc1]

2-[4-(5-Amino-4-cyano-1-isopropylpyrazol-3-yl)phenyl]propanoic acid (500 mg) is separated by prep-chiral with the following conditions: Column: (R,R)Whelk-O1, 21.1*250 mm, 5 μm; mobile phase A: hexanes (0.1% FA), mobile phase B:IPA; eluting with a gradient of 0-30% B in 17 min at 20 mL/min; UV 254 nm; t$_{(R)}$ isomer 1 9.2 min (209.6 mg, 41.2%, 100% ee) as a white solid, ES/MS (m/z) 299.1 (M+H), t$_{(R)}$ isomer 2 12 min (206.8 mg, 41.03%, 100% ee) as a white solid, ES/MS (m/z) 299.1 (M+H).

Preparation 63

2-[6-(5-Amino-4-cyano-1-isopropylpyrazol-3-yl)pyridin-3-yl]propanoic acid, Isomer 1 and

Preparation 64

2-[6-(5-Amino-4-cyano-1-isopropylpyrazol-3-yl)pyridin-3-yl]propanoic acid, Isomer 2

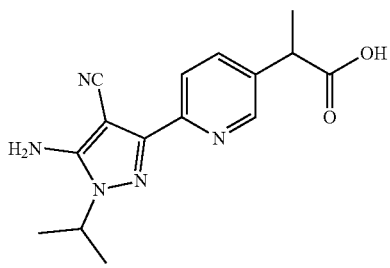 [SMILES: CC(C(=O)O)c1ccc(-c2nn(C(C)C)c(N)c2C#N)nc1]

2-[6-(5-Amino-4-cyano-1-isopropylpyrazol-3-yl)pyridin-3-yl]propanoic acid (290.00 mg) is separated by prep-chiral with the following conditions: Column: CHIRALPAK AD-H, 2.0*25 cm L; mobile phase A: hexanes (0.1% TFA), mobile phase B: IPA eluting with a gradient of 30%-0% B in 9.5 min; flow rate 20 mL/min; UV 230/254 nm, $t_{(R)}$ Isomer 1 6.2 min, (102.5 mg, 35.3%) as a white solid with 100% ee; ES/MS (m/z) 300.1 (M+H), $t_{(R)}$ Isomer 2 7.8 min (104.8 mg, 36.1%) as a white solid with 100% ee, ES/MS (m/z) 300.1 (M+H).

Preparation 64a

2-[4-(5-Amino-4-carbamoyl-1-isopropylpyrazol-3-yl)phenyl]propanoic acid

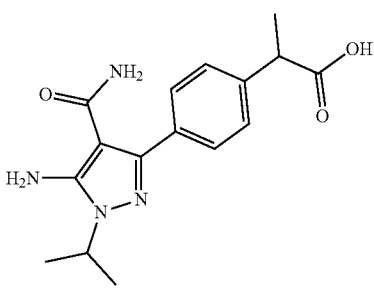 [SMILES: CC(C(=O)O)c1ccc(-c2nn(C(C)C)c(N)c2C(N)=O)cc1]

A mixture of 2-[4-(5-amino-4-cyano-1-isopropylpyrazol-3-yl)phenyl]propanoic acid (1.00 g, 3.352 mmol), NaOH (671 mg, 16.759 mmol) and $H_2O_2$ (7.81 mL, 68.873 mmol, 30%) in EtOH (20.00 mL)/DMSO (2.00 mL) is stirred overnight at 50° C. The reaction is quenched with saturated $Na_2SO_3$ aqueous (20 mL) at 0° C. The resulting mixture is diluted with $H_2O$ (200 mL) and acidified to pH 3-4 with 6 N HCl. The precipitated solids are collected by filtration and washed with $H_2O$ (2×10 mL). The solid is purified by reverse Combi-flash chromatography with the following conditions: column, C18; mobile phase, ACN in $H_2O$ eluting with a gradient of 30% to 60% in 25 min; detector, UV 220 nm and then lyophilized to give the title compound (670 mg, 62.5%) as an off-white solid. ES/MS (m/z) 317.2 (M+H).

Preparation 64b

2-[4-(5-Amino-4-carbamoyl-1-isopropylpyrazol-3-yl)phenyl]propanoic acid, Isomer 1 and

Preparation 64c

2-[4-(5-Amino-4-carbamoyl-1-isopropylpyrazol-3-yl)phenyl]propanoic acid, Isomer 2

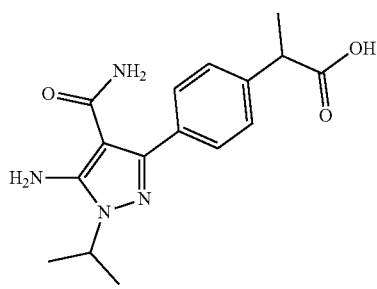 [SMILES: CC(C(=O)O)c1ccc(-c2nn(C(C)C)c(N)c2C(N)=O)cc1]

2-[4-(5-Amino-4-carbamoyl-1-isopropylpyrazol-3-yl)phenyl]propanoic acid (280 mg) is separated by prep-chiral HPLC with the following conditions: Column: CHIRALPAK AD-H, 2.0*25 cm; mobile phase A: hexanes (0.1% FA), mobile phase B: IPA; flow rate: 20 mL/min eluting with 15% B in 21 min; UV 210Y254 nm; $t_{(R)}$ Isomer 1 16 min, (106.2 mg, 37.6%, 100% ee) as a white solid, ES/MS (m/z) 317.1 (M+H); $t_{(R)}$ Isomer 2 19 min, (94.96 mg, 33.3%, 98.3% ee) as a white solid, ES/MS (m/z) 317.1 (M+H).

Preparation 65

(Z/E)-5,5-Difluoro-N'-hydroxy-4,4-dimethyl-3-oxo-hexanimidamide

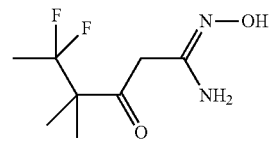

A solution of 5,5-difluoro-4,4-dimethyl-3-oxohexanenitrile (1.50 g, 8.56 mmol), $NaHCO_3$ (1.80 g, 21.427 mmol), and bis(hydroxylammonium); sulfate (1.69 g, 10.30 mmol) in $H_2O$ (27.00 mL) and MeOH (3.00 mL) is stirred overnight at 65° C. under $N_2$. The mixture is used directly without further purification. ES/MS m/z 209.2 (M+H).

Preparation 66

3-(3,3-Dimethylcyclobutyl)-1,2-oxazol-5-amine

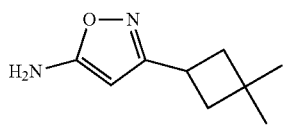

A solution of 3-(3,3-dimethylcyclobutyl)-3-oxopropanenitrile (1.50 g, 9.92 mmol), NH$_2$OH.HCl (0.76 g, 10.94 mmol), and NaOH (0.79 g, 19.84 mmol) in H$_2$O (15.00 mL) is stirred for 2 hrs at 100° C. under N$_2$. The mixture is allowed to cool to RT. The precipitated solids are collected by filtration and washed with H$_2$O (3×30 mL). The resulting mixture is concentrated under reduced pressure to give the title compound (1.5 g, 90.97%) as an off-white solid. ES/MS (m/z) 167.3 (M+H).

The following compound in Table 11 is prepared essentially as described for 3-(3,3-dimethylcyclobutyl)-1,2-oxazol-5-amine using the appropriate reagents and adjusting the reaction time to determine completion of the reaction. The base can be added in portions and the reaction mixture can be extracted with DCM or filtered as appropriate.

TABLE 11

| Prep. No. | Chemical name | Structure | NMR (300 MHz, CDCl$_3$) δ or ES/MS (m/z) (M + H) |
|---|---|---|---|
| 67 | 3-(2-Methylbutan-2-yl)-1,2-oxazol-5-amine | 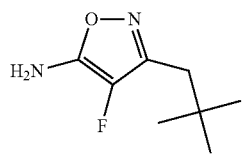 | 5.01 (s, 1H), 4.35 (br, s, 2H), 1.60(q, 2H), 1.25 (s, 6H), 0.83 (t, 3H) |
| 67a | 3-(4-(Trifluoromethyl)bicyclo[2.2.1]heptan-1-yl)isoxazol-5-amine | 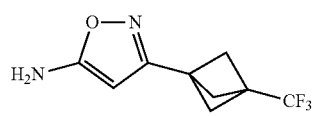 [SMILES: Nc1cc(C23CC(C(F)(F)F)(C2)C3)no1] | 247.1 |

Preparation 67b

3-(3-Methyl-1-bicyclo[1.1.1]pentanyl)isoxazol-5-amine

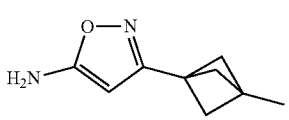

To a stirred mixture of 3-[3-methylbicyclo[1.1.1]pentan-1-yl]-3-oxopropanenitrile (350.00 mg, 2.41 mmol) and hydroxylamine HCl (183.83 mg, 2.65 mmol) in H$_2$O (8.00 mL) is added NaOH (192.38 mg, 4.81 mmol) in portions at RT under N$_2$. The mixture is stirred for 1 hr at 100° C. under N$_2$. The mixture is allowed to cool to RT. The precipitated solids are collected by filtration and washed with H$_2$O (3×20 mL), to give the title compound (300 mg, 77.9%) as a light yellow solid. ES/MS m/z (M+H) 165.1.

Preparation 67c

3-(2,2-Dimethylpropyl)-4-fluoro-1,2-oxazol-5-amine

A solution of 3-(2,2-dimethylpropyl)-1,2-oxazol-5-amine (5.00 g, 32.42 mmol) and Selectfluor™ (13.78 g, 38.90 mmol) in MeOH (100 mL, 780.04 mmol) is stirred for 30 mins at 50° C. under N$_2$. The reaction is cooled to RT, diluted with H$_2$O (100 mL) and extracted with EtOAc (3×100 mL). The organic extract is dried over anhydrous Na$_2$SO$_4$ and concentrated under reduced pressure. The crude product is purified by silica gel chromatography (PE:EtOAc=10:1 to 5:1) to give the title compound (1.55 g, 27.7%) as a light yellow solid. LC-MS: (ES+H, m/z):[M+H]+=173.10

Preparation 67d

3-(3-(Trifluoromethyl)bicyclo[1.1.1]pentan-1-yl)isoxazol-5-amine

A mixture of 3-oxo-3-[3-(trifluoromethyl)bicyclo[1.1.1]pentan-1-yl]propanenitrile (280.00 mg, 1.38 mmol), hydroxylamine HCl (105.35 mg, 1.52 mmol) and H$_2$O (10 mL) is added NaOH (110.25 mg, 2.76 mmol) in portions at RT under N$_2$. The resulting mixture is heated to 100° C. for 1 hr. The mixture is allowed to cool to RT and is extracted with DCM (3×50 mL). The combined organic extracts are washed with brine, dried over anhydrous Na$_2$SO$_4$, filtered, and concentrated under reduced pressure. The resulting solid is triturated with Et$_2$O (10 mL). The resulting solids are collected by filtration and washed with Et$_2$O to give the title compound (220 mg, 73%). ES/MS m/z (M+H) 219.2.

Preparation 68

5-(3,3-Difluoro-2-methylbutan-2-yl)-1,2-oxazol-3-amine

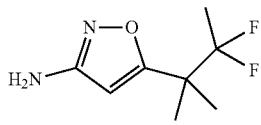

The crude solution of (Z)-5,5-difluoro-N'-hydroxy-4,4-dimethyl-3-oxohexanimidamide is acidified to pH=1 with HCl (c) and the resulting mixture is stirred for 1 hr at 100° C. under $N_2$. The mixture is slowly cooled to RT and concentrated under reduced pressure. The residue is purified by reversed combi-flash chromatography with the following conditions: Column, C18; mobile phase, ACN in $H_2O$ eluting with a 30% to 50% gradient in 20 min; UV 220 nm to give the title compound (230 mg, 14%) as a yellow solid. ES/MS (m/z) 191.2 (M+H).

Preparation 69

3-(2-Chloro-4-fluorophenyl)-1,2-oxazol-5-amine

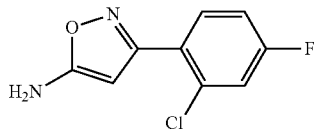

To a crude mixture of 3-(2-chloro-4-fluorophenyl)-3,2-oxopropanenitrile (2.8 g, 14 mmol) is added $NH_2OH.HCl$ (0.98 g, 14.17 mmol), KOAc (2.09 g, 21.30 mmol) and 1,4-dioxane (30.00 mL). The resulting mixture is stirred at 100° C. overnight. The mixture is allowed to cool to RT and diluted with $H_2O$ (30 mL) and EtOAc (30 mL). The mixture is extracted with EtOAc (3×30 mL). The combined organic extracts are dried over anhydrous $Na_2SO_4$, filtered, and concentrated under reduced pressure. The residue is purified by silica gel column chromatography eluting with a gradient of PE/EtOAc (9:1-2:1) to give the title compound (1.2 g, 39.83%) as a yellow solid. ES/MS (m/z) ($^{35}Cl/^{37}Cl$) 213.0/215.0 (M+H).

The following compound in Table 12 is prepared essentially as described for 3-(2-chloro-4-fluorophenyl)-1,2-oxazol-5-amine using the appropriate reagents, adjusting the reaction time to determine completion of the reaction, and purification conditions as appropriate. The reaction temperature can range from about 70° C. to 100° C. NaOAc can be substituted for KOAc and EtOH can be substituted for 1,4-dioxane.

TABLE 12

| Prep. No. | Chemical name | Structure | ES/MS (m/z) (M + H) |
|---|---|---|---|
| 70 | 3-(3-Bicyclo[1.1.1]pentanylmethyl)isoxazol-5-amine | 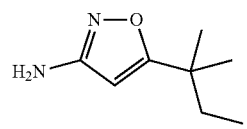 | 165.1 |

Preparation 71

5-(2-Methylbutan-2-yl)-1,2-oxazol-3-amine

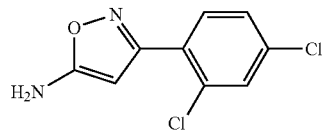 [SMILES: Nc1cc(-c2ccc(Cl)cc2Cl)no1]

To a stirred mixture of 4,4-dimethyl-3-oxohexanenitrile (3.00 g, 21.55 mmol) and hydroxylamine sulfate (3.89 g, 23.71 mmol) in MeOH (5.00 mL) and $H_2O$ (45 mL) is added $NaHCO_3$ (4.53 g, 53.88 mmol) in portions at RT under $N_2$. The resulting mixture is stirred for 5 hrs at 65° C. under $N_2$. The mixture is allowed to cool to RT. The mixture is acidified to pH 1 with HCl (c) and stirred for 20 min at 130° C. under $N_2$. The mixture is allowed to cool to RT and the pH adjusted to 8 with NaOH. The resulting mixture is extracted with DCM (3×200 mL). The combined organic extracts are washed with saturated aqueous NaCl solution (2×200 mL), dried over anhydrous $Na_2SO_4$, filtered, and concentrated under reduced pressure. The residue is purified by reverse phase combi-flash chromatography with the following conditions: Column, C18; mobile phase, ACN in $H_2O$ (0.1% $NH_4HCO_3$), eluting with a 30% to 40% gradient in 10 min; UV 220 nm, to give the title compound (1.2 g, 36%) as a light yellow solid. $^1H$ NMR (CDCl$_3$) δ5.53 (s, 1H), 1.66 (q, 2H), 1.27 (s, 6H), 0.82 (t, 3H).

Preparation 72

3-(2,4-Dichlorophenyl)-1,2-oxazol-5-amine

A solution of $NH_2OH.HCl$ (535.66 mg, 7.71 mmol) and KOAc (756.53 mg, 7.71 mmol) in MeOH (10.00 mL) is stirred for 1 hr at RT under $N_2$. To the mixture is added 3-(2,4-dichlorophenyl)-3-oxopropanenitrile (550.00 mg, 2.57 mmol) and the reaction is stirred for an additional 1 hr at RT. The resulting mixture is filtered, the filter cake is washed with MeOH (3×20 mL), and the filtrate is concentrated under reduced pressure. The residue is diluted with $H_2O$ (30 mL) and the precipitated solids are collected by filtration, washed with H$_2$O (3×20 mL), and dried under reduced pressure to give the title compound (200 mg, 35.0%) as a yellow solid. ES/MS m/z ($^{35}$Cl/$^{37}$Cl) 229.0/231.0 (M+H).

Preparation 72a 5-(2,5-Dimethyl-1H-pyrrol-1-yl)-3-(1,1,1-trifluoro-2-methylpropan-2-yl)-1H-pyrazole

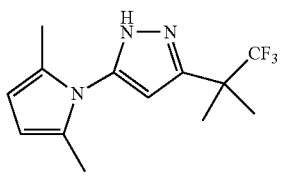 [SMILES: Cc1ccc(C)n1-c1cc(C(C)(C)C(F)(F)F)n[nH]1]

A solution of 3-(1,1,1-trifluoro-2-methylpropan-2-yl)-1H-pyrazol-5-amine (500.0 mg, 2.59 mmol), hexane-2,5-dione (886.3 mg, 7.77 mmol) and HOAc (15.5 mg, 0.26 mmol) in toluene (10.00 mL) is stirred for 2 hr at 100° C. under N$_2$. The mixture is concentrated under reduced pressure. The residue is purified by reversed Combi-flash chromatography eluting with the following conditions: Column, C18 gel eluting with a gradient of 30% to 50% ACN in H$_2$O (0.1% FA) over 10 min; UV 254 nm to give the title compound (610 mg, 87%) as a yellow solid. ES/MS m/z (M+H) 272.1.

Preparation 72b 3-(2,5-Dimethyl-1H-pyrrol-1-yl)-1-methyl-5-(1,1,1-trifluoro-2-methylpropan-2-yl)-1H-pyrazole

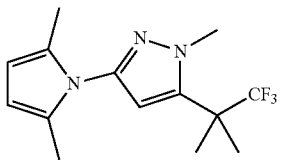 [SMILES: Cc1ccc(C)n1-c1cc(C(C)(C)C(F)(F)F)n(C)n1]

A solution of 5-(2,5-dimethyl-1H-pyrrol-1-yl)-3-(1,1,1-trifluoro-2-methylpropan-2-yl)-1H-pyrazole (500.0 mg, 1.84 mmol), MeI (1046.4 mg, 7.37 mmol) and K$_2$CO$_3$ (509.4 mg, 3.69 mmol) in ACN (10.00 mL) is stirred for 4 hr at 80° C. under N$_2$. The mixture is concentrated under reduced pressure. The residue is purified by Prep-TLC eluting with 5:1 PE/EtOAc, 254 nm to give the title compound (95 mg, 18%) as a white solid. ES/MS m/z (M+H) 286.2.

Preparation 72c

1-Methyl-5-(1,1,1-trifluoro-2-methylpropan-2-yl)-1H-pyrazol-3-amine

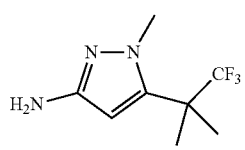

A solution of KOH (53.1 mg, 0.95 mmol) in EtOH (1.00 mL) and H$_2$O (1.00 mL) is added to a solution of hydroxylamine HCl (131.5 mg, 1.89 mmol) in EtOH (2.00 mL). 3-(2,5-Dimethyl-1H-pyrrol-1-yl)-1-methyl-5-(1,1,1-trifluoro-2-methylpropan-2-yl)-1H-pyrazole (90.0 mg, 0.32 mmol) is added and the mixture is stirred for 4 hr at 100° C. under N$_2$. The mixture is concentrated under reduced pressure. The residue is purified by reversed Combi-flash chromatography with the following conditions: Column, C18 gel eluting with a gradient of 10% to 30% ACN in H$_2$O (0.1% FA) over 10 min; UV 254 nm to give the title compound (45 mg, 68%) as a white solid. ES/MS m/z (M+H) 208.1.

Preparation 73

Tert-Butyl N-[4-cyano-5-[6-[2-[[5-(1,1-dimethylpropyl)isoxazol-3-yl]amino]-1-methyl-2-oxo-ethyl]-3-pyridyl]-2-isopropyl-pyrazol-3-yl]carbamate

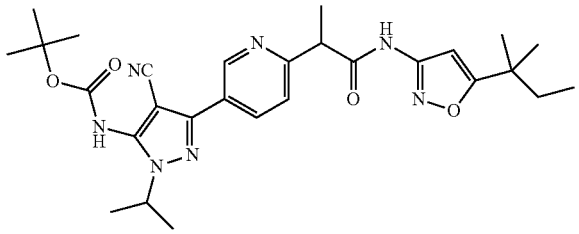 [SMILES: CCC(C)(C)c1cc(NC(=O)C(C)c2ccc(-c3nn(C(C)C)c(NC(=O)OC(C)(C)C)c3C#N)cn2)no1]

To a suspension of lithium; 2-[5-[5-(tert-butoxycarbonylamino)-4-cyano-1-isopropyl-pyrazol-3-yl]-2-pyridyl]propanoate (300 mg, 0.740 mmol) in pyridine (1.85 mL) under N$_2$ is added MeTHF (1.85 mL), 5-(1,1-dimethylpropyl)isoxazol-3-amine (171 mg, 1.11 mmol) then T3P® solution in MeTHF (50%, 1413 mg, 2.22 mmol). The reaction mixture is stirred at RT overnight and then poured into a saturated aqueous solution of NH$_4$Cl. The aqueous layer is extracted with EtOAc (2×). The combined organic extracts are washed with saturated aqueous NaCl solution, dried over Na$_2$SO$_4$, filtered, and concentrated under reduced pressure. The crude material is purified by silica gel flash chromatography eluting with a gradient of acetone in DCM from 1 to 10% to give the title compound (181.3 mg, 43%). $^1$H NMR (d$^6$-DMSO) δ11.17 (s, 1H), 9.91 (s, 1H), 8.92 (d, J=2.3 Hz, 1H), 8.16 (dd, J=8.2, 2.4 Hz, 1H), 7.60 (d, J=8.2 Hz, 1H), 6.61 (s, 1H), 4.58 (p, J=6.5 Hz, 1H), 4.16 (q, J=6.9 Hz, 1H), 1.61 (q, J=7.5 Hz, 2H), 1.50 (d, J=8.4 Hz, 13H), 1.41 (d, J=6.6 Hz, 7H), 1.24 (s, 7H), 1.08 (s, 1H), 0.73 (t, J=7.5 Hz, 3H).

The following compounds in Table 13 are prepared essentially as described for tert-butyl N-[4-cyano-5-[6-[2-[[5-(1,1-dimethylpropyl)isoxazol-3-yl]amino]-1-methyl-2-oxo-ethyl]-3-pyridyl]-2-isopropyl-pyrazol-3-yl]carbamate adjusting the reaction time to determine completion of the reaction and using appropriate chromatography conditions for purification.

TABLE 13

| Prep. No. | Chemical name | Structure | ES/MS (m/z) (M + H) |
|---|---|---|---|
| 74 | tert-Butyl N-[4-cyano-2-isopropyl-5-[6-[1-methyl-2-oxo-2-[[5-(2,2,2-trifluoro-1,1-dimethyl-ethyl)isoxazol-3-yl]amino]ethyl]-3-pyridyl]pyrazol-3-yl]carbamate | 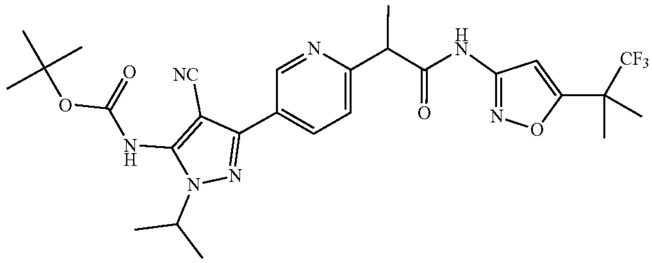 [SMILES: CC(C(=O)Nc1cc(C(C)(C)C(F)(F)F)on1)c1ccc(-c2nn(C(C)C)c(NC(=O)OC(C)(C)C)c2C#N)cn1] | 576 |
| 75 | tert-Butyl N-[4-cyano-2-isopropyl-5-[6-[1-methyl-2-oxo-2-[[3-(2,2,2-trifluoro-1,1-dimethyl-ethyl)isoxazol-5-yl]amino]ethyl]-3-pyridyl]pyrazol-3-yl]carbamate | 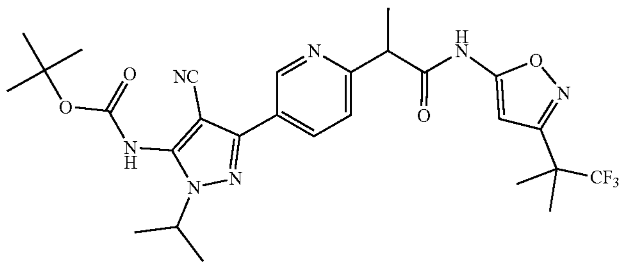 [SMILES: CC(C(=O)Nc1cc(C(C)(C)C(F)(F)F)no1)c1ccc(-c2nn(C(C)C)c(NC(=O)OC(C)(C)C)c2C#N)cn1] | a |
| 76 | tert-Butyl N-[4-cyano-5-[6-[2-[[3-(2,2-dimethylpropyl)isoxazol-5-yl]amino]-1-methyl-2-oxo-ethyl]-3-pyridyl]-2-isopropyl-pyrazol-3-yl]carbamate | 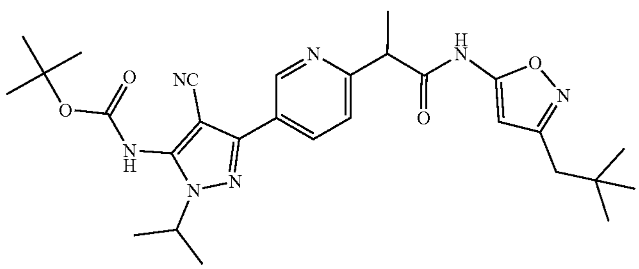 [SMILES: CC(C(=O)Nc1cc(CC(C)(C)C)no1)c1ccc(-c2nn(C(C)C)c(NC(=O)OC(C)(C)C)c2C#N)cn1] | b |
| 77 | tert-Butyl N-[4-cyano-5-[6-[2-[[5-(2,2-dimethylpropyl)isoxazol-3-yl]amino]-1-methyl-2-oxo-ethyl]-3-pyridyl]-2-isopropyl-pyrazol-3-yl]carbamate | 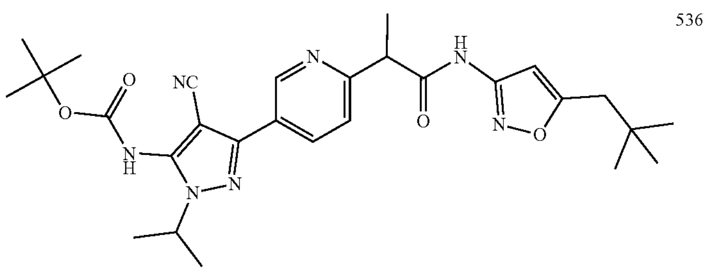 | 536 |
| 78 | tert-Butyl N-[4-cyano-5-[6-[2-[[3-(2,4-dichlorophenyl)isoxazol-5-yl]amino]-1-methyl-2-oxo-ethyl]-3-pyridyl]-2-isopropyl-pyrazol-3-yl]carbamate | 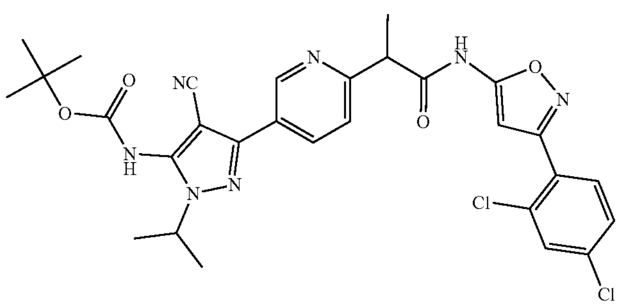 [SMILES: CC(C(=O)Nc1cc(-c2ccc(Cl)cc2Cl)no1)c1ccc(-c2nn(C(C)C)c(NC(=O)OC(C)(C)C)c2C#N)cn1] | c |

TABLE 13-continued

| Prep. No. | Chemical name | Structure | ES/MS (m/z) (M + H) |
|---|---|---|---|
| 79 | tert-Butyl N-[4-cyano-5-[6-[2-[[3-(1,1-dimethylpropyl)isoxazol-5-yl]amino]-1-methyl-2-oxo-ethyl]-2-pyridyl]-2-isopropyl-pyrazol-3-yl]carbamate | 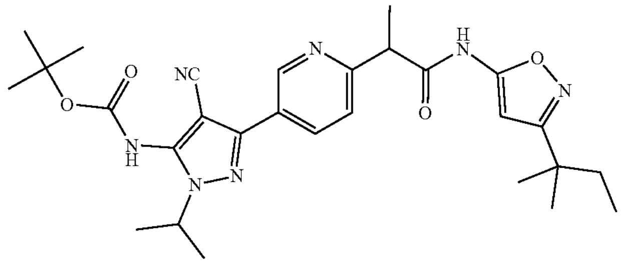 [SMILES: CCC(C)(C)c1cc(NC(=O)C(C)c2ccc(-c3nn(C(C)C)c(NC(=O)OC(C)(C)C)c3C#N)cn2)on1] | |

[a] 1H NMR (400 MHz, d6-DMSO) δ 8.95-8.90 (m, 1H), 8.58 (dd, J = 5.8, 1.6 Hz, 1H), 8.17 (dd, J = 8.2, 2.4 Hz, 1H), 7.60 (d, J = 8.2 Hz, 1H), 7.39 (ddd, J = 7.6, 4.3, 1.5 Hz, 1H), 6.38 (s, 1H), 4.58 (p, J = 6.5 Hz, 1H), 4.17 (q, J =7.0 Hz, 1H), 1.55-1.46 (m, 20H), 1.41 (d, J = 6.6 Hz, 8H).
[b] 1H NMR (400 MHz, d6-DMSO) δ 11.76 (s, 1H), 9.91 (s, 1H), 8.93 (d, J = 2.4 Hz, 1H), 8.17 (dd, J = 8.2, 2.4 Hz, 1H), 7.60 (d, J = 8.2 Hz, 1H), 6.12 (s, 1H), 4.58 (p, J = 6.6 Hz, 1H), 4.15 (q, J = 7.0 Hz, 1H), 2.45 (s, 2H), 1.52-1.49 (m, 12H), 1.41 (d, J = 6.6 Hz, 6H), 0.93 (s, 9H).
[c] 2-[5-[5-(tert-Butoxycarbonylamino)-4-cyano-1-isopropyl-pyrazol-3-yl]-2-pyridyl]propanoic acid used instead of the lithium salt

Preparation 80

2-[4-(5-Amino-4-cyano-1-isopropylpyrazol-3-yl)phenyl]-N-[3-(2,2-dimethylpropyl)-1,2-oxazol-5-yl]propanamide

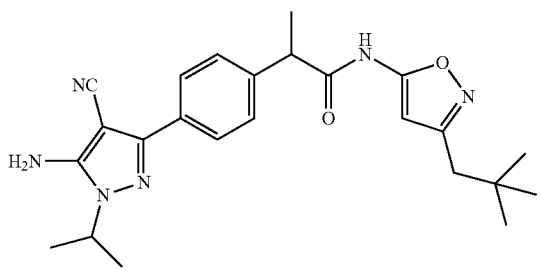 [SMILES: CC(C(=O)Nc1cc(CC(C)(C)C)no1)c1ccc(-c2nn(C(C)C)c(N)c2C#N)cc1]

To a mixture of 3-(2,2-dimethylpropyl)-1,2-oxazol-5-amine (62 mg, 0.402 mmol), 2-[4-(5-amino-4-cyano-1-isopropylpyrazol-3-yl)phenyl]propanoic acid (120 mg, 0.402 mmol), and NMI (99 mg, 1.206 mmol) in ACN (5.00 mL) is added TCFH (338 mg, 1.206 mmol). The resulting mixture is stirred at 50° C. for 2 hrs under $N_2$ and then concentrated under reduced pressure. The residue is purified by reverse Combi-flash chromatography with the following conditions: Column, C18; mobile phase, ACN in $H_2O$ (0.1% $NH_4CO_3$) and eluting with a gradient of 0% to 50% in 25 min; UV 254 nm to give the title compound (130 mg, 74.41%) as a white solid. ES/MS (m/z) 435.2 (M+H).

The following compounds in Table 14 are prepared essentially as described for 2-[4-(5-amino-4-cyano-1-isopropylpyrazol-3-yl)phenyl]-N-[3-(2,2-dimethylpropyl)-1,2-oxazol-5-yl]propanamide using the appropriate reagents, adjusting reaction time to determine completion of the reaction, and purification conditions as appropriate. The reaction temperature can range from about 50° C. to 80° C.

TABLE 14

| Prep. No. | Chemical name | Structure | ES/MS m/z (M + H) |
|---|---|---|---|
| 81 | 2-[6-(5-Amino-4-cyano-1-isopropylpyrazol-3-yl)pyridin-3-yl]-N-[3-(2,2-dimethylpropyl)-1,2-oxazol-5-yl]propanamide | 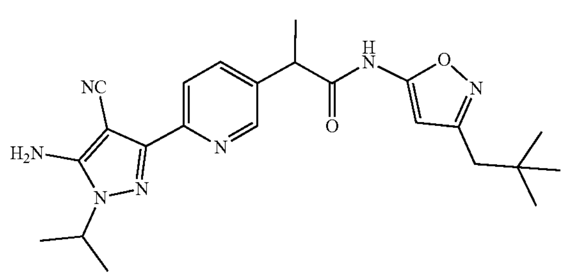 [SMILES: CC(C(=O)Nc1cc(CC(C)(C)C)no1)c1ccc(-c2nn(C(C)C)c(N)c2C#N)nc1] | 436.4 |

TABLE 14-continued

| Prep. No. | Chemical name | Structure | ES/MS m/z (M + H) |
|---|---|---|---|
| 82 | 2-[4-[5-Amino-4-cyano-1-(1-methylcyclopropyl)pyrazol-3-yl]phenyl]-N-[3-(2,2-dimethylpropyl)-1,2-oxazol-5-yl]propanamide | 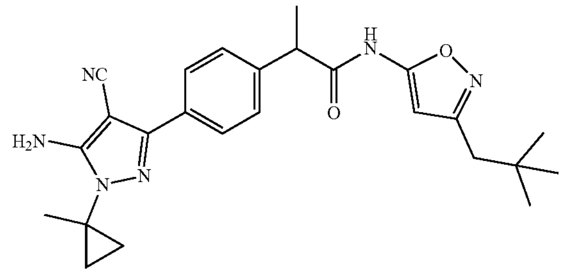 [SMILES: CC(C(=O)Nc1cc(CC(C)(C)C)no1)c1ccc(-c2nn(C3(C)CC3)c(N)c2C#N)cc1] | 477.3 |
| 83 | 2-(4-[5-Amino-4-cyano-1-[1,1,1-trifluoropropan-2-yl]pyrazol-3-yl]phenyl)-N-[3-(2,2-dimethylpropyl)-1,2-oxazol-5-yl]propanamide, Isomer 2 | 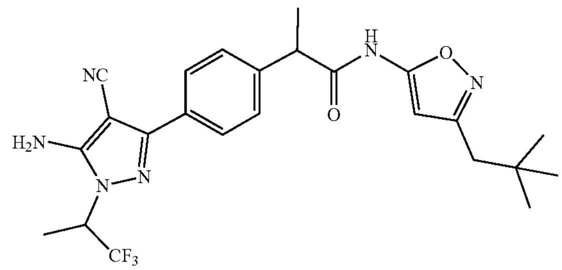 [SMILES: CC(C(=O)Nc1cc(CC(C)(C)C)no1)c1ccc(-c2nn(C(C)C(F)(F)F)c(N)c2C#N)cc1] | 489.1 |
| 84 | 2-[4-[5-Amino-4-cyano-1-(1,1,1-trifluoro-2-methylpropan-2-yl)pyrazol-3-yl]phenyl]-N-[3-(2,2-dimethylpropyl)-1,2-oxazol-5-yl]propanamide | 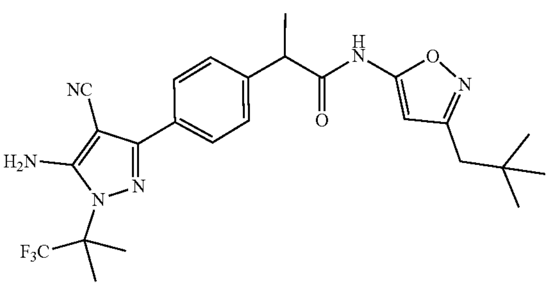 [SMILES: CC(C(=O)Nc1cc(CC(C)(C)C)no1)c1ccc(-c2nn(C(C)(C)C(F)(F)F)c(N)c2C#N)cc1] | 503.3 |
| 85 | 2-[4-(5-Amino-4-cyano-1-isopropylpyrazol-3-yl)phenyl]-N-[5-(4,4,4-trifluoro-2-methylbutan-2-yl)-1,2-oxazol-3-yl]propenamide | 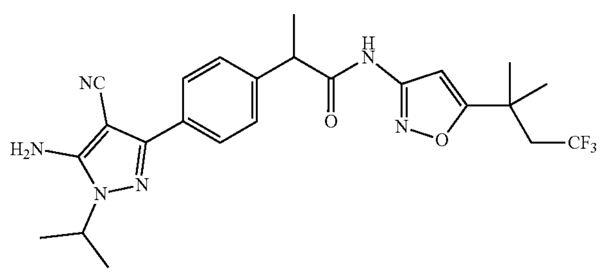 [SMILES: CC(C(=O)Nc1cc(C(C)(C)CC(F)(F)F)on1)c1ccc(-c2nn(C(C)C)c(N)c2C#N)cc1] | 489.2 |
| 86 | 2-[6-(5-Amino-4-cyano-1-isopropylpyrazol-3-yl)pyridin-3-yl]-N-[5-(1,1,1-trifluoro-2-methylpropan-2-yl)-1,2-oxazol-3-yl]propenamide | 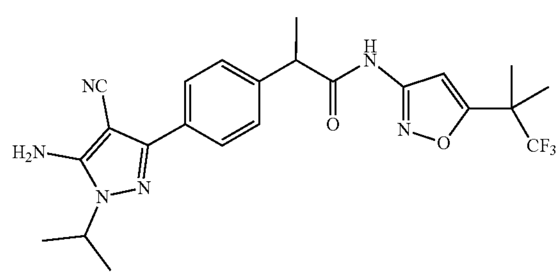 [SMILES: CC(C(=O)Nc1cc(C(C)(C)C(F)(F)F)on1)c1ccc(-c2nn(C(C)C)c(N)c2C#N)cc1] | 476.2 |

TABLE 14-continued

| Prep. No. | Chemical name | Structure | ES/MS m/z (M + H) |
|---|---|---|---|
| 87 | 2-[6-(5-Amino-4-cyano-1-isopropylpyrazol-3-yl)pyridin-3-yl]-N-[5-(2-methylbutan-2-yl)-1,2-oxazol-3-yl]propanamide | 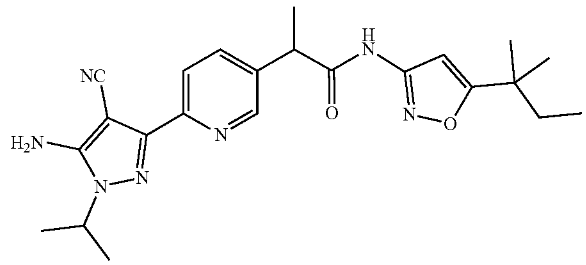 [SMILES: CCC(C)(C)c1cc(NC(=O)C(C)c2ccc(-c3nn(C(C)C)c(N)c3C#N)nc2)no1] | 436.2 |
| 88* | 2-[6-(5-Amino-4-cyano-1-isopropylpyrazol-3-yl)pyridin-3-yl]-N-[5-(4,4,4-trifluoro-2-methylbutan-2-yl)-1,2-oxazol-3-yl]propenamide | 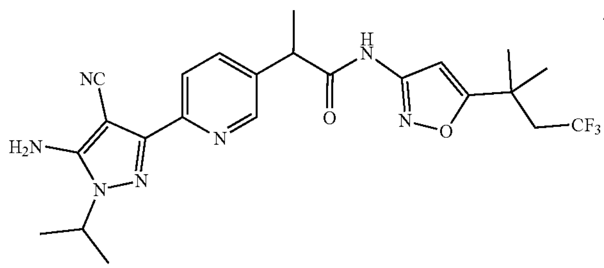 [SMILES: CC(C(=O)Nc1cc(C(C)(C)CC(F)(F)F)on1)c1ccc(-c2nn(C(C)C)c(N)c2C#N)nc1] | 490.2 |
| 89* | 2-(6-(5-Amino-4-cyano-1-isopropyl-1H-pyrazol-3-yl)pyridin-3-yl)-N-(3-(1,1,1-trifluoro-2-methylpropan-2-yl)isoxazol-5-yl)propenamide | 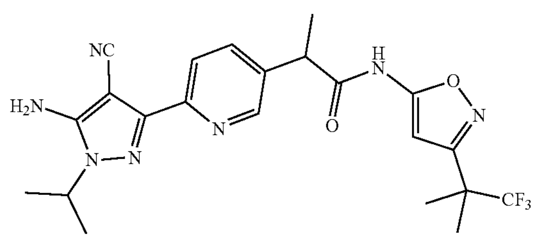 [SMILES: CC(C(=O)Nc1cc(C(C)(C)C(F)(F)F)no1)c1ccc(-c2nn(C(C)C)c(N)c2C#N)nc1] | 476.2 |
| 90 | 2-[6-(5-Amino-4-cyano-1-isopropylpyrazol-3-yl)pyridin-3-yl]-N-[3-(2,4-dichlorophenyl)-1,2-oxazol-5-yl]propenamide | 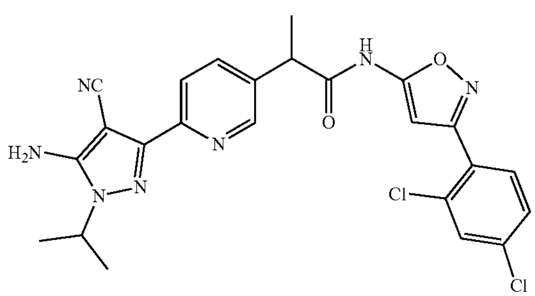 [SMILES: CC(C(=O)Nc1cc(-c2ccc(Cl)cc2Cl)no1)c1ccc(-c2nn(C(C)C)c(N)c2C#N)nc1] | 510.3, 512.3 |
| 91 | 2-(6-(5-Amino-4-cyano-1-isopropyl-1H-pyrazol-3-yl)pyridin-3-yl)-N-(3-(2-chloro-4-fluorophenyl)isoxazol-5-yl)propenamide | 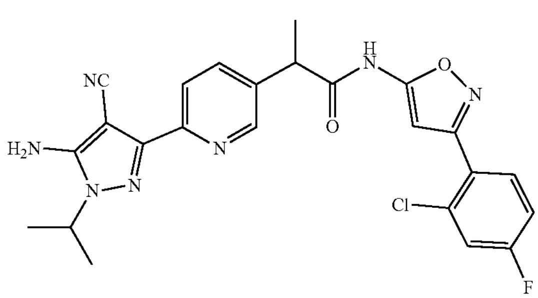 [SMILES: CC(C(=O)Nc1cc(-c2ccc(F)cc2Cl)no1)c1ccc(-c2nn(C(C)C)c(N)c2C#N)nc1] | 494.1, 496.1 |

TABLE 14-continued

| Prep. No. | Chemical name | Structure | ES/MS m/z (M + H) |
|---|---|---|---|
| 92 | 2-[4-(5-Amino-4-cyano-1-isopropylpyrazol-3-yl)phenyl]-N-[5-(2-methylbutan-2-yl)-1,2-oxazol-3-yl]propanamide | 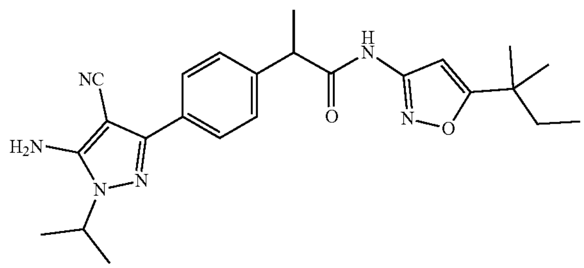 [SMILES: CCC(C)(C)c1cc(NC(=O)C(C)c2ccc(-c3nn(C(C)C)c(N)c3C#N)cc2)no1] | 435.2 |
| 93 | 2-[4-(5-Amino-4-cyano-1-isopropylpyrazol-3-yl)phenyl]-N-[3-(2,4-dichlorophenyl)-1,2-oxazol-5-yl]propenamide | 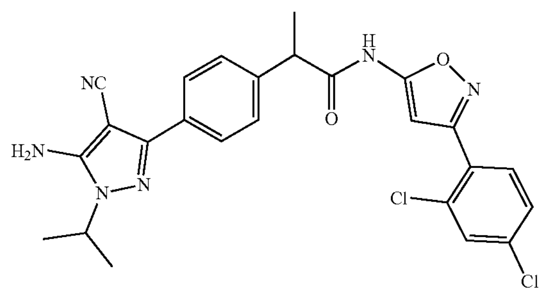 [SMILES: CC(C(=O)Nc1cc(-c2ccc(Cl)cc2Cl)no1)c1ccc(-c2nn(C(C)C)c(N)c2C#N)cc1] | 509.2, 511.2 |
| 94 | 2-[4-(5-Amino-4-cyano-1-isopropylpyrazol-3-yl)phenyl]-N-(5-tert-butyl-1,2-thiazol-3-yl)propenamide | 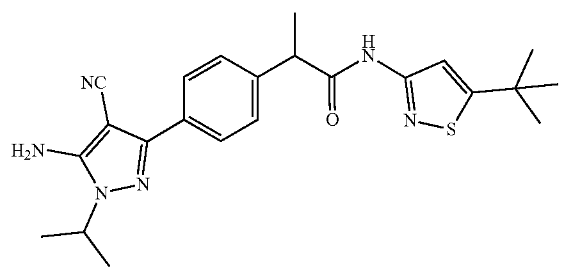 [SMILES: CC(C(=O)Nc1cc(C(C)(C)C)sn1)c1ccc(-c2nn(C(C)C)c(N)c2C#N)cc1] | 437.3 |
| 95 | 2-[4-(5-Amino-4-cyano-1-isopropylpyrazol-3-yl)phenyl]-N-[5-(1-methylcyclopropyl)-1,2-oxazol-3-yl]propanamide | 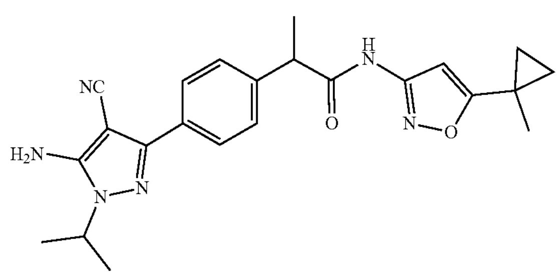 [SMILES: CC(C(=O)Nc1cc(C2(C)CC2)on1)c1ccc(-c2nn(C(C)C)c(N)c2C#N)cc1] | 419.2 |
| 96 | 2-[4-(5-Amino-4-cyano-1-isopropylpyrazol-3-yl)phenyl]-N-[3-(1-methylcyclopropyl)-1,2-oxazol-5-yl]propanamide | 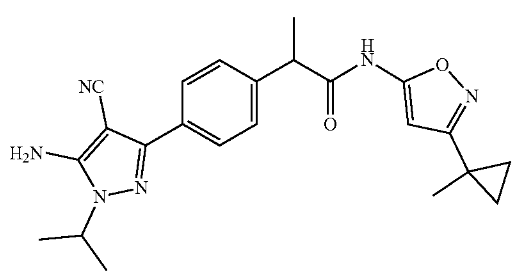 [SMILES: CC(C(=O)Nc1cc(C2(C)CC2)no1)c1ccc(-c2nn(C(C)C)c(N)c2C#N)cc1] | 419.2 |

TABLE 14-continued

| Prep. No. | Chemical name | Structure | ES/MS m/z (M + H) |
|---|---|---|---|
| 96a | 2-[4-[5-Amino-4-cyano-1-(2,2,2-trideuterio-1-methyl-ethyl)pyrazol-3-yl]phenyl]-N-[3-(2,2-dimethylpropyl)isoxazol-5-yl]propanamide | 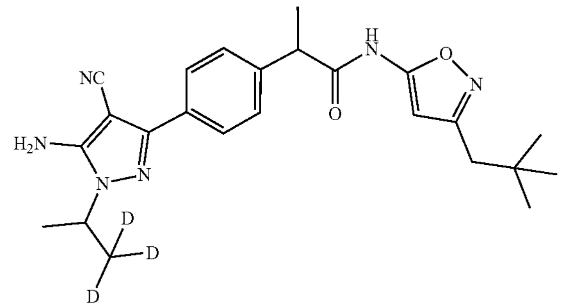 [SMILES: [2H]C([2H])([2H])C(C)n1nc(-c2ccc(C(C)C(=O)Nc3cc(CC(C)(C)C)no3)cc2)c(C#N)c1N] | 438.3 |
| 96b | 2-[4-[5-Amino-4-cyano-1-[2,2,2-trideuterio-1-(trideuteriomethyl)ethyl]pyrazol-3-yl]phenyl]-N-[3-(2,2-dimethylpropyl)isoxazol-5-yl]propanamide | 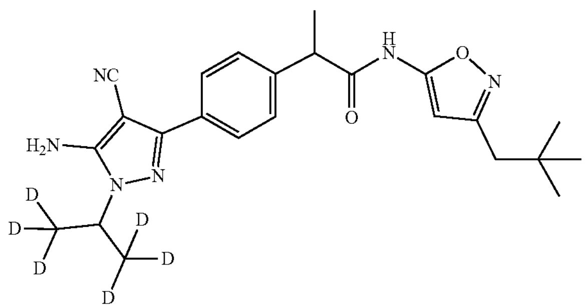 [SMILES: [2H]C([2H])([2H])C(n1nc(-c2ccc(C(C)C(=O)Nc3cc(CC(C)(C)C)no3)cc2)c(C#N)c1N)C([2H])([2H])[2H]] | 441.4 |
| 96c | 2-[4-[5-Amino-4-cyano-1-(1,2,2,2-tetradeuterio-1-methyl-ethyl)pyrazol-3-yl]phenyl]-N-[3-(2,2-dimethylpropyl)isoxazol-5-yl]propanamide | 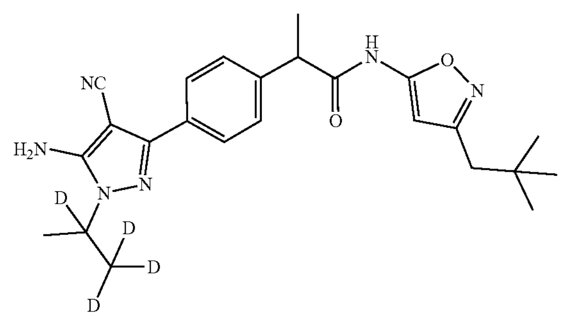 [SMILES: [2H]C([2H])([2H])C([2H])(C)n1nc(-c2ccc(C(C)C(=O)Nc3cc(CC(C)(C)C)no3)cc2)c(C#N)c1N] | 439.3 |
| 96d | 2-[4-[5-Amino-4-cyano-1-[1,2,2,2-tetradeuterio-1-(trideuteriomethyl)ethyl]pyrazol-3-yl]phenyl]-N-[3-(2,2-dimethylpropyl)isoxazol-5-yl]propanamide | 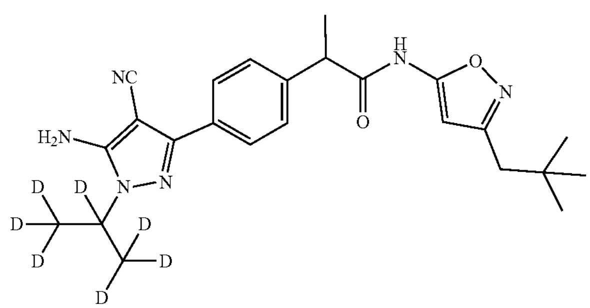 [SMILES: [2H]C([2H])([2H])C([2H])(n1nc(-c2ccc(C(C)C(=O)Nc3cc(CC(C)(C)C)no3)cc2)c(C#N)c1N)C([2H])([2H])[2H]] | 442.3 |
| 96e | 2-(4-[5-Amino-4-cyano-1-[1,1-difluoropropan-2-yl]pyrazol-3-yl]phenyl)-N-[3-(2,2-dimethylpropyl)-1,2-oxazol-5-yl]propanamide, Isomer 1 | 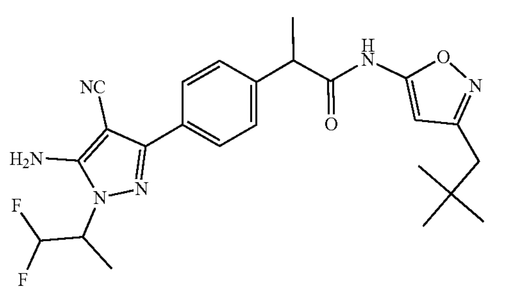 [SMILES: CC(C(=O)Nc1cc(CC(C)(C)C)no1)c1ccc(-c2nn(C(C)C(F)F)c(N)c2C#N)cc1] | 471.3 |

TABLE 14-continued

| Prep. No. | Chemical name | Structure | ES/MS m/z (M + H) |
|---|---|---|---|
| 96f | 2-(4-[5-Amino-4-cyano-1-[1,1-difluoropropan-2-yl]pyrazol-3-yl]phenyl)-N-[3-(2,2-dimethylpropyl)-1,2-oxazol-5-yl]propanamide, Isomer 2 | 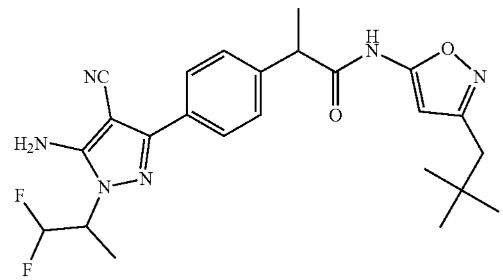 [SMILES: CC(C(=O)Nc1cc(CC(C)(C)C)no1)c1ccc(-c2nn(C(C)C(F)F)c(N)c2C#N)cc1] | 471.3 |
| 96g | 2-[4-[5-Amino-4-cyano-1-[2,2,2-trifluoro-1-(trideuteriomethyl)ethyl]pyrazol-3-yl]phenyl]-N-[3-(2,2-dimethylpropyl)isoxazol-5-yl]propanamide, Isomer 1 | 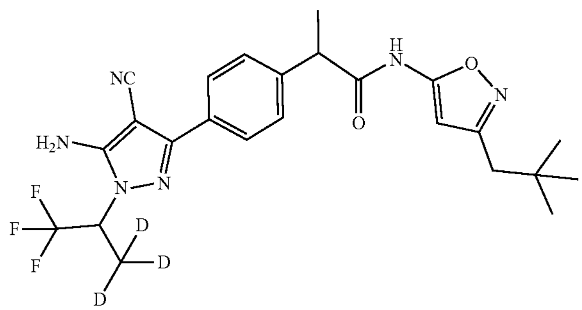 [SMILES: [2H]C([2H])([2H])C(n1nc(-c2ccc(C(C)C(=O)Nc3cc(CC(C)(C)C)no3)cc2)c(C#N)c1N)C(F)(F)F] | 492.2 |
| 96h | 2-[4-[5-Amino-4-cyano-1-[2,2,2-trifluoro-1-(trideuteriomethyl)ethyl]pyrazol-3-yl]phenyl]-N-[3-(2,2-dimethylpropyl)isoxazol-5-yl]propanamide, Isomer 2 | 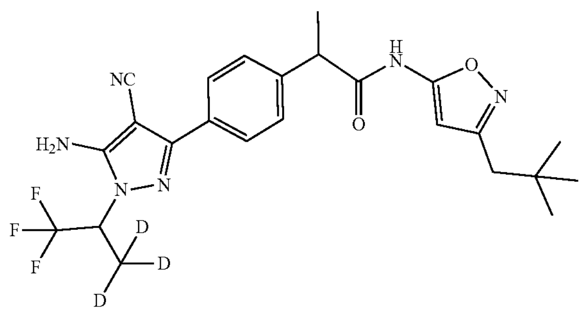 [SMILES: [2H]C([2H])([2H])C(n1nc(-c2ccc(C(C)C(=O)Nc3cc(CC(C)(C)C)no3)cc2)c(C#N)c1N)C(F)(F)F] | 492.1 |
| 96i | 2-[4-(5-Amino-4-cyano-1-isopropylpyrazol-3-yl)phenyl]-N-[3-(2,2-dimethylpropyl)-4-fluoro-1,2-oxazol-5-yl]propanamide | 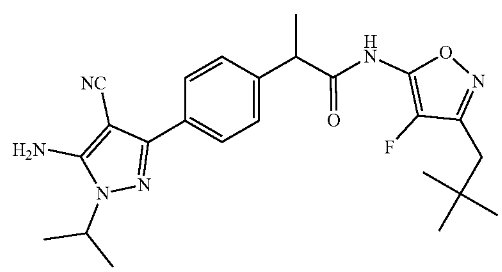 [SMILES: CC(C(=O)Nc1onc(CC(C)(C)C)c1F)c1ccc(-c2nn(C(C)C)c(N)c2C#N)cc1] | 453.3 |
| 96j | 2-[4-[5-Amino-4-cyano-1-(2-deuterio-2,2-difluoro-1-methyl-ethyl)pyrazol-3-yl]phenyl]-N-[3-(2,2-dimethylpropyl)isoxazol-5-yl]propanamide, Isomer 1 | 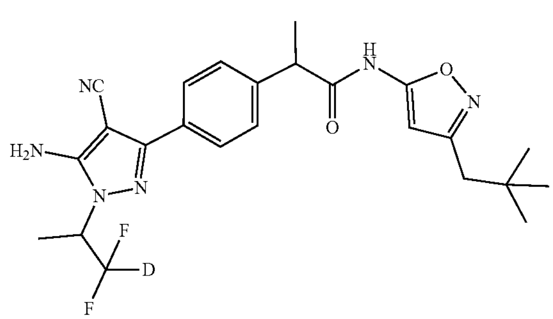 [SMILES: [2H]C(F)(F)C(C)n1nc(-c2ccc(C(C)C(=O)Nc3cc(CC(C)(C)C)no3)cc2)c(C#N)c1N] | 472.1 |

TABLE 14-continued

| Prep. No. | Chemical name | Structure | ES/MS m/z (M + H) |
|---|---|---|---|
| 96k | 2-[4-[5-Amino-4-cyano-1-(2-deuterio-2,2-difluoro-1-methyl-ethyl)pyrazol-3-yl]phenyl]-N-[3-(2,2-dimethylpropyl)isoxazol-5-yl]propanamide, Isomer 2 | 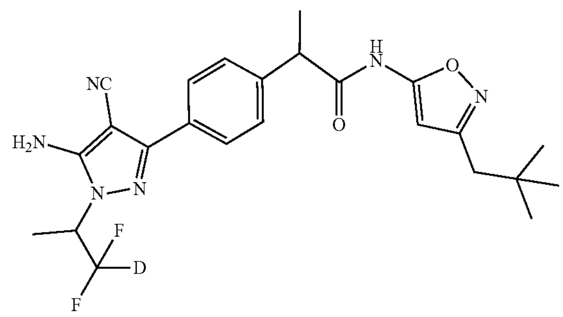 [SMILES: [2H]C(F)(F)C(C)n1nc(-c2ccc(C(C)C(=O)Nc3cc(CC(C)(C)C)no3)cc2)c(C#N)c1N] | 472.3 |

*4Å molecular sieves added to reaction

Alternate Preparation 82

2-[4-[5-Amino-4-cyano-1-(1-methylcyclopropyl)pyrazol-3-yl]phenyl]-N-[3-(2,2-dimethylpropyl)-1,2-oxazol-5-yl]propanamide

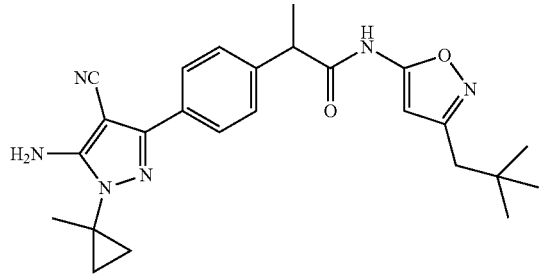 [SMILES: CC(C(=O)Nc1cc(CC(C)(C)C)no1)c1ccc(-c2nn(C3(C)CC3)c(N)c2C#N)cc1]

To a stirred mixture of 2-[4-[5-amino-4-cyano-1-(1-methylcyclopropyl)pyrazol-3-yl]phenyl]propanoic acid (220 mg, 0.71 mmol) and 3-(2,2-dimethylpropyl)-1,2-oxazol-5-amine (131 mg, 0.85 mmol) in ACN (3.00 mL) is added NMI (291 mg, 3.54 mmol) and TCFH (995 mg, 3.54 mmol). The mixture is stirred for 3 hr at 50° C. The mixture is purified by reversed Combi-flash chromatography with following conditions: C18; eluting with a gradient of 50% to 80% ACN in H₂O (0.1% FA) to give the title compound (200 mg, 63.1%) as an off-white solid. ES/MS (m/z) 447.3 (M+H).

Preparation 96l

2-[4-[5-Amino-4-cyano-1-(1-methylcyclopropyl)pyrazol-3-yl]phenyl]-N-(3-[3-methylbicyclo[1.1.1]pentan-1-yl]-1,2-oxazol-5-yl)propanamide

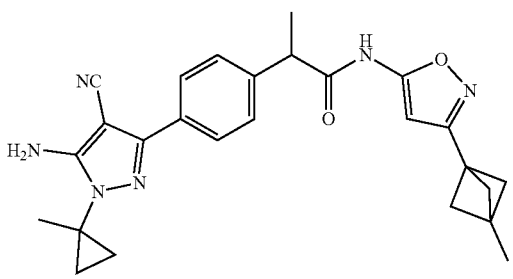 [SMILES: CC(C(=O)Nc1cc(C23CC(C)(C2)C3)no1)c1ccc(-c2nn(C3(C)CC3)c(N)c2C#N)cc1]

To a stirred mixture of 2-[4-[5-amino-4-cyano-1-(1-methylcyclopropyl)pyrazol-3-yl]phenyl]propanoic acid (150 mg, 0.48 mmol) and 3-[3-methylbicyclo[1.1.1]pentan-1-yl]-1,2-oxazol-5-amine (79.36 mg, 0.48 mmol) in ACN (5.00 mL) is added NMI (119.05 mg, 1.45 mmol) and TCFH (271.22 mg, 0.97 mmol) in portions at RT under N₂. The mixture is stirred for 2 hr at 50° C. under N₂. The mixture is allowed to cool to RT and concentrated under reduced pressure. The residue is purified by silica gel column chromatography, eluting with PE/EtOAc (3/1 to 2/1) to give the title compound (130 mg, 58.9%) as an off-white solid. ES/MS (m/z) 457.2 (M+H).

Preparation 96m

2-[4-[5-Amino-4-cyano-1-(1-methylcyclopropyl)pyrazol-3-yl]-3-fluorophenyl]-N-(3-[3-methylbicyclo[1.1.1]pentan-1-yl]-1,2-oxazol-5-yl)propanamide

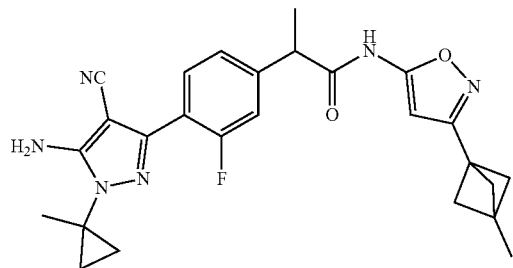 [SMILES: CC(C(=O)Nc1cc(C23CC(C)(C2)C3)no1)c1ccc(-c2nn(C3(C)CC3)c(N)c2C#N)c(F)c1]

To a solution of 2-[4-[5-amino-4-cyano-1-(1-methylcyclopropyl)pyrazol-3-yl]-3-fluorophenyl]propanoic acid (150 mg, 0.46 mmol), 3-[3-methylbicyclo[1.1.1]pentan-1-yl]-1,2-oxazol-5-amine (90.02 mg, 0.55 mmol) and NMI (112.52 mg, 1.37 mmol) in ACN (5.00 mL) is added TCFH (192.27 mg, 0.68 mmol). The reaction is stirred for 1 hr at 50° C. The mixture is allowed to cool to RT and concentrated under reduced pressure. The residue is purified by reversed Combi-flash chromatography with the following conditions: Column, C18; eluting with a gradient of 20% to 40% ACN in $H_2O$ (0.1% $NH_4HCO_3$) to give the title compound (110 mg, 50.74%) as a white solid. ES/MS (m/z) 475.1 (M+H).

Preparation 96n

2-[4-(5-Amino-4-cyano-1-isopropylpyrazol-3-yl)phenyl]-N-[3-[3-(trifluoromethyl)bicyclo[1.1.1]pentan-1-yl]-1,2-oxazol-5-yl]propanamide

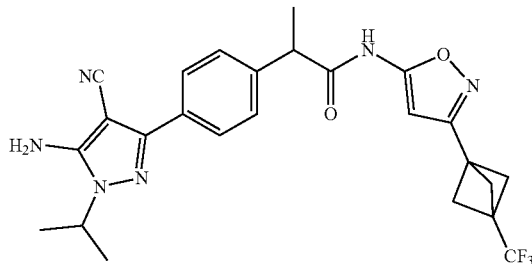 [SMILES: CC(C(=O)Nc1cc(C23CC(C(F)(F)F)(C2)C3)no1)c1ccc(-c2nn(C(C)C)c(N)c2C#N)cc1]

To a solution of 2-[4-(5-amino-4-cyano-1-isopropylpyrazol-3-yl)phenyl]propanoic acid (300 mg, 1.01 mmol), 3-[3-(trifluoromethyl)bicyclo[1.1.1]pentan-1-yl]-1,2-oxazol-5-amine (264 mg, 1.21 mmol) and NMI (248 mg, 3.02 mmol) in ACN (20 mL), TCFH (1.41 g, 5.03 mmol) is added and the mixture is stirred for 1 hr at 50° C. under $N_2$ in a sealed tube. The mixture is cooled to RT and concentrated under reduced pressure. The residue is purified by reserved phase Combi-flash chromatography with the following condition: Column, C18, eluting with a gradient of 10% to 50% ACN in $H_2O$ (0.1% $NH_4HCO_3$) to give the title compound (250 mg, 49.9%) as light brown solid. ES/MS (m/z) 499.10 (M+H).

Preparation 96o

2-[4-[5-Amino-4-cyano-1-[2,2,2-trideuterio-1-(trideuteriomethyl)ethyl]pyrazol-3-yl]phenyl]-N-[3-(2,2-dimethylpropyl)-4-fluoro-isoxazol-5-yl]propanamide

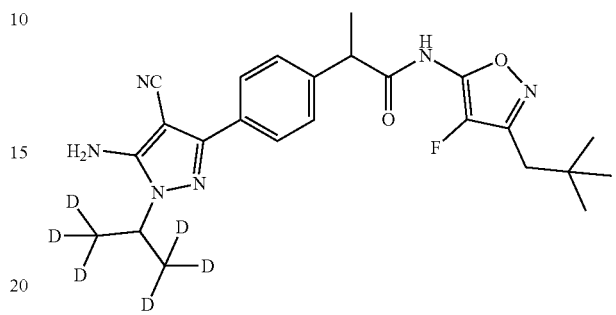

To a stirred solution of 2-[4-[5-amino-4-cyano-1-[2,2,2-trideuterio-1-(trideuteriomethyl)ethyl]pyrazol-3-yl]phenyl]propanoic acid (700 mg, 2.30 mmol) and 3-(2,2-dimethylpropyl)-4-fluoro-1,2-oxazol-5-amine (435.62 mg, 2.53 mmol) in ACN (5.00 mL) is added NMI (1.89 g, 22.99 mmol) and TCFH (6.45 g, 22.99 mmol) dropwise at RT under $N_2$. The mixture is stirred for 3 hrs at 50° C. under $N_2$. The mixture is concentrated under reduced pressure. The residue is purified by silica gel column chromatography, eluting with PE:EtOAc (3:2-1:1) to give the title compound (400 mg, 39.93%) as an off-white solid. ES/MS (m/z) 459.2 (M+H).

Preparation 97

2-[4-(5-Amino-4-cyano-1-isopropyl-pyrazol-3-yl)phenyl]-N-[3-(3-bicyclo[1.1.1]pentanylmethyl)isoxazol-5-yl]propanamide, Isomer 1

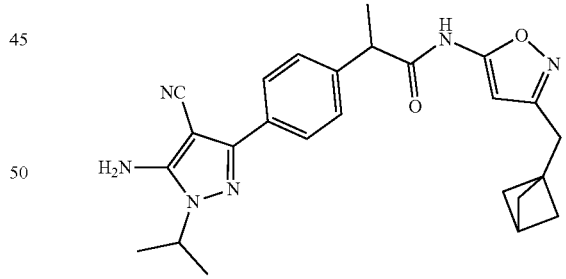

T3P® (250 μL, 0.427 mmol, 50% solution in EtOAc) is added dropwise to a stirring solution of 2-[4-(5-amino-4-cyano-1-isopropylpyrazol-3-yl)phenyl]propanoic acid, Isomer 1 (51 mg, 0.171 mmol), 3-(3-bicyclo[1.1.1]pentanylmethyl)isoxazol-5-amine (28.1 mg, 0.171 mmol) and pyridine (27.7 μL, 0.342 mmol) in EtOAc (2 mL, 0.1 M). The reaction is stirred at RT for 18 hrs. The reaction mixture is partitioned between EtOAc (5 mL) and saturated aqueous NaCl solution (5 mL). The organic layer is isolated and concentrated to dryness. The crude product is purified by C18 HPLC eluting with $H_2O$:ACN (5-95%) with 0.1% TFA to give the title compound as a salt. The free base of the desired product is formed by eluting the desired product through a cartridge of carbonate resin to give the title compound (10 mg, 0.0225 mmol, 13%). ES/MS (m/z) 445.2 (M+H).

Preparation 98

2-(6-[5-Amino-4-cyano-1-[1,1,1-trifluoropropan-2-yl]pyrazol-3-yl]pyridin-3-yl)-N-[3-(2-chloro-4-fluorophenyl)-1,2-oxazol-5-yl]propanamide, Isomer 2

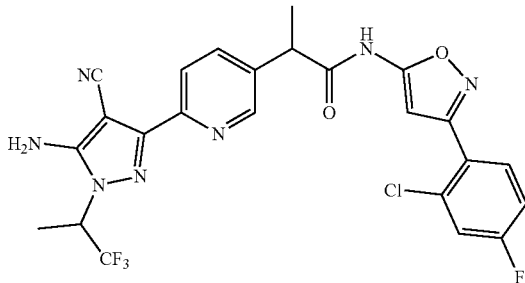 [SMILES: CC(C(=O)Nc1cc(-c2ccc(F)cc2Cl)no1)c1ccc(-c2nn(C(C)C(F)(F)F)c(N)c2C#N)nc1]

To a solution of 2-(6-[5-amino-4-cyano-1-[1,1,1-trifluoropropan-2-yl]pyrazol-3-yl]pyridin-3-yl)propanoic acid, Isomer 2 (200 mg, 0.57 mmol), 3-(2-chloro-4-fluorophenyl)-1,2-oxazol-5-amine (180 mg, 0.84 mmol), and DIPEA (273 mg, 2.11 mmol) in DCM (15 mL) is added T3P® (2.24 g, 3.52 mmol, 50% in EtOAc) and the mixture is stirred overnight at 50° C. The reaction is cooled to RT and concentrated under reduced pressure. The residue is purified by reversed phase Combi-flash with the following conditions: Column, C18; mobile phase, ACN in H₂O (0.1% NH₄CO₃) eluting with a gradient of 10% to 50% in 10 min; UV 254 nm to give the title compound (100 mg, 32.2%) as an off-white solid. ES/MS (m/z) 548.10 (M+H).

The following compounds in Table 15 are prepared essentially as described for 2-(6-[5-amino-4-cyano-1-[1,1,1-trifluoropropan-2-yl]pyrazol-3-yl]pyridin-3-yl)-N-[3-(2-chloro-4-fluorophenyl)-1,2-oxazol-5-yl]propanamide, Isomer 2 using the appropriate reagents, adjusting reaction time to determine completion of the reaction, and using appropriate chromatography conditions for purification. Temperature can range from RT to 80° C. and can be completed in a sealed tube if appropriate. Dimethylacetamide (DMA) can be substituted for DCM.

TABLE 15

| Prep. No. | Chemical name | Structure | ES/MS m/z (M + H) |
|---|---|---|---|
| 99 | 2-(6-[5-Amino-4-cyano-1-[1,1,1-trifluoropropan-2-yl]pyrazol-3-yl]pyridin-3-yl)-N-[3-(2-chloro-4-fluorophenyl)-1,2-oxazol-5-yl]propanamide, Isomer 1 | 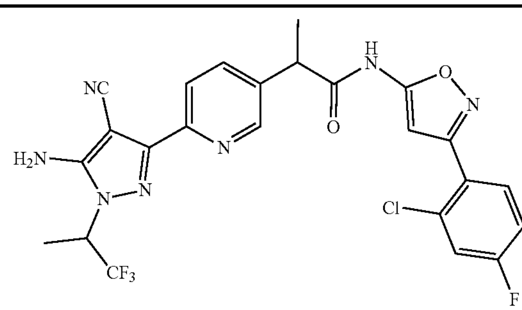 | 548.1, 550.1 |
| 100 | 2-(6-[5-Amino-4-cyano-1-[1,1,1-trifluoropropan-2-yl]pyrazol-3-yl]pyridin-3-yl)-N-[3-(2,4-dichlorophenyl)-1,2-oxazol-5-yl]propanamide, Isomer 1 | 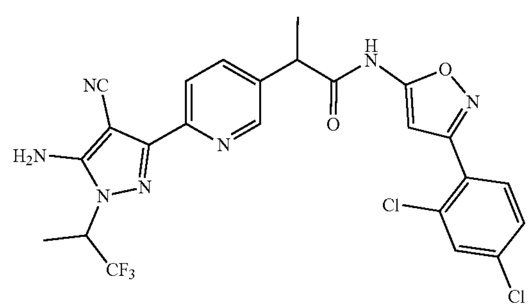 [SMILES: CC(C(=O)Nc1cc(-c2ccc(Cl)cc2Cl)no1)c1ccc(-c2nn(C(C)C(F)(F)F)c(N)c2C#N)nc1] | 564.3, 566.3 |
| 101 | 2-(6-[5-Amino-4-cyano-1-[1,1,1-trifluoropropan-2-yl]pyrazol-3-yl]pyridin-3-yl)-N-[3-(2,2-dimethylpropyl)-1,2-oxazol-5-yl]propanamide, Isomer 1 | 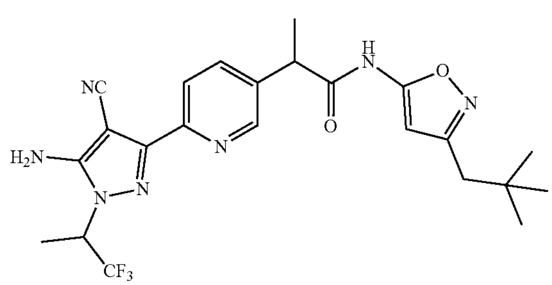 [SMILES: CC(C(=O)Nc1cc(CC(C)(C)C)no1)c1ccc(-c2nn(C(C)C(F)(F)F)c(N)c2C#N)nc1] | 490.2 |

TABLE 15-continued

| Prep. No. | Chemical name | Structure | ES/MS m/z (M + H) |
|---|---|---|---|
| 102 | 2-(6-[5-Amino-4-cyano-1-[1,1,1-trifluoropropan-2-yl]pyrazol-3-yl]pyridin-3-yl)-N-[5-(1,1,1-trifluoro-2-methylpropan-2-yl)-1,2-oxazol-3-yl]propanamide, Isomer 2 | 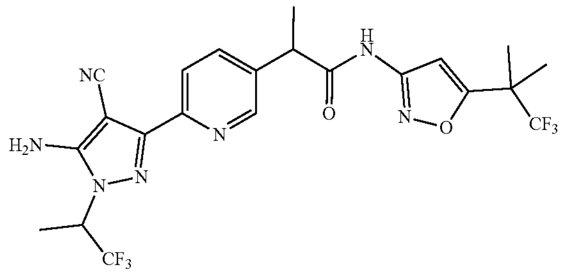 [SMILES: CC(C(=O)Nc1cc(C(C)(C)C(F)(F)F)on1)c1ccc(-c2nn(C(C)C(F)(F)F)c(N)c2C#N)nc1] | 530.3 |
| 103 | 2-(6-[5-Amino-4-cyano-1-[1,1,1-trifluoropropan-2-yl]pyrazol-3-yl]pyridin-3-yl)-N-[3-(2,2-dimethylpropyl)-1,2-oxazol-5-yl]propanamide, Isomer 2 | 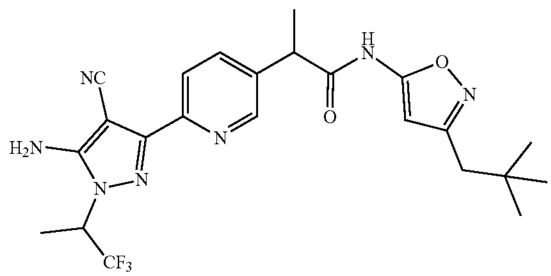 | 490.3 |
| 104 | 2-(6-[5-Amino-4-cyano-1-[1,1,1-trifluoropropan-2-yl]pyrazol-3-yl]pyridin-3-yl)-N-[3-(2,4-dichlorophenyl)-1,2-oxazol-5-yl]propanamide, Isomer 2 | 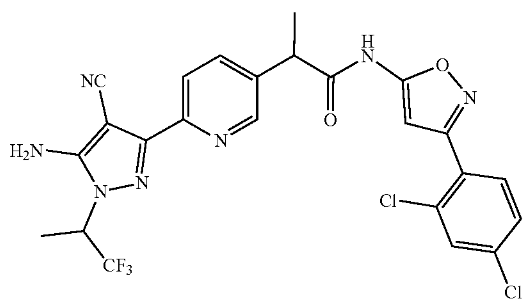 | 564.3, 566.3 |
| 105 | 2-[4-[5-Amino-4-cyano-1-[2,2,2-trifluoro-1-methylethyl]pyrazol-3-yl]phenyl]-N-[3-(2,2-dimethylpropyl)isoxazol-5-yl]propanamide, Isomer 1 | 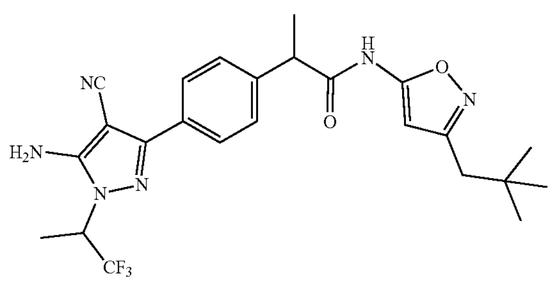 [SMILES: CC(C(=O)Nc1cc(CC(C)(C)C)no1)c1ccc(-c2nn(C(C)C(F)(F)F)c(N)c2C#N)cc1] | 489.3 |
| 106 | 2-[4-[5-Amino-4-cyano-1-(1-methylcyclopropyl)pyrazol-3-yl]phenyl]-N-[3-(3,3-dimethylcyclobutyl)-1,2-oxazol-5-yl]propanamide | 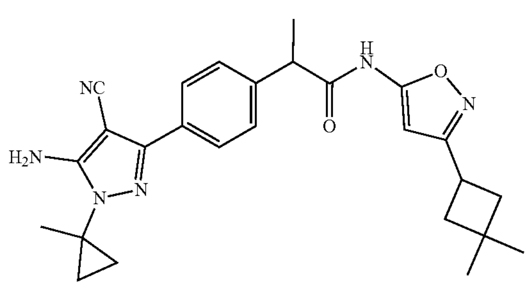 [SMILES: CC(C(=O)Nc1cc(C2CC(C)(C)C2)no1)c1ccc(-c2nn(C3(C)CC3)c(N)c2C#N)cc1] | 459.3 |

TABLE 15-continued

| Prep. No. | Chemical name | Structure | ES/MS m/z (M + H) |
|---|---|---|---|
| 107 | 2-[4-[5-Amino-4-cyano-1-(1-methylcyclopropyl)pyrazol-3-yl]phenyl]-N-[5-(2,2-dimethylpropyl)-1,2-oxazol-3-yl]propanamide | 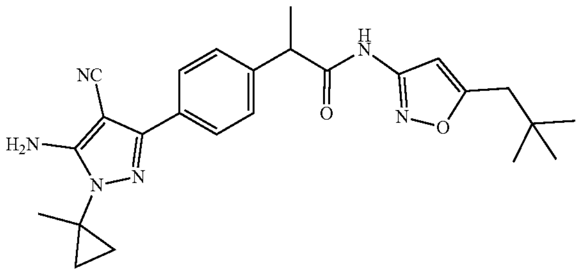 [SMILES: CC(C(=O)Nc1cc(CC(C)(C)C)on1)c1ccc(-c2nn(C3(C)CC3)c(N)c2C#N)cc1] | 447.2 |
| 108 | 2-[4-[5-Amino-4-cyano-1-(1-methoxy-2-methylpropan-2-yl)pyrazol-3-yl]phenyl]-N-[3-(2,2-dimethylpropyl)-1,2-oxazol-5-yl]propanamide | 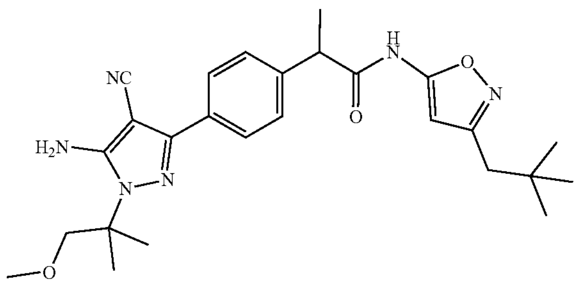 [SMILES: COCC(C)(C)n1nc(-c2ccc(C(C)C(=O)Nc3cc(CC(C)(C)C)no3)cc2)c(C#N)c1N] | 479.3 |
| 109 | 2-[4-(5-Amino-4-cyano-1-isopropylpyrazol-3-yl)phenyl]-N-[3-(2-methylbutan-2-yl)-1,2-oxazol-5-yl]propanamide | 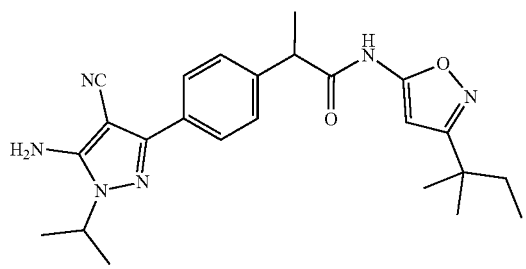 [SMILES: CCC(C)(C)c1cc(NC(=O)C(C)c2ccc(-c3nn(C(C)C)c(N)c3C#N)cc2)on1] | 434.6 |
| 110 | 2-[4-(5-Amino-4-cyano-1-isopropylpyrazol-3-yl)phenyl]-N-[5-(3,3-difluoro-2-methylbutan-2-yl)-1,2-oxazol-3-yl]propanamide | 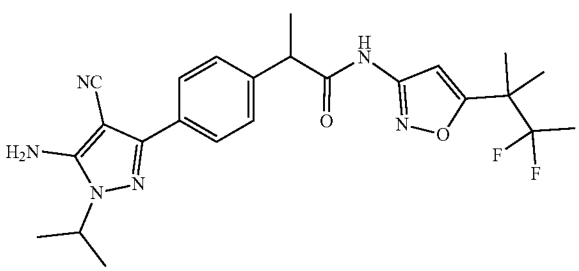 [SMILES: CC(C(=O)Nc1cc(C(C)(C)C(C)(F)F)on1)c1ccc(-c2nn(C(C)C)c(N)c2C#N)cc1] | 493.1 |
| 111 | 2-[6-(5-Amino-4-cyano-1-isopropylpyrazol-3-yl)pyridin-3-yl]-N-[5-(3,3-difluoro-2-methylbutan-2-yl)-1,2-oxazol-3-yl]propanamide | 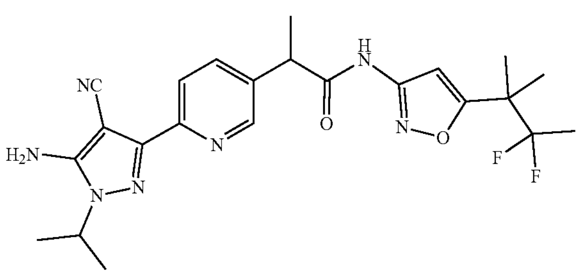 [SMILES: CC(C(=O)Nc1cc(C(C)(C)C(C)(F)F)on1)c1ccc(-c2nn(C(C)C)c(N)c2C#N)nc1] | 472.5 |

TABLE 15-continued

| Prep. No. | Chemical name | Structure | ES/MS m/z (M + H) |
|---|---|---|---|
| 112 | 2-[6-[5-Amino-4-cyano-1-(1-methylcyclopropyl)pyrazol-3-yl]pyridin-3-yl]-N-[5-(1,1,1-trifluoro-2-methylpropan-2-yl)-1,2-oxazol-3-yl]propanamide | 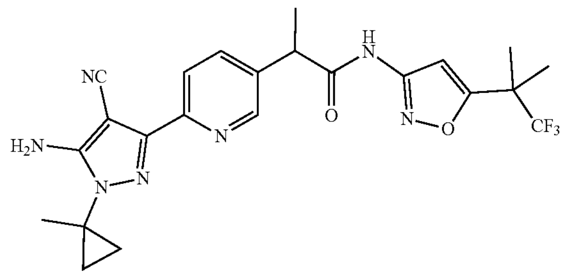 [SMILES: CC(C(=O)Nc1cc(C(C)(C)C(F)(F)F)on1)c1ccc(-c2nn(C3(C)CC3)c(N)c2C#N)nc1] | 488.2 |
| 113 | 2-[6-[5-Amino-4-cyano-1-methylcyclopropyl)pyrazol-3-yl]pyridin-3-yl]-N-[3-(2,2-dimethylpropyl)-1,2-oxazol-5-yl]propanamide | 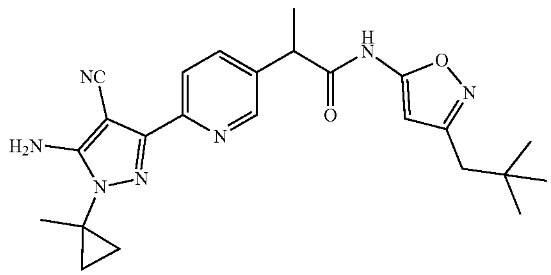 [SMILES: CC(C(=O)Nc1cc(CC(C)(C)C)no1)c1ccc(-c2nn(C3(C)CC3)c(N)c2C#N)nc1] | 448.3 |
| 114 | 2-[6-[5-Amino-4-cyano-1-(1-methylcyclopropyl)pyrazol-3-yl]pyridin-3-yl]-N-[3-(2,4-dichlorophenyl)-1,2-oxazol-5-yl]propanamide | 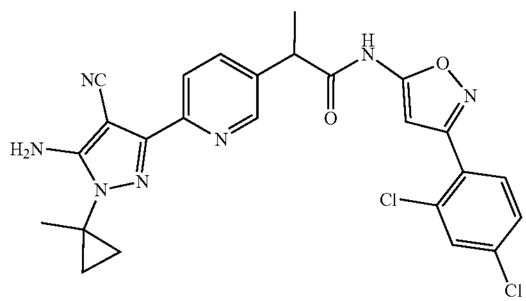 [SMILES: CC(C(=O)Nc1cc(-c2ccc(Cl)cc2Cl)no1)c1ccc(-c2nn(C3(C)CC3)c(N)c2C#N)nc1] | 522.1, 524.1 |
| 115 | 2-[6-[5-Amino-4-cyano-1-(1-methylcyclopropyl)pyrazol-3-yl]pyridin-3-yl]-N-[3-(2-chloro-4-fluorophenyl)-1,2-oxazol-5-yl]propanamide | 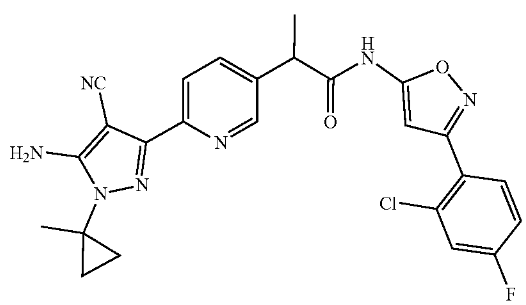 [SMILES: CC(C(=O)Nc1cc(-c2ccc(F)cc2Cl)no1)c1ccc(-c2nn(C3(C)CC3)c(N)c2C#N)nc1] | 506.1 |
| 116 | 2-(6-[5-Amino-4-cyano-[1,1,1-trifluoropropan-2-yl]pyrazol-3-yl]pyridin-3-yl)-N-[5-(1,1,1-trifluoro-2-methylpropan-2-yl)-1,2-oxazol-3-yl]propanamide, Isomer 1 | 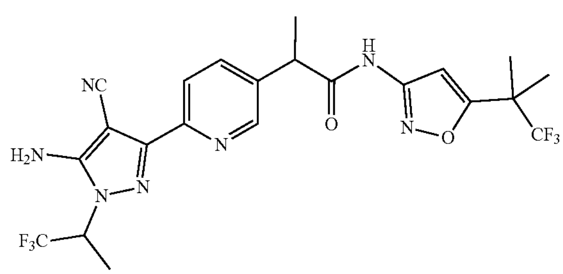 [SMILES: CC(C(=O)Nc1cc(C(C)(C)C(F)(F)F)on1)c1ccc(-c2nn(C(C)C(F)(F)F)c(N)c2C#N)nc1] | 530.3 |

TABLE 15-continued

| Prep. No. | Chemical name | Structure | ES/MS m/z (M + H) |
|---|---|---|---|
| 117 | 2-[4-(5-Amino-4-cyano-1-isopropylpyrazol-3-yl)phenyl]-N-[3-(trifluoromethyl)phenyl]propanamide | 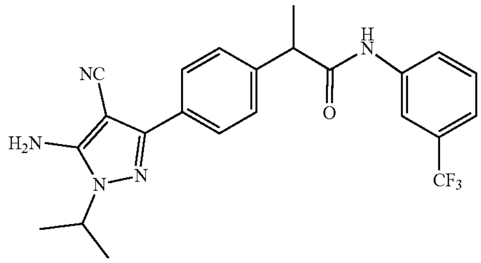 [SMILES: CC(C(=O)Nc1cccc(C(F)(F)F)c1)c1ccc(-c2nn(C(C)C)c(N)c2C#N)cc1] | 442.3 |
| 118 | 2-[4-(5-Amino-4-cyano-1-isopropylpyrazol-3-yl)phenyl]-N-[3-(1,1,1-trifluoro-2-methylpropan-2-yl)-1,2-oxazol-5-yl]propanamide | 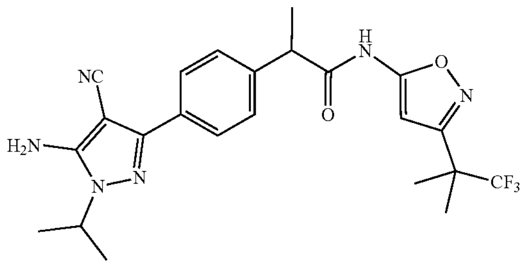 [SMILES: CC(C(=O)Nc1cc(C(C)(C)C(F)(F)F)no1)c1ccc(-c2nn(C(C)C)c(N)c2C#N)cc1] | 475.2 |
| 119 | 2-[4-(5-Amino-4-cyano-1-isopropylpyrazol-3-yl)phenyl]-N-[5-(1,1,1-trifluoro-2-methylpropan-2-yl)-1,2-oxazol-3-yl]propanamide | 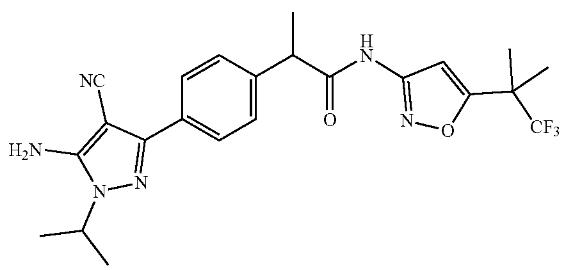 [SMILES: CC(C(=O)Nc1cc(C(C)(C)C(F)(F)F)on1)c1ccc(-c2nn(C(C)C)c(N)c2C#N)cc1] | 475.1 |
| 119a | 2-[4-(5-Amino-4-cyano-1-isopropylpyrazol-3-yl)phenyl]-N-[5-(1,1,1-trifluoro-2-methylpropan-2-yl)-1H-pyrazol-3-yl]propanamide | 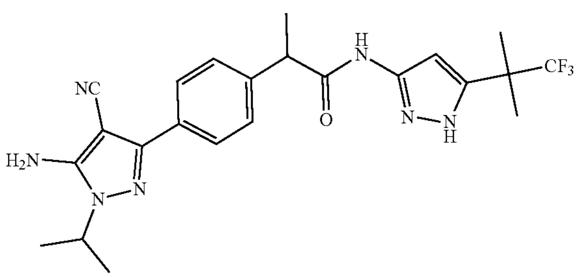 [SMILES: CC(C(=O)Nc1cc(C(C)(C)C(F)(F)F)[nH]n1)c1ccc(-c2nn(C(C)C)c(N)c2C#N)cc1] | 474.2 |
| 119b | 2-[4-(5-Amino-4-cyano-1-isopropylpyrazol-3-yl)phenyl]-N-[1-methyl-5-(1,1,1-trifluoro-2-methylpropan-2-yl)pyrazol-3-yl]propanamide | 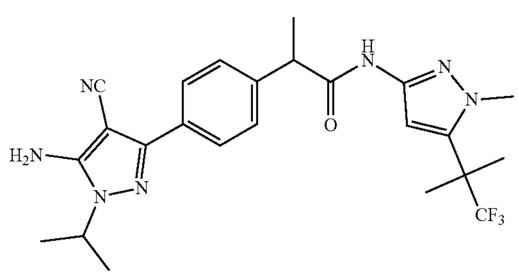 [SMILES: CC(C(=O)Nc1cc(C(C)(C)C(F)(F)F)n(C)n1)c1ccc(-c2nn(C(C)C)c(N)c2C#N)cc1] | 488.4 |

TABLE 15-continued

| Prep. No. | Chemical name | Structure | ES/MS m/z (M + H) |
|---|---|---|---|
| 119c | 2-[4-(5-Amino-4-cyano-1-(1-methylcyclopropyl)pyrazol-3-yl]-3-fluorophenyl]-N-[3-[3-(trifluoromethyl)bicyclo[1.1.1]pentan-1-yl]-1,2-oxazol-5-yl]propanamide | 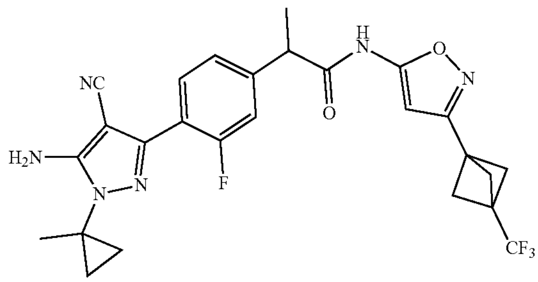 [SMILES: CC(C(=O)Nc1cc(C23CC(C(F)(F)F)(C2)C3)no1)c1ccc(-c2nn(C3(C)CC3)c(N)c2C#N)c(F)c1] | 529.3 |
| 119e | 2-[4-[5-Amino-4-cyano-1-(1-methylcyclopropyl)pyrazol-3-yl]-3-fluorophenyl]-N-[3-[4-(trifluoromethyl)bicyclo[2.2.1]heptan-1-yl]-1,2-oxazol-5-yl]propanamide | 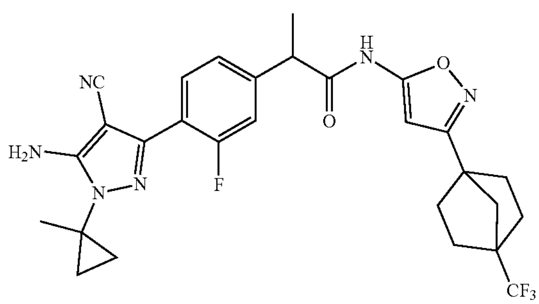 [SMILES: CC(C(=O)Nc1cc(C23CCC(C(F)(F)F)(CC2)C3)no1)c1ccc(-c2nn(C3(C)CC3)c(N)c2C#N)c(F)c1] | 557.4 |
| 119f | 2-[4-(5-Amino-4-cyano-1-isopropylpyrazol-3-yl)-2,3-difluorophenyl]-N-[3-(2,2-dimethylpropyl)-1,2-oxazol-5-yl]propanamide | 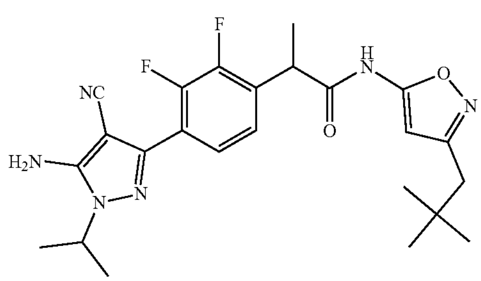 [SMILES: CC(C(=O)Nc1cc(CC(C)(C)C)no1)c1ccc(-c2nn(C(C)C)c(N)c2C#N)c(F)c1F] | 471.3 |

Preparation 119 g

2-[4-[5-Amino-4-cyano-1-(1-methylcyclopropyl)pyrazol-3-yl]phenyl]-N-[3-[3-(trifluoromethyl)bicyclo[1.1.1]pentan-1-yl]-1,2-oxazol-5-yl]propanamide

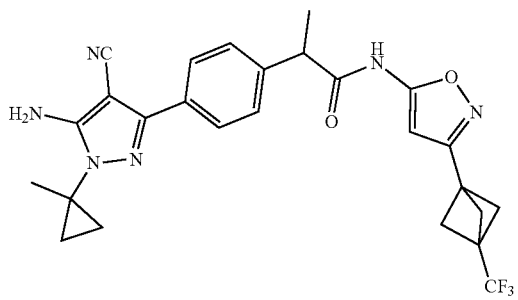 [SMILES: CC(C(=O)Nc1cc(C23CC(C(F)(F)F)(C2)C3)no1)c1ccc(-c2nn(C3(C)CC3)c(N)c2C#N)cc1]

To a stirred mixture of 2-[4-[5-amino-4-cyano-1-(1-methylcyclopropyl)pyrazol-3-yl]phenyl]propanoic acid (400 mg, 1.29 mmol) and 3-[3-(trifluoromethyl)bicyclo[1.1.1]pentan-1-yl]-1,2-oxazol-5-amine (281.20 mg, 1.29 mmol) in DCM (5.00 mL) is added DIPEA (499.72 mg, 3.87 mmol) and T3P® (4.10 g, 6.44 mmol, 50 wt % in EtOAc) dropwise in sealed tube at RT under $N_2$. The mixture is stirred for 1 hr at 80° C. under $N_2$. The mixture is concentrated under reduced pressure. The residue is purified by reverse combiflash chromatography with the following conditions: C18; eluting with a gradient of 30% to 50% ACN in $H_2O$ to give the title compound (230 mg, 34%) as a light yellow solid. ES/MS (m/z) 511.2 (M+H).

Preparation 119h

2-[4-(5-Amino-4-cyano-1-isopropyl-pyrazol-3-yl)phenyl]-N-[3-(3-methyl-1-bicyclo[1.1.1]pentanyl)isoxazol-5-yl]propanamide, Isomer 1

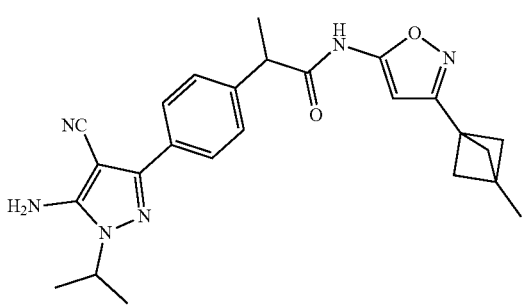 [SMILES: CC(C(=O)Nc1cc(C23CC(C)(C2)C3)no1)c1ccc(-c2nn(C(C)C)c(N)c2C#N)cc1]

2-[4-(5-Amino-4-cyano-1-isopropylpyrazol-3-yl)phenyl]propanoic acid, Isomer 1 (78 mg, 0.25 mmol), 3-(3-methylbicyclo[1.1.1]pentan-1-yl)isoxazol-5-amine (34 mg, 0.21 mmol) and 1-methylimidazole (39 mg, 0.038 mL, 0.48 mmol) are combined in EtOAc (3 mL). The orange solution is stirred for 2 mins at RT then T3P® (0.31 g, 0.29 mL, 50% Wt in EtOAc, 0.49 mmol) is added. The reaction is stirred for 16 hrs. The reaction is then diluted with 5 mL $H_2O$ and extracted with EtOAc (3×25 mL). The combined organic extracts are dried over $Na_2SO_4$, and the solvent is removed under reduced pressure. The residue is used without further purification. ES/MS (m/z) 511.2 (M+H). ES/MS (m/z) 445.2 (M+H).

Preparation 120

Tert-Butyl N-[4-carbamoyl-2-isopropyl-5-[6-[1-methyl-2-oxo-2-[[5-(2,2,2-trifluoro-1,1-dimethylethyl)isoxazol-3-yl]amino]ethyl]-3-pyridyl]pyrazol-3-yl]carbamate

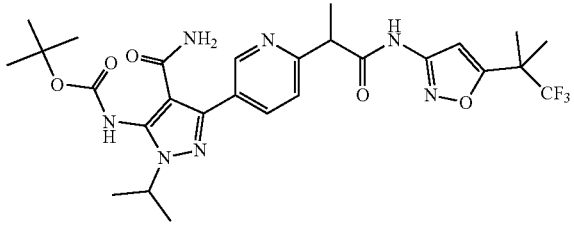 [SMILES: CC(C(=O)Nc1cc(C(C)(C)C(F)(F)F)on1)c1ccc(-c2nn(C(C)C)c(NC(=O)OC(C)(C)C)c2C(N)=O)cn1]

tert-Butyl N-[4-cyano-2-isopropyl-5-[6-[1-methyl-2-oxo-2-[[5-(2,2,2-trifluoro-1,1-dimethyl-ethyl)isoxazol-3-yl]amino]ethyl]-3-pyridyl]pyrazol-3-yl]carbamate (130 mg, 0.226 mmol) and platinate(2-), tris(dimethylphosphinito-P)hydro-, dihydrogen (Parkins catalyst, CAS #173416-05-2) (116 mg, 0.271 mmol) are added together in a mixture of tert-BuOH (2.6 mL) and $H_2O$ (1.3 mL). The reaction mixture is stirred at 60° C. overnight, filtered through a pad of talcum powder, and washed with EtOAc. The organic phase is washed with $H_2O$ and the aqueous phase is extracted with EtOAc. The organic extracts are combined, dried over $Na_2SO_4$, filtered, and concentrated under vacuum to give the title compound as a white solid (147.8 mg, 104.73%). The material is used directly without purification.

The following compounds in Table 16 are prepared essentially as described for tert-butyl N-[4-carbamoyl-2-isopropyl-5-[6-[1-methyl-2-oxo-2-[[5-(2,2,2-trifluoro-1,1-dimethyl-ethyl)isoxazol-3-yl]amino]ethyl]-3-pyridyl]pyrazol-3-yl]carbamate using the appropriate reagents, adjusting reaction time to determine completion of the reaction and using appropriate chromatography conditions for purification if needed. Temperature can vary from about 60 to 70° C.

TABLE 16

| Prep. No. | Chemical name | Structure | ES/MS m/z (M + H) |
|---|---|---|---|
| 121 | tert-Butyl N-[4-carbamoyl-2-isopropyl-5-[6-[1-methyl-2-oxo-2-[[3-(2,2,2-trifluoro-1,1-dimethyl-ethyl)isoxazol-5-yl]amino]ethyl]-3-pyridyl]pyrazol-3-yl]carbamate | 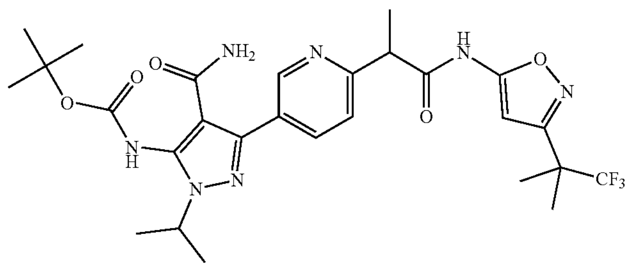 [SMILES: CC(C(=O)Nc1cc(C(C)(C)C(F)(F)F)no1)c1ccc(-c2nn(C(C)C)c(NC(=O)OC(C)(C)C)c2C(N)=O)cn1] | 594 |
| 122 | tert-Butyl N-[4-carbamoyl-5-[6-[2-[[3-(2,4-dichlorophenyl)isoxazol-5-yl]amino]-1-methyl-2-oxo-ethyl]-3-pyridyl]-2-isopropyl-pyrazol-3-yl]carbamate | 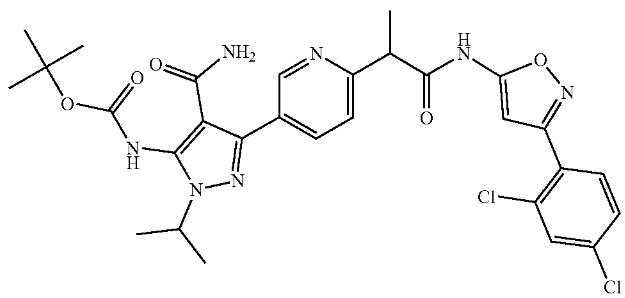 [SMILES: CC(C(=O)Nc1cc(-c2ccc(Cl)cc2Cl)no1)c1ccc(-c2nn(C(C)C)c(NC(=O)OC(C)(C)C)c2C(N)=O)cn1] | |
| 123 | tert-Butyl N-[4-carbamoyl-5-[6-[2-[[5-(1,1-dimethylpropyl)isoxazol-3-yl]amino]-1-methyl-2-oxo-ethyl]-3-pyridyl]-2-isopropyl-pyrazol-3-yl]carbamate | 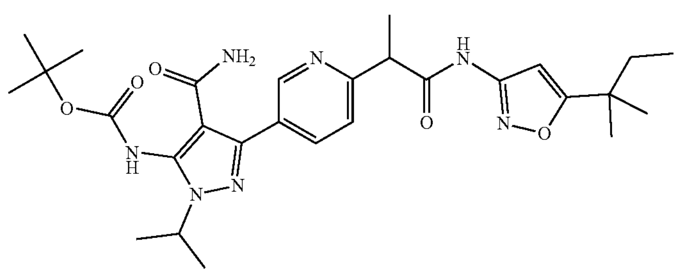 [SMILES: CCC(C)(C)c1cc(NC(=O)C(C)c2ccc(-c3nn(C(C)C)c(NC(=O)OC(C)(C)C)c3C(N)=O)cn2)no1] | |
| 124 | tert-Butyl N-[4-carbamoyl-5-[6-[2-[[5-(2,2-dimethylpropyl)isoxazol-3-yl]amino]-1-methyl-2-oxo-ethyl]-3-pyridyl]-2-isopropyl-pyrazol-3-yl]carbamate | 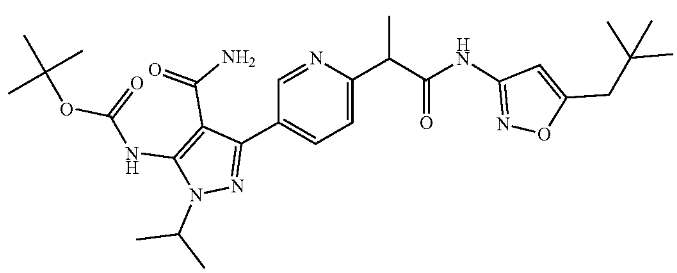 [SMILES: CC(C(=O)Nc1cc(CC(C)(C)C)on1)c1ccc(-c2nn(C(C)C)c(NC(=O)OC(C)(C)C)c2C(N)=O)cn1] | |
| 125 | tert-Butyl N-[4-carbamoyl-5-[6-[2-[[3-(2,2-dimethylpropyl)isoxazol-5-yl]amino]-1-methyl-2-oxo-ethyl]-3-pyridyl]-2-isopropyl-pyrazol-3-yl]carbamate | 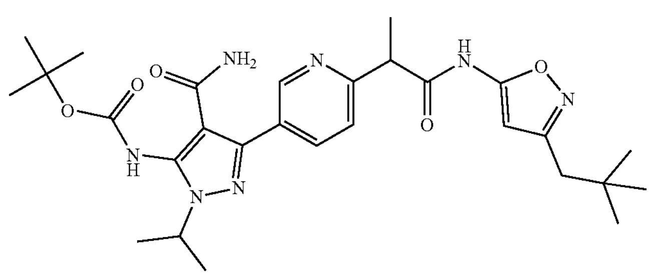 [SMILES: CC(C(=O)Nc1cc(CC(C)(C)C)no1)c1ccc(-c2nn(C(C)C)c(NC(=O)OC(C)(C)C)c2C(N)=O)cn1] | 554 |

TABLE 16-continued

| Prep. No. | Chemical name | Structure | ES/MS m/z (M + H) |
|---|---|---|---|
| 126 | tert-Butyl N-[4-carbamoyl-5-[5-[2-[[3-(1,1-dimethylpropyl)isoxazol-5-yl]amino]-1-methyl-2-oxo-ethyl]-2-pyridyl]-2-isopropyl-pyrazol-3-yl]carbamate | 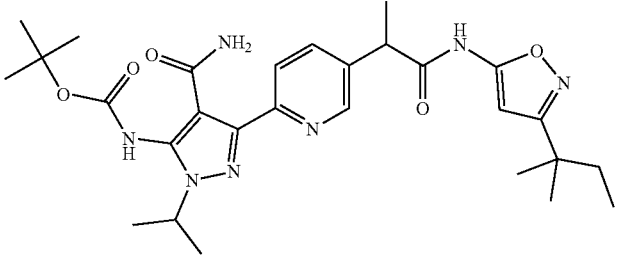 [SMILES: CCC(C)(C)c1cc(NC(=O)C(C)c2ccc(-c3nn(C(C)C)c(NC(=O)OC(C)(C)C)c3C(N)=O)nc2)on1] | |
| 127 | 5-Amino-1-cyclopropyl-3-[4-[2-[[3-(2,2-dimethylpropyl)isoxazol-5-yl]amino]-1-methyl-2-oxo-ethyl]phenyl]pyrazole-4-carboxamide | 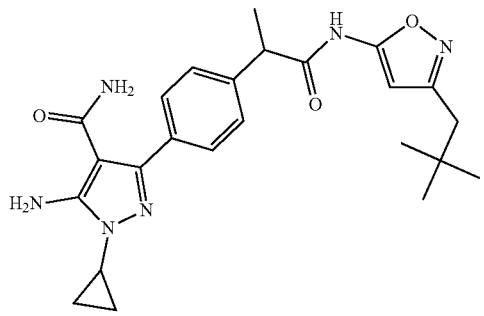 [SMILES: CC(C(=O)Nc1cc(CC(C)(C)C)no1)c1ccc(-c2nn(C3CC3)c(N)c2C(N)=O)cc1] | 451.3 |
| 128[1] | 5-Amino-1-isopropyl-3-[4-[1-methyl-2-[[3-[(1-methylcyclopropyl)methyl]isoxazol-5-yl]amino]-2-oxo-ethyl]phenyl]pyrazole-4-carboxamide | 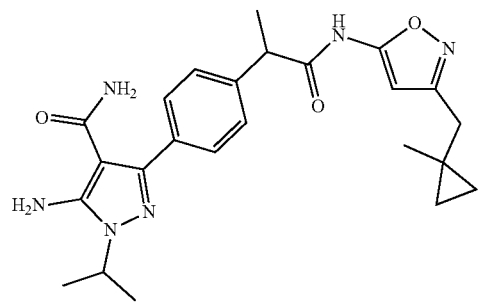 [SMILES: CC(C(=O)Nc1cc(CC2(C)CC2)no1)c1ccc(-c2nn(C(C)C)c(N)c2C(N)=O)cc1] | 451.1 |
| 129 | tert-Butyl N-[4-carbamoyl-5-[5-[2-[[3-(1,1-dimethylpropyl)isoxazol-5-yl]amino]-1-methyl-2-oxo-ethyl]-2-pyridyl]-2-isopropyl-pyrazol-3-yl]carbamate | 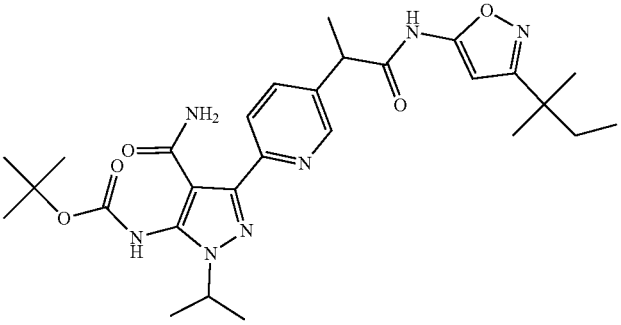 [SMILES: CCC(C)(C)c1cc(NC(=O)C(C)c2ccc(-c3nn(C(C)C)c(NC(=O)OC(C)(C)C)c3C(N)=O)nc2)on1] | 554.4 |

[1]EtOH can be substituted for tert-BuOH.

Preparation 129a

5-Amino-3-[4-(1-[[3-(2,2-dimethylpropyl)-1,2-oxazol-5-yl]carbamoyl]ethyl)phenyl]-1-isopropylpyrazole-4-carboxamide

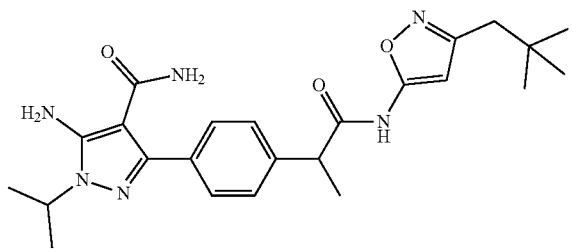 [SMILES: CC(C(=O)Nc1cc(CC(C)(C)C)no1)c1ccc(-c2nn(C(C)C)c(N)c2C(N)=O)cc1]

To a mixture of 2-[4-(5-amino-4-cyano-1-isopropylpyrazol-3-yl)phenyl]-N-[3-(2,2-dimethylpropyl)-1,2-oxazol-5-yl]propanamide (120 mg, 0.276 mmol), NaOH (55 mg, 1.38 mmol), H$_2$O (2.00 mL), and DMSO (1.00 mL) in EtOH (5.00 mL) is added H$_2$O$_2$ (187.86 mg, 5.523 mmol, 30% aq.). The resulting mixture is stirred at 40° C. for 4 hrs. The mixture is allowed to cool to RT and quenched by the addition of saturated Na$_2$SO$_3$ aqueous (10 mL). The mixture is extracted with EtOAc (3×50 mL). The combined organic extracts are washed with saturated aqueous NaCl solution (50 mL), dried over anhydrous Na$_2$SO$_4$, filtered, and concentrated under reduced pressure. The residue is purified by reverse Combi-flash chromatography with the following conditions: Column, C18; mobile phase ACN in H$_2$O (0.1% NH$_4$CO$_3$) eluting with a gradient of 0% to 50% in 25 min; UV 254 nm to give the title compound (100 mg, 80.02%) as a white solid. ES/MS (m/z) 453.4 (M+H).

The following compounds in Table 17 are prepared essentially as described for 5-amino-3-[4-(1-[[3-(2,2-dimethylpropyl)-1,2-oxazol-5-yl]carbamoyl]ethyl)phenyl]-1-isopropylpyrazole-4-carboxamide using the appropriate reagents, adjusting reaction time to determine completion of the reaction and using appropriate chromatography conditions for purification. NaOH and H$_2$O$_2$ can be added in portions and the relative amounts of solvents H$_2$O, EtOH, and DMSO may be varied. Temperature can vary from RT to 50° C.

TABLE 17

| Prep. No. | Chemical name | Structure | ES/MS m/z (M + H) |
|---|---|---|---|
| 130 | 5-Amino-3-[5-(1-[[3-(2,2-dimethylpropyl)-1,2-oxazol-5-yl]carbamoyl]ethyl)pyridin-2-yl]-1-isopropylpyrazole-4-carboxamide | 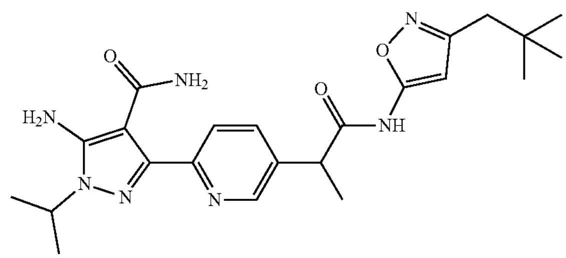 [SMILES: CC(C(=O)Nc1cc(CC(C)(C)C)no1)c1ccc(-c2nn(C(C)C)c(N)c2C(N)=O)nc1] | 454.2 |
| 131 | 5-Amino-3-[5-(1-[[3-(2-chloro-4-fluorophenyl)-1,2-oxazol-5-yl]carbamoyl]ethyl)pyridin-2-yl]-1[1,1,1-trifluoropropan-2-yl]pyrazole-4-carboxamide, Isomer 2 | 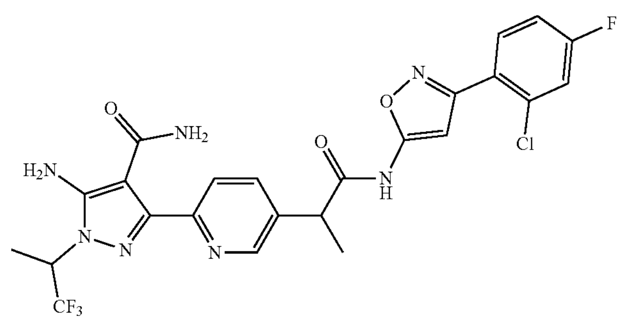 [SMILES: CC(C(=O)Nc1cc(-c2ccc(F)cc2Cl)no1)c1ccc(-c2nn(C(C)C(F)(F)F)c(N)c2C(N)=O)nc1] | 566.20 |
| 132 | 5-Amino-3-[5-(1-[[3-(2,4-dichlorophenyl)-1,2-oxazol-5-yl]carbamoyl]ethyl)pyridin-2-yl]-1[1,1,1-trifluoropropan-2-yl]pyrazole-4-carboxamide, Isomer 1 | 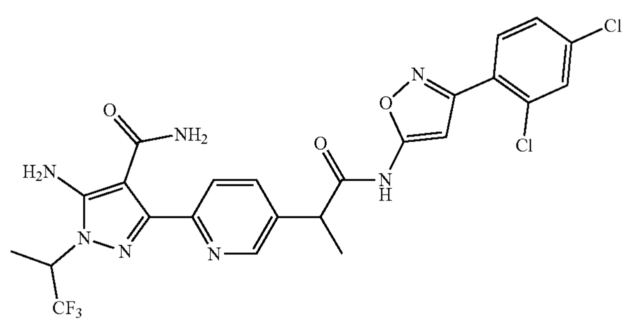 [SMILES: CC(C(=O)Nc1cc(-c2ccc(Cl)cc2Cl)no1)c1ccc(-c2nn(C(C)C(F)(F)F)c(N)c2C(N)=O)nc1] | 582.1, 584.1 |

TABLE 17-continued

| Prep. No. | Chemical name | Structure | ES/MS m/z (M + H) |
|---|---|---|---|
| 133 | 5-Amino-3-[5-(1-[[3-(2,2-dimethylpropyl)-1,2-oxazol-5-yl]carbamoyl]ethyl)pyridin-2-yl]-1-[1,1,1-trifluoropropan-2-yl]pyrazole-4-carboxamide, Isomer 1 | 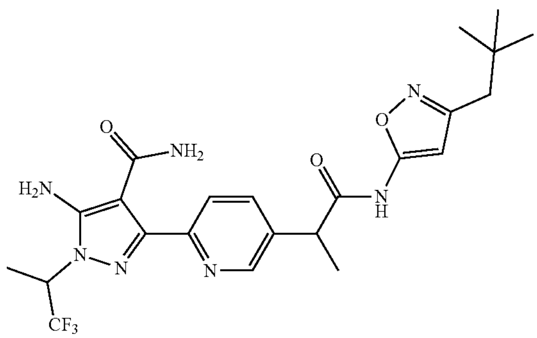 [SMILES: CC(C(=O)Nc1cc(CC(C)(C)C)no1)c1ccc(-c2nn(C(C)C(F)(F)F)c(N)c2C(N)=O)nc1] | 508.3 |
| 134 | 5-Amino-3-[5-(1-[[5-(1,1,1-trifluoro-2-methylpropan-2-yl)-1,2-oxazol-3-yl]carbamoyl]ethyl)pyridin-2-yl]-1-[1,1,1-trifluoropropan-2-yl]pyrazole-4-carboxamide, Isomer 2 | 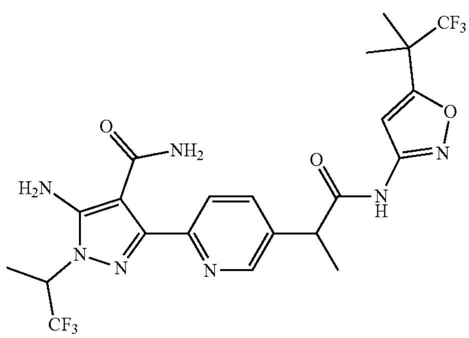 [SMILES: CC(C(=O)Nc1cc(C(C)(C)C(F)(F)F)on1)c1ccc(-c2nn(C(C)C(F)(F)F)c(N)c2C(N)=O)nc1] | 548.2 |
| 135 | 5-Amino-3-[5-(1-[[3-(2,2-dimethylpropyl)-1,2-oxazol-5-yl]carbamoyl]ethyl)pyridin-2-yl]-1-[1,1,1-trifluoropropan-2-yl]pyrazole-4-carboxamide, Isomer 2 | 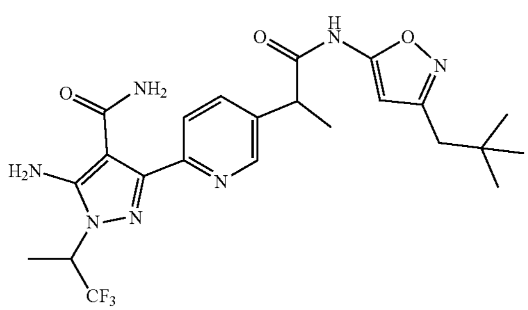 [SMILES: CC(C(=O)Nc1cc(CC(C)(C)C)no1)c1ccc(-c2nn(C(C)C(F)(F)F)c(N)c2C(N)=O)nc1] | 508.2 |
| 136 | 5-Amino-3-[5-(1-[[3-(2,4-dichlorophenyl)-1,2-oxazol-5-yl]carbamoyl]ethyl)pyridin-2-yl]-1-[1,1,1-trifluoropropan-2-yl]pyrazole-4-carboxamide, Isomer 2 | 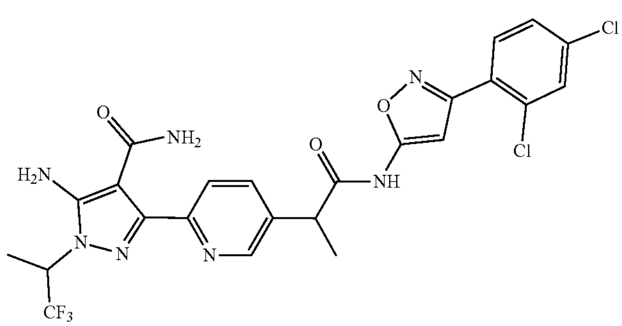 [SMILES: CC(C(=O)Nc1cc(-c2ccc(Cl)cc2Cl)no1)c1ccc(-c2nn(C(C)C(F)(F)F)c(N)c2C(N)=O)nc1] | 582.3, 584.3 |

TABLE 17-continued

| Prep. No. | Chemical name | Structure | ES/MS m/z (M + H) |
|---|---|---|---|
| 137 | 5-Amino-3-[5-(1-[[3-(2-chloro-4-fluorophenyl)-1,2-oxazol-5-yl]carbamoyl]ethyl)pyridin-2-yl]-1-[1,1,1-trifluoropropan-2-yl]pyrazole-4-carboxamide, Isomer 1 | 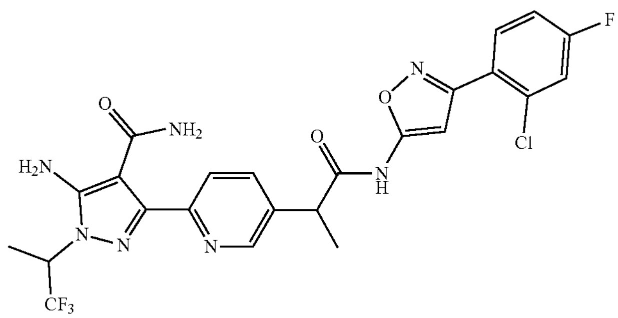 [SMILES: CC(C(=O)Nc1cc(-c2ccc(F)cc2Cl)no1)c1ccc(-c2nn(C(C)C(F)(F)F)c(N)c2C(N)=O)nc1] | 566.1, 568.1 |
| 138 | 5-Amino-3-[4-[1-[[3-(2,2-dimethylpropyl)-1,2-oxazol-5-yl]carbamoyl]ethyl]phenyl]-1-(1-methylcyclopropyl)pyrazole-4-carboxamide | 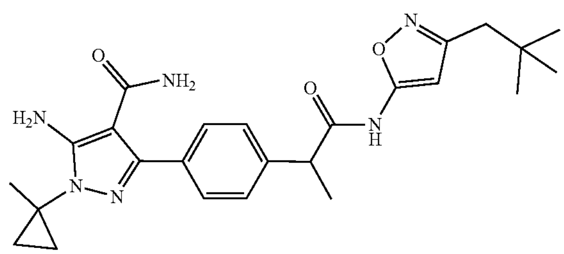 [SMILES: CC(C(=O)Nc1cc(CC(C)(C)C)no1)c1ccc(-c2nn(C3(C)CC3)c(N)c2C(N)=O)cc1] | 465.3 |
| 139 | 5-Amino-3-[4-[2-[[3-(2,2-dimethylpropyl)isoxazol-5-yl]amino]-1-methyl-2-oxo-ethyl]phenyl]-1-[3,3,3-trifluoro-1-methyl-propyl]pyrazole-4-carboxamide, Isomer 1 | 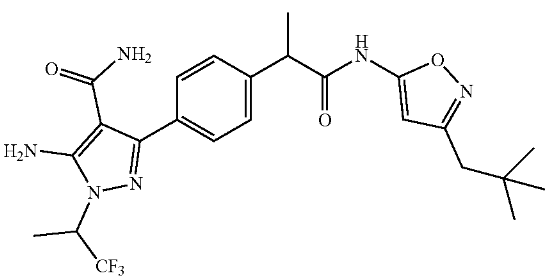 [SMILES: CC(C(=O)Nc1cc(CC(C)(C)C)no1)c1ccc(-c2nn(C(C)C(F)(F)F)c(N)c2C(N)=O)cc1] | 507.3 |
| 140 | 5-Amino-3-[4-(1-[[3-(2,2-dimethylpropyl)-1,2-oxazol-5-yl]carbamoyl]ethyl)phenyl]-1-[1,1,1-trifluoropropan-2-yl]pyrazole-4-carboxamide, Isomer 2 | 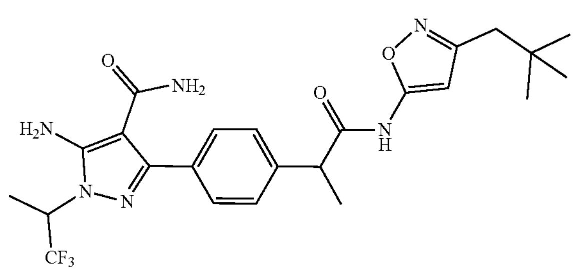 [SMILES: CC(C(=O)Nc1cc(CC(C)(C)C)no1)c1ccc(-c2nn(C(C)C(F)(F)F)c(N)c2C(N)=O)cc1] | 529.4 (M + Na) |
| 141 | 5-Amino-3-[4-(1-[[3-(2,2-dimethylpropyl)-1,2-oxazol-5-yl]carbamoyl]ethyl)phenyl]-1-(1,1,1-trifluoro-2-methylpropan-2-yl)pyrazole-4-carboxamide | 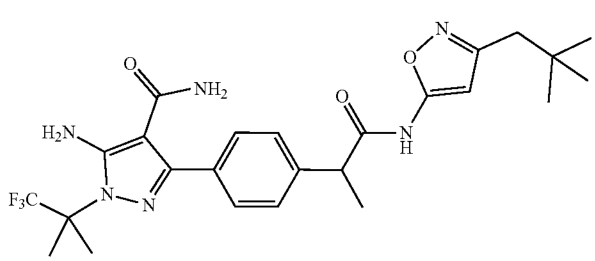 [SMILES: CC(C(=O)Nc1cc(CC(C)(C)C)no1)c1ccc(-c2nn(C(C)(C)C(F)(F)F)c(N)c2C(N)=O)cc1] | 521.3 |

TABLE 17-continued

| Prep. No. | Chemical name | Structure | ES/MS m/z (M + H) |
|---|---|---|---|
| 142 | 5-Amino-3-[4-(1-[[3-(3,3-dimethylcyclobutyl)-1,2-oxazol-5-yl]carbamoyl]ethyl)phenyl]-1-(1-methylcyclopropyl)pyrazole-4-carboxamide | 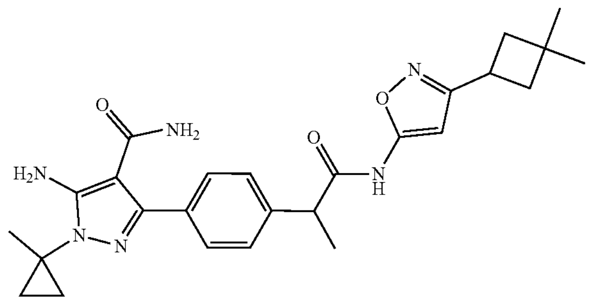 | 477.4 |
| 143 | 5-Amino-3-[4-(1-[[5-(2,2-dimethylpropyl)-1,2-oxazol-3-yl]carbamoyl]ethyl)phenyl]-1-(1-methylcyclopropyl)pyrazole-4-carboxamide | 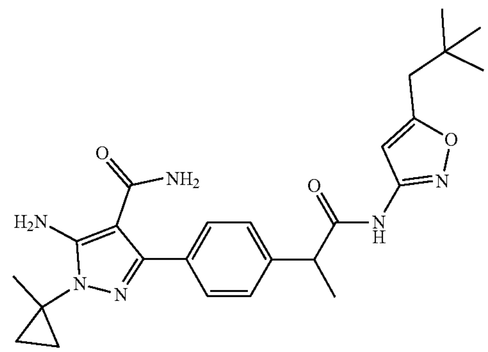 [SMILES: CC(C(=O)Nc1cc(CC(C)(C)C)on1)c1ccc(-c2nn(C3(C)CC3)c(N)c2C(N)=O)cc1] | 465.4 |
| 144 | 5-Amino-3-[4-(1-[[3-(2,2-dimethylpropyl)-1,2-oxazol-5-yl]carbamoyl]ethyl)phenyl]-1-(1-methoxy-2-methylpropan-2-yl)pyrazole-4-carboxamide | 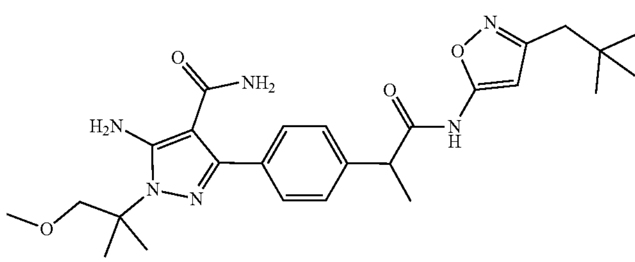 [SMILES: COCC(C)(C)n1nc(-c2ccc(C(C)C(=O)Nc3cc(CC(C)(C)C)no3)cc2)c(C(N)=O)c1N] | 497.3 |
| 145 | 5-Amino-1-isopropyl-3-[4-(1-[[3-(2-methylbutan-2-yl)-1,2-oxazol-5-yl]carbamoyl]ethyl)phenyl]pyrazole-4-carboxamide | 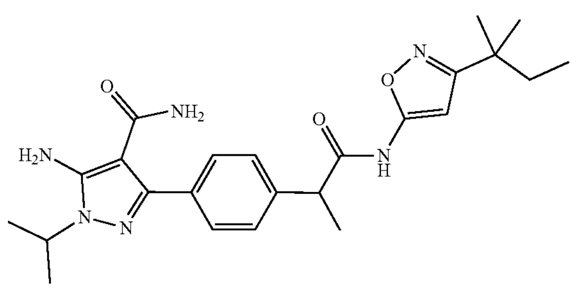 [SMILES: CCC(C)(C)c1cc(NC(=O)C(C)c2ccc(-c3nn(C(C)C)c(N)c3C(N)=O)cc2)on1] | 453.4 |
| 146 | 5-Amino-3-[4-(1-[[5-(3,3-difluoro-2-methylbutan-2-yl)-1,2-oxazol-3-yl]carbamoyl]ethyl)phenyl]-1-isopropylpyrazole-4-carboxamide | 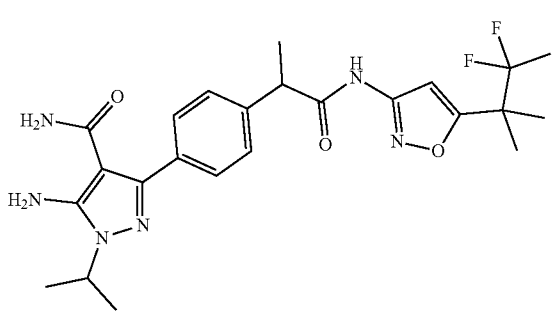 [SMILES: CC(C(=O)Nc1cc(C(C)(C)C(C)(F)F)on1)c1ccc(-c2nn(C(C)C)c(N)c2C(N)=O)cc1] | 489.2 |

TABLE 17-continued

| Prep. No. | Chemical name | Structure | ES/MS m/z (M + H) |
|---|---|---|---|
| 147* | 5-Amino-1-isopropyl-3-[4-(1[[5-(4,4,4-trifluoro-2-methylbutan-2-yl)-1,2-oxazol-3-yl]carbamoyl]ethyl)phenyl]pyrazole-4-carboxamide | 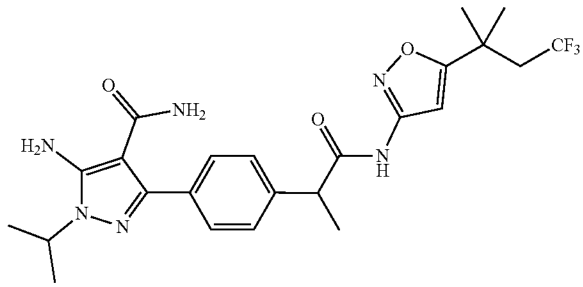 [SMILES: CC(C(=O)Nc1cc(C(C)(C)CC(F)(F)F)on1)c1ccc(-c2nn(C(C)C)c(N)c2C(N)=O)cc1] | 507.1 |
| 148* | 5-Amino-1-isopropyl-3-[5-(1-[[5-(1,1,1-trifluoro-2-methylpropan-2-yl)-1,2-oxazol-3-yl]carbamoyl]ethyl)pyridin-2-yl]pyrazole-4-carboxamide | 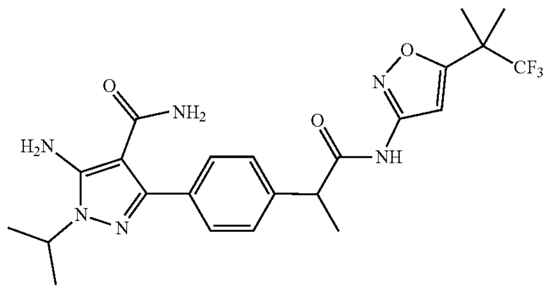 [SMILES: CC(C(=O)Nc1cc(C(C)(C)C(F)(F)F)on1)c1ccc(-c2nn(C(C)C)c(N)c2C(N)=O)cc1] | 494.1 |
| 149* | 5-Amino-1-isopropyl-3-[5-(1-[[5-(2-methylbutan-2-yl)-1,2-oxazol-3-yl]carbamoyl]ethyl)pyridin-2-yl]pyrazole-4-carboxamide | 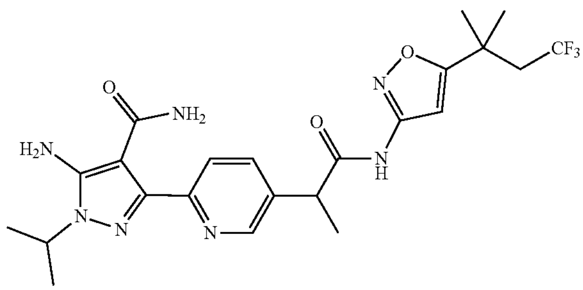 [SMILES: CC(C(=O)Nc1cc(C(C)(C)CC(F)(F)F)on1)c1ccc(-c2nn(C(C)C)c(N)c2C(N)=O)nc1] | 454.3 |
| 150 | 5-Amino-1-isopropyl-3-[5-(1-[[5-(4,4,4-trifluoro-2-methylbutan-2-yl)-1,2-oxazol-3-yl]carbamoyl]ethyl)pyridin-2-yl]pyrazole-4-carboxamide | 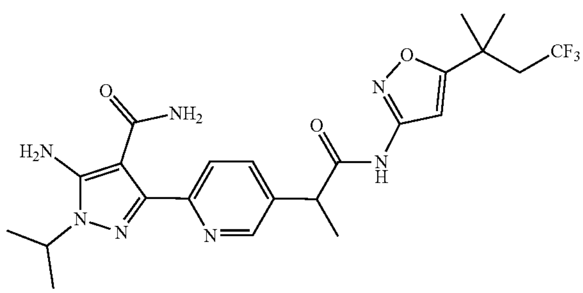 [SMILES: CC(C(=O)Nc1cc(C(C)(C)CC(F)(F)F)on1)c1ccc(-c2nn(C(C)C)c(N)c2C(N)=O)nc1] | 508.2 |
| 151* | 5-Amino-3-[5-(1-[[5-(3,3-difluoro-2-methylbutan-2-yl)-1,2-oxazol-3-yl]carbamoyl]ethyl)pyridin-2-yl]-1-isopropylpyrazole-4-carboxamide | 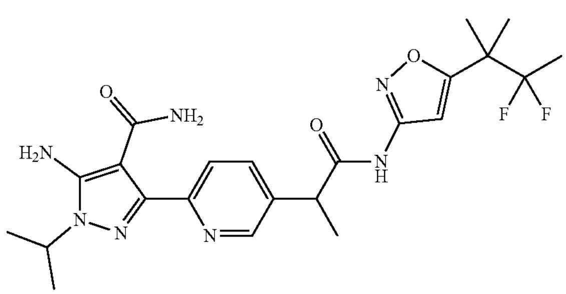 [SMILES: CC(C(=O)Nc1cc(C(C)(C)C(C)(F)F)on1)c1ccc(-c2nn(C(C)C)c(N)c2C(N)=O)nc1] | 490.4 |

TABLE 17-continued

| Prep. No. | Chemical name | Structure | ES/MS m/z (M + H) |
|---|---|---|---|
| 152 | 5-Amino-1-isopropyl-3-[5-(1-[[3-(1,1,1-trifluoro-2-methylpropan-2-yl)-1,2-oxazol-5-yl]carbamoyl]ethyl)pyridin-2-yl]pyrazole-4-carboxamide | 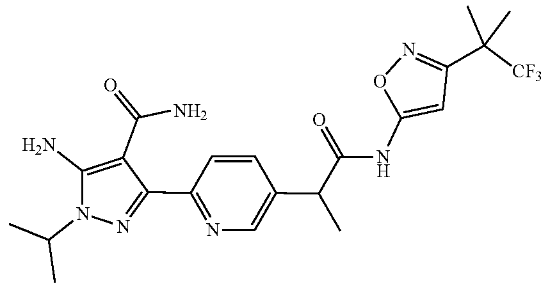 [SMILES: CC(C(=O)Nc1cc(C(C)(C)C(F)(F)F)no1)c1ccc(-c2nn(C(C)C)c(N)c2C(N)=O)nc1] | 494.2 |
| 153 | 5-Amino-3-(5-(1-((3-(2,4-dichlorophenyl)isoxazol-5-yl)amino)-1-oxopropan-2-yl)pyridin-2-yl)-1-isopropyl-1H-pyrazole-4-carboxamide | 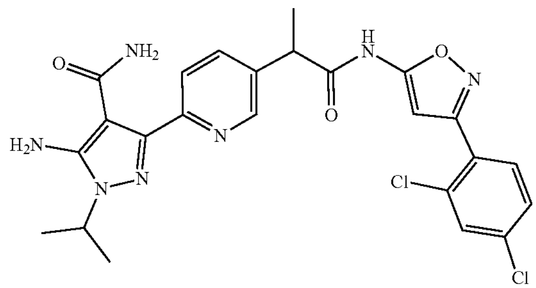 [SMILES: CC(C(=O)Nc1cc(-c2ccc(Cl)cc2Cl)no1)c1ccc(-c2nn(C(C)C)c(N)c2C(N)=O)nc1] | 528.2, 530.2 |
| 154 | 5-Amino-3-(5-(1-((3-(2-chloro-4-fluorophenyl)isoxazol-5-yl)amino)-1-oxopropan-2-yl)pyridin-2-yl)-1-isopropyl-1H-pyrazole-4-carboxamide | 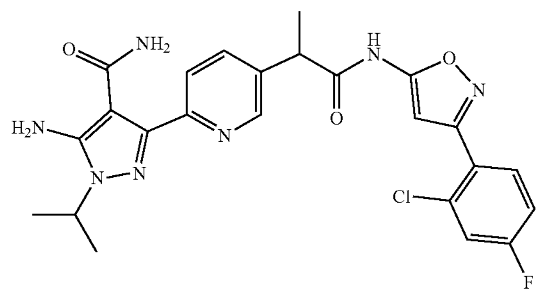 [SMILES: CC(C(=O)Nc1cc(-c2ccc(F)cc2Cl)no1)c1ccc(-c2nn(C(C)C)c(N)c2C(N)=O)nc1] | |
| 155 | 5-Amino-1-(1-methylcyclopropyl)-3-[5-(1-[[5-(1,1,1-trifluoro-2-methylpropan-2-yl)-1,2-oxazol-3-yl]carbamoyl]ethyl)pyridin-2-yl]pyrazole-4-carboxamide | 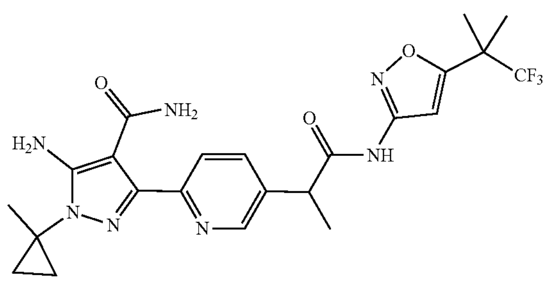 [SMILES: CC(C(=O)Nc1cc(C(C)(C)C(F)(F)F)on1)c1ccc(-c2nn(C3(C)CC3)c(N)c2C(N)=O)nc1] | 506.2 |
| 156 | 5-Amino-3-[5-(1-[[3-(2,2-dimethylpropyl)-1,2-oxazol-5-yl]carbamoyl]ethyl)pyridin-2-yl]-1-(1-methylcyclopropyl)pyrazole-4-carboxamide | 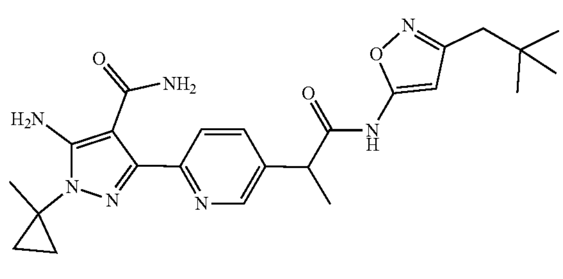 [SMILES: CC(C(=O)Nc1cc(CC(C)(C)C)no1)c1ccc(-c2nn(C3(C)CC3)c(N)c2C(N)=O)nc1] | 466.2 |

TABLE 17-continued

| Prep. No. | Chemical name | Structure | ES/MS m/z (M + H) |
|---|---|---|---|
| 157 | 5-Amino-3-[5-(1-[[3-(2,4-dichlorophenyl)-1,2-oxazol-5-yl]carbamoyl]ethyl)pyridin-2-yl]-1-(1-methylcyclopropyl)pyrazole-4-carboxamide | 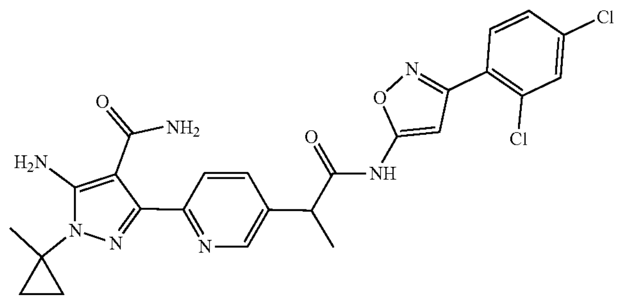 [SMILES: CC(C(=O)Nc1cc(-c2ccc(Cl)cc2Cl)no1)c1ccc(-c2nn(C3(C)CC3)c(N)c2C(N)=O)nc1] | 540.1, 542.1 |
| 158 | 5-Amino-3-[5-(1-[[3-(2-chloro-4-fluorophenyl)-1,2-oxazol-5-yl]carbamoyl]ethyl)pyridin-2-yl]-1-(1-methylcyclopropyl)pyrazole-4-carboxamide | 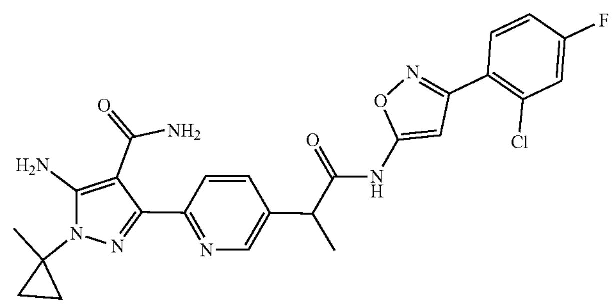 [SMILES: CC(C(=O)Nc1cc(-c2ccc(F)cc2Cl)no1)c1ccc(-c2nn(C3(C)CC3)c(N)c2C(N)=O)nc1] | 524.3 |
| 159 | 5-Amino-3-[5-(1-[[5-(1,1,1-trifluoro-2-methylpropan-2-yl)-1,2-oxazol-3-yl]carbamoyl]ethyl)pyridin-2-yl]-1-[1,1,1-trifluoropropan-2-yl]pyrazole-4-carboxamide, Isomer 1 | 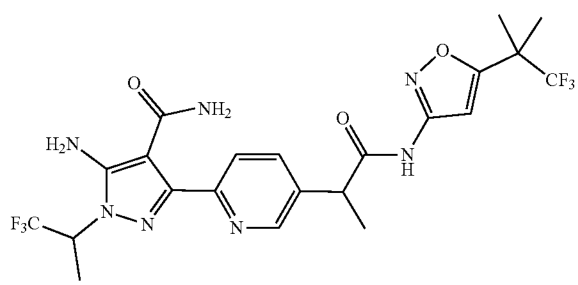 [SMILES: CC(C(=O)Nc1cc(C(C)(C)C(F)(F)F)on1)c1ccc(-c2nn(C(C)C(F)(F)F)c(N)c2C(N)=O)nc1] | 548.2 |
| 160* | 5-Amino-1-isopropyl-3-[4-(1-[[5-(2-methylbutan-2-yl)-1,2-oxazol-3-yl]carbamoyl]ethyl)phenyl]pyrazole-4-carboxamide | 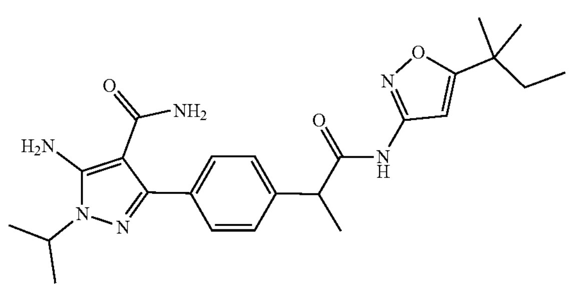 [SMILES: CCC(C)(C)c1cc(NC(=O)C(C)c2ccc(-c3nn(C(C)C)c(N)c3C(N)=O)cc2)no1] | 453.3 |
| 161 | 5-Amino-1-isopropyl-3-[4-(1-[[3-(trifluoromethyl)phenyl]carbamoyl]ethyl)phenyl]pyrazole-4-carboxamide | 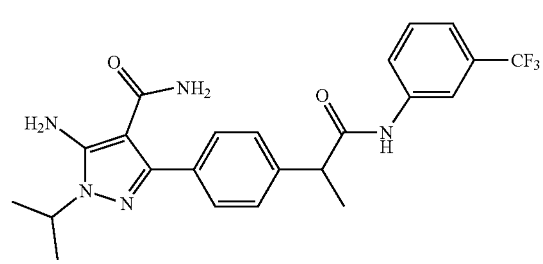 [SMILES: CC(C(=O)Nc1cccc(C(F)(F)F)c1)c1ccc(-c2nn(C(C)C)c(N)c2C(N)=O)cc1] | 460.3 |

TABLE 17-continued

| Prep. No. | Chemical name | Structure | ES/MS m/z (M + H) |
|---|---|---|---|
| 162 | 5-Amino-3-[4-(1-[[3-(2,4-dichlorophenyl)-1,2-oxazol-5-yl]carbamoyl]ethyl)phenyl]-1-isopropylpyrazole-4-carboxamide | 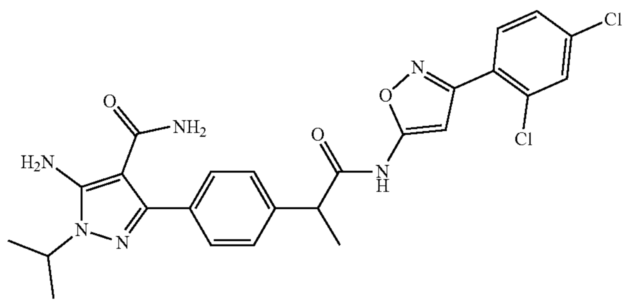 [SMILES: CC(C(=O)Nc1cc(-c2ccc(Cl)cc2Cl)no1)c1ccc(-c2nn(C(C)C)c(N)c2C(N)=O)cc1] | 527.1, 529.1 |
| 163 | 5-Amino-3-(4-[1-[(5-tert-butyl-1,2-thiazol-3-yl)carbamoyl]ethyl]phenyl)-1-isopropylpyrazole-4-carboxamide | 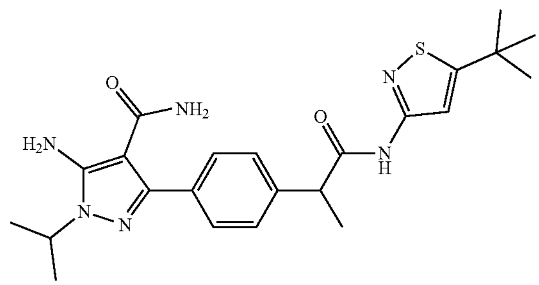 [SMILES: CC(C(=O)Nc1cc(C(C)(C)C)sn1)c1ccc(-c2nn(C(C)C)c(N)c2C(N)=O)cc1] | 455.2 |
| 164 | 5-Amino-1-isopropyl-3-[4-(1-[[5-(1-methylcyclopropyl)-1,2-oxazol-3-yl]carbamoyl]ethyl)phenyl]pyrazole-4-carboxamide | 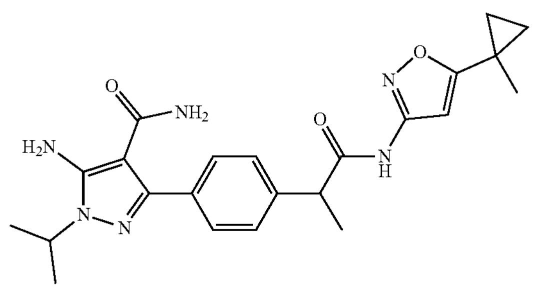 [SMILES: CC(C(=O)Nc1cc(C2(C)CC2)on1)c1ccc(-c2nn(C(C)C)c(N)c2C(N)=O)cc1] | 437.2 |
| 165 | 5-Amino-1-isopropyl-3-[4-(1-[[3-(1-methylcyclopropyl)-1,2-oxazol-5-yl]carbamoyl]ethyl)phenyl]pyrazole-4-carboxamide | 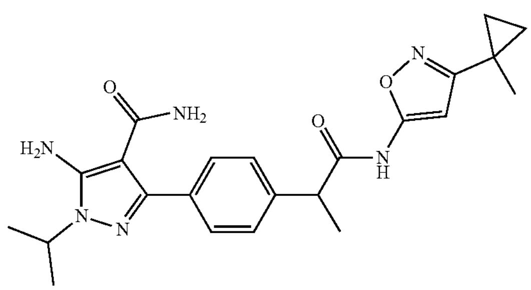 [SMILES: CC(C(=O)Nc1cc(C2(C)CC2)no1)c1ccc(-c2nn(C(C)C)c(N)c2C(N)=O)cc1] | 437.2 |
| 166 | 5-Amino-1-isopropyl-3-[4-(1-[[3-(1,1,1-trifluoro-2-methylpropan-2-yl)-1,2-oxazol-5-yl]carbamoyl]ethyl)phenyl]pyrazole-4-carboxamide | 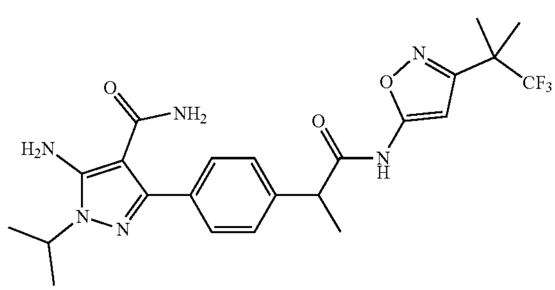 [SMILES: CC(C(=O)Nc1cc(C(C)(C)C(F)(F)F)no1)c1ccc(-c2nn(C(C)C)c(N)c2C(N)=O)cc1] | 493.2 |

TABLE 17-continued

| Prep. No. | Chemical name | Structure | ES/MS m/z (M + H) |
|---|---|---|---|
| 167 | 5-Amino-1-isopropyl-3-[4-(1-[[5-(1,1,1-trifluoro-2-methylpropan-2-yl)-1,2-oxazol-3-yl]carbamoyl]ethyl)phenyl]pyrazole-4-carboxamide | 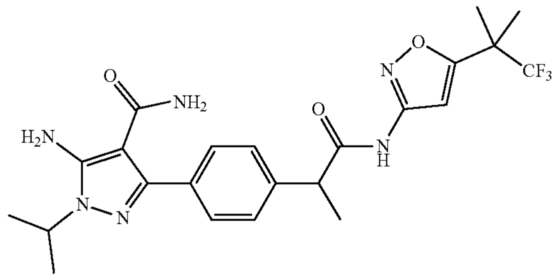 [SMILES: CC(C(=O)Nc1cc(C(C)(C)C(F)(F)F)on1)c1ccc(-c2nn(C(C)C)c(N)c2C(N)=O)cc1] | 493.2 |
| 167a | 5-Amino-1-isopropyl-3-[4-(1-[[5-(1,1,1-trifluoro-2-methylpropan-2-yl)-1H-pyrazol-3-yl]carbamoyl]ethyl)phenyl]pyrazole-4-carboxamide | 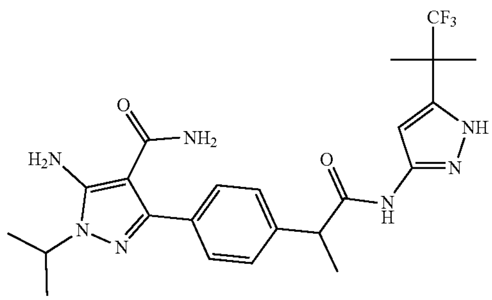 [SMILES: CC(C(=O)Nc1cc(C(C)(C)C(F)(F)F)[nH]n1)c1ccc(-c2nn(C(C)C)c(N)c2C(N)=O)cc1] | 492.2 |
| 167b | 5-Amino-3-[2-fluoro-4-[1-([3-[3-(trifluoromethyl)bicyclo[1.1.1]pentan-1-yl]-1,2-oxazol-5-yl]carbamoyl)ethyl]phenyl]-1-(1-methylcyclopropyl)pyrazole-4-carboxamide | 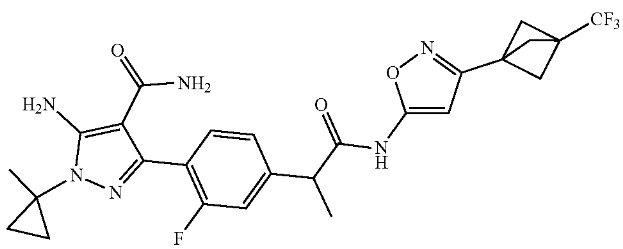 [SMILES: CC(C(=O)Nc1cc(C23CC(C(F)(F)F)(C2)C3)no1)c1ccc(-c2nn(C3(C)CC3)c(N)c2C(N)=O)c(F)c1] | 547.30 |
| 167c | 5-Amino-3-[2-fluoro-4-[1-([3-[4-(trifluoromethyl)bicyclo[2.2.1]heptan-1-yl]-1,2-oxazol-5-yl]carbamoyl)ethyl]phenyl]-1-(1-methylcyclopropyl)pyrazole-4-carboxamide | 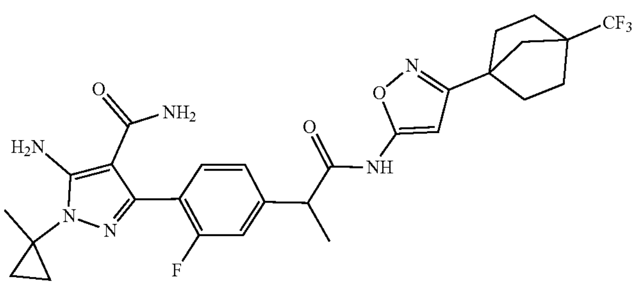 [SMILES: CC(C(=O)Nc1cc(C23CCC(C(F)(F)F)(CC2)C3)no1)c1ccc(-c2nn(C3(C)CC3)c(N)c2C(N)=O)c(F)c1] | 575.4 |
| 167d | 5-Amino-3-[4-[2-[[3-(2,2-dimethylpropyl)isoxazol-5-yl]amino]-1-methyl-2-oxo-ethyl]phenyl]-1-(2,2,2-trideuterio-1-methyl-ethyl)pyrazole-4-carboxamide | 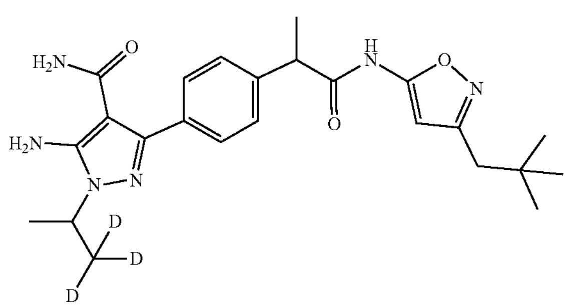 [SMILES: [2H]C([2H])([2H])C(C)n1nc(-c2ccc(C(C)C(=O)Nc3cc(CC(C)(C)C)no3)cc2)c(C(N)=O)c1N] | 456.4 |

TABLE 17-continued

| Prep. No. | Chemical name | Structure | ES/MS m/z (M + H) |
|---|---|---|---|
| 167e | 5-Amino-3-[4-[2-[[3-(2,2-dimethylpropyl)isoxazol-5-yl]amino]-1-methyl-2-oxo-ethyl]phenyl]-1-[2,2,2-trideuterio-1-(trideuteriomethyl)ethyl]pyrazole-4-carboxamide | 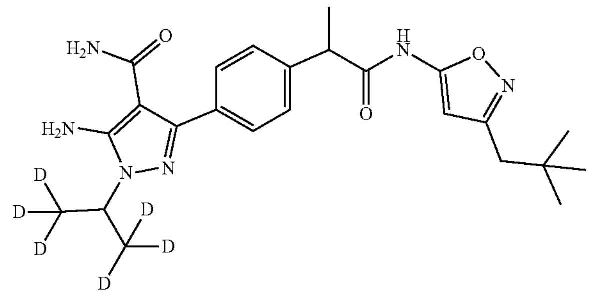 [SMILES: [2H]C([2H])([2H])C(n1nc(-c2ccc(C(C)C(=O)Nc3cc(CC(C)(C)C)no3)cc2)c(C(N)=O)c1N)C([2H])([2H])[2H]] | 459.5 |
| 167f | 5-Amino-3-[4-[2-[[3-(2,2-dimethylpropyl)isoxazol-5-yl]amino]-1-methyl-2-oxo-ethyl]phenyl]-1-(1,2,2,2-tetradeuterio-1-methyl-ethyl)pyrazole-4-carboxamide | 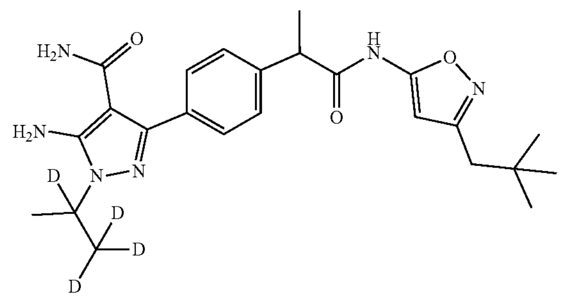 [SMILES: [2H]C([2H])([2H])C([2H])(C)n1nc(-c2ccc(C(C)C(=O)Nc3cc(CC(C)(C)C)no3)cc2)c(C(N)=O)c1N] | 457.3 |
| 167g | 5-Amino-3-[4-[2-[[3-(2,2-dimethylpropyl)isoxazol-5-yl]amino]-1-methyl-2-oxo-ethyl]phenyl]-1-[1,2,2,2-tetradeuterio-1-(trideuteriomethyl)ethyl]pyrazole-4-carboxamide | 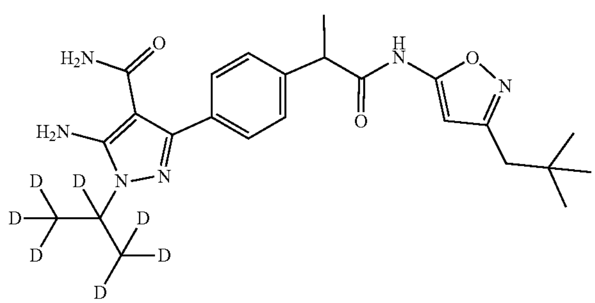 [SMILES: [2H]C([2H])([2H])C([2H])(n1nc(-c2ccc(C(C)C(=O)Nc3cc(CC(C)(C)C)no3)cc2)c(C(N)=O)c1N)C([2H])([2H])[2H]] | 460.3 |
| 167h | 5-Amino-1-[1,1-difluoropropan-2-yl]-3-[4-(1-[[3-(2,2-dimethylpropyl)-1,2-oxazol-5-yl]carbamoyl]ethyl)phenyl]pyrazole-4-carboxamide, Isomer 1 | 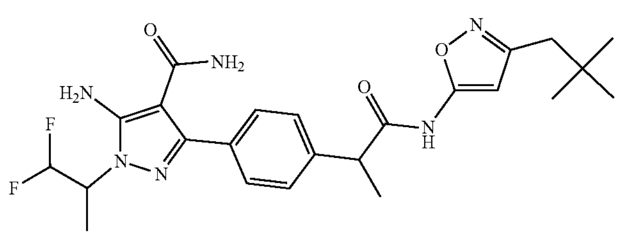 [SMILES: CC(C(=O)Nc1cc(CC(C)(C)C)no1)c1ccc(-c2nn(C(C)C(F)F)c(N)c2C(N)=O)cc1] | 489.3 |
| 167i | 5-Amino-1-[1,1-difluoropropan-2-yl]-3-[4-(1-[[3-[2,2-dimethylpropyl)-1,2-oxazol-5-yl]carbamoyl]ethyl)phenyl]pyrazole-4-carboxamide, Isomer 2 | 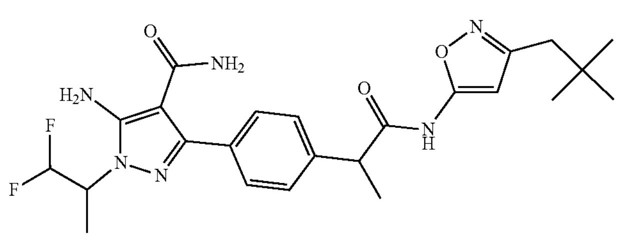 [SMILES: CC(C(=O)Nc1cc(CC(C)(C)C)no1)c1ccc(-c2nn(C(C)C(F)F)c(N)c2C(N)=O)cc1] | 489.3 |

TABLE 17-continued

| Prep. No. | Chemical name | Structure | ES/MS m/z (M + H) |
|---|---|---|---|
| 167j | 5-Amino-3-[4-(1-[[3-(2,2-dimethylpropyl)-1,2-oxazol-5-yl]carbamoyl]ethyl)-2,3-difluorophenyl]-1-isopropylpyrazole-4-carboxamide | 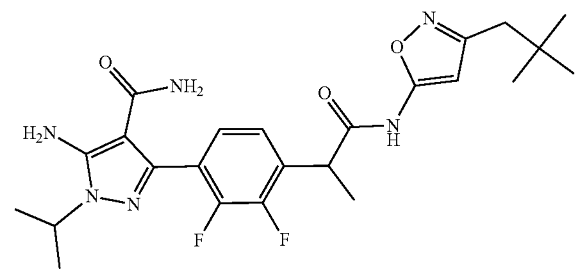 [SMILES: CC(C(=O)Nc1cc(CC(C)(C)C)no1)c1ccc(-c2nn(C(C)C)c(N)c2C(N)=O)c(F)c1F] | 489.3 |
| 167k | 5-Amino-3-[4-[2-[[3-(2,2-dimethylpropyl)isoxazol-5-yl]amino]-1-methyl-2-oxo-ethyl]phenyl]-1-[2,2,2-trifluoro-1-(trideuteriomethyl)ethyl]pyrazole-4-carboxamide, Isomer 1 | 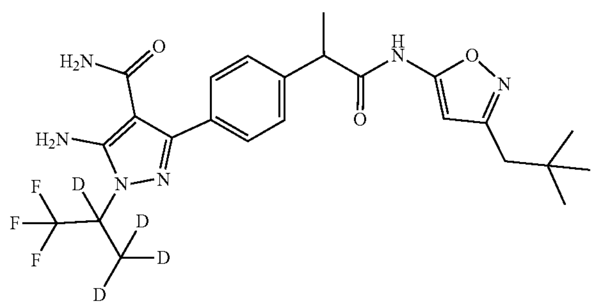 [SMILES: [2H]C([2H])([2H])C([2H])(n1nc(-c2ccc(C(C)C(=O)Nc3cc(CC(C)(C)C)no3)cc2)c(C(N)=O)c1N)C(F)(F)F] | 510.2 |
| 167l | 5-Amino-3-[4-[2-[[3-(2,2-dimethylpropyl)isoxazol-5-yl]amino]-1-methyl-2-oxo-ethyl]phenyl]-1-[2,2,2-trifluoro-1-(trideuteriomethyl)ethyl]pyrazole-4-carboxamide, Isomer 2 | 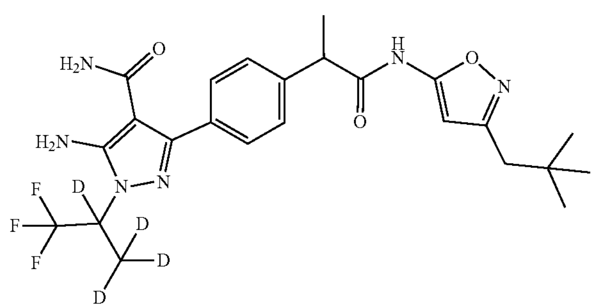 [SMILES: [2H]C([2H])([2H])C([2H])(n1nc(-c2ccc(C(C)C(=O)Nc3cc(CC(C)(C)C)no3)cc2)c(C(N)=O)c1N)C(F)(F)F] | 510.2 |
| 167m | 5-Amino-3-[4-(1-[[3-(2,2-dimethylpropyl)-4-fluoro-1,2-oxazol-5-yl]carbamoyl]ethyl)phenyl]-1-isopropylpyrazole-4-carboxamide | 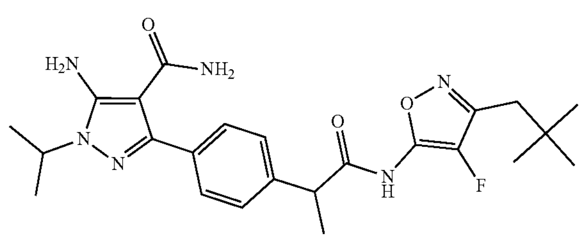 [SMILES: CC(C(=O)Nc1onc(CC(C)(C)C)c1F)c1ccc(-c2nn(C(C)C)c(N)c2C(N)=O)cc1] | 471.1 |
| 167n | 5-Amino-1-(2-deuterio-2,2-difluoro-1-methyl-ethyl)-3-[4-[2-[[3-(2,2-dimethylpropyl)isoxazol-5-yl]amino]-1-methyl-2-oxo-ethyl]phenyl]pyrazole-4-carboxamide, Isomer 1 | 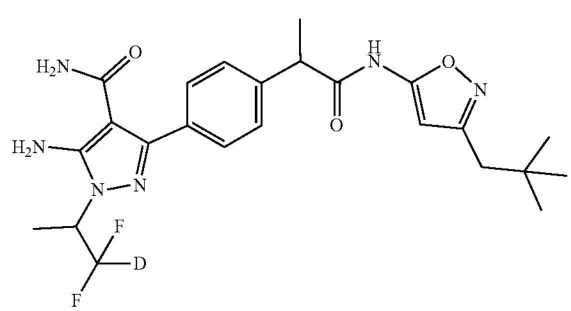 [SMILES: [2H]C(F)(F)C(C)n1nc(-c2ccc(C(C)C(=O)Nc3cc(CC(C)(C)C)no3)cc2)c(C(N)=O)c1N] | 490 |

TABLE 17-continued

| Prep. No. | Chemical name | Structure | ES/MS m/z (M + H) |
|---|---|---|---|
| 167o | 5-Amino-1-(2-deuterio-2,2-difluoro-1-methyl-ethyl)-3-[4-[2-[[3-(2,2-dimethylpropyl)isoxazol-5-yl]amino]-1-methyl-2-oxo-ethyl]phenyl]pyrazole-4-carboxamide, Isomer 2 | 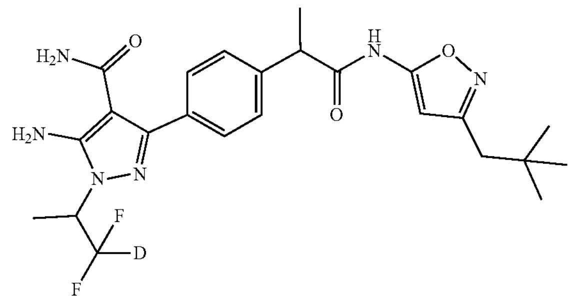 [SMILES: [2H]C(F)(F)C(C)n1nc(-c2ccc(C(C)C(=O)Nc3cc(CC(C)(C)C)no3)cc2)c(C(N)=O)c1N] | 490 |

*The mixture is acidified to pH = 3-6 with HCl (aq.) after quenching.

Alternate Preparation 129

5-Amino-3-[4-(1-[[3-(2,2-dimethylpropyl)-1,2-oxazol-5-yl]carbamoyl]ethyl)phenyl]-1-isopropylpyrazole-4-carboxamide A mixture of 2-[4-(5-amino-4-carbamoyl-1-isopropylpyrazol-3-yl)phenyl]propanoic acid (1.30 g, 4.109 mmol), 3-(2,2-dimethylpropyl)-1,2-oxazol-5-amine (0.70 g, 4.520 mmol), NMI (2.12 g, 16.437 mmol) and TCFH (2.31 g, 8.218 mmol) in DMF (50 mL) is stirred for 4 hrs at RT under $N_2$. The mixture is diluted with $H_2O$ (200 mL) and extracted with EtOAc (3×200 mL). The combined organic extracts are washed with saturated aqueous NaCl solution (3×100 mL) and concentrated under reduced pressure. The residue is purified by reverse Combi-flash chromatography with the following conditions: column, C18; mobile phase, ACN in $H_2O$ (0.1% FA) eluting with a gradient of 55% to 65% in 10 min; UV 220 nm to give the title compound (500 mg, 26.9%) as a light yellow solid. ES/MS (m/z) 453.4 (M+H).

Alternate Preparation 130

5-Amino-3-[5-(1-[[3-(2,2-dimethylpropyl)-1,2-oxazol-5-yl]carbamoyl]ethyl)pyridin-2-yl]-1-isopropylpyrazole-4-carboxamide

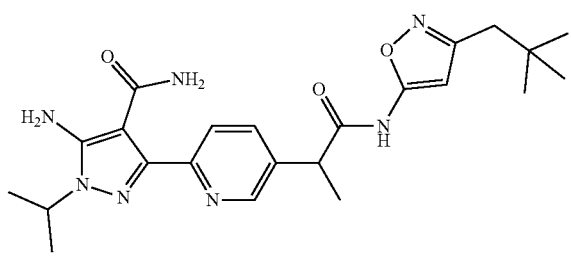 [SMILES: CC(C(=O)Nc1cc(CC(C)(C)C)no1)c1ccc(-c2nn(C(C)C)c(N)c2C(N)=O)nc1]

To a mixture of 2-[6-(5-amino-4-cyano-1-isopropylpyrazol-3-yl)pyridin-3-yl]-N-[3-(2,2-dimethylpropyl)-1,2-oxazol-5-yl]propanamide (120 mg, 0.28 mmol), NaOH (55 mg, 1.38 mmol), DMSO (0.40 mL), $H_2O$ (0.80 mL) in EtOH (2.00 mL) is added $H_2O_2$ (937 mg, 8.27 mmol 30%). The mixture is stirred at 40° C. for 4 hrs. The mixture is allowed to cool to RT, quenched by the addition of saturated $Na_2SO_3$ (aq 30 mL) and extracted with EtOAc (3×50 mL). The combined organic extracts are washed with brine (50 mL), dried over anhydrous $Na_2SO_4$, filtered, and concentrated under reduced pressure. The residue is purified by reversed Combi-flash chromatography with the following conditions: Column, C18, eluting with a gradient of 0 to 50% ACN in $H_2O$ (0.1% $NH_4CO_3$) to give the title compound (100 mg, 80%) as a white solid. ES/MS (m/z) 454.2 (M+H).

Alternate Preparation 138

5-Amino-3-[4-[1-[[3-(2,2-dimethylpropyl)-1,2-oxazol-5-yl]carbamoyl]ethyl]phenyl]-1-(1-methylcyclopropyl)pyrazole-4-carboxamide 2-[4-[5-Amino-4-cyano-1-(1-methylcyclopropyl)pyrazol-3-yl]phenyl]-N-[3-(2,2-dimethylpropyl)-1,2-oxazol-5-yl]propanamide (190 mg, 0.43 mmol), EtOH (5.00 mL), $H_2O$ (2.00 mL), DMSO (1.00 mL), NaOH (170.00 mg, 4.26 mmol) and $H_2O_2$ (2.43 g, 21.30 mmol, 30%) are added together. The solution is stirred for 5 hrs at 40° C. The reaction is quenched by saturated $Na_2SO_3$ (10 mL). The solution is diluted with EtOAc (100 mL), washed with $H_2O$ (2×30 mL), and brine (20 mL). The organic phase is concentrated under reduced pressure. The residue is purified by reversed Combi-flash chromatography with following conditions: C18; eluting with a gradient of 50% to 80% ACN in $H_2O$ (0.1% $NH_4CO_3$) to give the title compound (190 mg, 95.9%) as a white solid. ES/MS (m/z) 465.3 (M+H).

Preparation 167p

5-Amino-1-(1-methylcyclopropyl)-3-[4-[1-([3-[3-(trifluoromethyl)bicyclo[1.1.1]pentan-1-yl]-1,2-oxazol-5-yl]carbamoyl)ethyl]phenyl]pyrazole-4-carboxamide

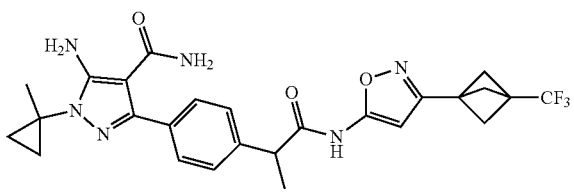 [SMILES: CC(C(=O)Nc1cc(C23CC(C(F)(F)F)(C2)C3)no1)c1ccc(-c2nn(C3(C)CC3)c(N)c2C(N)=O)cc1]

To a stirred solution of 2-[4-[5-amino-4-cyano-1-(1-methylcyclopropyl)pyrazol-3-yl]phenyl]-N-[3-[3-(trifluoromethyl)bicyclo[1.1.1]pentan-1-yl]-1,2-oxazol-5-yl]propanamide (225.00 mg, 0.44 mmol) in EtOH (5.00 mL) and DMSO (1.00 mL) is added NaOH (176.28 mg, 4.41 mmol) and H$_2$O$_2$ (30%, 999.40 mg, 8.82 mmol, 30 wt %) in portions at RT under N$_2$. The mixture is stirred for 2 hr at 50° C. in sealed tube under N$_2$. The mixture is cooled down to RT. The reaction is quenched by the addition of saturated Na$_2$SO$_3$ (20 mL) at RT. The mixture is extracted with EtOAc (3×50 mL). The combined organic extracts are washed with brine (2×100 mL), dried over anhydrous Na$_2$SO$_4$, and concentrated under reduced pressure. The residue is purified by reverse combi-flash chromatography with the following conditions: column, C18; eluting with a gradient of 40% to 50% ACN in H$_2$O (0.1% NH$_4$HCO$_3$) to give the title compound (70 mg, 30%) as a white solid. ES/MS (m/z) 529.2 (M+H)

Preparation 167q

5-Amino-3-(4-[1-[(3-[3-methylbicyclo[1.1.1]pentan-1-yl]-1,2-oxazol-5-yl)carbamoyl]ethyl]phenyl)-1-(1-methylcyclopropyl)pyrazole-4-carboxamide

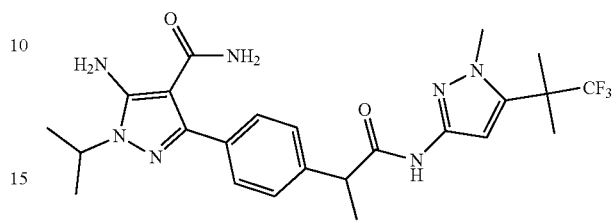

To a stirred solution of 2-[4-[5-amino-4-cyano-1-(1-methylcyclopropyl)pyrazol-3-yl]phenyl]-N-(3-[3-methylbicyclo[1.1.1]pentan-1-yl]-1,2-oxazol-5-yl)propanamide (130 mg, 0.29 mmol) in EtOH (5.00 mL) and DMSO (1.00 mL) is added NaOH (113.89 mg, 2.85 mmol) and H$_2$O$_2$ (30%, 645.70 mg, 5.70 mmol, 30 wt %) in portions at RT under N$_2$. The mixture is stirred for 4 hr at 50° C. under N$_2$. The mixture is allowed to cool to RT and quenched by the addition of saturated Na$_2$SO$_3$ (30 mL) at RT. The mixture is extracted with DCM (3×50 mL) and the combined organic extracts are washed with brine (2×100 mL), dried over anhydrous Na$_2$SO$_4$, filtered, and the filtrate is concentrated under reduced pressure. The residue is purified by reverse combi-flash chromatography with the following conditions: Column, C18; eluting with a gradient of 40% to 50% ACN in H$_2$O (0.1% NH$_4$HCO$_3$) to give the title compound (95 mg, 70%) as a pink solid. ES/MS (m/z) 497.2 (M+Na).

Preparation 167r

5-Amino-1-isopropyl-3-[4-(1-[[1-methyl-5-(1,1,1-trifluoro-2-methylpropan-2-yl)pyrazol-3-yl]carbamoyl]ethyl)phenyl]pyrazole-4-carboxamide

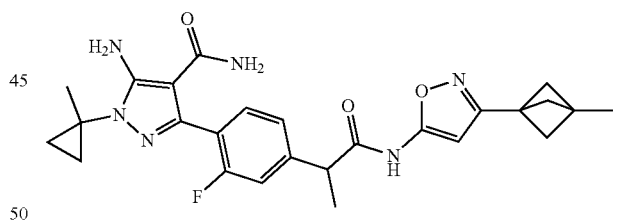

A solution of 2-[4-(5-amino-4-cyano-1-isopropylpyrazol-3-yl)phenyl]-N-[1-methyl-5-(1,1,1-trifluoro-2-methylpropan-2-yl)pyrazol-3-yl]propanamide (130 mg, 0.27 mmol), NaOH (53.33 mg, 1.33 mmol) in EtOH/DMSO (6 mL, 5:1), H$_2$O$_2$ (907 mg, 7.99 mmol, 30%) is added together and stirred for 2 hrs at 50° C. The solution is cooled to RT, quenched with saturated Na$_2$SO$_3$ solution (10 mL) and extracted with EtOAc (3×20 mL), the organic extracts are dried over anhydrous Na$_2$SO$_4$ and concentrated under reduced pressure. The crude product is purified by reversed phase Combi-flash with the following condition: Column, C18; eluting with a gradient of 40% to 60% ACN in H$_2$O (0.1% NH$_4$HCO$_3$), to give the title compound (100 mg, 74.18%). ES/MS (m/z) 506.4 (M+H).

Preparation 167s

5-Amino-3-(2-fluoro-4-[1-[(3-[3-methylbicyclo[1.1.1]pentan-1-yl]-1,2-oxazol-5-yl)carbamoyl]ethyl]phenyl)-1-(1-methylcyclopropyl)pyrazole-4-carboxamide To a solution of 2-[4-[5-amino-4-cyano-1-(1-methylcyclopropyl)pyrazol-3-yl]-3-fluorophenyl]-N-(3-[3-methylbicyclo[1.1.1]pentan-1-yl]-1,2-oxazol-5-yl)propanamide (100 mg, 0.21 mmol) and NaOH (42.14 mg, 1.05 mmol) in EtOH (5.00 mL) and DMSO (1.00 mL) is added H$_2$O$_2$ (358.39 mg, 3.161 mmol, 30%). The reaction is stirred for 2 hrs at 50° C. The reaction is quenched with saturated Na$_2$SO$_3$ (aq. 10 mL) at 0° C. The aqueous layer is extracted with EtOAc (3×30 mL). The combined organic layers are washed with brine (2×20 mL), dried over anhydrous Na$_2$SO$_4$, filtered, and the filtrate is concentrated under reduced pressure. The residue is purified by reversed Combi-flash chromatography with the following conditions: Column, C18; eluting with a gradient of 20% to 40% ACN in H$_2$O (0.1% NH$_4$HCO$_3$) to give the title compound (70 mg, 67.44%) as a white solid. ES/MS (m/z) 493.2 (M+H).

Preparation 167t

5-Amino-1-isopropyl-3-[4-[1-([3-[3-(trifluoromethyl)bicyclo[1.1.1]pentan-1-yl]-1,2-oxazol-5-yl]carbamoyl)ethyl]phenyl]pyrazole-4-carboxamide

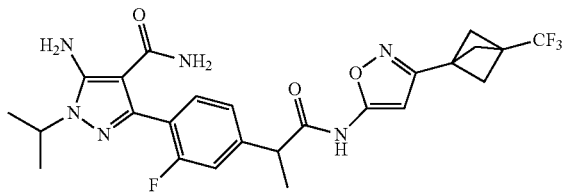 [SMILES: CC(C(=O)Nc1cc(C23CC(C(F)(F)F)(C2)C3)no1)c1ccc(-c2nn(C(C)C)c(N)c2C(N)=O)c(F)c1]

A solution of 2-[4-(5-amino-4-cyano-1-isopropylpyrazol-3-yl)phenyl]-N-[3-[3-(trifluoromethyl)bicyclo[1.1.1]pentan-1-yl]-1,2-oxazol-5-yl]propanamid (230 mg, 0.46 mmol), $H_2O_2$ (1.05 g, 9.23 mmol, 30%) and NaOH (93 mg, 2.31 mmol) in EtOH/DMSO (20 mL, 4:1) is stirred for 2 hr at 40° C. The solution is cooled to RT, saturated $Na_2SO_3$ solution (10 mL) is added and the mixture is stirred for 10 mins at RT. The mixture is concentrated under reduced pressure and purified by reversed phase Combi-flash with the following condition: Column, C18; eluting with a gradient of 20% to 50% MeOH in $H_2O$ (0.1% $NH_4HCO_3$) to give the title compound (166 mg, 69.7%) as white solid. ES/MS (m/z) 517.10 (M+H).

Preparation 167u

5-Amino-3-[4-[2-[[3-(2,2-dimethylpropyl)-4-fluoro-isoxazol-5-yl]amino]-1-methyl-2-oxo-ethyl]phenyl]-1-[2,2,2-trideuterio-1-(trideuteriomethyl)ethyl]pyrazole-4-carboxamide

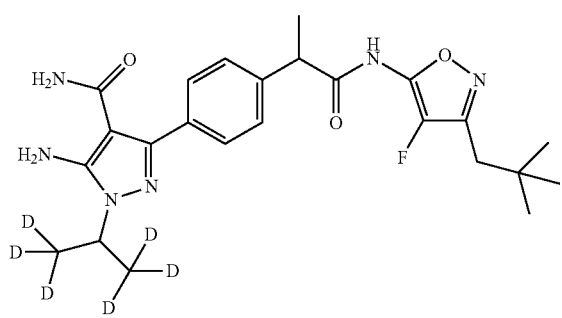 [SMILES: [2H]C([2H])([2H])C(n1nc(-c2ccc(C(C)C(=O)Nc3onc(CC(C)(C)C)c3F)cc2)c(C(N)=O)c1N)C([2H])([2H])[2H]]

To a stirred solution of 2-[4-[5-amino-4-cyano-1-[2,2,2-trideuterio-1-(trideuteriomethyl)ethyl]pyrazol-3-yl]phenyl]-N-[3-(2,2-dimethylpropyl)-4-fluoro-isoxazol-5-yl]propanamide (400 mg, 0.87 mmol) in EtOH (5.00 mL) and DMSO (1.00 mL) is added NaOH (174.44 mg, 4.36 mmol) and $H_2O_2$ (1.98 g, 17.45 mmol 30 wt %) dropwise at RT under $N_2$. The mixture is stirred for 1 hr at 50° C. under $N_2$ and then is quenched with saturated $Na_2SO_3$. The mixture is extracted with EtOAc (3×100 mL). The combined organic extracts are washed with brine (3×100 mL), dried over anhydrous $Na_2SO_4$, filtered, and concentrated under reduced pressure. The residue is purified by reverse combi-flash chromatography with the following conditions: Column C18; eluting with 30% to 50% ACN in $H_2O$ to give the title compound (120.00 mg, 28.87%) as a yellow solid. ES/MS (m/z) 477.3 (M+H).

Preparation 168

5-Amino-3-[6-[2-[[3-(1,1-dimethylpropyl)isoxazol-5-yl]amino]-1-methyl-2-oxo-ethyl]-3-pyridyl]-1-isopropyl-pyrazole-4-carboxamide

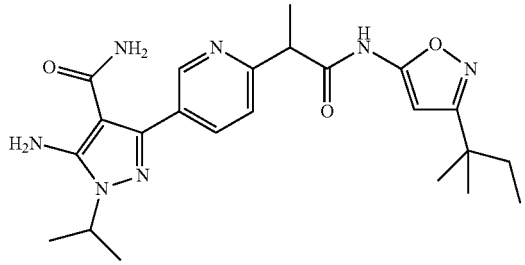 [SMILES: CCC(C)(C)c1cc(NC(=O)C(C)c2ccc(-c3nn(C(C)C)c(N)c3C(N)=O)cn2)on1]

To tert-butyl N-[4-carbamoyl-5-[6-[2-[[3-(1,1-dimethylpropyl)isoxazol-5-yl]amino]-1-methyl-2-oxo-ethyl]-3-pyridyl]-2-isopropyl-pyrazol-3-yl]carbamate (134 mg, 0.242 mmol) in DCM (1.45 mL) is added TFA (0.72 mL, 9.68 mmol). The reaction mixture is stirred at RT for 3 hrs. The reaction mixture is quenched with cold saturated aqueous solution of $NaHCO_3$ and the aqueous layer is extracted with EtOAc. The combined organic extract is washed with saturated aqueous NaCl solution, dried over $Na_2SO_4$, filtered, and concentrated under reduced pressure. The crude material is purified by silica gel flash chromatography eluting with a gradient of MeOH in DCM from 0% to 5% to give the title compound (68 mg, 61.95%).

The following compounds in Table 18 are prepared essentially as described for 5-amino-3-[6-[2-[[3-(1,1-dimethylpropyl)isoxazol-5-yl]amino]-1-methyl-2-oxo-ethyl]-3-pyridyl]-1-isopropyl-pyrazole-4-carboxamide adjusting reaction time to determine completion of the reaction and using appropriate chromatography conditions for purification. The product can also be triturated in isopropyl ether, filtered, and dried under vacuum.

TABLE 18

| Prep. No. | Chemical name | Structure | ES/MS m/z (M + H) | t(R) |
|---|---|---|---|---|
| 169 | 5-Amino-3-[6-[2-[[5-(2,2-dimethylpropyl)isoxazol-3-yl]amino]-1-methyl-2-oxo-ethyl]-3-pyridyl]-1-isopropyl-pyrazole-4-carboxamide | 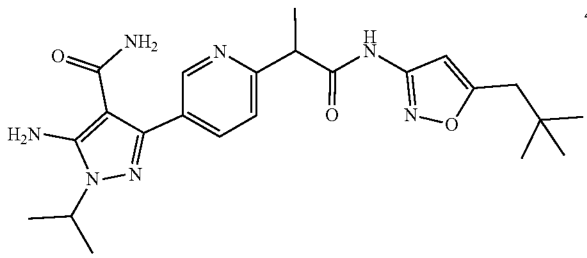 [SMILES: CC(C(=O)Nc1cc(CC(C)(C)C)on1)c1ccc(-c2nn(C(C)C)c(N)c2C(N)=O)cn1] | 454.4 | 18.4 |
| 170 | 5-Amino-1-isopropyl-3-[6-[1-methyl-2-oxo-2-[[5-(2,2,2-trifluoro-1,1-dimethyl-ethyl)isoxazol-3-yl]amino]ethyl]-3-pyridyl]pyrazole-4-carboxamide | 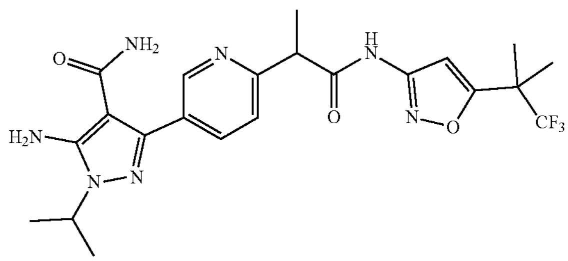 [SMILES: CC(C(=O)Nc1cc(C(C)(C)C(F)(F)F)on1)c1ccc(-c2nn(C(C)C)c(N)c2C(N)=O)cn1] | 494.4 | 5.2 |
| 171 | 5-Amino-1-isopropyl-3-[6-[1-methyl-2-oxo-2-[[3-(2,2,2-trifluoro-1,1-dimethyl-ethyl)isoxazol-5-yl]amino]ethyl]-3-pyridyl]pyrazole-4-carboxamide | 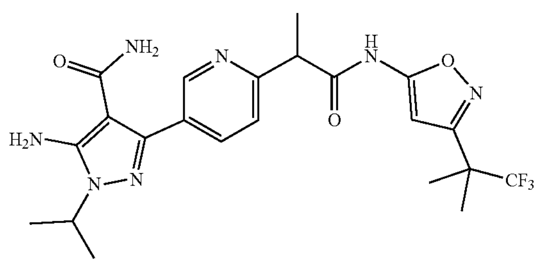 [SMILES: CC(C(=O)Nc1cc(C(C)(C)C(F)(F)F)no1)c1ccc(-c2nn(C(C)C)c(N)c2C(N)=O)cn1] | 494 | 3.5 |
| 172 | 5-Amino-3-[6-[2-[[3-(2,2-dimethylpropyl)isoxazol-5-yl]amino]-1-methyl-2-oxo-ethyl]-3-pyridyl]-1-isopropyl-pyrazole-4-carboxamide | 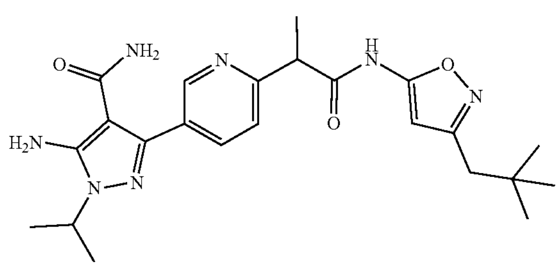 [SMILES: CC(C(=O)Nc1cc(CC(C)(C)C)no1)c1ccc(-c2nn(C(C)C)c(N)c2C(N)=O)cn1] | 454 | 28.5 |
| 173 | 5-Amino-3-[6-[2-[[3-(2,4-dichlorophenyl)isoxazol-5-yl]amino]-1-methyl-2-oxo-ethyl]-3-pyridyl]-1-isopropyl-pyrazole-4-carboxamide | 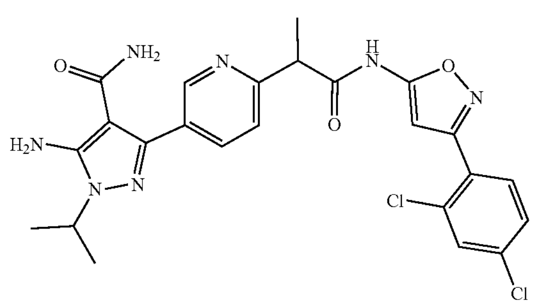 [SMILES: CC(C(=O)Nc1cc(-c2ccc(Cl)cc2Cl)no1)c1ccc(-c2nn(C(C)C)c(N)c2C(N)=O)cn1] | | 13.7 |

TABLE 18-continued

| Prep. No. | Chemical name | Structure | ES/MS m/z (M + H) | $t_{(R)}$ |
|---|---|---|---|---|
| 174 | 5-Amino-3-[6-[2-[[5-(1,1-dimethylpropyl)isoxazol-3-yl]amino]-1-methyl-2-oxo-ethyl]-3-pyridyl]-1-isopropyl-pyrazole-4-carboxamide | 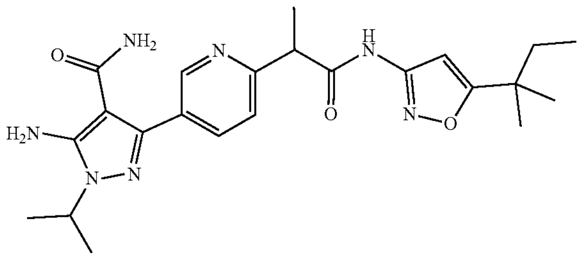 [SMILES: CCC(C)(C)c1cc(NC(=O)C(C)c2ccc(-c3nn(C(C)C)c(N)c3C(N)=O)cn2)no1] | | 7.8 |

Example 1

5-Amino-3-[4-(1-[[3-(2,2-dimethylpropyl)-1,2-oxazol-5-yl]carbamoyl]ethyl)phenyl]-1-isopropylpyrazole-4-carboxamide, Isomer 1 and

Example 2

5-Amino-3-[4-(1-[[3-(2,2-dimethylpropyl)-1,2-oxazol-5-yl]carbamoyl]ethyl)phenyl]-1-isopropylpyrazole-4-carboxamide, Isomer 2

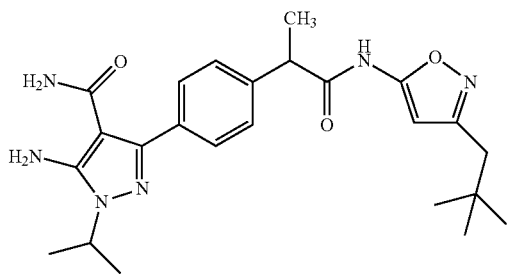 [SMILES: CC(C(=O)Nc1cc(CC(C)(C)C)no1)c1ccc(-c2nn(C(C)C)c(N)c2C(N)=O)cc1]

5-Amino-3-[4-(1-[[3-(2,2-dimethylpropyl)-1,2-oxazol-5-yl]carbamoyl]ethyl)phenyl]-1-isopropylpyrazole-4-carboxamide (100.00 mg, 0.22 mmol) is separated by prep-chiral chromatography with the following conditions: Column: CHIRAL ART Cellulose-SB, 2*25 cm, 5 µm; mobile phase A: hexanes (10 mM $NH_3$), mobile phase B:IPA; flow rate 20 mL/min; eluting 30% B in 15 min; 254 nm; $t_{(R)}$ Isomer 1 is 8.2 min (33.3 mg, 33.3%), $[\alpha]D^{20}$=0.22696° (C=0.1, MeOH) as a white solid with 100% ee. $t_{(R)}$ Isomer 2 is 11.0 min (33.1 mg, 33.1%), $[\alpha]D^{20}$=−0.2113° (C=0.1, MeOH) as a white solid with 100% ee. ES/MS (m/z) 453.4 (M+H).

The following compounds in Table 19 are prepared essentially as described for 5-amino-3-[4-(1-[[3-(2,2-dimethylpropyl)-1,2-oxazol-5-yl]carbamoyl]ethyl)phenyl]-1-isopropylpyrazole-4-carboxamide, Isomer 1 and Isomer 2 and adjusting the purification system as appropriate.

TABLE 19

| Prep. No. | Chemical name | Structure | ES/MS m/z (M + H) | $t_{(R)}$ |
|---|---|---|---|---|
| 3[1] | 5-Amino-3-[4-[1-[[3-(2,2-dimethylpropyl)-1,2-oxazol-5-yl]carbamoyl]ethyl]phenyl]-1-[1,1,1-trifluoropropan-2-yl]pyrazole-4-carboxamide, Isomer 1, Diastereomer A | 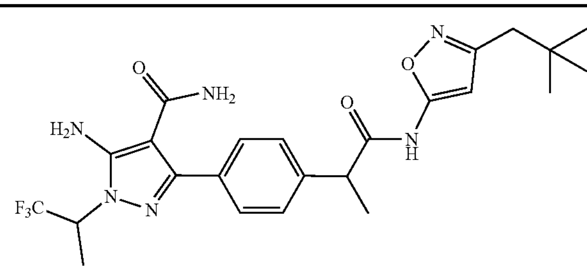 | 508.2 | 13.1 |

TABLE 19-continued

| Prep. No. | Chemical name | Structure | ES/MS m/z (M + H) | $t_{(R)}$ |
|---|---|---|---|---|
| 4[1] | 5-Amino-3-[4-[1-[[3-(2,2-dimethylpropyl)-1,2-oxazol-5-yl]carbamoyl]ethyl]phenyl]-1-[1,1,1-trifluoropropan-2-yl]pyrazole-4-carboxamide, Isomer 1, Diastereomer B | 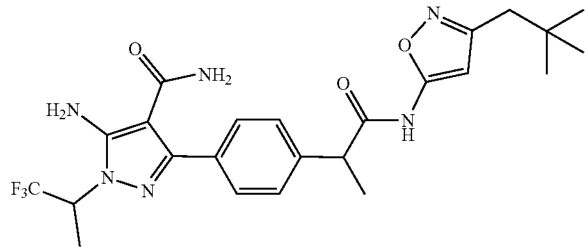 [SMILES: CC(C(=O)Nc1cc(CC(C)(C)C)no1)c1ccc(-c2nn(C(C)C(F)(F)F)c(N)c2C(N)=O)cc1] | 508.2 | 15.8 |
| 5[1] | 5-Amino-3-[4-[1-[[3-(2,2-dimethylpropyl)-1,2-oxazol-5-yl]carbamoyl]ethyl]phenyl]-1-[1,1,1-trifluoropropan-2-yl]pyrazole-4-carboxamide, Isomer 2, Diastereomer A | 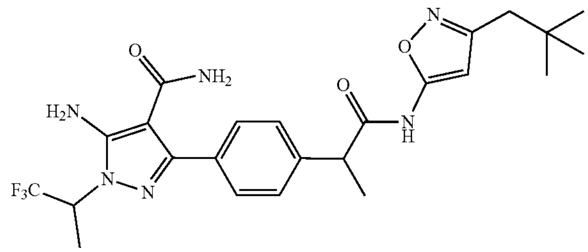 [SMILES: CC(C(=O)Nc1cc(CC(C)(C)C)no1)c1ccc(-c2nn(C(C)C(F)(F)F)c(N)c2C(N)=O)cc1] | 529.3 (M + Na) | 6.2 |
| 6[1] | 5-Amino-3-[4-[1-[[3-(2,2-dimethylpropyl)-1,2-oxazol-5-yl]carbamoyl]ethyl]phenyl]-1-[1,1,1-trifluoropropan-2-yl]pyrazole-4-carboxamide, Isomer 2, Diastereomer B | 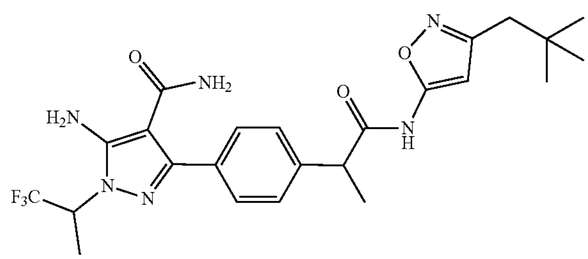 [SMILES: CC(C(=O)Nc1cc(CC(C)(C)C)no1)c1ccc(-c2nn(C(C)C(F)(F)F)c(N)c2C(N)=O)cc1] | 529.3 (M + Na) | 12.6 |
| 7 | 5-Amino-3-[4-[1-[[3-(2,2-dimethylpropyl)-1,2-oxazol-5-yl]carbamoyl]ethyl]phenyl]-1-(1,1,1-trifluoro-2-methylpropan-2-yl)pyrazole-4-carboxamide, Isomer 1 | 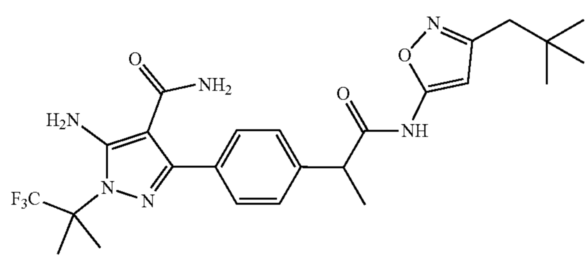 [SMILES: CC(C(=O)Nc1cc(CC(C)(C)C)no1)c1ccc(-c2nn(C(C)(C)C(F)(F)F)c(N)c2C(N)=O)cc1] | 521.4 | 12.2 |
| 8 | 5-Amino-3-[4-[1-[[3-(2,2-dimethylpropyl)-1,2-oxazol-5-yl]carbamoyl]ethyl]phenyl]-1-(1,1,1-trifluoro-2-methylpropan-2-yl)pyrazole-4-carboxamide, Isomer 2 | 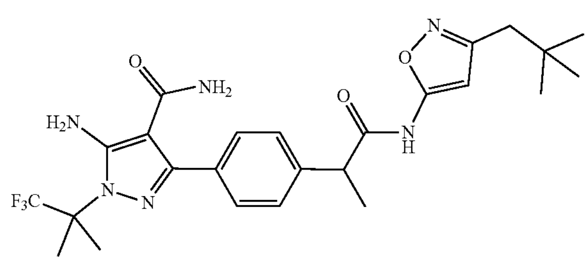 [SMILES: CC(C(=O)Nc1cc(CC(C)(C)C)no1)c1ccc(-c2nn(C(C)(C)C(F)(F)F)c(N)c2C(N)=O)cc1] | 521.4 | 14.3 |

TABLE 19-continued

| Prep. No. | Chemical name | Structure | ES/MS m/z (M + H) | t(R) |
|---|---|---|---|---|
| 9 | 5-Amino-3-[4-[1-[[3-(3,3-dimethylcyclobutyl)-1,2-oxazol-5-yl]carbamoyl]ethyl]phenyl]-1-(1-methylcyclopropyl)pyrazole-4-carboxamide, Isomer 1 | 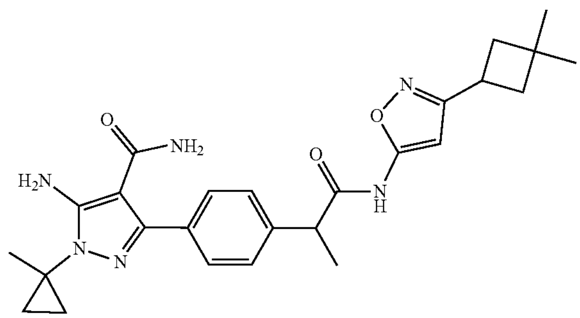 | 477.4 | 8.6 |
| 10 | 5-Amino-3-[4-[1-[[3-(3,3-dimethylcyclobutyl)-1,2-oxazol-5-yl]carbamoyl]ethyl]phenyl]-1-(1-methylcyclopropyl)pyrazole-4-carboxamide, Isomer 2 | 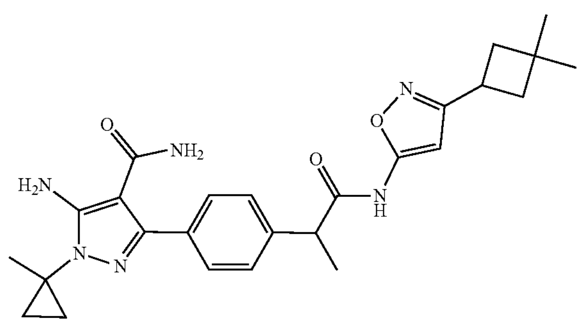 | 477.4 | 11.1 |
| 11 | 5-Amino-3-[4-[1-[[5-(2,2-dimethylpropyl)-1,2-oxazol-3-yl]carbamoyl]ethyl]phenyl]-1-(1-methylcyclopropyl)pyrazole-4-carboxamide, Isomer 1 | 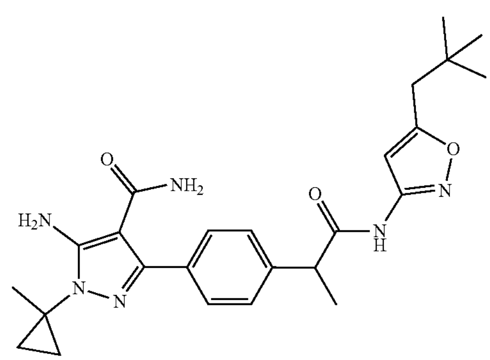 [SMILES: CC(C(=O)Nc1cc(CC(C)(C)C)on1)c1ccc(-c2nn(C3(C)CC3)c(N)c2C(N)=O)cc1] | 465.2 | 11.9 |
| 12 | 5-Amino-3-[4-[1-[[5-(2,2-dimethylpropyl)-1,2-oxazol-3-yl]carbamoyl]ethyl]phenyl]-1-(1-methylcyclopropyl)pyrazole-4-carboxamide, Isomer 2 | 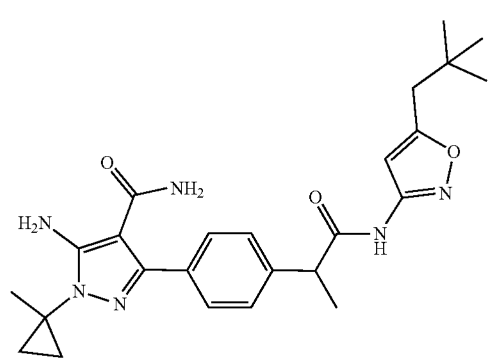 [SMILES: CC(C(=O)Nc1cc(CC(C)(C)C)on1)c1ccc(-c2nn(C3(C)CC3)c(N)c2C(N)=O)cc1] | 465.2 | 14.4 |

TABLE 19-continued

| Prep. No. | Chemical name | Structure | ES/MS m/z (M + H) | $t_{(R)}$ |
|---|---|---|---|---|
| 13 | 5-Amino-3-[4-[1-[[3-(2,2-dimethylpropyl)-1,2-oxazol-5-yl]carbamoyl]ethyl]phenyl]-1-(1-methoxy-2-methylpropan-2-yl)pyrazole-4-carboxamide, Isomer 1 | 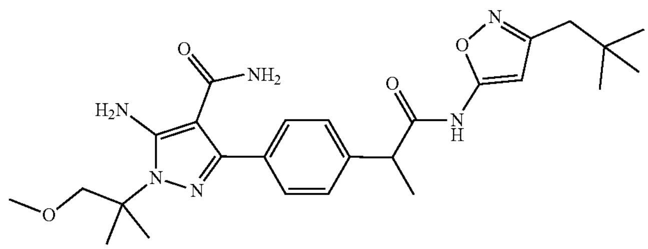 [SMILES: COCC(C)(C)n1nc(-c2ccc(C(C)C(=O)Nc3cc(CC(C)(C)C)no3)cc2)c(C(N)=O)c1N] | 497.2 | 14.2 |
| 14 | 5-Amino-3-[4-[1-[[3-(2,2-dimethylpropyl)-1,2-oxazol-5-yl]carbamoyl]ethyl]phenyl]-1-(1-methoxy-2-methylpropan-2-yl)pyrazole-4-carboxamide, Isomer 2 | 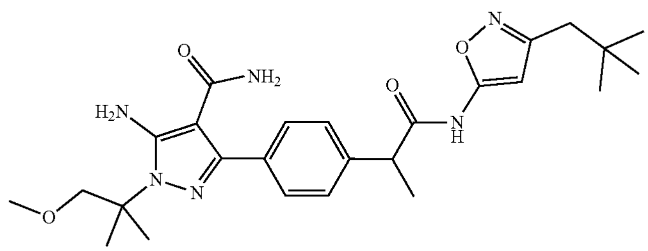 [SMILES: COCC(C)(C)n1nc(-c2ccc(C(C)C(=O)Nc3cc(CC(C)(C)C)no3)cc2)c(C(N)=O)c1N] | 497.2 | 17.6 |
| 15 | 5-Amino-1-isopropyl-3-[4-(1-[[3-(2-methylbutan-2-yl)-1,2-oxazol-5-yl]carbamoyl]ethyl)phenyl]pyrazole-4-carboxamide, Isomer 1 | 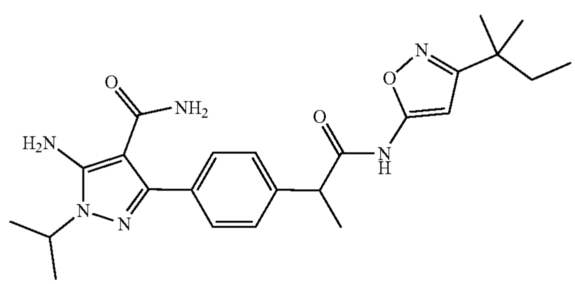 [SMILES: CCC(C)(C)c1cc(NC(=O)C(C)c2ccc(-c3nn(C(C)C)c(N)c3C(N)=O)cc2)on1] | 453.2 | 9.3 |
| 16 | 5-Amino-1-isopropyl-3-[4-(1-[[3-(2-methylbutan-2-yl)-1,2-oxazol-5-yl]carbamoyl]ethyl)phenyl]pyrazole-4-carboxamide, Isomer 2 | 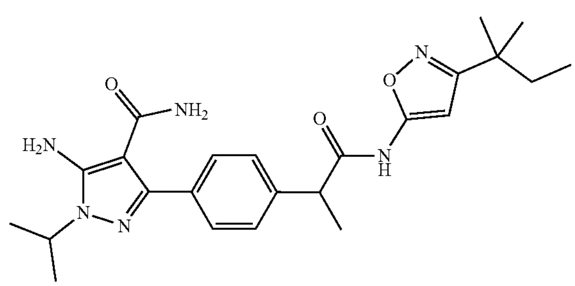 [SMILES: CCC(C)(C)c1cc(NC(=O)C(C)c2ccc(-c3nn(C(C)C)c(N)c3C(N)=O)cc2)on1] | 453.2 | 11.4 |
| 17 | 5-Amino-1-isopropyl-3-[4-(1-[[3-(1,1,1-trifluoro-2-methylpropan-2-yl)-1,2-oxazol-5-yl]carbamoyl]ethyl)phenyl]pyrazole-4-carboxamide, Isomer 1 | 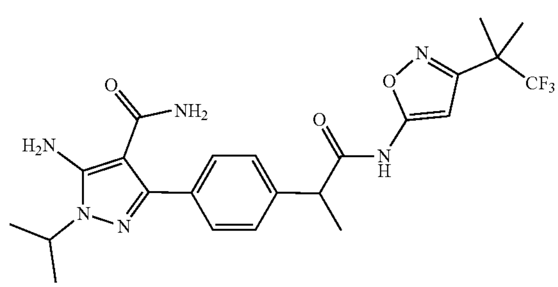 [SMILES: CC(C(=O)Nc1cc(C(C)(C)C(F)(F)F)no1)c1ccc(-c2nn(C(C)C)c(N)c2C(N)=O)cc1] | 493.2 | 6.9 |

TABLE 19-continued

| Prep. No. | Chemical name | Structure | ES/MS m/z (M + H) | t(R) |
|---|---|---|---|---|
| 18 | 5-Amino-1-isopropyl-3-[4-(1-[[3-(1,1,1-trifluoro-2-methylpropan-2-yl)-1,2-oxazol-5-yl]carbamoyl]ethyl)phenyl]pyrazole-4-carboxamide, Isomer 2 | 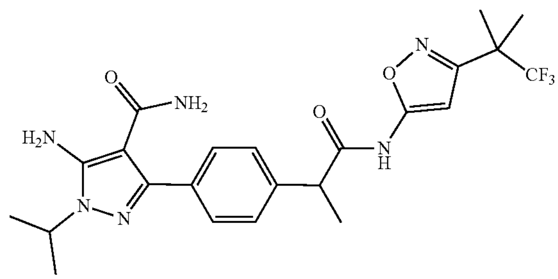 [SMILES: CC(C(=O)Nc1cc(C(C)(C)C(F)(F)F)no1)c1ccc(-c2nn(C(C)C)c(N)c2C(N)=O)cc1] | 493.2 | 8.0 |
| 19[2] | 5-Amino-3-[5-[1-[[3-(2-chloro-4-fluorophenyl)-1,2-oxazol-5-yl]carbamoyl]ethyl]pyridin-2-yl]-1-[1,1,1-trifluoropropan-2-yl]pyrazole-4-carboxamide, Isomer 1, Diastereomer A | 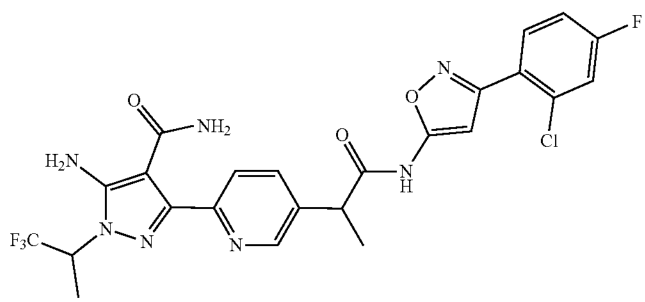 [SMILES: CC(C(=O)Nc1cc(-c2ccc(F)cc2Cl)no1)c1ccc(-c2nn(C(C)C(F)(F)F)c(N)c2C(N)=O)nc1] | 566.1, 568.1 | 13.7 |
| 20[2] | 5-Amino-3-[5-[1-[[3-(2-chloro-4-fluorophenyl)-1,2-oxazol-5-yl]carbamoyl]ethyl]pyridin-2-yl]-1-[1,1,1-trifluoropropan-2-yl]pyrazole-4-carboxamide, Isomer 1, Diastereomer B | 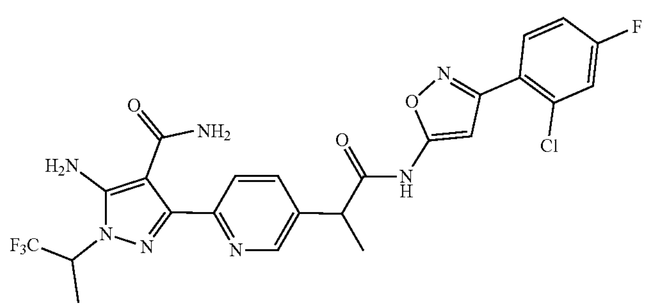 [SMILES: CC(C(=O)Nc1cc(-c2ccc(F)cc2Cl)no1)c1ccc(-c2nn(C(C)C(F)(F)F)c(N)c2C(N)=O)nc1] | 566.1, 568.1 | 21.2 |
| 21[3] | 5-Amino-1-isopropyl-3-[4-(1-[[3-(trifluoromethyl)phenyl]carbamoyl]ethyl)phenyl]pyrazole-4-carboxamide, Isomer 1 | 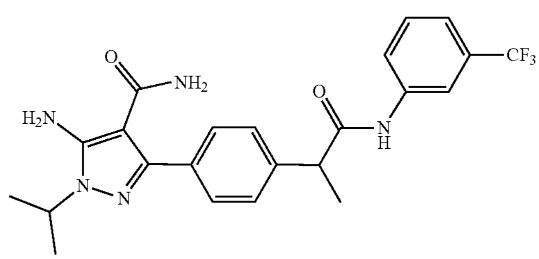 [SMILES: CC(C(=O)Nc1cccc(C(F)(F)F)c1)c1ccc(-c2nn(C(C)C)c(N)c2C(N)=O)cc1] | 460.3 | 9.0 |
| 22[3] | 5-Amino-1-isopropyl-3-[4-(1-[[3-(trifluoromethyl)phenyl]carbamoyl]ethyl)phenyl]pyrazole-4-carboxamide, Isomer 2 | 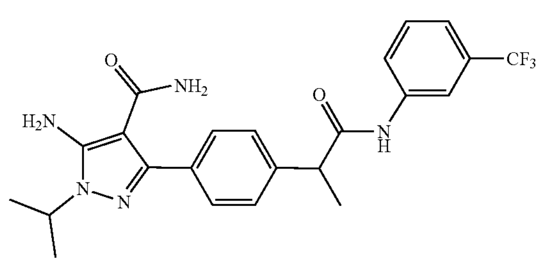 [SMILES: CC(C(=O)Nc1cccc(C(F)(F)F)c1)c1ccc(-c2nn(C(C)C)c(N)c2C(N)=O)cc1] | 460.3 | 12.8 |

TABLE 19-continued

| Prep. No. | Chemical name | Structure | ES/MS m/z (M + H) | $t_{(R)}$ |
|---|---|---|---|---|
| 23[4] | 5-Amino-3-[5-[1-[[3-(2,2-dimethylpropyl)-1,2-oxazol-5-yl]carbamoyl]ethyl]pyridin-2-yl]-1-[1,1,1-trifluoropropan-2-yl]pyrazole-4-carboxamide, Isomer 2, Diastereomer A | 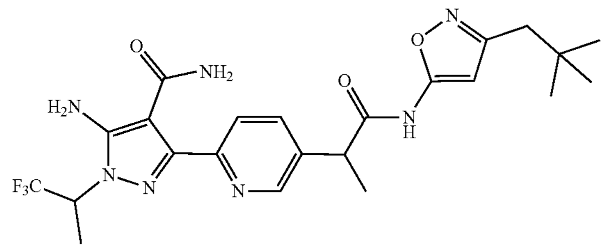 [SMILES: CC(C(=O)Nc1cc(CC(C)(C)C)no1)c1ccc(-c2nn(C(C)C(F)(F)F)c(N)c2C(N)=O)nc1] | 508.15 | 4.0 |
| 24[4] | 5-Amino-3-[5-[1-[[3-(2,2-dimethylpropyl)-1,2-oxazol-5-yl]carbamoyl]ethyl]pyridin-2-yl]-1-[1,1,1-trifluoropropan-2-yl]pyrazole-4-carboxamide, Isomer 2, Diastereomer B | 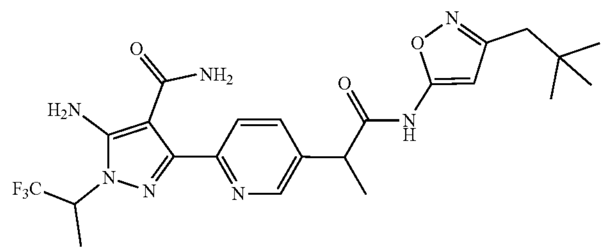 [SMILES: CC(C(=O)Nc1cc(CC(C)(C)C)no1)c1ccc(-c2nn(C(C)C(F)(F)F)c(N)c2C(N)=O)nc1] | 508.15 | 11 |
| 25[5] | 5-Amino-3-[5-[1-[[5-(1,1,1-trifluoro-2-methylpropan-2-yl)-1,2-oxazol-3-yl]carbamoyl]ethyl]pyridin-2-yl]-1-[1,1,1-trifluoropropan-2-yl]pyrazole-4-carboxamide, Isomer 1 | 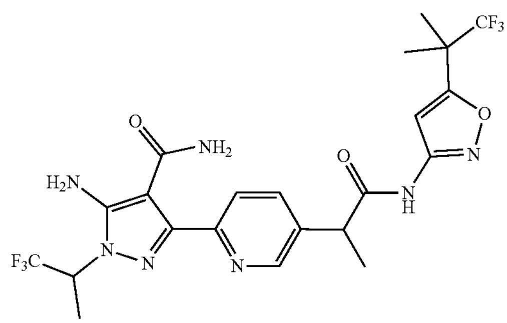 [SMILES: CC(C(=O)Nc1cc(C(C)(C)C(F)(F)F)on1)c1ccc(-c2nn(C(C)C(F)(F)F)c(N)c2C(N)=O)nc1] | 548.2 | 7.5 |
| 26[5] | 5-Amino-3-[5-[1-[[5-(1,1,1-trifluoro-2-methylpropan-2-yl)-1,2-oxazol-3-yl]carbamoyl]ethyl]pyridin-2-yl]-1-[1,1,1-trifluoropropan-2-yl]pyrazole-4-carboxamide, Isomer 2 | 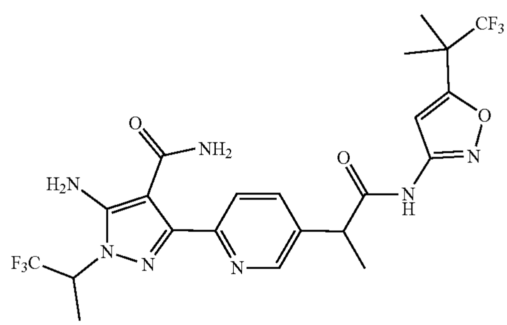 [SMILES: CC(C(=O)Nc1cc(C(C)(C)C(F)(F)F)on1)c1ccc(-c2nn(C(C)C(F)(F)F)c(N)c2C(N)=O)nc1] | 548.2 | 11 |
| 27[5] | 5-Amino-1-isopropyl-3-[4-(1-[[5-(4,4,4-trifluoro-2-methylbutan-2-yl)-1,2-oxazol-3-yl]carbamoyl]ethyl)phenyl]pyrazole-4-carboxamide, Isomer 1 | 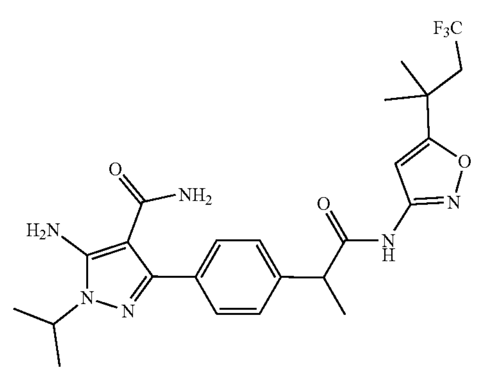 [SMILES: CC(C(=O)Nc1cc(C(C)(C)CC(F)(F)F)on1)c1ccc(-c2nn(C(C)C)c(N)c2C(N)=O)cc1] | 507.15 | 8 |

TABLE 19-continued

| Prep. No. | Chemical name | Structure | ES/MS m/z (M + H) | $t_{(R)}$ |
|---|---|---|---|---|
| 28[5] | 5-Amino-1-isopropyl-3-[4-(1-[[5-(4,4,4-trifluoro-2-methylbutan-2-yl)-1,2-oxazol-3-yl]carbamoyl]ethyl)phenyl]pyrazole-4-carboxamide, Isomer 2 | 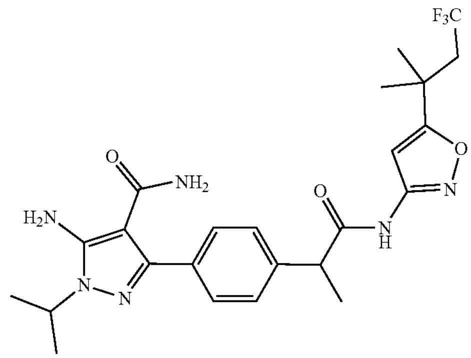 [SMILES: CC(C(=O)Nc1cc(C(C)(C)CC(F)(F)F)on1)c1ccc(-c2nn(C(C)C)c(N)c2C(N)=O)cc1] | 507.15 | 10.8 |
| 29[6] | 5-Amino-3-[5-[1-[[3-(2,4-dichlorophenyl)-1,2-oxazol-5-yl]carbamoyl]ethyl]pyridin-2-yl]-1-[1,1,1-trifluoropropan-2-yl]pyrazole-4-carboxamide, Isomer 1, Diastereomer A | 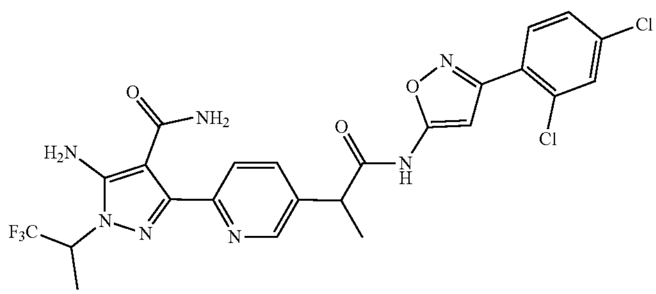 [SMILES: CC(C(=O)Nc1cc(-c2ccc(Cl)cc2Cl)no1)c1ccc(-c2nn(C(C)C(F)(F)F)c(N)c2C(N)=O)nc1] | 582.0, 584.0 | 11.7 |
| 30[6] | 5-Amino-3-[5-[1-[[3-(2,4-dichlorophenyl)-1,2-oxazol-5-yl]carbamoyl]ethyl]pyridin-2-yl]-1-[1,1,1-trifluoropropan-2-yl]pyrazole-4-carboxamide, Isomer 1, Diastereomer B | 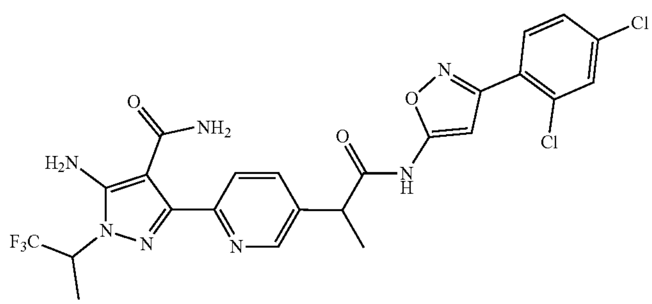 [SMILES: CC(C(=O)Nc1cc(-c2ccc(Cl)cc2Cl)no1)c1ccc(-c2nn(C(C)C(F)(F)F)c(N)c2C(N)=O)nc1] | 582.1, 584.1 | 15.8 |
| 31[7] | 5-Amino-1-(1-methylcyclopropyl)-3-[5-[(1-[[5-[1,1,1-trifluoro-2-methylpropan-2-yl)-1,2-oxazol-3-yl]carbamoyl]ethyl]pyridin-2-yl]pyrazole-4-carboxamide, Isomer 1 | 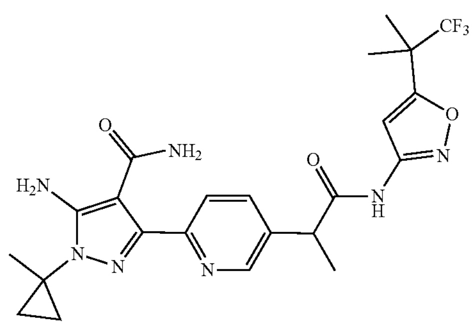 [SMILES: CC(C(=O)Nc1cc(C(C)(C)C(F)(F)F)on1)c1ccc(-c2nn(C3(C)CC3)c(N)c2C(N)=O)nc1] | 506.3 | 8.6 |

TABLE 19-continued

| Prep. No. | Chemical name | Structure | ES/MS m/z (M + H) | t$_{(R)}$ |
|---|---|---|---|---|
| 32[7] | 5-Amino-1-(1-methylcyclopropyl)-3-[5-[(1-[[5-[1,1,1-trifluoro-2-methylpropan-2-yl]-1,2-oxazol-3-yl]carbamoyl]ethyl]pyridin-2-yl]pyrazole-4-carboxamide, Isomer 2 | 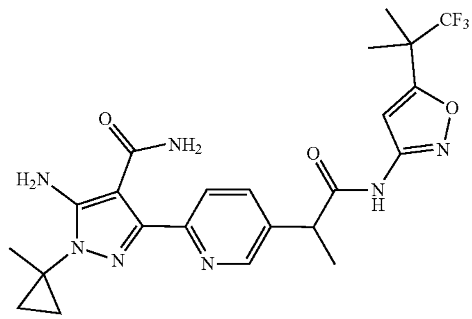 [SMILES: CC(C(=O)Nc1cc(C(C)(C)C(F)(F)F)on1)c1ccc(-c2nn(C3(C)CC3)c(N)c2C(N)=O)nc1] | 506.3 | 10.0 |
| 33[8] | 5-Amino-3-[5-[1-[[3-(2,2-dimethylpropyl)-1,2-oxazol-5-yl]carbamoyl]ethyl]pyridin-2-yl]-1-(1-methylcyclopropyl)pyrazole-4-carboxamide, Isomer 1 | 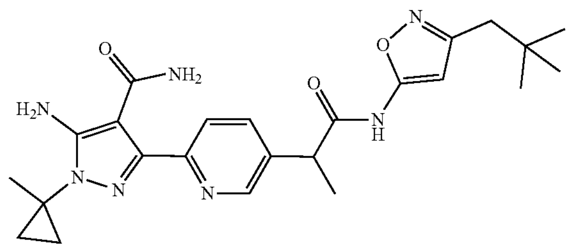 [SMILES: CC(C(=O)Nc1cc(CC(C)(C)C)no1)c1ccc(-c2nn(C3(C)CC3)c(N)c2C(N)=O)nc1] | 466.35 | 8.8 |
| 34[8] | 5-Amino-3-[5-[1-[[3-(2,2-dimethylpropyl)-1,2-oxazol-5-yl]carbamoyl]ethyl]pyridin-2-yl]-1-(1-methylcyclopropyl)pyrazole-4-carboxamide, Isomer 2 | 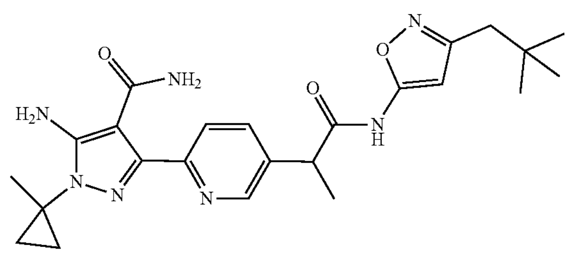 [SMILES: CC(C(=O)Nc1cc(CC(C)(C)C)no1)c1ccc(-c2nn(C3(C)CC3)c(N)c2C(N)=O)nc1] | 466.35 | 13.6 |
| 35 | 5-Amino-1-isopropyl-3-[4-(1-[[3-(1-methylcyclopropyl)-1,2-oxazol-5-yl]carbamoyl]ethyl)phenyl]pyrazole-4-carboxamide, Isomer 1 | 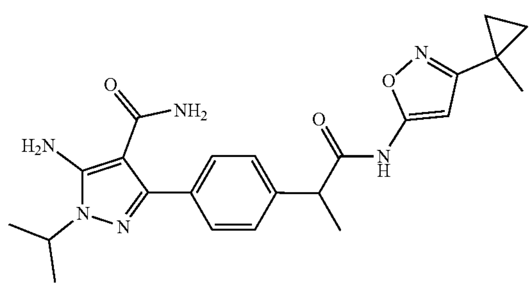 [SMILES: CC(C(=O)Nc1cc(C2(C)CC2)no1)c1ccc(-c2nn(C(C)C)c(N)c2C(N)=O)cc1] | 437.2 | 8.2 |
| 36 | 5-Amino-1-isopropyl-3-[4-(1-[[3-(1-methylcyclopropyl)-1,2-oxazol-5-yl]carbamoyl]ethyl)phenyl]pyrazole-4-carboxamide, Isomer 2 | 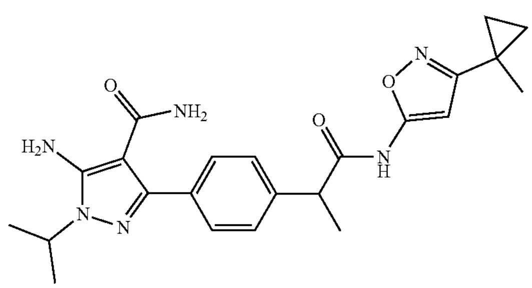 [SMILES: CC(C(=O)Nc1cc(C2(C)CC2)no1)c1ccc(-c2nn(C(C)C)c(N)c2C(N)=O)cc1] | 437.2 | 11 |

TABLE 19-continued

| Prep. No. | Chemical name | Structure | ES/MS m/z (M + H) | $t_{(R)}$ |
|---|---|---|---|---|
| 36a[9] | 5-Amino-3-[4-(1-[[3-(2,2-dimethylpropyl)-1,2-oxazol-5-yl]carbamoyl]ethyl)-2,3-difluorophenyl]-1-isopropylpyrazole-4-carboxamide, Isomer 1 | 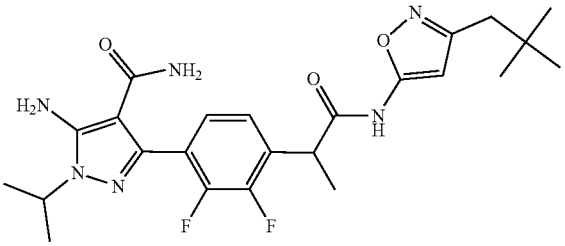 [SMILES: CC(C(=O)Nc1cc(CC(C)(C)C)no1)c1ccc(-c2nn(C(C)C)c(N)c2C(N)=O)c(F)c1F] | 489.2 | 10 |
| 36b[9] | 5-Amino-3-[4-(1-[[3-(2,2-dimethylpropyl)-1,2-oxazol-5-yl]carbamoyl]ethyl)-2,3-difluorophenyl]-1-isopropylpyrazole-4-carboxamide, Isomer 2 | 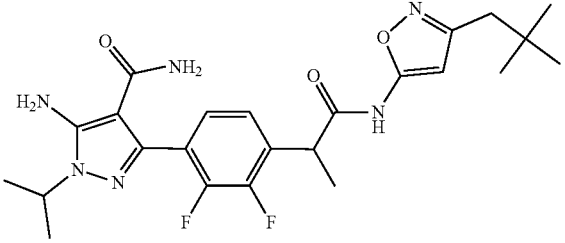 [SMILES: CC(C(=O)Nc1cc(CC(C)(C)C)no1)c1ccc(-c2nn(C(C)C)c(N)c2C(N)=O)c(F)c1F] | 489.2 | 12.8 |

[1] Column Chiralpak AD-H, 2*25 cm, 5 μm.
[2] Column: (R,R)Whelk-O 1, 21.1*250 mm, 5 μm.
[3] Column: (R,R)Whelk-O 1, Kromasil(02), 5*25 cm, 5 μm.
[4] CHIRALPAK IF, 2*25 cm, 5 μm.
[5] CHIRALPAK IA, 2*25 cm, 5 μm.
[6] CHIRALPAK IA, 2*25 cm, 5 μm.
[7] Mobile phase B, EtOH.
[8] (R,R)-Whelk-01, 2.12*25, 5 μm, mobile phase B, EtOH.
[9] Eluting with 25% IPA, 246/210 nm

Alternate Example 1

5-Amino-3-[4-(1-[[3-(2,2-dimethylpropyl)-1,2-oxazol-5-yl]carbamoyl]ethyl)phenyl]-1-isopropylpyrazole-4-carboxamide, Isomer 1

5-Amino-3-[4-(1-[[3-(2,2-dimethylpropyl)-1,2-oxazol-5-yl]carbamoyl]ethyl)phenyl]-1-isopropylpyrazole-4-carboxamide (17 g) is isolated by prep-chiral with the following conditions: Column: CHIRAL ART Cellulose-SB, 2*25 cm, 5 μm; mobile phase A hexanes (10 mM NH$_3$-MeOH), mobile phase B IPA; flow rate 20 mL/min; eluting with 30% B in 12 min; UV 254/220 nm; $t_{(R)}$ Isomer 1 is 7.0. The resulting solution is concentrated under reduced pressure. The residue is purified by reverse Combi-flash chromatography with the following conditions: column, C18; mobile phase, ACN in H$_2$O (0.1% FA) eluting with a gradient of 55% to 65% in 10 min; UV 220 nm, (6.1315 g, 35.7%) as white solid with 99.8% ee, MP 128° C., ES/MS (m/z) 453.2 (M+H).

Example 36c

5-Amino-3-[4-[1-[(3-[3-methylbicyclo[1.1.1]pentan-1-yl]-1,2-oxazol-5-yl)carbamoyl]ethyl]phenyl]-1-(1-methylcyclopropyl)pyrazole-4-carboxamide, Isomer 1 and

Example 36d

5-Amino-3-[4-[1-[(3-[3-methylbicyclo[1.1.1]pentan-1-yl]-1,2-oxazol-5-yl)carbamoyl]ethyl]phenyl]-1-(1-methylcyclopropyl)pyrazole-4-carboxamide, Isomer 2

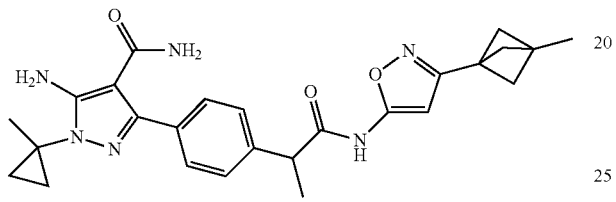

5-Amino-3-(4-[1-[(3-[3-methylbicyclo[1.1.1]pentan-1-yl]-1,2-oxazol-5-yl)carbamoyl]ethyl]phenyl)-1-(1-methylcyclopropyl)pyrazole-4-carboxamide (93 mg) is purified by Prep-HPLC with the following conditions: Column CHIRAL ART Cellulose-SB, 2*25 cm, 5 μm; eluting with 20% IPA in hexanes (10 mM NH$_3$-MeOH), flow rate 20 mL/min; 254/210 nm to give Isomer 1, t$_{(R)}$ 12.22, (30.8 mg, 33% yield, 100% ee) as a white solid, ES/MS (m/z) 475.3 (M+H) and Isomer 2, t$_{(R)}$ 16.56, (30.5 mg, 33% yield 100% ee) as a white solid, ES/MS (m/z) 475.3 (M+H).

Example 36e

5-Amino-1-isopropyl-3-[4-[1-[[1-methyl-5-(1,1,1-trifluoro-2-methylpropan-2-yl)pyrazol-3-yl]carbamoyl]ethyl]phenyl]pyrazole-4-carboxamide, Isomer 1 and

Example 36f

5-Amino-1-isopropyl-3-[4-[1-[[1-methyl-5-(1,1,1-trifluoro-2-methylpropan-2-yl)pyrazol-3-yl]carbamoyl]ethyl]phenyl]pyrazole-4-carboxamide, Isomer 2

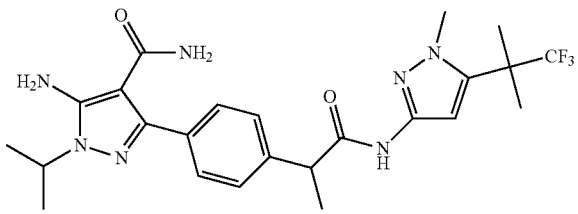 [SMILES: CC(C(=O)Nc1cc(C(C)(C)C(F)(F)F)n(C)n1)c1ccc(-c2nn(C(C)C)c(N)c2C(N)=O)cc1]

5-Amino-1-isopropyl-3-[4-(1-[[1-methyl-5-(1,1,1-trifluoro-2-methylpropan-2-yl)pyrazol-3-yl]carbamoyl]ethyl)phenyl]pyrazole-4-carboxamide (90 mg) is purified by Prep-CHIRAL-HPLC with the following conditions: Column CHIRALPAK IC, 2*25 cm, 5 μm; eluting with 30% IPA in hexanes (10 mM NH$_3$-MeOH), flow rate 20 mL/min; 240/210 nm to give the title compound of Isomer 1, t$_{(R)}$ 15.48, (35.2 mg, 39.22% yield, 100% ee), ES/MS (m/z) 506.3 (M+H) as a white solid and the title compound of Isomer 2, t$_{(R)}$ 20.74, (32.3 mg, 35.89% yield 97.7% ee), ES/MS (m/z) 506.3 (M+H) as a white solid.

Example 36g

5-Amino-1-isopropyl-3-(4-(1-((3-(3-methylbicyclo[1.1.1]pentan-1-yl)isoxazol-5-yl)amino)-1-oxopropan-2-yl)phenyl)-1H-pyrazole-4-carboxamide, Isomer 1

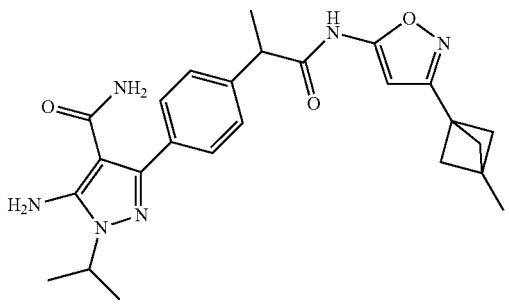 [SMILES: CC(C(=O)Nc1cc(C23CC(C)(C2)C3)no1)c1ccc(-c2nn(C(C)C)c(N)c2C(N)=O)cc1]

2-[4-(5-Amino-4-cyano-1-isopropyl-pyrazol-3-yl)phenyl]-N-[3-(3-methyl-1-bicyclo[1.1.1]pentanyl)isoxazol-5-yl]propanamide, Isomer 1 (110 mg, 247 μmol) and Parkins catalyst (106 mg, 247 μmol) are combined in EtOH (4 mL) and H$_2$O (1 mL). The mixture is heated to 60° C. for 24 hrs. The mixture is passed through a 0.45 μM filter and the solvent is removed under reduced pressure. The residue is purified via silica gel flash chromatography eluting with a gradient of 0-100% heptane:EtOAc to give the title compound (26 mg, 23%) as a yellow solid. ES/MS (m/z) 463.2 (M+H).

Example 36h

5-Amino-1-(1-methylcyclopropyl)-3-[4-[1-([3-[3-(trifluoromethyl)bicyclo[1.1.1]pentan-1-yl]-1,2-oxazol-5-yl]carbamoyl)ethyl]phenyl]pyrazole-4-carboxamide, Isomer 1 and

Example 36i

5-Amino-1-(1-methylcyclopropyl)-3-[4-[1-([3-[3-(trifluoromethyl)bicyclo[1.1.1]pentan-1-yl]-1,2-oxazol-5-yl]carbamoyl)ethyl]phenyl]pyrazole-4-carboxamide, Isomer 2

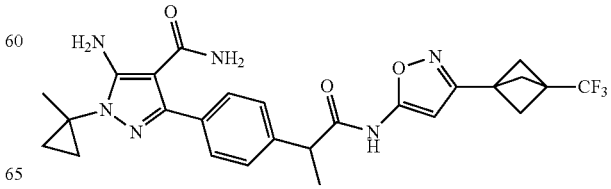

5-Amino-1-(1-methylcyclopropyl)-3-[4-[1-([3-[3-(trifluoromethyl)bicyclo[1.1.1]pentan-1-yl]-1,2-oxazol-5-yl]carbamoyl)ethyl]phenyl]pyrazole-4-carboxamide (68 mg) is purified by Prep-CHIRAL-HPLC with the following conditions: Column: CHIRAL ART Cellulose-SB, 2*25 cm, 5 μm; eluting with 15% EtOH in hexanes (10 mM $NH_3$-MeOH), flow rate 20 mL/min in 18 min, 254/210 nm to give the title compound of Isomer 1, $t_{(R)}$ 11.72, (15.3 mg, 22% yield with 100% ee) as a white solid, ES/MS (m/z) 529.2 (M+H) and the title compound of Isomer 2, $t_{(R)}$ 14.41, (16.8 mg, 24% yield with 100% ee) as a white solid, ES/MS (m/z) 529.2 (M+H).

The following compounds in Table 19a are prepared essentially as described for 5-amino-1-(1-methylcyclopropyl)-3-[4-[1-([3-[3-(trifluoromethyl)bicyclo[1.1.1]pentan-1-yl]-1,2-oxazol-5-yl]carbamoyl)ethyl]phenyl]pyrazole-4-carboxamide, Isomer 1 and Isomer 2 and adjusting chromatography conditions as appropriate.

TABLE 19a

| Ex. No. | Chemical name | Structure | ES/MS m/z (M + H) | $t_{(R)}$ min |
|---|---|---|---|---|
| 36j | 5-Amino-3-[4-[2-[[3-(2,2-dimethylpropyl)isoxazol-5-yl]amino]-1-methyl-2-oxo-ethyl]phenyl]-1-(2,2,2-trideuterio-1-methyl-ethyl)pyrazole-4-carboxamide, Isomer 1 | 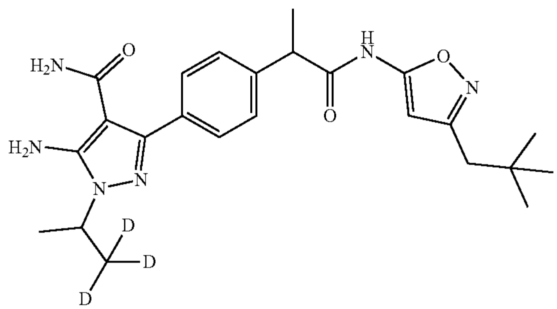 | 456.2 | 11.62 |
| 36k | 5-Amino-3-[4-[2-[[3-(2,2-dimethylpropyl)isoxazol-5-yl]amino]-1-methyl-2-oxo-ethyl]phenyl]-1-(2,2,2-trideuterio-1-methyl-ethyl)pyrazole-4-carboxamide, Isomer 2 | 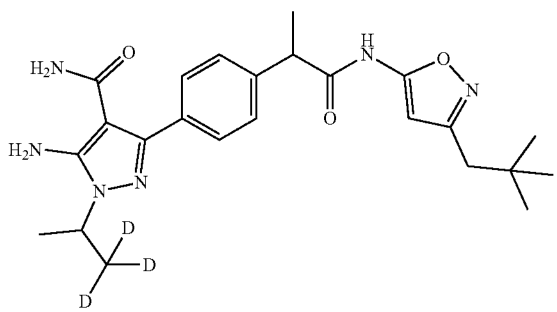 | 456.2 | 14.55 |
| 36l[1] | 5-Amino-3-[4-[2-[[3-(2,2-dimethylpropyl)isoxazol-5-yl]amino]-1-methyl-2-oxo-ethyl]phenyl]-1-[2,2,2-trifluoro-1-(trideuteriomethyl)ethyl]pyrazole-4-carboxamide, Isomer 1, Diastereomer A | 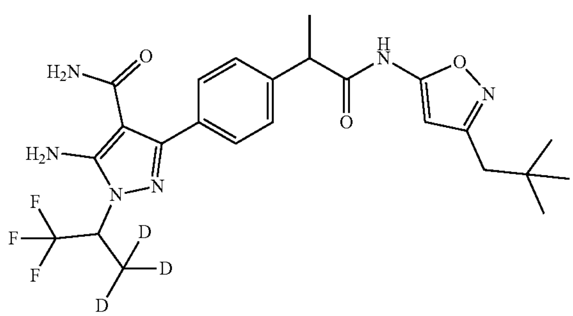 [SMILES: [2H]C([2H])([2H])C(n1nc(-c2ccc(C(C)C(=O)Nc3cc(CC(C)(C)C)no3)cc2)c(C(N)=O)c1N)C(F)(F)F] | 510.2 | 7.4 |
| 36m[1] | 5-Amino-3-[4-[2-[[3-(2,2-dimethylpropyl)isoxazol-5-yl]amino]-1-methyl-2-oxo-ethyl]phenyl]-1-[2,2,2-trifluoro-1-(trideuteriomethyl)ethyl]pyrazole-4-carboxamide, Isomer 1, Diastereomer B | 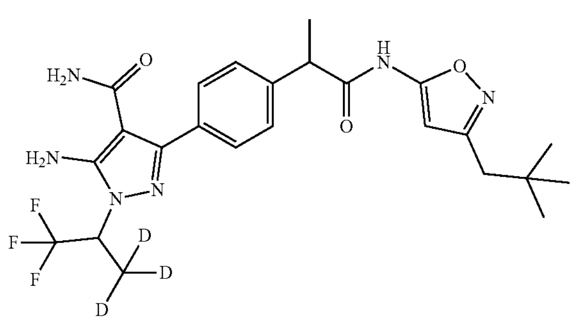 [SMILES: [2H]C([2H])([2H])C(n1nc(-c2ccc(C(C)C(=O)Nc3cc(CC(C)(C)C)no3)cc2)c(C(N)=O)c1N)C(F)(F)F] | 510.2 | 11.6 |

TABLE 19a-continued

| Ex. No. | Chemical name | Structure | ES/MS m/z (M + H) | t(R) min |
|---|---|---|---|---|
| 36n[3] | 5-Amino-3-[4-[2-[[3-(2,2-dimethylpropyl)isoxazol-5-yl]amino]-1-methyl-2-oxo-ethyl]phenyl]-1-[2,2,2-trifluoro-1-(trideuteriomethyl)ethyl]pyrazole-4-carboxamide, Isomer 2, Diastereomer A | 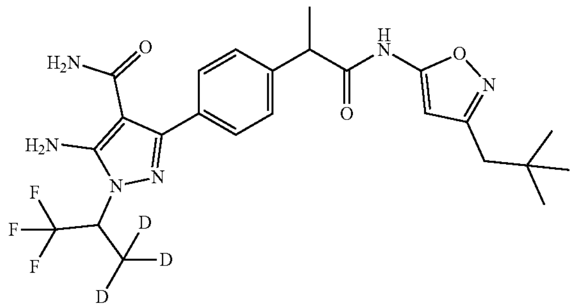 [SMILES: [2H]C([2H])([2H])C(n1nc(-c2ccc(C(C)C(=O)Nc3cc(CC(C)(C)C)no3)cc2)c(C(N)=O)c1N)C(F)(F)F] | 510.05 | 6.05 |
| 36o[3] | 5-Amino-3-[4-[2-[[3-(2,2-dimethylpropyl)isoxazol-5-yl]amino]-1-methyl-2-oxo-ethyl]phenyl]-1-[2,2,2-trifluoro-1-(trideuteriomethyl)ethyl]pyrazole-4-carboxamide, Isomer 2, Diastereomer B | 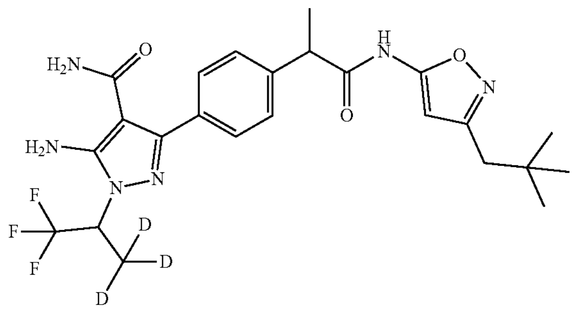 [SMILES: [2H]C([2H])([2H])C(n1nc(-c2ccc(C(C)C(=O)Nc3cc(CC(C)(C)C)no3)cc2)c(C(N)=O)c1N)C(F)(F)F] | 510.05 | 7.59 |
| 36p[2] | 5-Amino-1-(2-deuterio-2,2-difluoro-1-methyl-ethyl)-3-[4-[2-[[3-(2,2-dimethylpropyl)isoxazol-5-yl]amino]-1-methyl-2-oxo-ethyl]phenyl]pyrazole-4-carboxamide, Isomer 1, Diastereomer A | 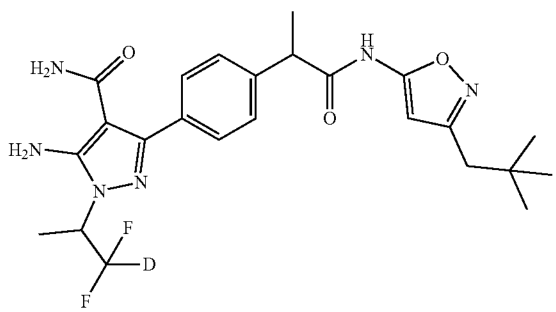 | 490.2 | 26.3 |
| 36q[2] | 5-Amino-1-(2-deuterio-2,2-difluoro-1-methyl-ethyl)-3-[4-[2-[[3-(2,2-dimethylpropyl)isoxazol-5-yl]amino]-1-methyl-2-oxo-ethyl]phenyl]pyrazole-4-carboxamide, Isomer 1, Diastereomer B | 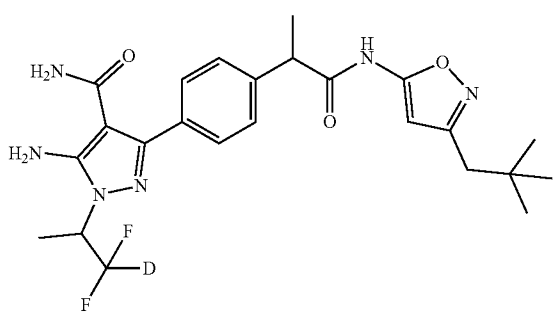 [SMILES: [2H]C(F)(F)C(C)n1nc(-c2ccc(C(C)C(=O)Nc3cc(CC(C)(C)C)no3)cc2)c(C(N)=O)c1N] | 490.2 | 29.45 |
| 36r[4] | 5-Amino-1-(2-deuterio-2,2-difluoro-1-methyl-ethyl)-3-[4-[2-[[3-(2,2-dimethylpropyl)isoxazol-5-yl]amino]-1-methyl-2-oxo-ethyl]phenyl]pyrazole-4-carboxamide carboxamide, Isomer 2, Diastereomer A | 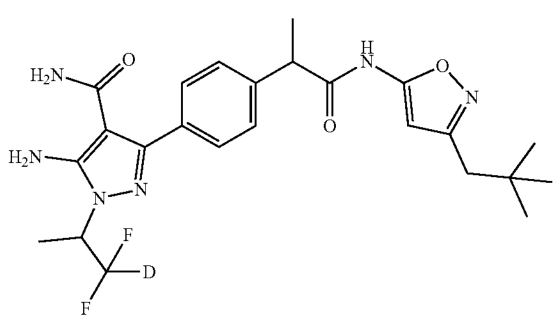 [SMILES: [2H]C(F)(F)C(C)n1nc(-c2ccc(C(C)C(=O)Nc3cc(CC(C)(C)C)no3)cc2)c(C(N)=O)c1N] | 490.15 | 11.8 |

TABLE 19a-continued

| Ex. No. | Chemical name | Structure | ES/MS m/z (M + H) | $t_{(R)}$ min |
|---|---|---|---|---|
| 36s[4] | 5-Amino-1-(2-deuterio-2,2-difluoro-1-methyl-ethyl)-3-[4-[2-[[3-(2,2-dimethylpropyl)isoxazol-5-yl]amino]-1-methyl-2-oxo-ethyl]phenyl]pyrazole-4-carboxamide, Isomer 2, Diastereomer B | 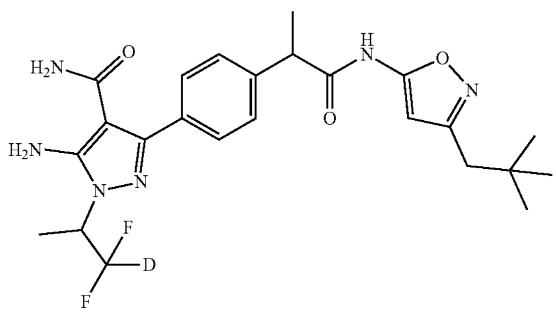 [SMILES: [2H]C(F)(F)C(C)n1nc(-c2ccc(C(C)C(=O)Nc3cc(CC(C)(C)C)no3)cc2)c(C(N)=O)c1N] | 490.15 | 14.5 |

[1]Eluting with 10% EtOH in 1:1 hexanes:MTBE (0.5% 2M NH$_3$—MeOH).
[2]Eluting with 10% EtOH in hexanes (10 mM NH$_3$—MeOH), 245/210 nm.
[3]Column: CHIRALPAK ID 2*25 cm, 5 μm; eluting with 8% IPA in 1:1 hexanes:MTBE (0.5% 2M NH$_3$—MeOH), 245/210 nm.
[4]UV 245/210 nm.

Example 36t

5-Amino-3-(2-fluoro-4-[1-[(3-[3-methylbicyclo[1.1.1]pentan-1-yl]-1,2-oxazol-5-yl)carbamoyl]ethyl]phenyl)-1-(1-methylcyclopropyl)pyrazole-4-carboxamide, Isomer 1 and

Example 36u

5-Amino-3-(2-fluoro-4-[1-[(3-[3-methylbicyclo[1.1.1]pentan-1-yl]-1,2-oxazol-5-yl)carbamoyl]ethyl]phenyl)-1-(1-methylcyclopropyl)pyrazole-4-carboxamide, Isomer 2

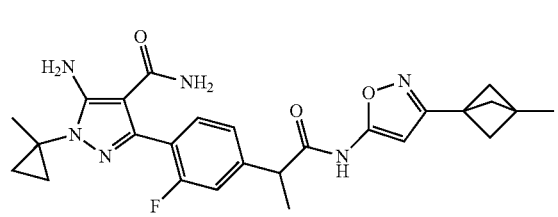

5-Amino-3-(2-fluoro-4-[1-[(3-[3-methylbicyclo[1.1.1]pentan-1-yl]-1,2-oxazol-5-yl)carbamoyl]ethyl]phenyl)-1-(1-methylcyclopropyl)pyrazole-4-carboxamide (70 mg) is purified by Prep-Chiral-HPLC by following conditions: Column CHIRAL ART Cellulose-SB, 2*25 cm, 5 μm eluting with 30% IPA in hexanes (10 mM NH$_3$-MeOH), 250/210 nm to give the title compound of Isomer 1 $t_{(R)}$ 7.04, (20.3 mg, 29.0%, 99.76% ee) as a white solid, ES/MS (m/z) 454.2 (M+H) and the title compound of Isomer 2 trio 9.48, (18.9 mg, 27.0%, 99.26% ee) as a white solid, ES/MS (m/z) 454.2 (M+H).

Example 36v

5-Amino-1-isopropyl-3-[4-[1-([3-[3-(trifluoromethyl)bicyclo[1.1.1]pentan-1-yl]-1,2-oxazol-5-yl]carbamoyl)ethyl]phenyl]pyrazole-4-carboxamide, Isomer 1 and

Example 36w

5-Amino-1-isopropyl-3-[4-[1-([3-[3-(trifluoromethyl)bicyclo[1.1.1]pentan-1-yl]-1,2-oxazol-5-yl]carbamoyl)ethyl]phenyl]pyrazole-4-carboxamide, Isomer 2

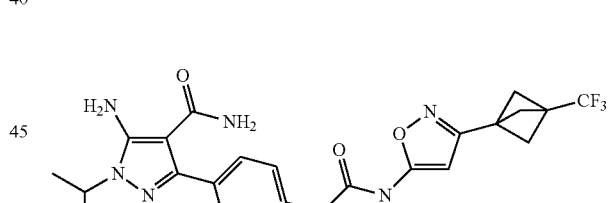

5-Amino-1-isopropyl-3-[4-[1-([3-[3-(trifluoromethyl)bicyclo[1.1.1]pentan-1-yl]-1,2-oxazol-5-yl]carbamoyl)ethyl]phenyl]pyrazole-4-carboxamide (162 mg) is purified by Prep-Chiral-HPLC by following conditions: Column CHIRAL ART Cellulose-SB, 2*25 cm, 5 μm eluting with 20% EtOH in hexanes (10 mM NH$_3$-MeOH), 254/210 nm to give the title compound of Isomer 1 $t_{(R)}$ 10.66, (48.1 mg, 29.6%, 100% ee) as a white solid, ES/MS (m/z) 517.05 (M+H) and the title compound of Isomer 2 $t_{(R)}$ 13.23, (50.4 mg, 30.6%, 99.74% ee) as a white solid, ES/MS (m/z) 517.05 (M+H).

The following compounds in Table 19b are prepared essentially as described for 5-amino-1-isopropyl-3-[4-[1-([3-[3-(trifluoromethyl)bicyclo[1.1.1]pentan-1-yl]-1,2-oxazol-5-yl]carbamoyl)ethyl]phenyl]pyrazole-4-carboxamide, Isomer 1 and Isomer 2 and adjusting chromatography conditions as appropriate.

TABLE 19b

| Ex. No. | Chemical name | Structure | ES/MS m/z (M + H) | t(R) min |
|---|---|---|---|---|
| 36x | 5-Amino-3-[4-[2-[[3-(2,2-dimethylpropyl)isoxazol-5-yl]amino]-1-methyl-2-oxo-ethyl]phenyl]-1-[2,2,2-trideuterio-1-(trideuteriomethyl)ethyl]pyrazole-4-carboxamide, Isomer 1 | 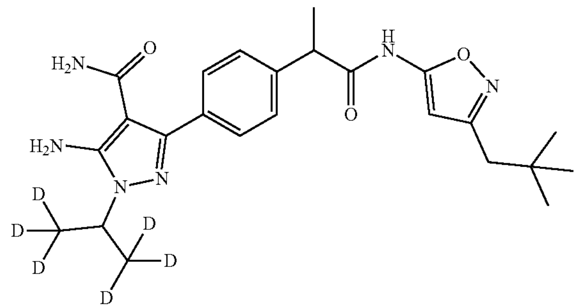 | 459.1 | 7.55 |
| 36y | 5-Amino-3-[4-[2-[[3-(2,2-dimethylpropyl)isoxazol-5-yl]amino]-1-methyl-2-oxo-ethyl]phenyl]-1-[2,2,2-trideuterio-1-(trideuteriomethyl)ethyl]pyrazole-4-carboxamide, Isomer 2 | 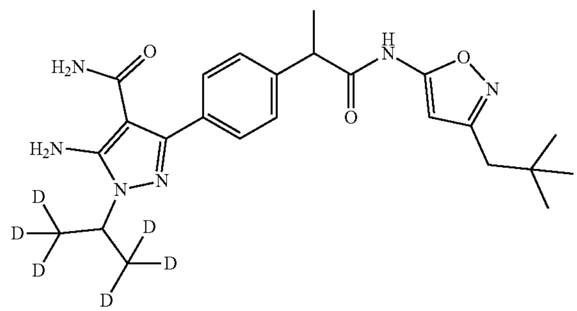 | 459.1 | 9.18 |
| 36z | 5-Amino-3-[4-[2-[[3-(2,2-dimethylpropyl)isoxazol-5-yl]amino]-1-methyl-2-oxo-ethyl]phenyl]-1-(1,2,2,2-tetradeuterio-1-methyl-ethyl)pyrazole-4-carboxamide, Isomer 1 | 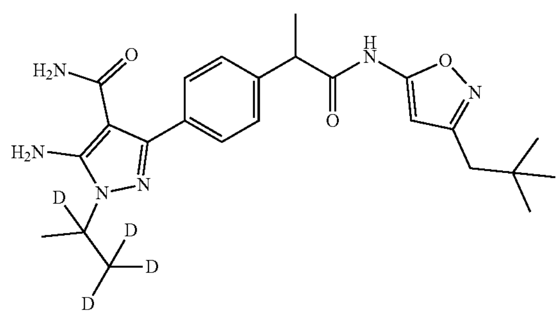 [SMILES: [2H]C([2H])([2H])C([2H])(C)n1nc(-c2ccc(C(C)C(=O)Nc3cc(CC(C)(C)C)no3)cc2)c(C(N)=O)c1N] | 457.1 | 7.9 |
| 36za | 5-Amino-3-[4-[2-[[3-(2,2-dimethylpropyl)isoxazol-5-yl]amino]-1-methyl-2-oxo-ethyl]phenyl]-1-(1,2,2,2-tetradeuterio-1-methyl-ethyl)pyrazole-4-carboxamide, Isomer 2 | 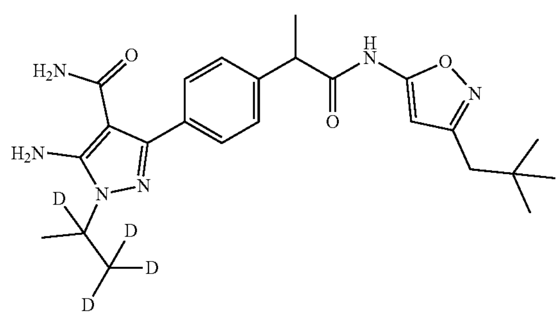 [SMILES: [2H]C([2H])([2H])C([2H])(C)n1nc(-c2ccc(C(C)C(=O)Nc3cc(CC(C)(C)C)no3)cc2)c(C(N)=O)c1N] | 457.1 | 9.65 |
| 36zb | 5-Amino-3-[4-[2-[[3-(2,2-dimethylpropyl)isoxazol-5-yl]amino]-1-methyl-2-oxo-ethyl]phenyl]-1-[1,2,2,2-tetradeuterio-1-(trideuteriomethyl)ethyl]pyrazole-4-carboxamide, Isomer 1 | 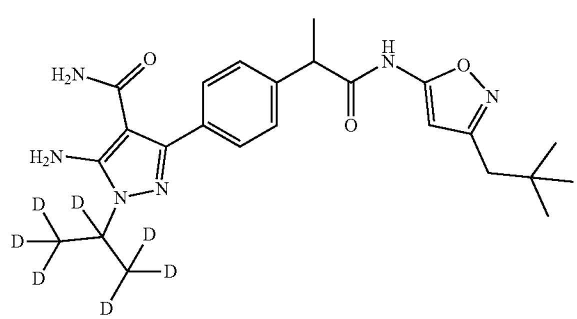 [SMILES: [2H]C([2H])([2H])C([2H])(n1nc(-c2ccc(C(C)C(=O)Nc3cc(CC(C)(C)C)no3)cc2)c(C(N)=O)c1N)C([2H])([2H])[2H]] | 460.3 | 7.42 |

TABLE 19b-continued

| Ex. No. | Chemical name | Structure | ES/MS m/z (M + H) | t$_{(R)}$ min |
|---|---|---|---|---|
| 36zc | 5-Amino-3-[4-[2-[[3-(2,2-dimethylpropyl)isoxazol-5-yl]amino]-1-methyl-2-oxo-ethyl]phenyl]-1-[1,2,2,2-tetradeuterio-1-(trideuteriomethyl)ethyl]pyrazole-4-carboxamide, Isomer 2 | 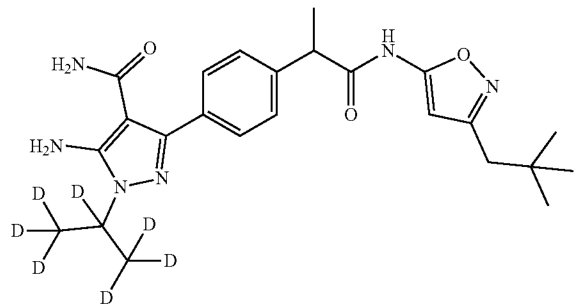 [SMILES: [2H]C([2H])([2H])C([2H])(n1nc(-c2ccc(C(C)C(=O)Nc3cc(CC(C)(C)C)no3)cc2)c(C(N)=O)c1N)C([2H])([2H])[2H]] | 460.3 | 9.04 |
| 36zd[1] | 5-Amino-3-[4-(1-[[3-(2,2-dimethylpropyl)-4-fluoro-1,2-oxazol-5-yl]carbamoyl]ethyl)phenyl]-1-isopropylpyrazole-4-carboxamide, Isomer 1 | 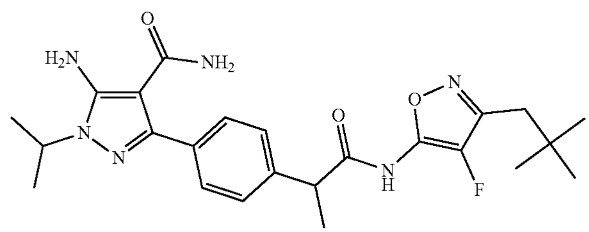 [SMILES: CC(C(=O)Nc1onc(CC(C)(C)C)c1F)c1ccc(-c2nn(C(C)C)c(N)c2C(N)=O)cc1] | 471.1 | 8 |
| 36ze[1] | 5-Amino-3-[4-(1-[[3-(2,2-dimethylpropyl)-4-fluoro-1,2-oxazol-5-yl]carbamoyl]ethyl)phenyl]-1-isopropylpyrazole-4-carboxamide, Isomer 2 | 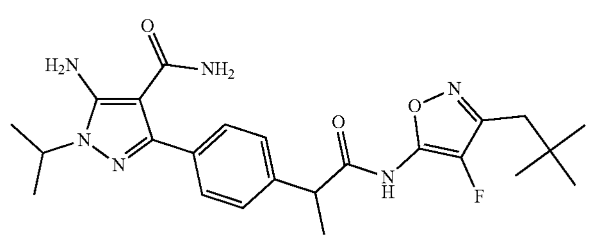 [SMILES: CC(C(=O)Nc1onc(CC(C)(C)C)c1F)c1ccc(-c2nn(C(C)C)c(N)c2C(N)=O)cc1] | 471.1 | 9.7 |

[1]UV is 210/237 nm

Example 36zf

5-Amino-3-[4-[2-[[3-(2,2-dimethylpropyl)-4-fluoro-isoxazol-5-yl]amino]-1-methyl-2-oxo-ethyl]phenyl]-1-[2,2,2-trideuterio-1-(trideuteriomethyl)ethyl]pyrazole-4-carboxamide, Isomer 1 and

Example 36zg

5-Amino-3-[4-[2-[[3-(2,2-dimethylpropyl)-4-fluoro-isoxazol-5-yl]amino]-1-methyl-2-oxo-ethyl]phenyl]-1-[2,2,2-trideuterio-1-(trideuteriomethyl)ethyl]pyrazole-4-carboxamide, Isomer 2

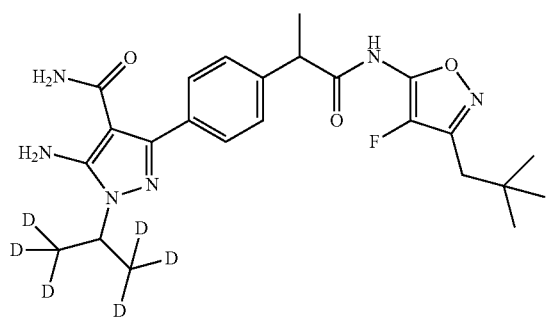 [SMILES: [2H]C([2H])([2H])C(n1nc(-c2ccc(C(C)C(=O)Nc3onc(CC(C)(C)C)c3F)cc2)c(C(N)=O)c1N)C([2H])([2H])[2H]]

5-Amino-3-[4-[2-[[3-(2,2-dimethylpropyl)-4-fluoro-isoxazol-5-yl]amino]-1-methyl-2-oxo-ethyl]phenyl]-1-[2,2,2-trideuterio-1-(trideuteriomethyl)ethyl]pyrazole-4-carboxamide (120 mg) is purified by Prep-Chiral-HPLC by following conditions: Column CHIRAL ART Cellulose-SB, 2*25 cm, 5 μm eluting with 20% EtOH in hexanes (10 mM $NH_3$-MeOH), 213/237 nm to give the title compound of Isomer 1 $t_{(R)}$ 7.78, (22.2 mg, 18.5%, 100% ee) as a beige solid, ES/MS (m/z) 477.25 (M+H) and the title compound of Isomer 2 $t_{(R)}$ 9.43, (27.1 mg, 22.6%, 98.14% ee) as a beige solid, ES/MS (m/z) 477.25 (M+H).

Example 37

5-Amino-3-[5-(1-[[3-(2,2-dimethylpropyl)-1,2-oxazol-5-yl]carbamoyl]ethyl)pyridin-2-yl]-1-isopropylpyrazole-4-carboxamide, Isomer 1 and

Example 38

5-Amino-3-[5-(1-[[3-(2,2-dimethylpropyl)-1,2-oxazol-5-yl]carbamoyl]ethyl)pyridin-2-yl]-1-isopropylpyrazole-4-carboxamide, Isomer 2

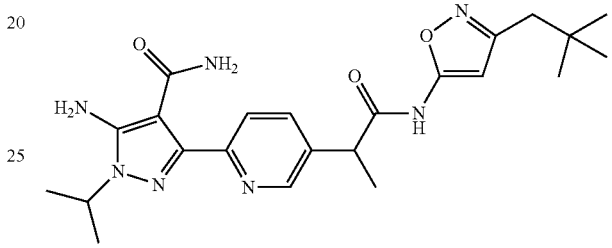

5-Amino-3-[5-(1-[[3-(2,2-dimethylpropyl)-1,2-oxazol-5-yl]carbamoyl]ethyl)pyridin-2-yl]-1-isopropylpyrazole-4-carboxamide (97.00 mg, 0.21 mmol) is separated by prep-chiral chromatography with the following conditions: Column: CHIRAL ART Cellulose-SB, 2*25 cm, 5 μm; mobile phase A: hexanes (10 mM $NH_3$), mobile phase B: EtOH; flow rate 20 mL/min; eluting with 40% B in 11 min; 254/220 nm; $t_{(R)}$ Isomer 1 is 5.2 min (35.8 mg, 36.9%) as a white solid with 100% ee. ES/MS (m/z) 454.2 (M+H). $t_{(R)}$ Isomer 2 is 7.5 min (42.1 mg, 43.4%) as a white solid with 100% ee. ES/MS (m/z) 454.2 (M+H).

The following compounds in Table 20 are prepared essentially as described for 5-amino-3-[5-(1-[[3-(2,2-dim ethyl-propyl)-1,2-oxazol-5-yl]carbamoyl]ethyl)pyridin-2-yl]-1-isopropylpyrazole-4-carboxamide, Isomer 1 and Isomer 2 and adjusting the purification system as appropriate.

TABLE 20

| Ex. No. | Chemical name | Structure | ES/MS m/z (M + H) | $t_{(R)}$ min |
|---|---|---|---|---|
| 39[1] | 5-Amino-3-[5-(1-[[3-(2,4-dichlorophenyl)-1,2-oxazol-5-yl]carbamoyl]ethyl)pyridin-2-yl]-1-isopropylpyrazole-4-carboxamide, Isomer 1 | 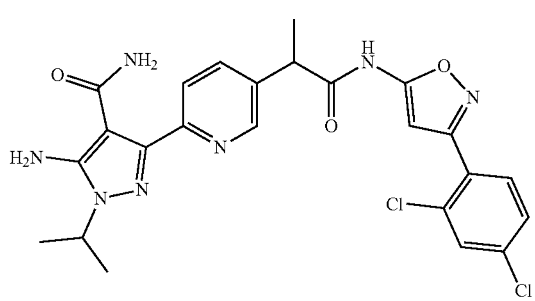 [SMILES: CC(C(=O)Nc1cc(-c2ccc(Cl)cc2Cl)no1)c1ccc(-c2nn(C(C)C)c(N)c2C(N)=O)nc1] | 528.3, 530.3 | 6 |

TABLE 20-continued

| Ex. No. | Chemical name | Structure | ES/MS m/z (M + H) | t(R) min |
|---|---|---|---|---|
| 40[1] | 5-Amino-3-[5-(1-[[3-(2,4-dichlorophenyl)-1,2-oxazol-5-yl]carbamoyl]ethyl)pyridin-2-yl]-1-isopropylpyrazole-4-carboxamide, Isomer 2 | 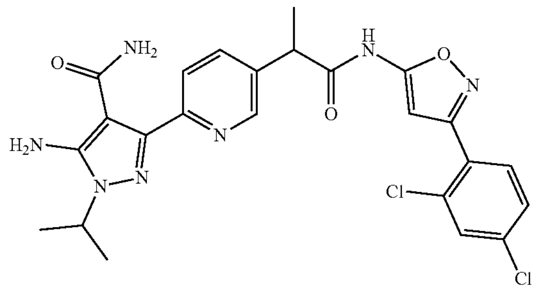 [SMILES: CC(C(=O)Nc1cc(-c2ccc(Cl)cc2Cl)no1)c1ccc(-c2nn(C(C)C)c(N)c2C(N)=O)nc1] | 528.3, 530.3 | 8.5 |
| 41[2] | 5-Amino-3-(5-(1-((3-(2-chloro-4-fluorophenyl)isoxazol-5-yl)amino)-1-oxopropan-2-yl)pyridin-2-yl)-1-isopropyl-1H-pyrazole-4-carboxamide, Isomer 1 | 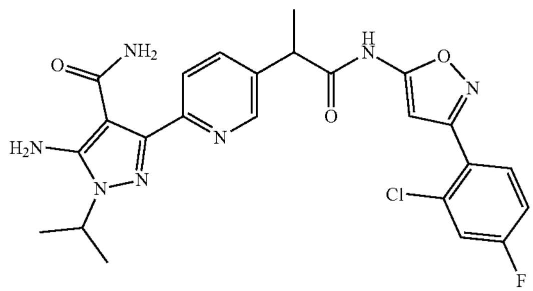 [SMILES: CC(C(=O)Nc1cc(-c2ccc(F)cc2Cl)no1)c1ccc(-c2nn(C(C)C)c(N)c2C(N)=O)nc1] | 512.05, 514.05 | 5.8 |
| 42[2] | 5-Amino-3-(5-(1-((3-(2-chloro-4-fluorophenyl)isoxazol-5-yl)amino)-1-oxopropan-2-yl)pyridin-2-yl)-1-isopropyl-1H-pyrazole-4-carboxamide, Isomer 2 | 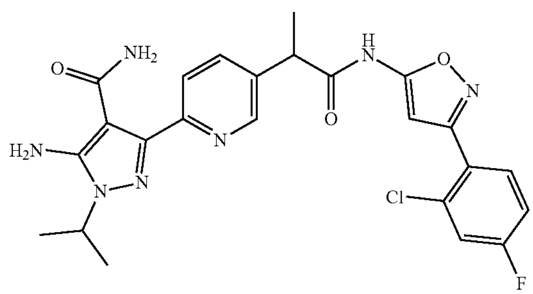 | 512.05, 514.05 | 7.5 |
| 43[3] | 5-Amino-3-[5-[1-[[3-(2,4-dichlorophenyl)-1,2-oxazol-5-yl]carbamoyl]ethyl]pyridin-2-yl]-1-(1-methylcyclopropyl)pyrazole-4-carboxamide, Isomer 1 | 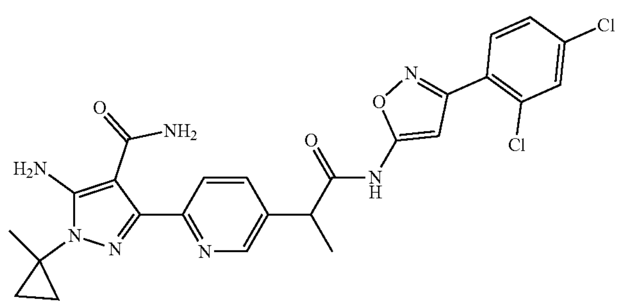 [SMILES: CC(C(=O)Nc1cc(-c2ccc(Cl)cc2Cl)no1)c1ccc(-c2nn(C3(C)CC3)c(N)c2C(N)=O)nc1] | 540.4, 542.4 | 7.9 |
| 44[3] | 5-Amino-3-[5-[1-[[3-(2,4-dichlorophenyl)-1,2-oxazol-5-yl]carbamoyl]ethyl]pyridin-2-yl]-1-(1-methylcyclopropyl)pyrazole-4-carboxamide, Isomer 2 | 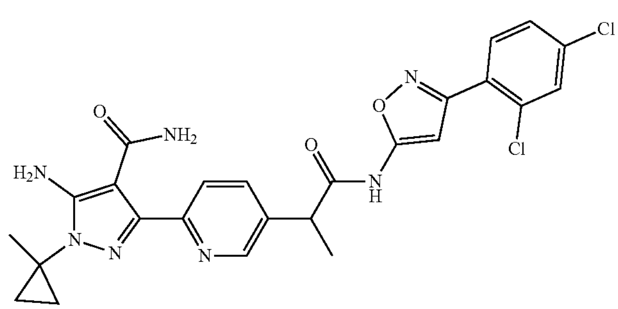 [SMILES: CC(C(=O)Nc1cc(-c2ccc(Cl)cc2Cl)no1)c1ccc(-c2nn(C3(C)CC3)c(N)c2C(N)=O)nc1] | 540.4, 542.4 | 17.6 |

TABLE 20-continued

| Ex. No. | Chemical name | Structure | ES/MS m/z (M + H) | t(R) min |
|---|---|---|---|---|
| 45 | 5-Amino-3-[4-(1-[[3-(2,4-dichlorophenyl)-1,2-oxazol-5-yl]carbamoyl]ethyl)phenyl]-1-isopropylpyrazole-4-carboxamide, Isomer 1 | 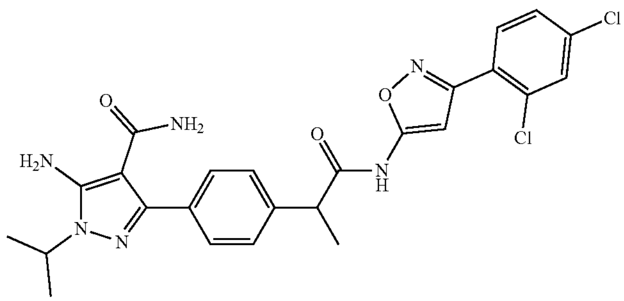 [SMILES: CC(C(=O)Nc1cc(-c2ccc(Cl)cc2Cl)no1)c1ccc(-c2nn(C(C)C)c(N)c2C(N)=O)cc1] | 527.05, 529.05 | 7.5 |
| 46 | 5-Amino-3-[4-(1-[[3-(2,4-dichlorophenyl)-1,2-oxazol-5-yl]carbamoyl]ethyl)phenyl]-1-isopropylpyrazole-4-carboxamide, Isomer 2 | 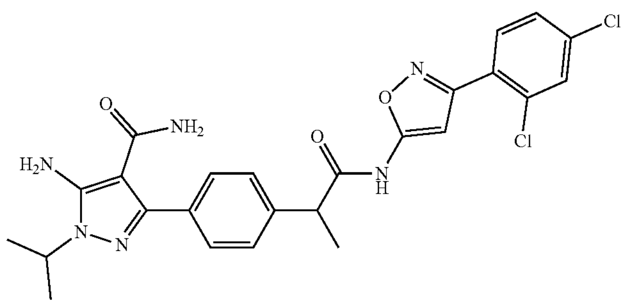 [SMILES: CC(C(=O)Nc1cc(-c2ccc(Cl)cc2Cl)no1)c1ccc(-c2nn(C(C)C)c(N)c2C(N)=O)cc1] | 527.05, 529.05 | 9.5 |
| 47[4] | 5-Amino-1-cyclopropyl-3-[4-[2-[[3-(2,2-dimethylpropyl)isoxazol-5-yl]amino]-1-methyl-2-oxo-ethyl]phenyl]pyrazole-4-carboxamide, Isomer 1 | 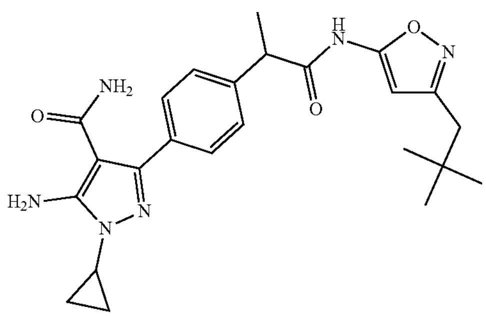 [SMILES: CC(C(=O)Nc1cc(CC(C)(C)C)no1)c1ccc(-c2nn(C3CC3)c(N)c2C(N)=O)cc1] | 451.3 | 1.89 |
| 48[4] | 5-Amino-1-cyclopropyl-3-[4-[2-[[3-(2,2-dimethylpropyl)isoxazol-5-yl]amino]-1-methyl-2-oxo-ethyl]phenyl]pyrazole-4-carboxamide, Isomer 2 | 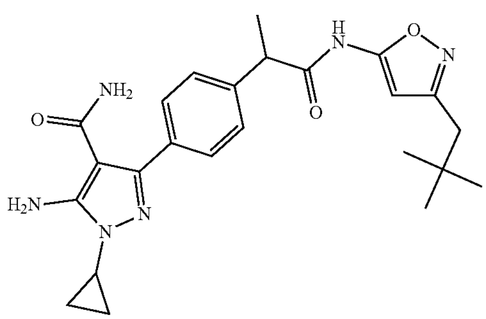 [SMILES: CC(C(=O)Nc1cc(CC(C)(C)C)no1)c1ccc(-c2nn(C3CC3)c(N)c2C(N)=O)cc1] | 451.3 | 2.77 |
| 49[4] | 5-Amino-1-isopropyl-3-[4-[1-methyl-2-[[3-[(1-methylcyclopropyl)methyl]isoxazol-5-yl]amino]-2-oxo-ethyl]phenyl]pyrazole-4-carboxamide, Isomer 1 | 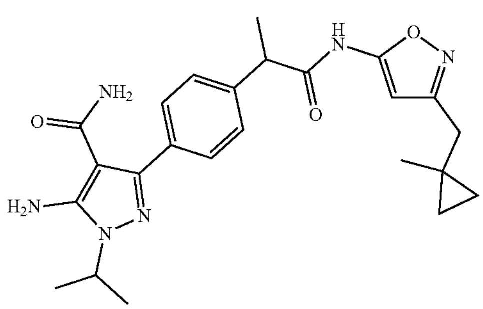 [SMILES: CC(C(=O)Nc1cc(CC2(C)CC2)no1)c1ccc(-c2nn(C(C)C)c(N)c2C(N)=O)cc1] | 451.3 | 1.65 |

TABLE 20-continued

| Ex. No. | Chemical name | Structure | ES/MS m/z (M + H) | t(R) min |
|---|---|---|---|---|
| 50[4] | 5-Amino-1-isopropyl-3-[4-[1-methyl-2-[[3-[(1-methylcyclopropyl)methyl]isoxazol-5-yl]amino]-2-oxo-ethyl]phenyl]pyrazole-4-carboxamide, Isomer 2 | 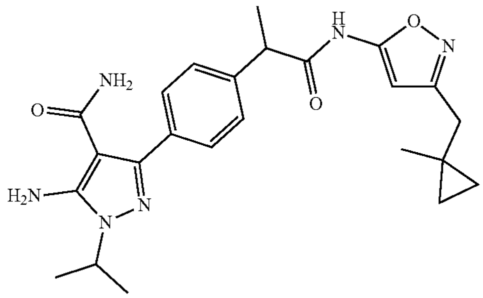 [SMILES: CC(C(=O)Nc1cc(CC2(C)CC2)no1)c1ccc(-c2nn(C(C)C)c(N)c2C(N)=O)cc1] | 451.3 | 2.32 |
| 51 | 5-Amino-1-isopropyl-3-[4-(1-[[5-(2-methylbutan-2-yl)-1,2-oxazol-3-yl]carbamoyl]ethyl)phenyl]pyrazole-4-carboxamide, Isomer 1 | 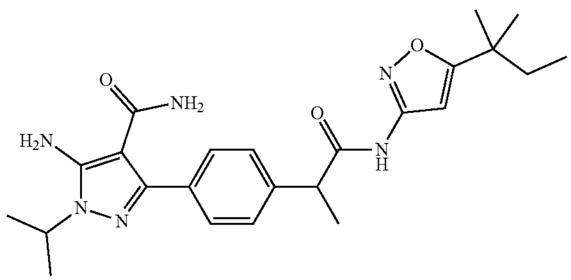 [SMILES: CCC(C)(C)c1cc(NC(=O)C(C)c2ccc(-c3nn(C(C)C)c(N)c3C(N)=O)cc2)no1] | 453.4 | 10 |
| 52 | 5-Amino-1-isopropyl-3-[4-(1-[[5-(2-methylbutan-2-yl)-1,2-oxazol-3-yl]carbamoyl]ethyl)phenyl]pyrazole-4-carboxamide, Isomer 2 | 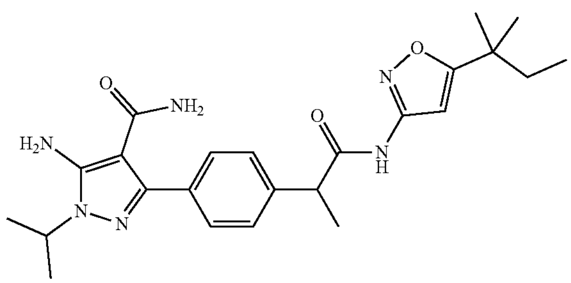 [SMILES: CCC(C)(C)c1cc(NC(=O)C(C)c2ccc(-c3nn(C(C)C)c(N)c3C(N)=O)cc2)no1] | 453.4 | 13.5 |
| 53 | 5-Amino-3-[5-[1-[[3-(2,2-dimethylpropyl)-1,2-oxazol-5-yl]carbamoyl]ethyl]pyridin-2-yl]-1-[1,1,1-trifluoropropan-2-yl]pyrazole-4-carboxamide, Isomer 1, Diastereomer A | 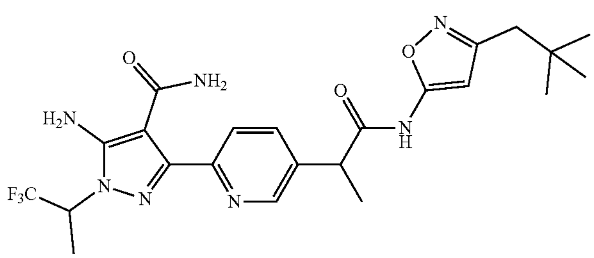 [SMILES: CC(C(=O)Nc1cc(CC(C)(C)C)no1)c1ccc(-c2nn(C(C)C(F)(F)F)c(N)c2C(N)=O)nc1] | 508.2 | 4.5 |
| 54 | 5-amino-3-[5-[1-[[3-(2,2-dimethylpropyl)-1,2-oxazol-5-yl]carbamoyl]ethyl]pyridin-2-yl]-1-[1,1,1-trifluoropropan-2-yl]pyrazole-4-carboxamide, Isomer 1, Diastereomer B | 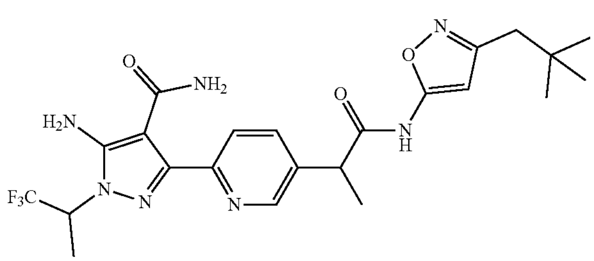 [SMILES: CC(C(=O)Nc1cc(CC(C)(C)C)no1)c1ccc(-c2nn(C(C)C(F)(F)F)c(N)c2C(N)=O)nc1] | 508.2 | 5.7 |

TABLE 20-continued

| Ex. No. | Chemical name | Structure | ES/MS m/z (M + H) | t(R) min |
|---|---|---|---|---|
| 55[5] | 5-Amino-3-[5-[1-[[3-(2-chloro-4-fluorophenyl)-1,2-oxazol-5-yl]carbamoyl]ethyl]pyridin-2-yl]-1-(1-methylcyclopropyl)pyrazole-4-carboxamide, Isomer 1 | 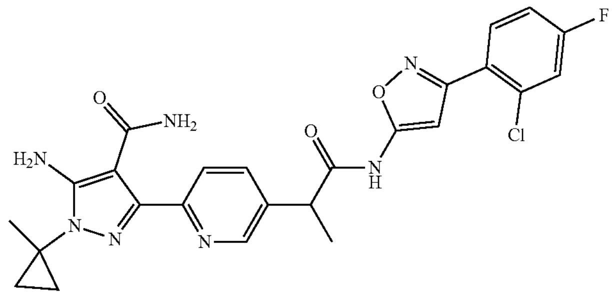 [SMILES: CC(C(=O)Nc1cc(-c2ccc(F)cc2Cl)no1)c1ccc(-c2nn(C3(C)CC3)c(N)c2C(N)=O)nc1] | 524.1 | 6.4 |
| 56[5] | 5-Amino-3-[5-[1-[[3-(2-chloro-4-fluorophenyl)-1,2-oxazol-5-yl]carbamoyl]ethyl]pyridin-2-yl]-1-(1-methylcyclopropyl)pyrazole-4-carboxamide, Isomer 2 | 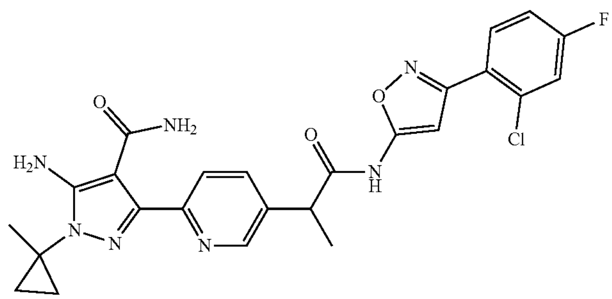 [SMILES: CC(C(=O)Nc1cc(-c2ccc(F)cc2Cl)no1)c1ccc(-c2nn(C3(C)CC3)c(N)c2C(N)=O)nc1] | 524.1 | 8.9 |
| 57[6] | 5-Amino-3-[5-[1-[[3-(2-chloro-4-fluorophenyl)-1,2-oxazol-5-yl]carbamoyl]ethyl]pyridin-2-yl]-1-[1,1,1-trifluoropropan-2-yl]pyrazole-4-carboxamide, Isomer 2, Diastereomer A | 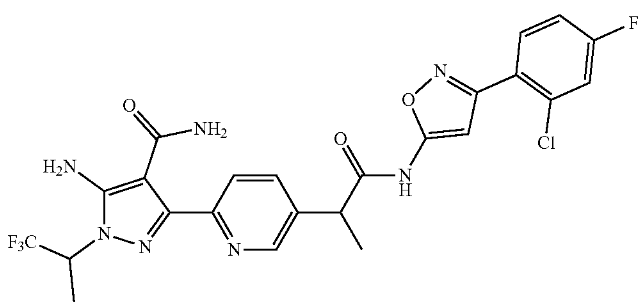 [SMILES: CC(C(=O)Nc1cc(-c2ccc(F)cc2Cl)no1)c1ccc(-c2nn(C(C)C(F)(F)F)c(N)c2C(N)=O)nc1] | 566.10 | 8.6 |
| 58[6] | 5-Amino-3-[5-[1-[[3-(2-chloro-4-fluorophenyl)-1,2-oxazol-5-yl]carbamoyl]ethyl]pyridin-2-yl]-1-[1,1,1-trifluoropropan-2-yl]pyrazole-4-carboxamide, Isomer 2, Diastereomer B | 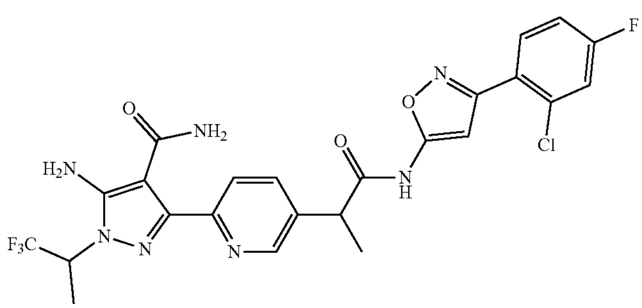 [SMILES: CC(C(=O)Nc1cc(-c2ccc(F)cc2Cl)no1)c1ccc(-c2nn(C(C)C(F)(F)F)c(N)c2C(N)=O)nc1] | 566.10 | 13.5 |
| 59[6] | 5-Amino-3-[5-[1-[[3-(2,4-dichlorophenyl)-1,2-oxazol-5-yl]carbamoyl]ethyl]pyridin-2-yl]-1-[1,1,1-trifluoropropan-2-yl]pyrazole-4-carboxamide, Isomer 2, Diastereomer A | 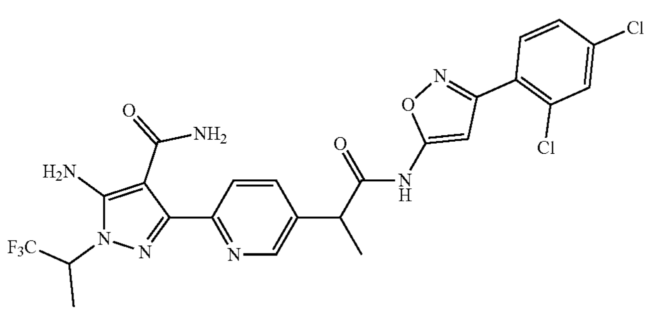 [SMILES: CC(C(=O)Nc1cc(-c2ccc(Cl)cc2Cl)no1)c1ccc(-c2nn(C(C)C(F)(F)F)c(N)c2C(N)=O)nc1] | 582.25, 584.25 | 9.2 |

TABLE 20-continued

| Ex. No. | Chemical name | Structure | ES/MS m/z (M + H) | t(R) min |
|---|---|---|---|---|
| 60[6] | 5-Amino-3-[5-[1-[[3-(2,4-dichlorophenyl)-1,2-oxazol-5-yl]carbamoyl]ethyl]pyridin-2-yl]-1-[1,1,1-trifluoropropan-2-yl]pyrazole-4-carboxamide, Isomer 2, Diastereomer B | 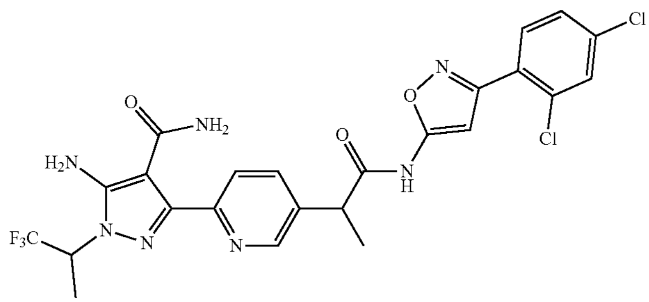 [SMILES: CC(C(=O)Nc1cc(-c2ccc(Cl)cc2Cl)no1)c1ccc(-c2nn(C(C)C(F)(F)F)c(N)c2C(N)=O)nc1] | 582.25, 584.25 | 13.5 |
| 61[7] | 5-Amino-3-[4-[1-[[3-(2,2-dimethylpropyl)-1,2-oxazol-5-yl]carbamoyl]ethyl]phenyl]-1-(1-methylcyclopropyl)pyrazole-4-carboxamide, Isomer 1 | 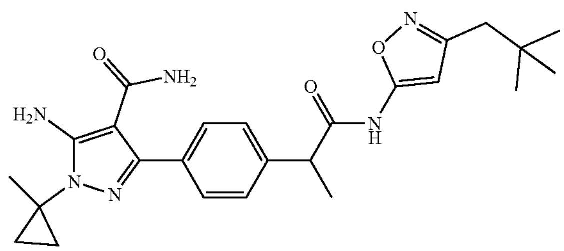 [SMILES: CC(C(=O)Nc1cc(CC(C)(C)C)no1)c1ccc(-c2nn(C3(C)CC3)c(N)c2C(N)=O)cc1] | 465.3 | 11.5 |
| 62[7] | 5-Amino-3-[4-[1-[[3-(2,2-dimethylpropyl)-1,2-oxazol-5-yl]carbamoyl]ethyl]phenyl]-1-(1-methylcyclopropyl)pyrazole-4-carboxamide, Isomer 2 | 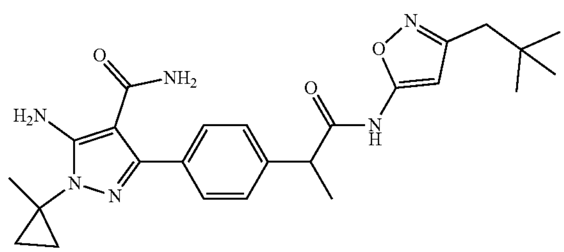 [SMILES: CC(C(=O)Nc1cc(CC(C)(C)C)no1)c1ccc(-c2nn(C3(C)CC3)c(N)c2C(N)=O)cc1] | 465.3 | 20 |
| 63[6] | 5-Amino-1-isopropyl-3-[5-(1-[[5-(1,1,1-trifluoro-2-methylpropan-2-yl)-1,2-oxazol-3-yl]carbamoyl]ethyl)pyridin-2-yl]pyrazole-4-carboxamide, Isomer 1 | 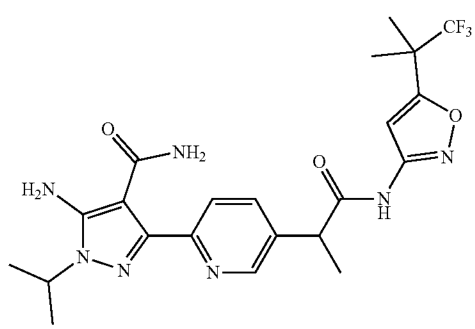 [SMILES: CC(C(=O)Nc1cc(C(C)(C)C(F)(F)F)on1)c1ccc(-c2nn(C(C)C)c(N)c2C(N)=O)nc1] | 494.15 | 8.5 |
| 64[6] | 5-Amino-1-isopropyl-3-[5-(1-[[5-(1,1,1-trifluoro-yl)-1,2-oxazol-3-2-methylpropan-2-yl]carbamoyl]ethyl)pyridin-2-yl]pyrazole-4-carboxamide, Isomer 2 | 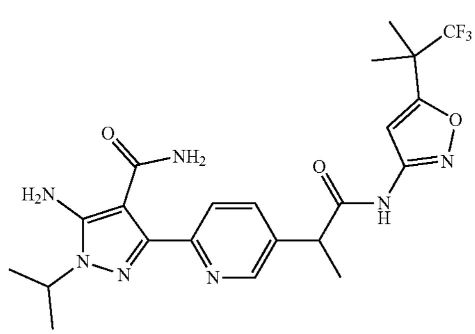 [SMILES: CC(C(=O)Nc1cc(C(C)(C)C(F)(F)F)on1)c1ccc(-c2nn(C(C)C)c(N)c2C(N)=O)nc1] | 494.2 | 12.5 |

TABLE 20-continued

| Ex. No. | Chemical name | Structure | ES/MS m/z (M + H) | $t_{(R)}$ min |
|---|---|---|---|---|
| 65[6,8] | 5-Amino-1-isopropyl-3-[5-(1-[[5-(2-methylbutan-2-yl)-1,2-oxazol-3-yl]carbamoyl]ethyl)pyridin-2-yl]pyrazole-4-carboxamide, Isomer 1 | 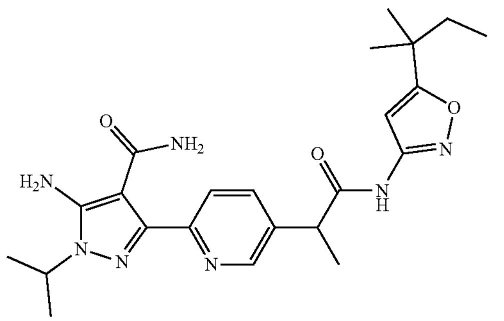 [SMILES: CCC(C)(C)c1cc(NC(=O)C(C)c2ccc(-c3nn(C(C)C)c(N)c3C(N)=O)nc2)no1] | 454.4 | 5 |
| 66[6,8] | 5-Amino-1-isopropyl-3-[5-(1-[[5-(2-methylbutan-2-yl)-1,2-oxazol-3-yl]carbamoyl]ethyl)pyridin-2-yl]pyrazole-4-carboxamide, Isomer 2 | 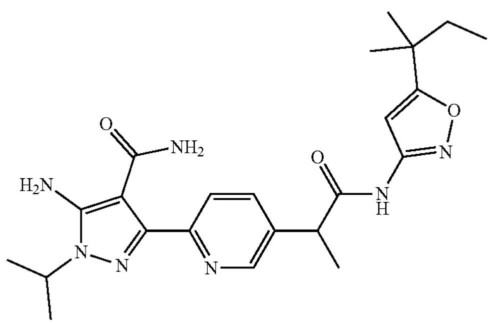 [SMILES: CCC(C)(C)c1cc(NC(=O)C(C)c2ccc(-c3nn(C(C)C)c(N)c3C(N)=O)nc2)no1] | 454.4 | 6.7 |
| 67[7] | 5-Amino-1-isopropyl-3-(5-(1-oxo-1-((5-(4,4,4-trifluoro-2-methylbutan-2-yl)isoxazol-3-yl)amino)propan-2-yl)pyridin-2-yl)-1H-pyrazole-4-carboxamide, Isomer 1 | 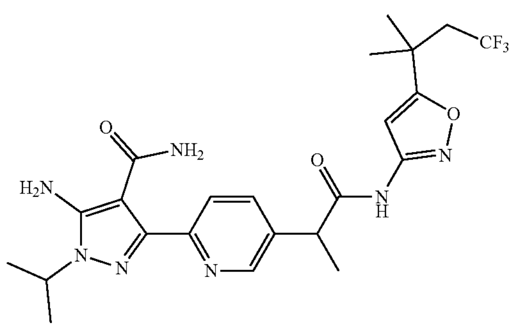 [SMILES: CC(C(=O)Nc1cc(C(C)(C)CC(F)(F)F)on1)c1ccc(-c2nn(C(C)C)c(N)c2C(N)=O)nc1] | 508.4 | 8.5 |
| 68[7] | 5-Amino-1-isopropyl-3-(5-(1-oxo-1-((5-(4,4,4-trifluoro-2-methylbutan-2-yl)isoxazol-3-yl)amino)propan-2-yl)pyridin-2-yl)-1H-pyrazole-4-carboxamide, Isomer 2 | 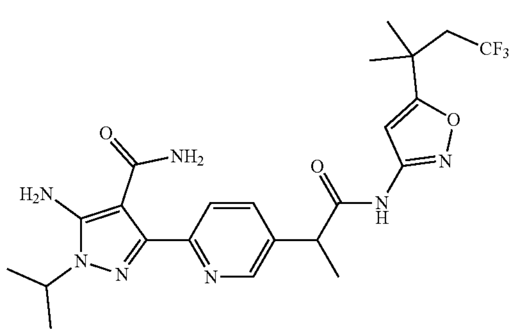 [SMILES: CC(C(=O)Nc1cc(C(C)(C)CC(F)(F)F)on1)c1ccc(-c2nn(C(C)C)c(N)c2C(N)=O)nc1] | 508.4 | 13 |

| Ex. No. | Chemical name | Structure | ES/MS m/z (M + H) | t$_{(R)}$ min |
|---|---|---|---|---|
| 69[6] | 5-Amino-3-[5-(1-[[5-(3,3-difluoro-2-methylbutan-2-yl)-1,2-oxazol-3-yl]carbamoyl]ethyl)pyridin-2-yl]-1-isopropylpyrazole-4-carboxamide, Isomer 1 | 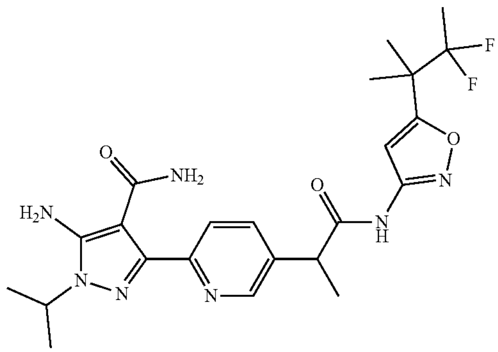 [SMILES: CC(C(=O)Nc1cc(C(C)(C)C(C)(F)F)on1)c1ccc(-c2nn(C(C)C)c(N)c2C(N)=O)nc1] | 490.10 | 6 |
| 70[6] | 5-Amino-3-[5-(1-[[5-(3,3-difluoro-2-methylbutan-2-yl)-1,2-oxazol-3-yl]carbamoyl]ethyl)pyridin-2-yl]-1-isopropylpyrazole-4-carboxamide, Isomer 2 | 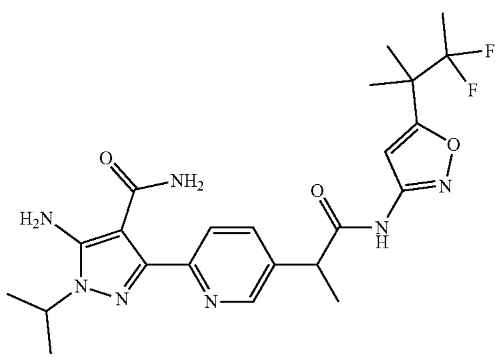 [SMILES: CC(C(=O)Nc1cc(C(C)(C)C(C)(F)F)on1)c1ccc(-c2nn(C(C)C)c(N)c2C(N)=O)nc1] | 490.15 | 8.5 |
| 71[10] | 5-Amino-1-isopropyl-3-[5-(1-[[3-(1,1,1-trifluoro-2-methylpropan-2-yl)-1,2-oxazol-5-yl]carbamoyl]ethyl)pyridin-2-yl]pyrazole-4-carboxamide, Isomer 1 | 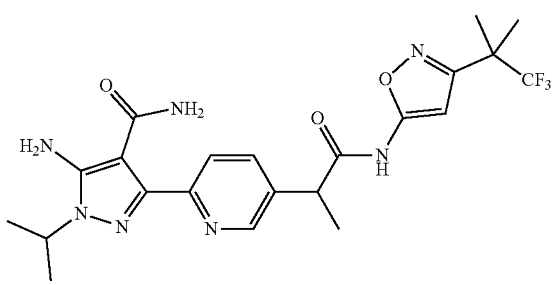 [SMILES: CC(C(=O)Nc1cc(C(C)(C)C(F)(F)F)no1)c1ccc(-c2nn(C(C)C)c(N)c2C(N)=O)nc1] | 494.2 | 7.2 |
| 72[10] | 5-Amino-1-isopropyl-3-[5-(1-[[3-(1,1,1-trifluoro-2-methylpropan-2-yl)-1,2-oxazol-5-yl]carbamoyl]ethyl)pyridin-2-yl]pyrazole-4-carboxamide, Isomer 2 | 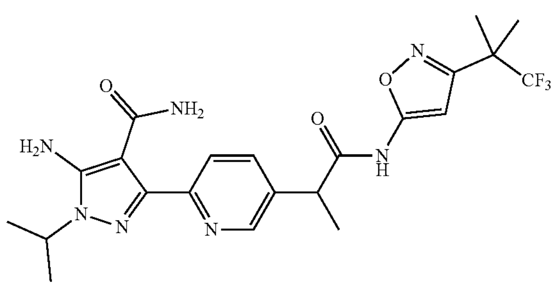 [SMILES: CC(C(=O)Nc1cc(C(C)(C)C(F)(F)F)no1)c1ccc(-c2nn(C(C)C)c(N)c2C(N)=O)nc1] | 494.2 | 11 |

TABLE 20-continued

| Ex. No. | Chemical name | Structure | ES/MS m/z (M + H) | $t_{(R)}$ min |
|---|---|---|---|---|
| 73[9] | 5-Amino-3-[5-[1-[[5-(1,1,1-trifluoro-2-methylpropan-2-yl)-1,2-oxazol-3-yl]carbamoyl]ethyl]pyridin-2-yl]-1-[1,1,1-trifluoropropan-2-yl]pyrazole-4-carboxamide, Isomer 1 | 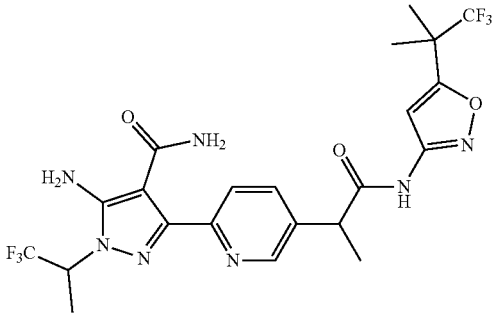 [SMILES: CC(C(=O)Nc1cc(C(C)(C)C(F)(F)F)on1)c1ccc(-c2nn(C(C)C(F)(F)F)c(N)c2C(N)=O)nc1] | 548.2 | 3.2 |
| 74[9] | 5-Amino-3-[5-[1-[[5-(1,1,1-trifluoro-2-methylpropan-2-yl)-1,2-oxazol-3-yl]carbamoyl]ethyl]pyridin-2-yl]-1-[1,1,1-trifluoropropan-2-yl]pyrazole-4-carboxamide, Isomer 2 | 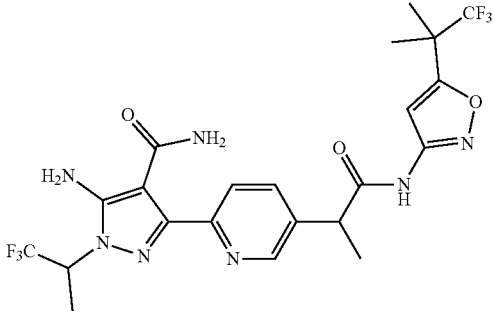 [SMILES: CC(C(=O)Nc1cc(C(C)(C)C(F)(F)F)on1)c1ccc(-c2nn(C(C)C(F)(F)F)c(N)c2C(N)=O)nc1] | 548.2 | 6.2 |
| 75[11] | 5-Amino-3-[4-(1-[[5-(3,3-difluoro-2-methylbutan-2-yl)-1,2-oxazol-3-yl]carbamoyl]ethyl)phenyl]-1-isopropylpyrazole-4-carboxamide, Isomer 1 | 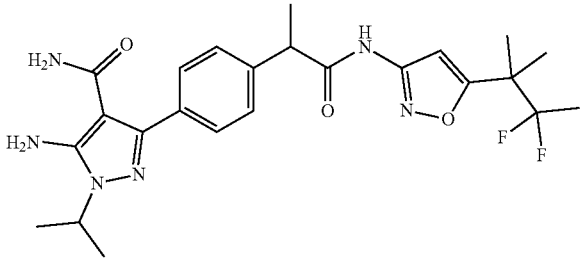 [SMILES: CC(C(=O)Nc1cc(C(C)(C)C(C)(F)F)on1)c1ccc(-c2nn(C(C)C)c(N)c2C(N)=O)cc1] | 511.10 | 5.2 |
| 76[11] | 5-Amino-3-[4-(1-[[5-(3,3-difluoro-2-methylbutan-2-yl)-1,2-oxazol-3-yl]carbamoyl]ethyl)phenyl]-1-isopropylpyrazole-4-carboxamide, Isomer 2 | 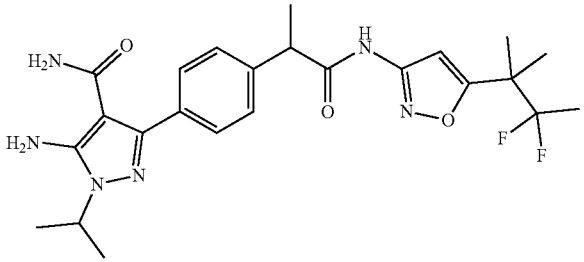 [SMILES: CC(C(=O)Nc1cc(C(C)(C)C(C)(F)F)on1)c1ccc(-c2nn(C(C)C)c(N)c2C(N)=O)cc1] | 511.10 | 7.5 |
| 77[12] | 5-Amino-1-isopropyl-3-[4-(1-[[5-(1-methylcyclopropyl)-1,2-oxazol-3-yl]carbamoyl]ethyl)phenyl]pyrazole-4-carboxamide, Isomer 1 | 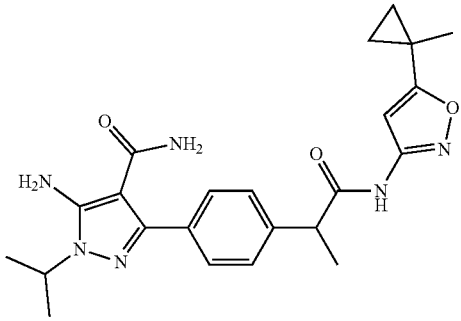 [SMILES: CC(C(=O)Nc1cc(C2(C)CC2)on1)c1ccc(-c2nn(C(C)C)c(N)c2C(N)=O)cc1] | 437.25 | 7.5 |

TABLE 20-continued

| Ex. No. | Chemical name | Structure | ES/MS m/z (M + H) | t(R) min |
|---|---|---|---|---|
| 78[12] | 5-Amino-1-isopropyl-3-[4-(1-[[5-(1-methylcyclopropyl)-1,2-oxazol-3-yl]carbamoyl]ethyl)phenyl]pyrazole-4-carboxamide, Isomer 2 | 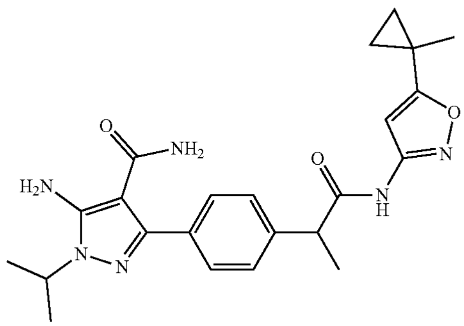 [SMILES: CC(C(=O)Nc1cc(C2(C)CC2)on1)c1ccc(-c2nn(C(C)C)c(N)c2C(N)=O)cc1] | 437.2 | 16 |
| 78a[13] | 5-Amino-1-isopropyl-3-[4-[1-[[5-(1,1,1-trifluoro-2-methylpropan-2-yl)-1H-pyrazol-3-yl]carbamoyl]ethyl]phenyl]pyrazole-4-carboxamide, Isomer 1 | 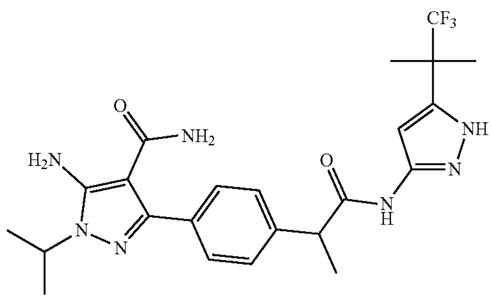 [SMILES: CC(C(=O)Nc1cc(C(C)(C)C(F)(F)F)[nH]n1)c1ccc(-c2nn(C(C)C)c(N)c2C(N)=O)cc1] | 492.2 | 5.97 |
| 78b[13] | 5-Amino-1-isopropyl-3-[4-[1-[[5-(1,1,1-trifluoro-2-methylpropan-2-yl)-1H-pyrazol-3-yl]carbamoyl]ethyl]phenyl]pyrazole-4-carboxamide, Isomer 2 | 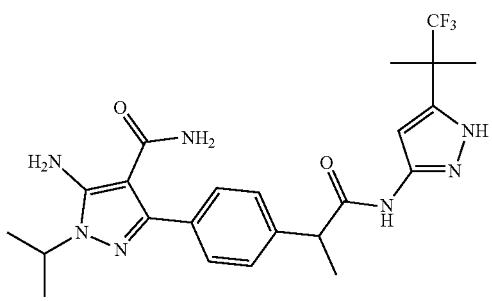 [SMILES: CC(C(=O)Nc1cc(C(C)(C)C(F)(F)F)[nH]n1)c1ccc(-c2nn(C(C)C)c(N)c2C(N)=O)cc1] | 492.2 | 10.34 |
| 78c[14] | 5-Amino-1-isopropyl-3-[4-[1-[[1-methyl-5-(1,1,1-trifluoro-2-methylpropan-2-yl)pyrazol-3-yl]carbamoyl]ethyl]phenyl]pyrazole-4-carboxamide, Isomer 1 | 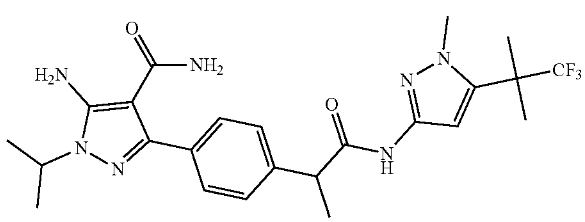 [SMILES: CC(C(=O)Nc1cc(C(C)(C)C(F)(F)F)n(C)n1)c1ccc(-c2nn(C(C)C)c(N)c2C(N)=O)cc1] | 506.3 | 15.48 |
| 78d[14] | 5-Amino-1-isopropyl-3-[4-[1-[[1-methyl-5-(1,1,1-trifluoro-2-methylpropan-2-yl)pyrazol-3-yl]carbamoyl]ethyl]phenyl]pyrazole-4-carboxamide, Isomer 2 | 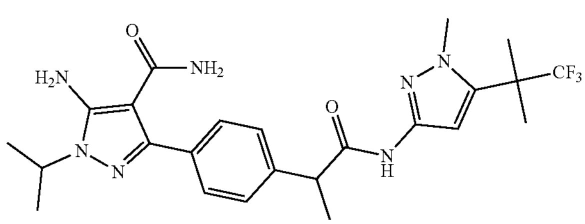 [SMILES: CC(C(=O)Nc1cc(C(C)(C)C(F)(F)F)n(C)n1)c1ccc(-c2nn(C(C)C)c(N)c2C(N)=O)cc1] | 506.3 | 20.74 |

TABLE 20-continued

| Ex. No. | Chemical name | Structure | ES/MS m/z (M + H) | t(R) min |
|---|---|---|---|---|
| 78e[14] | 5-Amino-3-[2-fluoro-4-[1-([3-[3-(trifluoromethyl)bicyclo[1.1.1]pentan-1-yl]-1,2-oxazol-5-yl]carbamoyl)ethyl]phenyl]-1-(1-methylcyclopropyl)pyrazole-4-carboxamide, Isomer 1 | 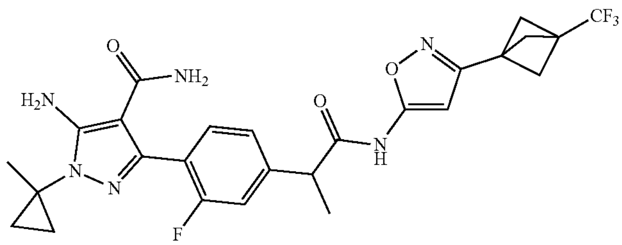 [SMILES: CC(C(=O)Nc1cc(C23CC(C(F)(F)F)(C2)C3)no1)c1ccc(-c2nn(C3(C)CC3)c(N)c2C(N)=O)c(F)c1] | 547.3 | 5.30 |
| 78f[14] | 5-Amino-3-[2-fluoro-4-[1-([3-[3-(trifluoromethyl)bicyclo[1.1.1]pentan-1-yl]-1,2-oxazol-5-yl]carbamoyl)ethyl]phenyl]-1-(1-methylcyclopropyl)pyrazole-4-carboxamide, Isomer 2 | 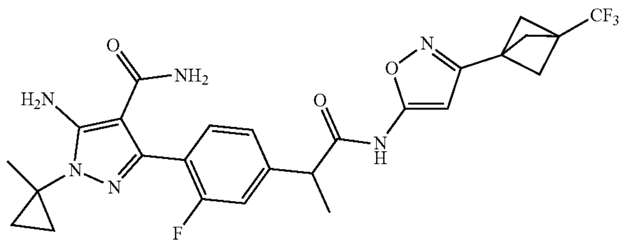 [SMILES: CC(C(=O)Nc1cc(C23CC(C(F)(F)F)(C2)C3)no1)c1ccc(-c2nn(C3(C)CC3)c(N)c2C(N)=O)c(F)c1] | 547.3 | 6.44 |
| 78g | 5-Amino-3-[2-fluoro-4-[1-([3-[4-(trifluoromethyl)bicyclo[2.2.1]heptan-1-yl]-1,2-oxazol-5-yl]carbamoyl)ethyl]phenyl]-1-(1-methylcyclopropyl)pyrazole-4-carboxamide, Isomer 1 | 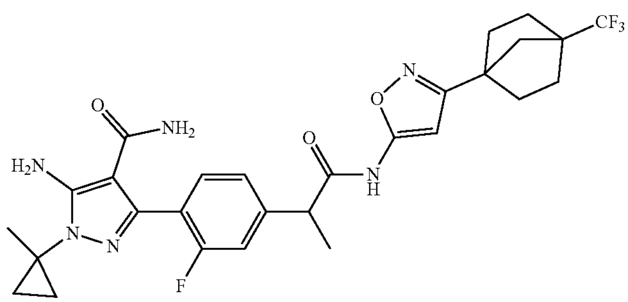 [SMILES: CC(C(=O)Nc1cc(C23CCC(C(F)(F)F)(CC2)C3)no1)c1ccc(-c2nn(C3(C)CC3)c(N)c2C(N)=O)c(F)c1] | 575.2 | 5.79 |
| 78h | 5-Amino-3-[2-fluoro-4-[1-([3-[4-(trifluoromethyl)bicyclo[2.2.1]heptan-1-yl]-1,2-oxazol-5-yl]carbamoyl)ethyl]phenyl]-1-(1-methylcyclopropyl)pyrazole-4-carboxamide, Isomer 2 | 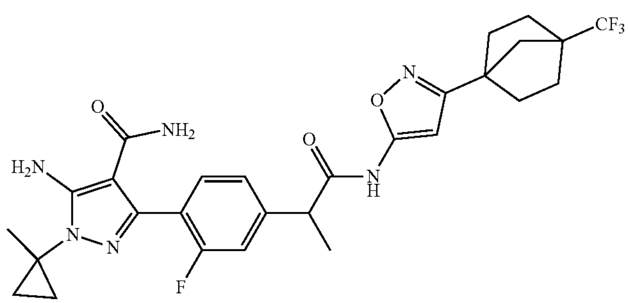 [SMILES: CC(C(=O)Nc1cc(C23CCC(C(F)(F)F)(CC2)C3)no1)c1ccc(-c2nn(C3(C)CC3)c(N)c2C(N)=O)c(F)c1] | 575.2 | 7.62 |
| 78i[15] | 5-Amino-1-[1,1-difluoropropan-2-yl]-3-[4-(1-[[3-(2,2-dimethylpropyl)-1,2-oxazol-5-yl]carbamoyl]ethyl)phenyl]pyrazole-4-carboxamide, Isomer 1 | 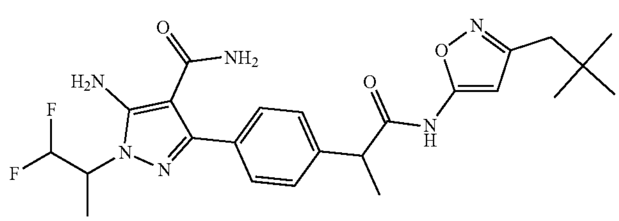 [SMILES: CC(C(=O)Nc1cc(CC(C)(C)C)no1)c1ccc(-c2nn(C(C)C(F)F)c(N)c2C(N)=O)cc1] | 489.2 | 5 |
| 78j[15] | 5-Amino-1-[1,1-difluoropropan-2-yl]-3-[4-(1-[[3-(2,2-dimethylpropyl)-1,2-oxazol-5-yl]carbamoyl]ethyl)phenyl]pyrazole-4-carboxamide, Isomer 2 | 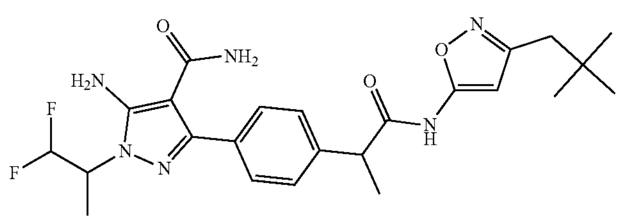 [SMILES: CC(C(=O)Nc1cc(CC(C)(C)C)no1)c1ccc(-c2nn(C(C)C(F)F)c(N)c2C(N)=O)cc1] | 489.2 | 7.4 |

TABLE 20-continued

| Ex. No. | Chemical name | Structure | ES/MS m/z (M + H) | $t_{(R)}$ min |
|---|---|---|---|---|
| 78k[16] | 5-Amino-1-[1,1-difluoropropan-2-yl]-3-[4-(1-[[3-(2,2-dimethylpropyl)-1,2-oxazol-5-yl]carbamoyl]ethyl)phenyl]pyrazole-4-carboxamide, Isomer 1 | 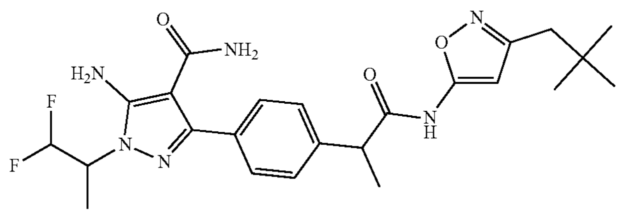 [SMILES: CC(C(=O)Nc1cc(CC(C)(C)C)no1)c1ccc(-c2nn(C(C)C(F)F)c(N)c2C(N)=O)cc1] | 489.2 | 6.1 |
| 78l[16] | 5-Amino-1-[1,1-difluoropropan-2-yl]-3-[4-(1-[[3-(2,2-dimethylpropyl)-1,2-oxazol-5-yl]carbamoyl]ethyl)phenyl]pyrazole-4-carboxamide, Isomer 2 | 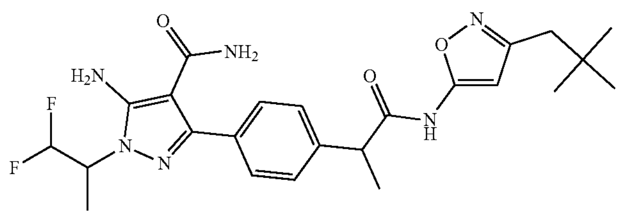 [SMILES: CC(C(=O)Nc1cc(CC(C)(C)C)no1)c1ccc(-c2nn(C(C)C(F)F)c(N)c2C(N)=O)cc1] | 489.2 | 12.1 |

[1]Column CHIRAL ART Cellulose-SB, S-5 μm, 50*250 mm, 5 μm.

[2]Column CHIRAL ART Cellulose-SB S-5 μm, 2*25 cm.

[3]Column CHIRALCEL OD-H, 2*25 mm.

[4]Column CHIRALCEL OD-H, 4.6X150 mm, 5 μm, 25% EtOH/CO$_2$, 5 mL/min, 225 nm.

[5]Column CHIRAL ART Cellulose-SC.

[6]Column: (R,R)Whelk-O 1, 21.1*250 mm, 5 μm.

[7]Column: (R,R)Whelk-O1, 2.12*25 cm, 5 μm.

[8]EtOH used for mobile phase A and B, 50% isocratic.

[9]Column: CHIRALPAK IH, 25*2 cm, 5 μm, mobile phase A CO$_2$, mobile phase B IPA, isocratic 45% B.

[10](R,R)-Whelk-01, 2*25 mm, 5 μm.

[11]Column: Chiralpak AD-H, 2*25 cm, 5 μm.

[12]Column: Chiralpak AD-H, 2*25 cm, 5 μm, eluting with a gradient of 50% B to 0 B.

[13]Column: Chiralpak ADH, 2*25 cm, 5 μm, eluting with hexanes (10 mM NH$_3$MeOH and 30% IPA.

[14]Solvent system is 30% EtOH in hexanes (10 mM NH$_3$—MeOH).

[15]Column: CHIRALPAK IG, 2*25 cm, 5 μm; eluting with 30% EtOH in hexanes (10 mM NH$_3$—MeOH), flow rate 20 mL/min, 234/274 nm.

[16]Column: CHIRAL ART Amylose-C NEO, 2.0*2 cm, 5 μm; eluting with 40% EtOH in hexanes (10 mM NH$_3$—MeOH), flow rate 20 mL/min, 245/254 nm.

Alternate Example 61

5-Amino-3-[4-[1-[[3-(2,2-dimethylpropyl)-1,2-oxazol-5-yl]carbamoyl]ethyl]phenyl]-1-(1-methylcyclopropyl)pyrazole-4-carboxamide, Isomer 1 and

Alternate Example 62

5-Amino-3-[4-[1-[[3-(2,2-dimethylpropyl)-1,2-oxazol-5-yl]carbamoyl]ethyl]phenyl]-1-(1-methylcyclopropyl)pyrazole-4-carboxamide, Isomer 2

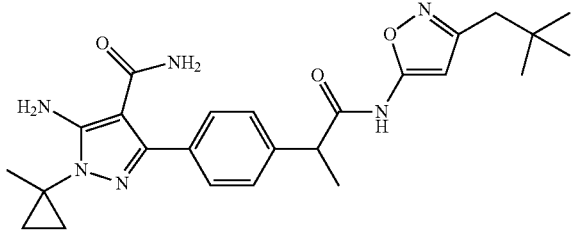 [SMILES: CC(C(=O)Nc1cc(CC(C)(C)C)no1)c1ccc(-c2nn(C3(C)CC3)c(N)c2C(N)=O)cc1]

5-Amino-3-[4-[1-[[3-(2,2-dimethylpropyl)-1,2-oxazol-5-yl]carbamoyl]ethyl]phenyl]-1-(1-methylcyclopropyl)pyrazole-4-carboxamide (95 mg) is separated with the following conditions: Column: (R,R)-Whelk-O1, 2.12*25 cm, 5 μm; eluting with 30% EtOH in hexanes (10 mM-MeOH), flow rate 20 mL/min, UV 254 nm to give the title compound of Isomer 1 $t_{(R)}$ 11.5 min, (38.6 mg, 40.6%, 100% ee) as a white solid, ES/MS (m/z) 465.3 (M+H) and the title compound of Isomer 2 trio 20 min (30.7 mg, 32.3%, 99.6% ee) as a white solid, ES/MS (m/z) 465.3 (M+H).

Example 79

5-Amino-3-(4-[1-[(5-tert-butyl-1,2-thiazol-3-yl)carbamoyl]ethyl]phenyl)-1-isopropylpyrazole-4-carboxamide, Isomer 1 and

Example 80

5-Amino-3-(4-[1-[(5-tert-butyl-1,2-thiazol-3-yl)carbamoyl]ethyl]phenyl)-1-isopropylpyrazole-4-carboxamide, isomer 2

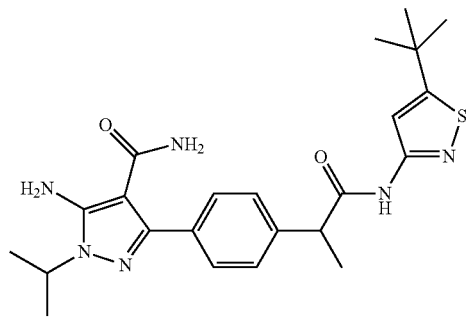 [SMILES: CC(C(=O)Nc1cc(C(C)(C)C)sn1)c1ccc(-c2nn(C(C)C)c(N)c2C(N)=O)cc1]

5-Amino-3-(4-[1-[(5-tert-butyl-1,2-thiazol-3-yl)carbamoyl]ethyl]phenyl)-1-isopropylpyrazole-4-carboxamide (90 mg, 0.20 mmol) is separated by prep-chiral chromatography with the following conditions: Column: CHIRALPAK IG-3, 4.6*50 mm, 3.0 μm, mobile phase A: hexanes (0.1% DEA); mobile phase B: EtOH eluting with a gradient of 70% to 30% B; flow rate 1 mL/min, UV 254 nm, $t_{(R)}$ Isomer 1 is 2.1 min (25 mg, 21.8%) as a white solid, $t_{(R)}$ Isomer 2 is 3.3 min (25 mg, 21.8%) as a white solid. ES/MS (m/z) 455.25 (M+H).

Example 81

5-Amino-1-isopropyl-3-[4-(1-[[5-(1,1,1-trifluoro-2-methylpropan-2-yl)-1,2-oxazol-3-yl]carbamoyl]ethyl)phenyl]pyrazole-4-carboxamide, Isomer 1 and

Example 82

5-Amino-1-isopropyl-3-[4-(1-[[5-(1,1,1-trifluoro-2-methylpropan-2-yl)-1,2-oxazol-3-yl]carbamoyl]ethyl)phenyl]pyrazole-4-carboxamide, Isomer 2

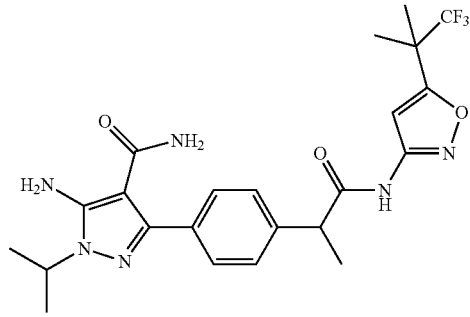 [SMILES: CC(C(=O)Nc1cc(C(C)(C)C(F)(F)F)on1)c1ccc(-c2nn(C(C)C)c(N)c2C(N)=O)cc1]

5-Amino-1-isopropyl-3-[4-(1-[[5-(1,1,1-trifluoro-2-methylpropan-2-yl)-1,2-oxazol-3-yl]carbamoyl]ethyl)phenyl]pyrazole-4-carboxamide (90 mg, 0.18 mmol) is separated by prep-chiral chromatography with the following conditions: Column: CHIRALPAK IE, 2*25 cm, 5 μm; mobile phase A: ACN; mobile phase B: MtBE eluting with 25% B; 210 nm, 254 nm; $t_{(R)}$ Isomer 1 is 5 min (39.3 mg, 43.6%, 100% ee) as a white solid. $t_{(R)}$ Isomer 2 is 6 min (36.1 mg, 40.1%, 100% ee) as a white solid. ES/MS (m/z) 493.3 (M+H).

Example 83

5-Amino-1-isopropyl-3-[6-[2-[[3-(1,1-dimethylpropyl)isoxazol-5-yl]amino]-1-methyl-2-oxo-ethyl]-3-pyridyl]pyrazole-4-carboxamide, Isomer 1 and

Example 84

5-Amino-1-isopropyl-3-[6-[2-[[3-(1,1-dimethylpropyl)isoxazol-5-yl]amino]-1-methyl-2-oxo-ethyl]-3-pyridyl]pyrazole-4-carboxamide, Isomer 2

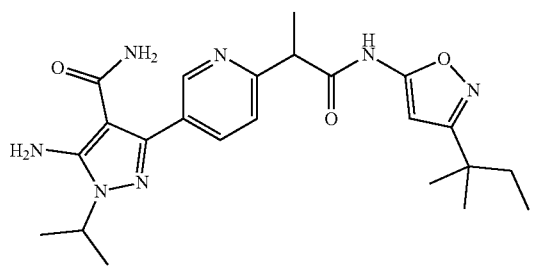 [SMILES: CCC(C)(C)c1cc(NC(=O)C(C)c2ccc(-c3nn(C(C)C)c(N)c3C(N)=O)cn2)on1]

5-Amino-3-[6-[2-[[3-(1,1-dimethylpropyl)isoxazol-5-yl]amino]-1-methyl-2-oxo-ethyl]-3-pyridyl]-1-isopropyl-pyrazole-4-carboxamide (68 mg, 0.18 mmol) is chirally separated with the following conditions: Column: Acquity UPLC CSH C18 (2.1×50 mm) 1.7 μm; mobile phase A: $H_2O$+ 0.02% FA; mobile phase B: ACN+0.02% FA eluting with a gradient of 2% B to 98% B over 4 min; flow rate of 1 ml/min, temperature of 55° C. $t_{(R)}$ isomer 1 is 3.3 min (22 mg, 20%). $t_{(R)}$ isomer 2 is 4.7 min (23 mg, 21%). ES/MS (m/z) 454 (M+H).

The following compounds in Table 21 are chirally separated essentially as described for 5-amino-1-isopropyl-3-[6-[2-[[3-(1,1-dimethylpropyl)isoxazol-5-yl]amino]-1-methyl-2-oxo-ethyl]-3-pyridyl]pyrazole-4-carboxamide, Isomer 1 and Isomer 2 adjusting the conditions as appropriate. The title compounds can be triturated with isopropyl ether and dried under vacuum at about 45° C. for 14 hrs to give white solids.

TABLE 21

| Ex. No. | Chemical name | Structure | ES/MS m/z (M + H) | $t_{(R)}$ |
|---|---|---|---|---|
| 85 | 5-Amino-1-isopropyl-3-[6-[2-[[5-(2,2-dimethylpropyl)isoxazol-3-yl]amino]-1-methyl-2-oxo-ethyl]-3-pyridyl]pyrazole-4-carboxamide, Isomer 2 | 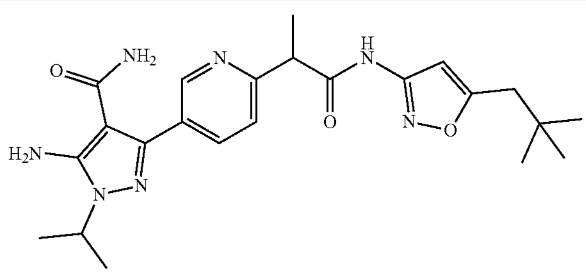 [SMILES: CC(C(=O)Nc1cc(CC(C)(C)C)on1)c1ccc(-c2nn(C(C)C)c(N)c2C(N)=O)cn1] | 454.4 | 17.2 |
| 86 | 5-Amino-1-isopropyl-3-[6-[2-[[5-(2,2-dimethylpropyl)isoxazol-3-yl]amino]-1-methyl-2-oxo-ethyl]-3-pyridyl]pyrazole-4-carboxamide, Isomer 1 | 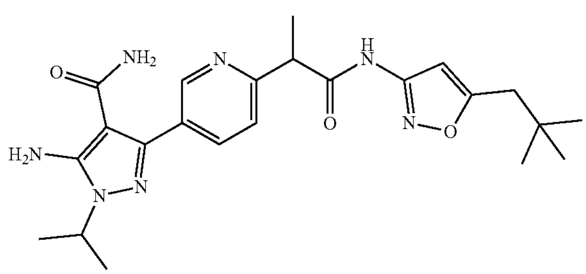 [SMILES: CC(C(=O)Nc1cc(CC(C)(C)C)on1)c1ccc(-c2nn(C(C)C)c(N)c2C(N)=O)cn1] | 454.3 | 16.1 |
| 87 | 5-Amino-1-isopropyl-3-[6-[1-methyl-2-oxo-2-[[5-(2,2,2-trifluoro-1,1-dimethyl-ethyl)isoxazol-3-yl]amino]ethyl]-3-pyridyl]pyrazole-4-carboxamide, Isomer 1 | 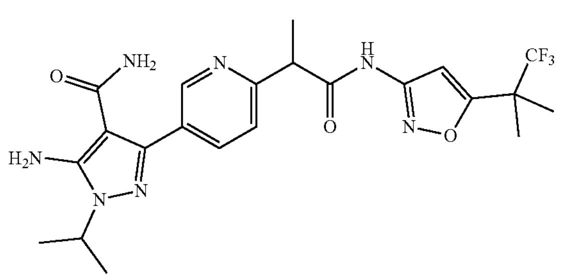 [SMILES: CC(C(=O)Nc1cc(C(C)(C)C(F)(F)F)on1)c1ccc(-c2nn(C(C)C)c(N)c2C(N)=O)cn1] | 494 | 3.2 |

TABLE 21-continued

| Ex. No. | Chemical name | Structure | ES/MS m/z (M + H) | t(R) |
|---|---|---|---|---|
| 88 | 5-Amino-1-isopropyl-3-[6-[1-methyl-2-oxo-2-[[5-(2,2,2-trifluoro-1,1-dimethyl-ethyl)isoxazol-3-yl]amino]ethyl]-3-pyridyl]pyrazole-4-carboxamide, Isomer 2 | 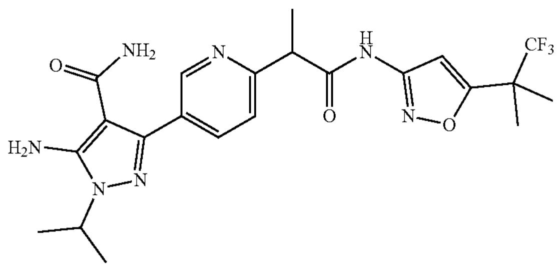 [SMILES: CC(C(=O)Nc1cc(C(C)(C)C(F)(F)F)on1)c1ccc(-c2nn(C(C)C)c(N)c2C(N)=O)cn1] | 494 | 5.2 |
| 89 | 5-Amino-1-isopropyl-3-[6-[1-methyl-2-oxo-2-[[3-(2,2,2-trifluoro-1,1-dimethyl-ethyl)isoxazol-5-yl]amino]ethyl]-3-pyridyl]pyrazole-4-carboxamide, Isomer 1 | 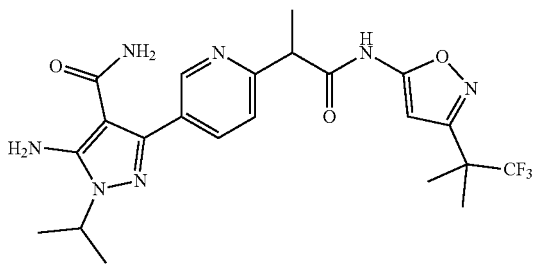 [SMILES: CC(C(=O)Nc1cc(C(C)(C)C(F)(F)F)no1)c1ccc(-c2nn(C(C)C)c(N)c2C(N)=O)cn1] | 494.4 | 2.5 |
| 90 | 5-Amino-1-isopropyl-3-[6-[1-methyl-2-oxo-2-[[3-(2,2,2-trifluoro-1,1-dimethyl-ethyl)isoxazol-5-yl]amino]ethyl]-3-pyridyl]pyrazole-4-carboxamide, Isomer 2 | 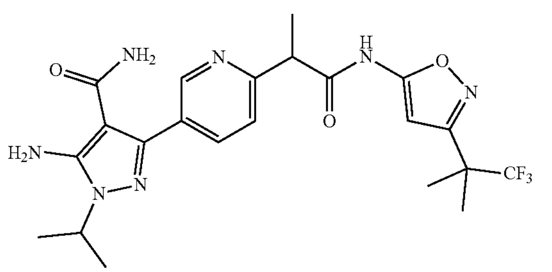 [SMILES: CC(C(=O)Nc1cc(C(C)(C)C(F)(F)F)no1)c1ccc(-c2nn(C(C)C)c(N)c2C(N)=O)cn1] | 494.4 | 3.5 |
| 91 | 5-Amino-1-isopropyl-3-[6-[2-[[3-(2,2-dimethylpropyl)isoxazol-5-yl]amino]-1-methyl-2-oxo-ethyl]-3-pyridyl]pyrazole-4-carboxamide, Isomer 2 | 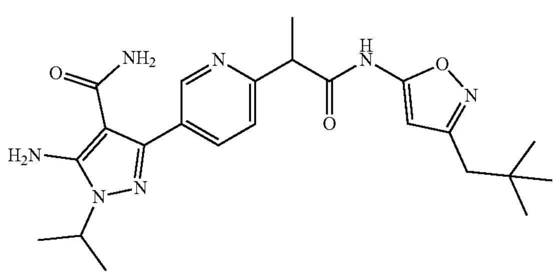 [SMILES: CC(C(=O)Nc1cc(CC(C)(C)C)no1)c1ccc(-c2nn(C(C)C)c(N)c2C(N)=O)cn1] | 454.4 | 20.2 |
| 92 | 5-Amino-1-isopropyl-3-[6-[2-[[3-(2,2-dimethylpropyl)isoxazol-5-yl]amino]-1-methyl-2-oxo-ethyl]-3-pyridyl]pyrazole-4-carboxamide, Isomer 1 | 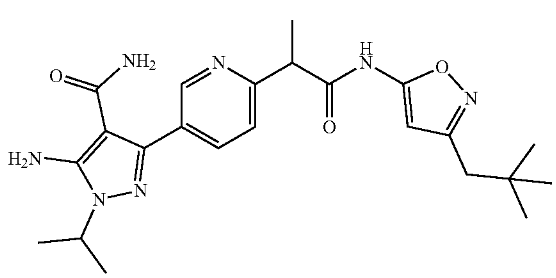 [SMILES: CC(C(=O)Nc1cc(CC(C)(C)C)no1)c1ccc(-c2nn(C(C)C)c(N)c2C(N)=O)cn1] | 454.4 | 20.1 |

TABLE 21-continued

| Ex. No. | Chemical name | Structure | ES/MS m/z (M + H) | t(R) |
|---|---|---|---|---|
| 93 | 5-Amino-1-isopropyl-3-[6-[2-[[3-(2,4-dichlorophenyl)isoxazol-5-yl]amino]-1-methyl-2-oxo-ethyl]-3-pyridyl]pyrazole-4-carboxamide, Isomer 1 | 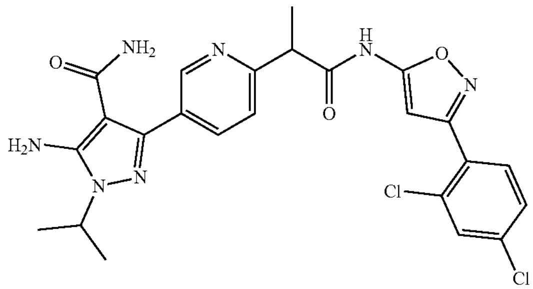 [SMILES: CC(C(=O)Nc1cc(-c2ccc(Cl)cc2Cl)no1)c1ccc(-c2nn(C(C)C)c(N)c2C(N)=O)cn1] | 528.3 | 14.6 |
| 94 | 5-Amino-1-isopropyl-3-[6-[2-[[3-(2,4-dichlorophenyl)isoxazol-5-yl]amino]-1-methyl-2-oxo-ethyl]-3-pyridyl]pyrazole-4-carboxamide, Isomer 2 | 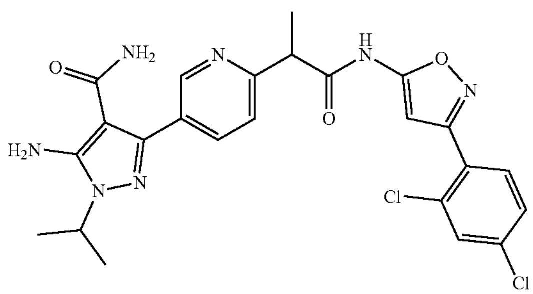 [SMILES: CC(C(=O)Nc1cc(-c2ccc(Cl)cc2Cl)no1)c1ccc(-c2nn(C(C)C)c(N)c2C(N)=O)cn1] | 528.3 | 16.8 |
| 95 | 5-Amino-1-isopropyl-3-[6-[2-[[5-(1,1-dimethylpropyl)isoxazol-3-yl]amino]-1-methyl-2-oxo-ethyl]-3-pyridyl]pyrazole-4-carboxamide, Isomer 2 | 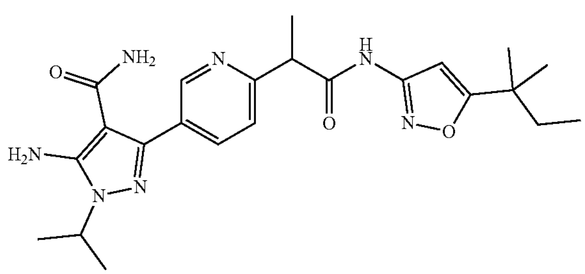 [SMILES: CCC(C)(C)c1cc(NC(=O)C(C)c2ccc(-c3nn(C(C)C)c(N)c3C(N)=O)cn2)no1] | 454 | 8.8 |
| 96 | 5-Amino-1-isopropyl-3-[6-[2-[[5-(1,1-dimethylpropyl)isoxazol-3-yl]amino]-1-methyl-2-oxo-ethyl]-3-pyridyl]pyrazole-4-carboxamide, Isomer 1 | 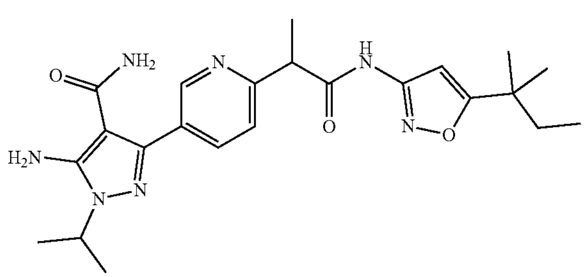 [SMILES: CCC(C)(C)c1cc(NC(=O)C(C)c2ccc(-c3nn(C(C)C)c(N)c3C(N)=O)cn2)no1] | 454 | 8.7 |

Example 97

5-Amino-3-[4-[2-[[3-(3-bicyclo[1.1.1]pentanylmethyl)isoxazol-5-yl]amino]-1-methyl-2-oxo-Ethyl]phenyl]-1-isopropyl-pyrazole-4-carboxamide, Isomer 1

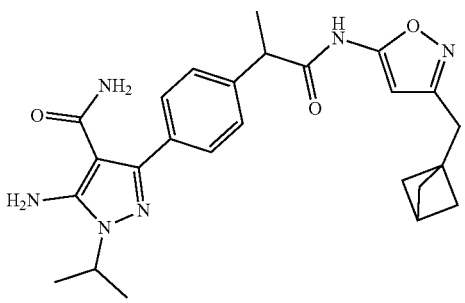 [SMILES: CC(C(=O)Nc1cc(CC23CC(C2)C3)no1)c1ccc(-c2nn(C(C)C)c(N)c2C(N)=O)cc1]

2-[4-(5-Amino-4-cyano-1-isopropyl-pyrazol-3-yl)phenyl]-N-[3-(3-bicyclo[1.1.1]pentanylmethyl)isoxazol-5-yl]

propanamide, Isomer 1 (10 mg, 0.023 mmol) and platinate (2-), tris(dimethylphosphinito-P)hydro-, dihydrogen (Parkins catalyst, CAS #173416-05-2) (10 mg, 0.023 mmol) are stirred in EtOH (0.2 ml) and H$_2$O (0.2 ml) at 70° C. for 90 min. The reaction mixture is filtered through diatomaceous earth and concentrated. The residue is purified by C18 HPLC eluting with H$_2$O:ACN (5-95%) with 0.1% TFA. The free base of the desired product is formed by eluting the material through a cartridge of carbonate resin to give the title compound (4.3 mg, 39%). ES/MS (m/z) 463.2 (M+H) 99% ee, chiral purity determination: YMA Chiral Cellulose-SB column, 4.6×100 mm, 3 μm eluting with 70/30 hexanes (0.1% ethylenediamine)/IPA 1 ml/min, t$_{(R)}$ 3.78.

The following compounds in Table 22 are prepared essentially as described for 5-amino-3-[4-[2-[[3-(3-bicyclo[1.1.1]pentanylmethyl)isoxazol-5-yl]amino]-1-methyl-2-oxo-ethyl]phenyl]-1-isopropyl-pyrazole-4-carboxamide, Isomer 1 using the appropriate reagents, adjusting reaction time to determine completion of the reaction and using appropriate chromatography conditions for purification if needed. Temperature can vary from about 60 to 80° C. Further Parkin's catalyst can be used to push the reaction to completion if needed.

TABLE 22

| Ex. No. | Chemical name | Structure | ES/MS m/z (M + H) | t$_{(R)}$ |
|---|---|---|---|---|
| 98[1] | 5-Amino-3-[4-[2-[[3-(3,3-dimethylcyclobutyl)isoxazol-5-yl]amino]-1-methyl-2-oxo-ethyl]phenyl]-1-isopropyl-pyrazole-4-carboxamide, Isomer 1 | 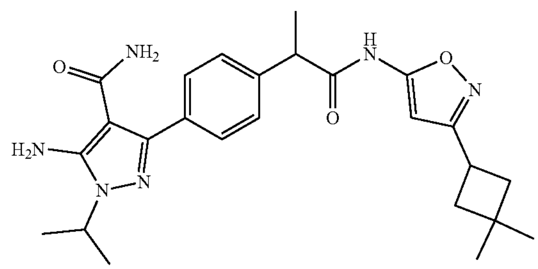 [SMILES: CC(C(=O)Nc1cc(C2CC(C)(C)C2)no1)c1ccc(-c2nn(C(C)C)c(N)c2C(N)=O)cc1] | 465.26 | 3.25 |
| 99 | 5-Amino-1-isopropyl-3-[4-[2-[[5-(2,2-dimethylpropyl)isoxazol-3-yl]amino]-1-methyl-2-oxo-ethyl]phenyl]pyrazole-4-carboxamide, Isomer 1 | 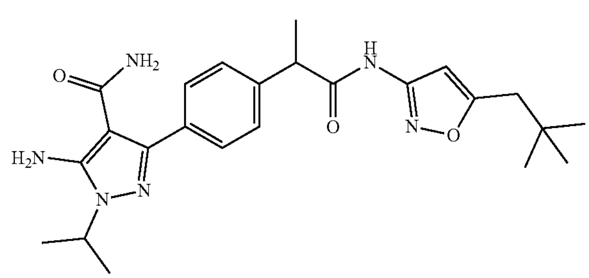 [SMILES: CC(C(=O)Nc1cc(CC(C)(C)C)on1)c1ccc(-c2nn(C(C)C)c(N)c2C(N)=O)cc1] | 453.3 | 4.96 |

While only certain representative compounds, materials, and method steps disclosed herein are specifically described, other combinations of the compounds, materials, and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising", and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

Biological Assays

The following assays demonstrate that the compounds described herein are RET kinase inhibitors.

Assay A: RET Enzyme Assay

Compounds of formulas I, II, or III are screened for their ability to inhibit wildtype, V804M, and G810S mutant RET kinase using CisBio's HTRF® KinEASE™TK assay technology. N-terminal GST tagged recombinant human RET cytoplasmic domain (aa 658-end) from Eurofins (T25 nM RET; Catalog No. 14-570M) or N-terminal GST tagged recombinant human V804M mutant RET cytoplasmic domain (aa 658-end) from Millipore (1.25 nM enzyme; Catalog No. 14-760) or N-Terminal GST-tagged recombinant human G810S (aa-658-end) (1.25 nM Enzyme; produced in insect cells) is incubated with 62.5 nM TK-substrate biotin (CisBio, part of Catalog No. 62TK0PEC) and 1 mM ATP along with test compound (0.4% final DMSO in the assay) in a 1× Cisbio enzymatic buffer consisting of 1 nM DTT, 5 mM MgCl$_2$, 0.04% BSA and 0.05% Tween20 in a volume of 10 μL. Compounds are typically prepared in a threefold serial dilution in DMSO and added to the assay to give the appropriate final concentration. After a 40-60 min (40 min for V804M, 60 min for WT and G810S) incubation at 22° C., the reaction is quenched by adding quench solution (10 μL) containing 7.8 nM Streptavidine-XL665 and 0.5×TK-ab-Cryptate in HTRF detection buffer (all from CisBio, part of Cat. No. 62TK0PEC). After a 60-80 min incubation (60 minutes for WT, 80 minutes for V804M and G810S) at 22° C., the extent of reaction is determined using a PHERastar plate reader via HTRF detection at excitation/emission 337/665 nm. Percent of inhibition is calculated with 0% inhibition referring to control conditions containing no compound (0.4% DMSO only) and 100% inhibition represented by conditions containing no enzyme. The % inhibition values are fit to a 4 parameter logistic curve, and the determined IC$_{50}$ value is defined as the estimated concentration of inhibitor at the inflexion point of the fitted curve. The compounds of Examples 1, 15, 17, 35, 45, 52, 64, 66, 68, 70, 76, 80, 81, 84, 90, 94, and 98 all exhibited IC$_{50}$ values of less than 100 nM for each of wildtype, V804M, and G810S mutant RET kinase in these assays. All of the compounds in Table A have IC$_{50}$ values of less than 700 nm in the wildtype, V804M, and G810S mutant RET kinase assays.

Assay B: RET Cell Assay

Compounds of formulas (I), (II), and (III) are screened for their ability to inhibit the intracellular autophosphorylation of RET at tyrosine 1062 as detected by In-Cell Western. HEK293 cells containing a doxycycline-inducible plasmid for inducible expression of KIF5B-RET WT and RET mutant forms V804M and G810S are seeded at 25,000 cells/well into black poly-D-lysine pre-coated 384-well plates (Corning, Catalog No. 356697). Expression of KIF5B-RET is induced with doxycycline at 1 μg/mL and cells are incubated at 37° C. overnight. Compounds are prepared in a threefold serial dilution in DMSO before further diluting 1:100 in media prior to the addition to the cells (0.1% final DMSO concentration). Compound treatment is performed for 1 hr at 37° C. followed by fixation of cells with 4% formaldehyde for 20 min at RT and cell permeabilisation with ice-cold MeOH for 10 min at RT. Cells are incubated with Intercept® blocking buffer (Li—COR, Catalogue No. 927-70010) for 1 hr at RT. Incubation with primary antibodies against human phospho-RET (Y1062) (R&D, Catalogue No. AF5009, 1/250 dilution) and human glyceraldehyde-3-phosphate dehydrogenase (clone 6C$_5$, Merck, Catalog No. MAB374, 1/1000 dilution) are performed overnight at 4° C. Incubation with secondary antibodies IRDye® 800CW goat anti-rabbit IgG (Li—COR, Catalogue No. 926-32211, 1/1000 dilution) and IRDye® 680CW goat anti-mouse IgG (Li—COR, Catalogue No. 926-68070, 1/1000 dilution) are performed for 1 hr at RT. All antibody dilutions are done in Intercept® blocking buffer containing 0.05% Tween20. After washing cells with PBS-T (Cell Signaling technology, Catalogue No. 9809), the images are acquired on a Li—COR Odyssey LCx at 700 and 800 nm. Percent of DMSO control is calculated with 100% signal referring to control conditions containing no compound (0.4% DMSO only) and 0% signal represented by conditions containing control compound. The % of DMSO control values are fit to a 4 parameter logistic curve, and the determined EC$_{50}$ value is defined as the estimated concentration of inhibitor at the inflexion point of the fitted curve. The compounds of Examples 1, 15, 17, 31, 33, 35, 45, 52, 64, 66, 68, 70, 76, 80, 81, 84, 90, 94, and 98 all inhibited the intracellular autophosphorylation of RET at tyrosine 1062 with EC$_{50}$ values of less than 100 nM in each of wildtype, V804M, and G810S RET mutant cells in these assays. All of the compounds in Table B have IC$_{50}$ values of less than 700 nm in the wildtype, V804M, and G810S mutant RET kinase assays.

What is claimed is:

1. A compound of the formula:

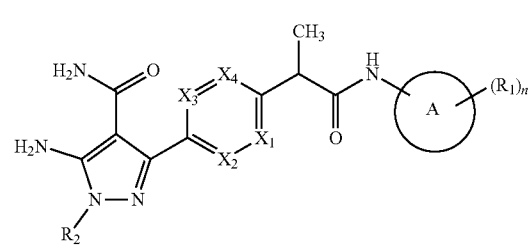

wherein

A is a five- or six-member aryl or heteroaryl;

Each $R_1$ is independently hydrogen, halogen, $C_1$-$C_6$ alkyl, $C_1$-$C_6$ heteroalkyl, —($C_0$-$C_4$ alkyl)($C_5$-$C_6$ heteroalkyl), —($C_0$-$C_4$ alkyl)($C_3$-$C_7$ cycloalkyl), —($C_0$-$C_4$ heteroalkyl)($C_3$-$C_7$ cycloalkyl), —($C_0$-$C_4$ alkyl)($C_4$-$C_7$ cycloheteroalkyl), —($C_0$-$C_4$ heteroalkyl)($C_3$-$C_7$ cycloheteroalkyl), —($C_0$-$C_4$ alkyl)($C_4$-$C_{10}$ bicyclic), —($C_0$-$C_4$ alkyl)($C_5$-$C_6$ aryl), —($C_0$-$C_4$ alkyl)($C_5$-$C_6$ heteroaryl), —($C_0$-$C_4$ alkyl)($C_4$-$C_{10}$ heterobicyclic), $C_5$-$C_{12}$ spirane, $C_5$-$C_{12}$ heterospirane, adamantane, difluoromethylsulfane, or pentafluorosulfane, wherein each $R_1$ is optionally substituted with one or more groups that are independently halogen, cyano, hydroxyl, oxo, methyl, methoxy, hydroxymethyl, ethyl, ethoxy, hydroxyethyl, methylamine, N,N-dimethylmethylamine, or mono-, di-, or tri-halomethyl, and wherein two $R_1$ groups can fuse to form a ring structure that includes a portion of A and is optionally aromatic, and n is 1, 2, or 3;

$X_1$, $X_2$, $X_3$, and $X_4$ are each independently N, CH, C—CH$_3$, C—CH$_2$—OH, C—OCH$_3$, C—CH$_2$—OCH$_3$, or C-halogen; and $R_2$ is $C_1$-$C_4$ alkyl, —($C_0$-$C_4$ alkyl)($C_3$-$C_7$ cycloalkyl), —($C_0$-$C_4$ alkyl)($C_4$-$C_7$ heterocycloalkyl), —($C_0$-$C_4$ alkyl)($C_4$-$C_{10}$ bicyclic) each optionally substituted with one or more groups that are independently deuterium, halogen, cyano, hydroxyl, oxo, methyl, methoxy, hydroxymethyl, ethyl, ethoxy, hydroxyethyl, cyclopropyl, or mono-, di-, or tri-halomethyl;

or a pharmaceutically acceptable salt thereof.

2. The compound according to claim 1, wherein each of $X_1$, $X_2$, $X_3$, and $X_4$ is CH, or a pharmaceutically acceptable salt thereof.

3. The compound according to claim 2, wherein A-$(R_1)_n$ is

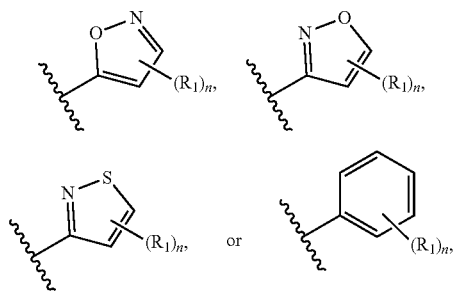

or a pharmaceutically acceptable salt thereof.

4. The compound according to claim 3, wherein A-$(R_1)_n$ is

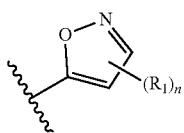

or or a pharmaceutically acceptable salt thereof.

5. The compound according to claim 3, wherein $R_1$ is 2,2-dimethylpropyl; 2-chloro-4-fluoro-phenyl; 2,4-dichlorophenyl; 1,1-dimethyl-2,2,2-trifluoroethyl; 1,1-dimethylethyl; 1,1-dimethylpropyl; trifluoromethyl; 1,1-dimethyl-2,2-difluoropropyl; 1,1-dimethyl-3,3,3-trifluoropropyl; 1-methylcyclopropyl; (1-methylcyclopropyl)methyl; 3-methylbicyclo[1.1.1]pentan-1-yl; 3-(trifluoromethyl)bicyclo[1.1.1]pentan-1-yl; (3,3-dimethylcyclobutyl)methyl or a pharmaceutically acceptable salt thereof.

6. The compound according to claim 3, wherein $R_1$ is 2,2-dimethylpropyl, or a pharmaceutically acceptable salt thereof.

7. The compound according to claim 4, wherein $R_1$ is 2,2-dimethylpropyl, or a pharmaceutically acceptable salt thereof.

8. The compound according to claim 3, wherein at least one $R_1$ is halogen, —CH$_2$C(CH$_3$)$_3$,

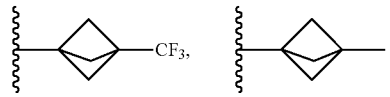

or a pharmaceutically acceptable salt thereof.

9. The compound according to claim 4, wherein at least one $R_1$ is halogen, —CH$_2$C(CH$_3$)$_3$,

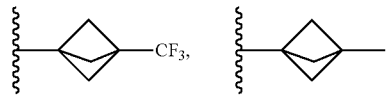

or a pharmaceutically acceptable salt thereof.

10. The compound according to claim 3, wherein $R_2$ is

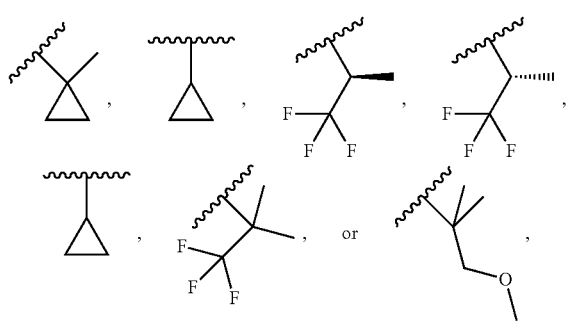

or a pharmaceutically acceptable salt thereof.

11. The compound according to claim 5, wherein $R_2$ is

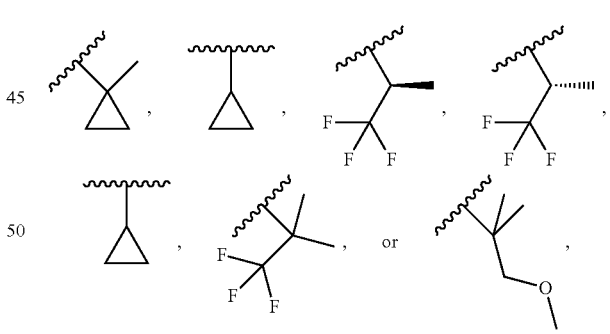

or a pharmaceutically acceptable salt thereof.

12. The compound according to claim 4, wherein $R_2$ is —CH(CH$_3$)$_2$, —CH(CF$_3$)CH$_3$, —CH(CH$_3$)CHF$_2$, or

or a pharmaceutically acceptable salt thereof.

13. The compound according to claim 5, wherein R₂ is —CH(CH₃)₂, —CH(CF₃)CH₃, —CH(CH₃)CHF₂, or

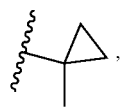, or a pharmaceutically acceptable salt thereof.

14. The compound according to claim 4, wherein R₂ is

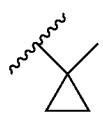 or 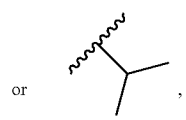, or a pharmaceutically acceptable salt thereof.

15. The compound according to claim 5, wherein R₂ is

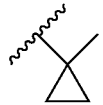 or , or a pharmaceutically acceptable salt thereof.

16. The compound according to claim 1, of the formula:

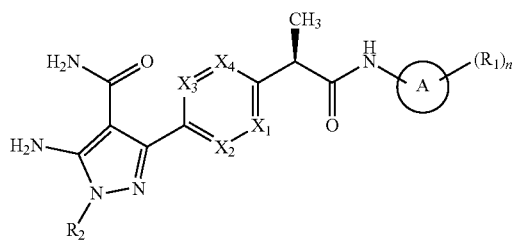

or a pharmaceutically acceptable salt thereof.

17. The compound according to claim 1, of the formula:

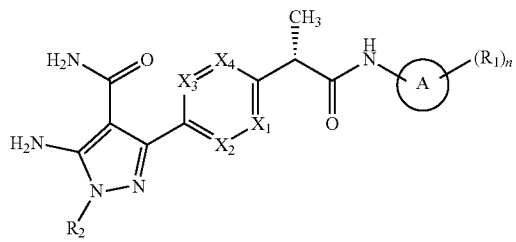

or a pharmaceutically acceptable salt thereof.

18. A compound that is:

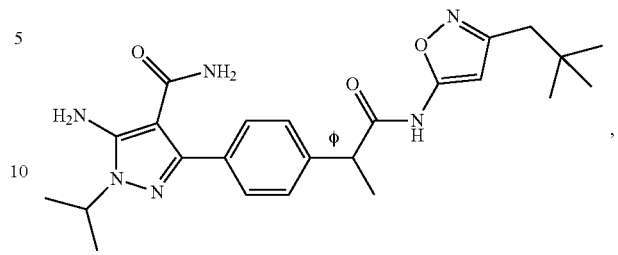,

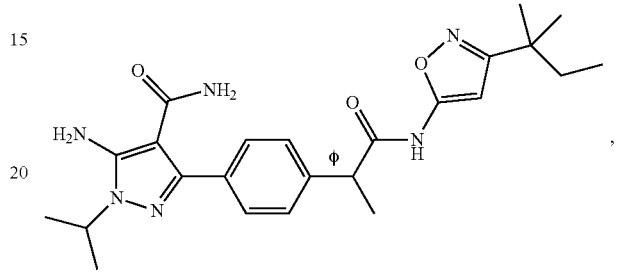,

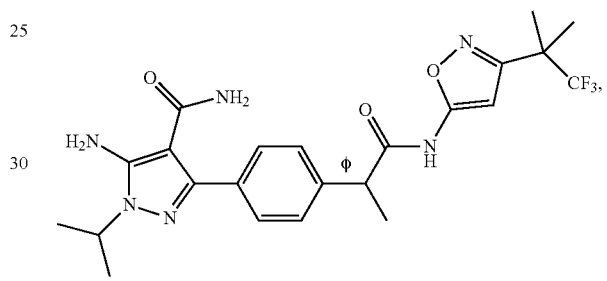,

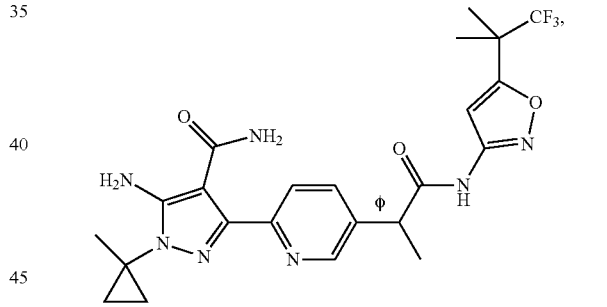,

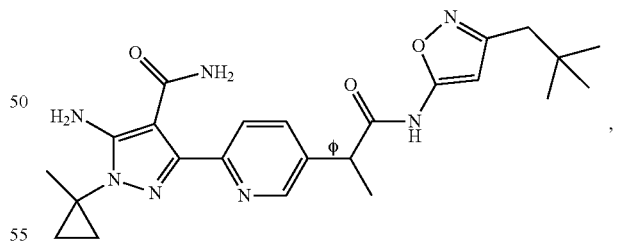,

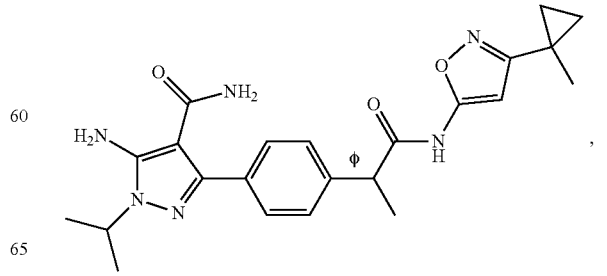,

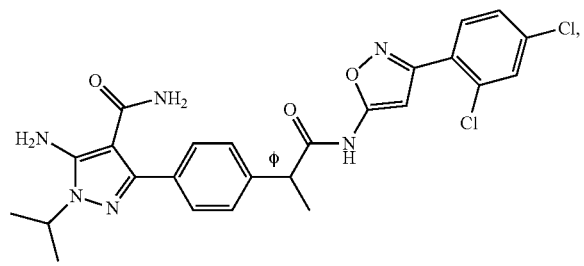
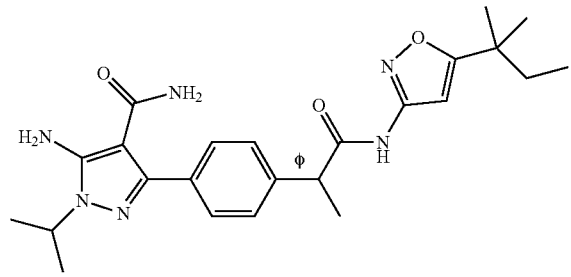
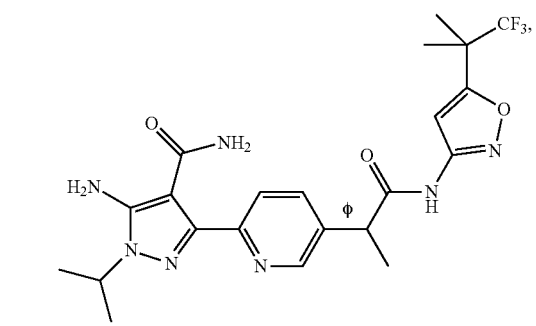
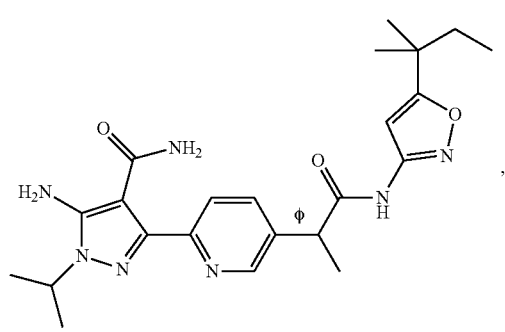
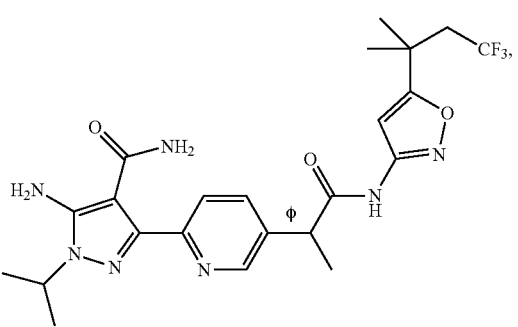
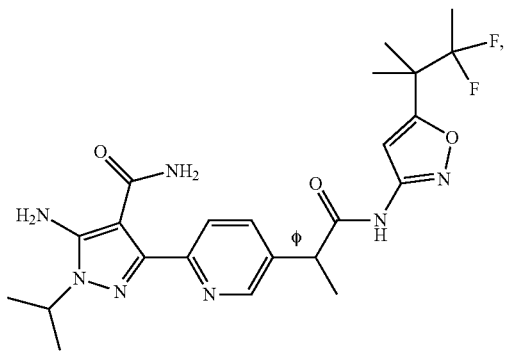
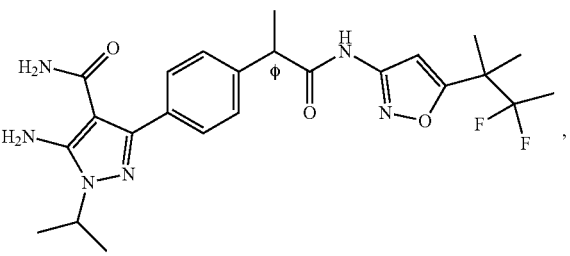
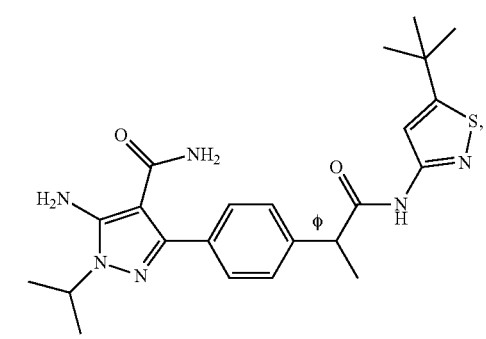
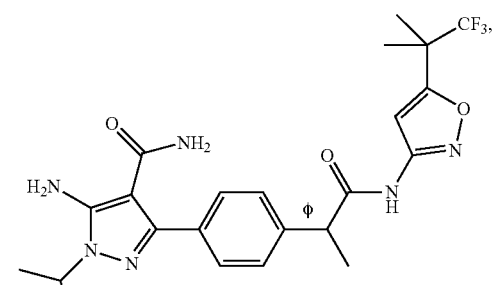
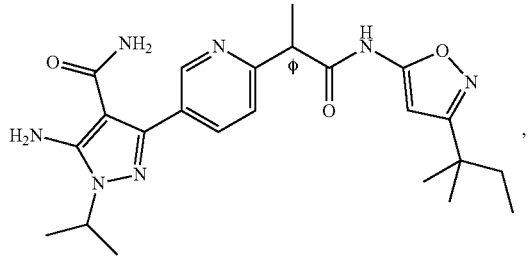

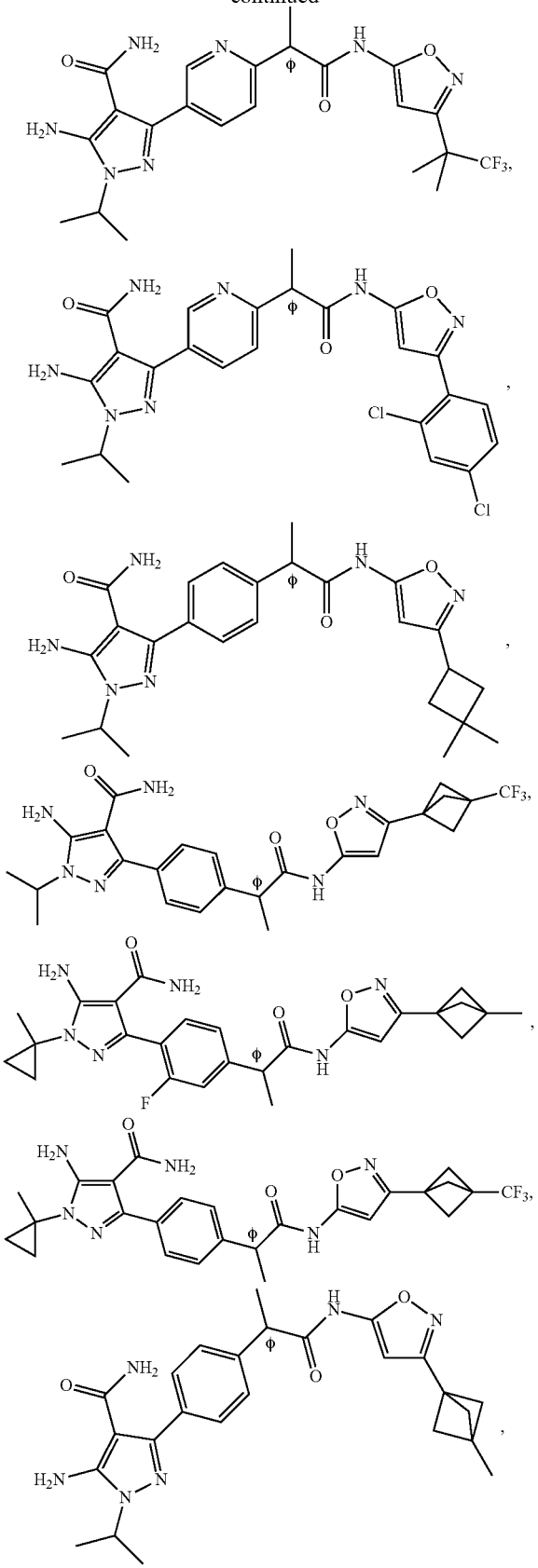

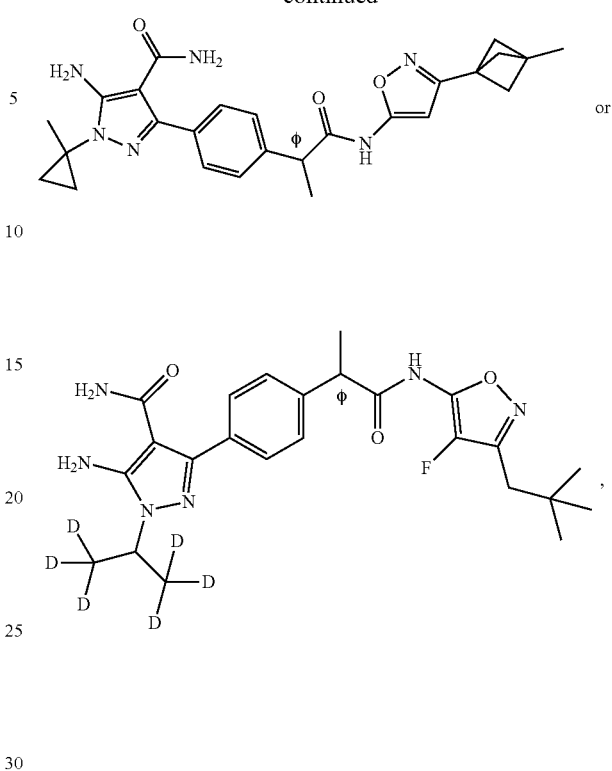

or a pharmaceutically acceptable salt thereof.

19. The compound according to claim 18, wherein the formulas have R-enantiomeric chirality at the φ position.

20. The compound according to claim 18, wherein the formulas have S-enantiomeric chirality at the φ position.

21. A method of treating cancer in a patient, comprising administering to a patient in need of such treatment an effective amount of a compound, or a pharmaceutically acceptable salt thereof, according to claim 1, wherein the cancer is a RET-associated cancer.

22. The method according to claim 21, wherein the cancer is selected from the group consisting of: lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

23. The method of claim 21, wherein the cancer is medullary thyroid cancer.

24. The method of claim 22, wherein the lung cancer is small cell lung carcinoma, non-small cell lung cancer, bronchioles lung cell carcinoma, RET fusion lung cancer, or lung adenocarcinoma.

25. A pharmaceutical composition comprising a compound, or a pharmaceutically acceptable salt thereof, according to claim 1 with one or more pharmaceutically acceptable carriers, diluents, or excipients.

* * * * *

UNITED STATES PATENT AND TRADEMARK OFFICE
CERTIFICATE OF CORRECTION

PATENT NO. : 11,613,533 B2
APPLICATION NO. : 17/238370
DATED : March 28, 2023
INVENTOR(S) : Erin D. Anderson et al.

It is certified that error appears in the above-identified patent and that said Letters Patent is hereby corrected as shown below:

In the Specification

In Column 2, Line 17, "N,N,-diethylmethylamine" should read -- N,N,-dimethylmethylamine --.

In Column 4, Lines 9-10, "N,N,-diethylmethylamine" should read -- N,N,-dimethylmethylamine --.

In the Claims

In Column 281, Line 49 of Claim 4, delete the word "or".

Signed and Sealed this
Fifteenth Day of August, 2023

Katherine Kelly Vidal
*Director of the United States Patent and Trademark Office*

SEQUENCE LISTING

<160> NUMBER OF SEQ ID NOS: 1

<210> SEQ ID NO 1
<211> LENGTH: 1114
<212> TYPE: PRT
<213> ORGANISM: Homo sapiens

<400> SEQUENCE: 1

```
Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400
```

```
Ser Leu His Leu Pro Ser Thr Tyr Ser Leu Ser Val Ser Arg Arg Ala
            405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
            435                 440                 445

Cys Ser Thr Leu Gly Val Val Thr Ser Ala Glu Asp Thr Ser Gly Ile
            450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
            485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
            515                 520                 525

Glu Glu Cys Gly Gly Leu Gly Ser Pro Thr Gly Arg Cys Glu Trp Arg
            530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
            565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
            595                 600                 605

Cys Asn Cys Phe Pro Glu Glu Lys Cys Phe Cys Glu Pro Glu Asp
            610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
            645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
            675                 680                 685

Ser Ser Gly Ala Arg Arg Pro Ser Leu Asp Ser Met Glu Asn Gln Val
            690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
            725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
            755                 760                 765

Leu Arg Asp Leu Leu Ser Glu Phe Asn Val Leu Lys Gln Val Asn His
            770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
            805                 810                 815
```

-continued

```
Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
    850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp Ile Ser Lys Asp Leu Glu Lys Met
            995                1000                1005

Met Val Lys Arg Arg Asp Tyr Leu Asp Leu Ala Ala  Ser Thr Pro
    1010                1015                1020

Ser Asp Ser Leu Ile Tyr Asp Gly Leu Ser Glu  Glu Glu Thr
    1025                1030                1035

Pro Leu Val Asp Cys Asn Asn Ala Pro Leu Pro Arg Ala Leu Pro
    1040                1045                1050

Ser Thr Trp Ile Glu Asn Lys Leu Tyr Gly Met Ser Asp Pro Asn
    1055                1060                1065

Trp Pro Gly Glu Ser Pro Val Pro Leu Thr Arg Ala Asp Gly Thr
    1070                1075                1080

Asn Thr Gly Phe Pro Arg Tyr Pro Asn Asp Ser Val Tyr Ala Asn
    1085                1090                1095

Trp Met Leu Ser Pro Ser Ala Ala Lys Leu Met Asp Thr Phe Asp
    1100                1105                1110

Ser
```